(12) United States Patent
Suzuki et al.

(10) Patent No.: US 10,377,713 B2
(45) Date of Patent: Aug. 13, 2019

(54) QUENCHER

(71) Applicant: Wako Pure Chemical Industries, Ltd., Osaka-shi, Osaka (JP)

(72) Inventors: Katsufumi Suzuki, Kawagoe (JP); Yoshihisa Tsurumi, Kawagoe (JP); Kei Kawano, Kawagoe (JP); Shigeaki Imazeki, Kawagoe (JP); Tetsuji Murase, Kawagoe (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 0 days.

(21) Appl. No.: 15/535,650

(22) PCT Filed: Dec. 18, 2015

(86) PCT No.: PCT/JP2015/085523
§ 371 (c)(1),
(2) Date: Jun. 13, 2017

(87) PCT Pub. No.: WO2016/098889
PCT Pub. Date: Jun. 23, 2016

(65) Prior Publication Data
US 2017/0342031 A1   Nov. 30, 2017

(30) Foreign Application Priority Data

Dec. 18, 2014 (JP) .................. 2014-256082
Jan. 27, 2015 (JP) .................. 2015-013679

(51) Int. Cl.
| | | |
|---|---|---|
| C07D 491/16 | (2006.01) |
| C07D 493/10 | (2006.01) |
| C07D 209/88 | (2006.01) |
| C08F 20/30 | (2006.01) |
| G02B 5/20 | (2006.01) |
| C09B 11/24 | (2006.01) |

(Continued)

(52) U.S. Cl.
CPC ......... C07D 209/88 (2013.01); C07D 491/16 (2013.01); C07D 493/10 (2013.01); C08F 20/30 (2013.01); C09B 11/24 (2013.01); C09B 69/06 (2013.01); C09B 69/103 (2013.01); G02B 5/20 (2013.01)

(58) Field of Classification Search
CPC .................. C07D 491/16; C07D 493/10
See application file for complete search history.

(56) References Cited

U.S. PATENT DOCUMENTS

2016/0040013 A1   2/2016 Shida et al.

FOREIGN PATENT DOCUMENTS

| CN | 102838578 A | 12/2012 |
| EP | 1493781 A1 | 1/2005 |

(Continued)

OTHER PUBLICATIONS

Marculescu et al., "Aryloxymaleimides for cysteine modification, disulfide bridging and the dual functionalization of disulfide bonds", Chem. Commun., 2014, vol. 50, pp. 7139-7142, cited in ISR (4 pages).

(Continued)

*Primary Examiner* — Shawquia Jackson
(74) *Attorney, Agent, or Firm* — Westerman, Hattori, Daniels & Adrian, LLP

(57) ABSTRACT

A quencher is disclosed having a compound represented by the following general formula (1):

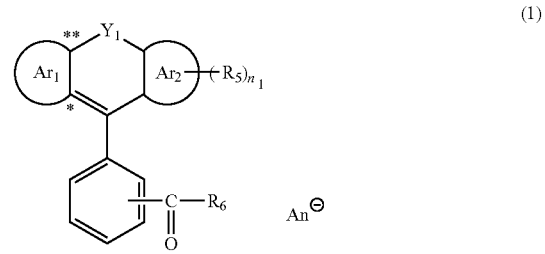

wherein $R_5$ each independently represent a halogen atom, an alkyl group, an alkoxy group, an alkylthio group, an amino group having a substituent or not having a substituent, a hydroxy group, an aryl group, an aryloxy group, or an arylalkyl group; $R_6$ represents a group having a polymerizable unsaturated group, a hydroxy group, or the like; $Y_1$ represents an oxygen atom, or the like; $An^-$ represents an anion; $Ar_1$ represents a specific ring structure; * and ** represent binding positions; $Ar_2$ represents a benzene ring, a naphthalene ring, or an anthracene ring; $n_1$ represents a specific integer;
and the following structure (1-10) in the general formula (1) is an asymmetric structure;

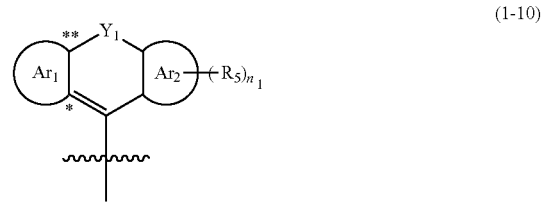

(wherein $R_5$, $Y_1$, $Ar_1$, $Ar_2$, $n_1$, * and ** are the same as described above.).

17 Claims, No Drawings

(51) Int. Cl.
*C09B 69/06* (2006.01)
*C09B 69/10* (2006.01)

(56) References Cited

FOREIGN PATENT DOCUMENTS

| EP | 2 957 578 A1 | 12/2015 |
|---|---|---|
| EP | 3165541 A1 | 5/2017 |
| FR | 2 889 064 A1 | 2/2007 |
| JP | 61-221265 A | 10/1986 |
| JP | 7-13082 A | 1/1995 |
| JP | 2010-249870 A | 11/2010 |
| JP | 2011-241372 A | 12/2011 |
| WO | 00/64988 A1 | 11/2000 |
| WO | 2014/126167 A1 | 8/2014 |

OTHER PUBLICATIONS

Yuan et al., Abstract of "A Unique Class of Near-Infrared Functional Fluorescent Dyes with Carboxylic- Acid-Modulated Fluorescene On/Off Switching: Rational Design, Synthesis, Optical Properties, Theoretical Calculations, and Applications for Fluorescene Imaging in Living Animals", J. Am. Chem. Soc., 2012, vol. 134, pp. 13510-13523, sited in ISR (2 pages).

Homma et al., Abstract of "A ratiometric fluorescent molecular probe for visualization of mitochondrial temperature in iving cells", Chem. Commun, Feb. 26, 2015, vol. 51, pp. 6194-6197, cited in ISR (5 pages).

International Search Report dated Feb. 9, 2016, issued in counterpart International Application No. PCT/JP2015/085523 (2 pages).

Fernando, C.A.N. et al, "Photoelectrochemical properties of Rhodamine-C18 sensitized p-CuSCN photoelectrochemical cell (PEC)", Solar Energy Materials and Solar Cells, Elsevier Science Publishers, Jul. 1, 1994, vol. 33, No. 3, pp. 301-315; cited in Extended (supplementary) European Search Report dated Aug. 10, 2018.

Tokita, S. et al, "Molecular Design for Low Radiation Dose Detection with Functional Dyes", Journal of Photopolymer Science and Technology, Jan. 1, 2000, vol. 13, No. 2, pp. 187-190; cited in Extended (supplementary) European Search Report dated Aug. 10, 2018.

Stepanov, B.I. et al, "Influence of structural elements of rhodamine dyes on lasing efficiency of their solutions", Acta Physica Et Chemica, Jate, Szege, Hu, Jan. 1, 1974, vol. 20, No. 3, pp. 207-213; cited in Extended (supplementary) European Search Report dated Aug. 10, 2018.

Extended (supplementary) European Search Report dated Aug. 10, 2018, issued in counterpart EP Application No. 15870088.0. (14 pages).

QUENCHER

TECHNICAL FIELD

The present invention relates to a quencher to be used in a color filter in a color liquid crystal display device or a color pickup tube element, or the like; a compound to be used as the quencher, or the like; and a polymer having a monomer unit derived from the compound.

BACKGROUND ART

In general, a color filter is composed of the one arranged with fine band(stripe)-like filter segments (pixels) made of filter layers of each color, which are formed, in parallel or crossed, on the surface of a transparent substrate such as glass; or the one arranged with fine filter segments in a constant array vertically and horizontally. A transparent electrode or an oriented film is formed on a color filter, and it is necessary to carry out a formation step at a high temperature of generally 150° C. or higher, and preferably 200° C. or higher, to sufficiently obtain performance thereof.

Quality items required to a color filter include brightness and contrast ratio. High contrast is needed, because a color filter having low contrast ratio causes a blurred screen. In addition, higher brightness of a color filter is required, because a color filter having low brightness results in a dark screen due to low light transmittance.

Accordingly, there have been reported various kinds of dyes having a xanthene skeleton, such as a Rhodamine-type coloring compound, or color filters which use the xanthene-based dye, as the one to solve the problem of brightness and contrast ratio. For example, in JP-A-2011-241372, there has been reported a Rhodamine dye to be suitably used in ink for a color filter, or the like. In addition, in JP-A-2010-249870, there have been reported a colored composition for a color filter, containing a xanthene-based dye, and the like; and in WO2014/126167, there have been reported a colored composition containing a cationic Rhodamine derivative having a specific anion, and the like.

CITATION LIST

Patent Literature

[PATENT LITERATURE 1] JP-A-2011-241372
[PATENT LITERATURE 2] JP-A-2010-249870
[PATENT LITERATURE 3] WO2014/126167

SUMMARY OF INVENTION

Technical Problem

However, the xanthene-based dye exhibits fluorescence emission, and thus has a problem that the contrast ratio is lowered. Therefore, the present inventors have investigated conventional quenchers, however, there were no quenchers having quenching ability enough to suppress fluorescence emission of the xanthene-based dye. Accordingly, it is an object of the present invention to provide a quencher capable of sufficiently quenching fluorescence of a compound having fluorescent property, including a xanthene-based dye.

Solution to Problem

In view of the circumstances, the present inventors have discovered, as the result of intensive investigation, that a compound having a specific structure is useful as a quencher for various compounds having fluorescent property, for example, a xanthene-based dye, and the like.

In addition, it has been discovered that high heat resistance, elution resistance and weather resistance, in addition to quenching effect on a compound having fluorescent property, are exerted by using a compound having a specific anion, as a counter anion, as well as having a polymerizable unsaturated group, or a polymer having a monomer unit derived from the compound; and thus the present invention has been completed.

That is, the present invention relates to "a quencher comprising a compound represented by the following general formula (1) (hereinafter, it may be abbreviated as the quencher of the present invention);

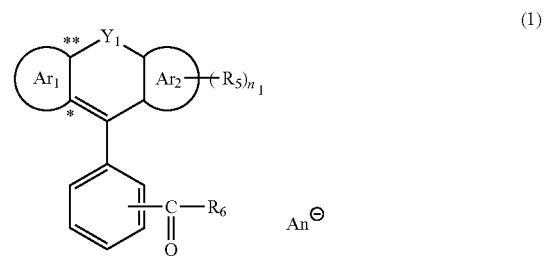

(1)

[wherein $n_1$ pieces of $R_5$ each independently represent a halogen atom, an alkyl group having 1 to 20 carbon atoms, an alkoxy group having 1 to 20 carbon atoms, an alkylthio group having 1 to 20 carbon atoms, an amino group having a substituent or not having a substituent, a hydroxy group, an aryl group having 6 to 14 carbon atoms, an aryloxy group having 6 to 14 carbon atoms, or an arylalkyl group having 7 to 20 carbon atoms; $R_6$ represents a group having a polymerizable unsaturated group, a hydroxy group, an alkoxy group having 1 to 20 carbon atoms, an amino group having a substituent or not having a substituent, or a heterocyclic amino group; $Y_1$ represents an oxygen atom, a sulfur atom or —$NR_{32}$—; $R_{32}$ represents an alkyl group having 1 to 6 carbon atoms; An⁻ represents an anion; $Ar_1$ represents a ring structure represented by the following general formulae (1-1) to (1-7);

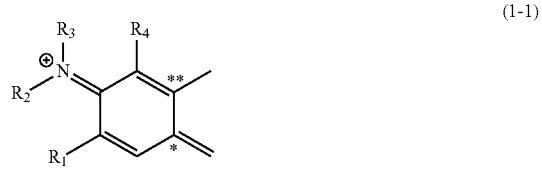

(1-1)

(wherein $R_1$ and $R_4$ represent a hydrogen atom; $R_2$ and $R_3$ each independently represent an alkyl group having 1 to 20 carbon atoms, or an aryl group having 6 to 14 carbon atoms which has a substituent or no substituent; $R_1$ and $R_2$ may form an alkylene group having 2 to 4 carbon atoms; and $R_3$ and $R_4$ may form an alkylene group having 2 to 4 carbon atoms.),

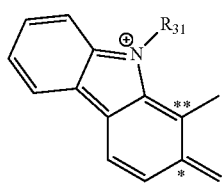

(1-2)

(wherein $R_{31}$ represents an alkyl group having 1 to 20 carbon atoms.),

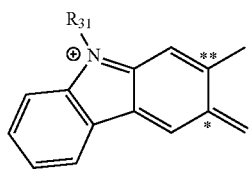

(1-3)

(wherein $R_{31}$ is the same as described above.),

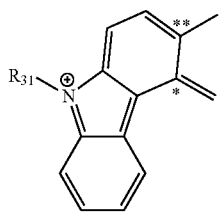

(1-4)

(wherein $R_{31}$ is the same as described above.),

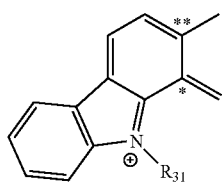

(1-5)

(wherein $R_{31}$ is the same as described above.),

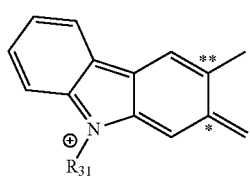

(1-6)

(wherein $R_{31}$ is the same as described above.),

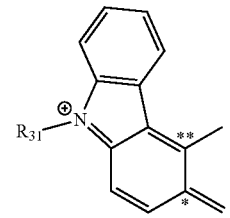

(1-7)

(wherein $R_{31}$ is the same as described above.),

* and ** represent each binding position; $Ar_2$ represents a benzene ring, a naphthalene ring or an anthracene ring; when $Ar_2$ is the benzene ring, $n_1$ represents an integer of 0 to 4, when $Ar_2$ is the naphthalene ring, $n_1$ represents an integer of 0 to 6, and when $Ar_2$ is the anthracene ring, $n_1$ represents an integer of 0 to 8;

and the following structure (1-10) in the general formula (1) is an asymmetric structure;

(1-10)

(wherein $n_1$ pieces of $R_5$, $Y_1$, $Ar_1$, $Ar_2$, $n_1$, * and ** are the same as described above.)]", "a compound represented by the following general formula (3) (hereinafter, it may be abbreviated as the compound of the present invention):

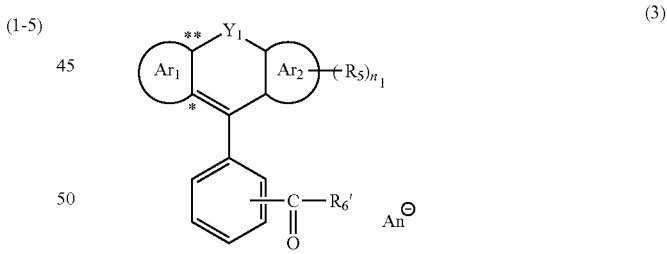

(3)

[wherein $n_1$ pieces of $R_5$ each independently represent a halogen atom, an alkyl group having 1 to 20 carbon atoms, an alkoxy group having 1 to 20 carbon atoms, an alkylthio group having 1 to 20 carbon atoms, an amino group having a substituent or not having a substituent, a hydroxy group, an aryl group having 6 to 14 carbon atoms, an aryloxy group having 6 to 14 carbon atoms, or an arylalkyl group having 7 to 20 carbon atoms; $R_6'$ represents a group having a polymerizable unsaturated group; $Y_1$ represents an oxygen atom, a sulfur atom or —$NR_{32}$—; $R_{32}$ represents an alkyl group having 1 to 6 carbon atoms; An⁻ represents an anion; $Ar_1$ represents a ring structure represented by the following general formulae (1-1) to (1-7);

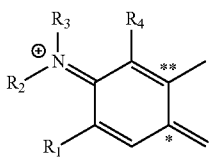

(1-1)

(wherein $R_1$ and $R_4$ represent a hydrogen atom; $R_2$ and $R_3$ each independently represent an alkyl group having 1 to 20 carbon atoms, or an aryl group having 6 to 14 carbon atoms which has a substituent or no substituent; $R_1$ and $R_2$ may form an alkylene group having 2 to 4 carbon atoms; and $R_3$ and $R_4$ may form an alkylene group having 2 to 4 carbon atoms.),

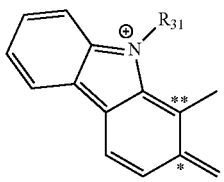

(1-2)

(wherein $R_{31}$ represents an alkyl group having 1 to 20 carbon atoms.),

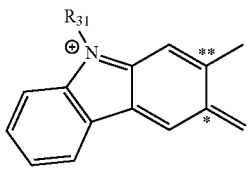

(1-3)

(wherein $R_{31}$ is the same as described above.),

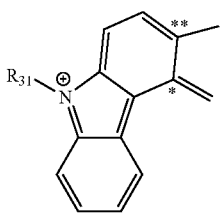

(1-4)

(wherein $R_{31}$ is the same as described above.),

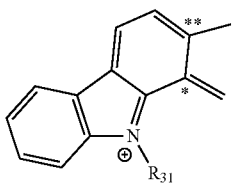

(1-5)

(wherein $R_{31}$ is the same as described above.),

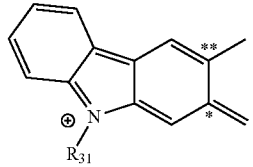

(1-6)

(wherein $R_{31}$ is the same as described above.),

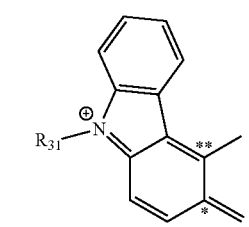

(1-7)

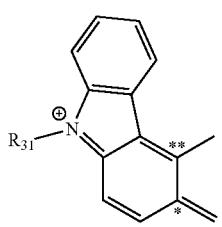

(wherein $R_{31}$ is the same as described above.),
* and ** represent each binding position; $Ar_2$ represents a benzene ring, a naphthalene ring or an anthracene ring; when $Ar_2$ is the benzene ring, $n_1$ represents an integer of 0 to 4, when $Ar_2$ is the naphthalene ring, $n_1$ represents an integer of 0 to 6, and when $Ar_2$ is the anthracene ring, $n_1$ represents an integer of 0 to 8;
and the following structure (1-10) in the general formula (3) is an asymmetric structure;

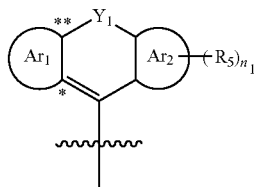

(1-10)

(wherein $n_1$ pieces of $R_5$, $Y_1$, $Ar_1$, $Ar_2$, $n_1$, * and ** are the same as described above.)]", and
"a polymer having a monomer unit derived from the compound represented by the general formula (3) (hereinafter, it may be abbreviated as the polymer of the present invention)".

Advantageous Effects of Invention

By using the quencher of the present invention, sufficient quenching effect is exerted on fluorescence which is emitted by, for example, a xanthene-based dye, or the like, which a conventional quencher has not been able to quench. That is, the color filter containing the quencher of the present invention suppresses fluorescence which is emitted by various compounds having fluorescent property, such as a xanthene-based dye, and exerts effect of having high contrast ratio.
In addition, the compound of the present invention or the polymer of the present invention has low color fading caused by heating, even in the case of heating at 150 to 250° C., and thus exerts high heat resistance effect, in addition to the quenching effect. That is, the colored composition containing the compound of the present invention or the polymer of the present invention is capable of forming a superior colored cured film, because it not only has high contrast ratio but also exerts effect to have heat resistance equivalent to or higher than that of a conventional colored composition. Therefore, the colored composition of the present invention can be used in an application of formation of a colored pixel such as a color filter, to be used in a liquid crystal display device (LCD) or a solid-state imaging element (CCD, CMOS, or the like), or in applications of printing ink, inkjet ink, paint, and the like; and it is particularly suitable for the color filter of the liquid crystal display device. Still more, the colored composition of the present invention can be used also as a colored resin molded articles by molding to sheets, films, bottles, cups, or the like, by a conventionally known molding method. Accordingly, it can be used also in applications of spectacles, color contact lenses, or the like; and can be used in similar applications also by making a multi-layered structure with a known resin. In addition, it can be used also in applications of, for example, optical films, hair coloring agents, labeling substances for compounds or biomaterials, materials of organic solar cells, or the like.

DESCRIPTION OF EMBODIMENTS

In the following description, Me represents a methyl group, Et represents an ethyl group, Pr represents a propyl group, Bu represents a butyl group, n⁻ represents a normal-form, and i⁻ represents an iso-form, respectively.

[Quencher of the Present Invention]

The quencher of the present invention is the one comprising the compound represented by the general formula (1).

(1)

[wherein $n_1$ pieces of $R_5$ each independently represent a halogen atom, an alkyl group having 1 to 20 carbon atoms, an alkoxy group having 1 to 20 carbon atoms, an alkylthio group having 1 to 20 carbon atoms, an amino group having a substituent or not having a substituent, a hydroxy group, an aryl group having 6 to 14 carbon atoms, an aryloxy group having 6 to 14 carbon atoms, or an arylalkyl group having 7 to 20 carbon atoms; $R_6$ represents a group having a polymerizable unsaturated group, a hydroxy group, an alkoxy group having 1 to 20 carbon atoms, an amino group having a substituent or not having a substituent, or a heterocyclic amino group; $Y_1$ represents an oxygen atom, a sulfur atom or —$NR_{32}$—; $R_{32}$ represents an alkyl group having 1 to 6 carbon atoms; An⁻ represents an anion; $Ar_1$ represents a ring structure represented by the following general formulae (1-1) to (1-7);

(1-1)

(wherein $R_1$ and $R_4$ represent a hydrogen atom; $R_2$ and $R_3$ each independently represent an alkyl group having 1 to 20 carbon atoms, or an aryl group having 6 to 14 carbon atoms which has a substituent or no substituent; $R_1$ and $R_2$ may form an alkylene group having 2 to 4 carbon atoms; and $R_3$ and $R_4$ may form an alkylene group having 2 to 4 carbon atoms.),

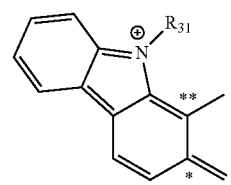
(1-2)

(wherein $R_{31}$ represents an alkyl group having 1 to 20 carbon atoms.),

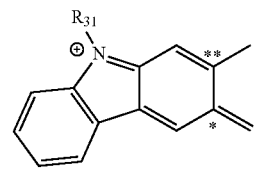
(1-3)

(wherein $R_{31}$ is the same as described above.),

(1-4)

(wherein $R_{31}$ is the same as described above.),

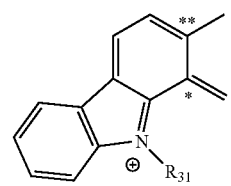
(1-5)

(wherein $R_{31}$ is the same as described above.),

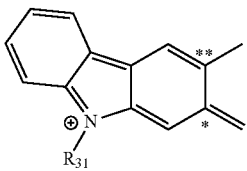
(1-6)

(wherein R$_{31}$ is the same as described above.),

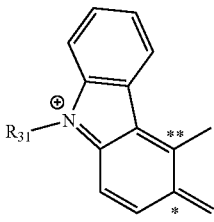
(1-7)

(wherein R$_{31}$ is the same as described above.),
* and ** represent each binding position; Ar$_2$ represents a benzene ring, a naphthalene ring or an anthracene ring; when Ar$_2$ is the benzene ring, n$_1$ represents an integer of 0 to 4, when Ar$_2$ is the naphthalene ring, n$_1$ represents an integer of 0 to 6, and when Ar$_2$ is the anthracene ring, n$_1$ represents an integer of 0 to 8;
and the following structure (1-10) in the general formula (1) is an asymmetric structure;

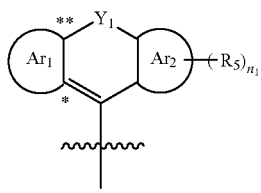
(1-10)

(wherein n$_1$ pieces of R$_5$, Y$_1$, Ar$_1$, Ar$_2$, n$_1$, * and ** are the same as described above.)]

The halogen atom in R$_5$ of the general formula (1) includes, for example, a fluorine atom, a chlorine atom, a bromine atom, an iodine atom, and the like, and among them, the fluorine atom is preferable.

The alkyl group having 1 to 20 carbon atoms, in R$_5$ of the general formula (1), may be any of the linear, branched and cyclic ones, and among them, the linear and branched ones are preferable. In addition, among the alkyl group having 1 to 20 carbon atoms, the one having 1 to 12 carbon atoms is preferable, the one having 1 to 6 carbon atoms is more preferable, and the one having 1 to 4 carbon atoms is particularly preferable. It specifically includes, for example, a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, an n-heptyl group, an isoheptyl group, a sec-heptyl group, a tert-heptyl group, a neoheptyl group, a cycloheptyl group, an n-octyl group, an isooctyl group, a sec-octyl group, a tert-octyl group, a neooctyl group, a 2-ethylhexyl group, a cyclooctyl group, an n-nonyl group, an isononyl group, a sec-nonyl group, a tert-nonyl group, a neononyl group, a cyclononyl group, an n-decyl group, an isodecyl group, a sec-decyl group, a tert-decyl group, a neodecyl group, a cyclodecyl group, an n-undecyl group, a cycloundecyl group, an n-dodecyl group, a cyclododecyl group, an n-tridecyl group, an isotridecyl group, an n-tetradecyl group, an isotetradecyl group, an n-pentadecyl group, an isopentadecyl group, an n-hexadecyl group, an isohexadecyl group, an n-heptadecyl group, an isoheptadecyl group, an n-octadecyl group, an isooctadecyl group, an n-nonadecyl group, an isononadecyl group, an n-icosyl group, an isoicosyl group, a cyclohexylmethyl group, a 1-cyclohexylethyl group, a 2-methylcyclohexyl group, a 3-methylcyclohexyl group, a 4-methylcyclohexyl group, a 2,6-dimethylcyclohexyl group, a 2,4-dimethylcyclohexyl group, a 3,5-dimethylcyclohexyl group, a 2,5-dimethylcyclohexyl group, a 2,3-dimethylcyclohexyl group, a 3,3,5-trimethylcyclohexyl group, a 4-tert-butylcyclohexyl group, a 1-adamantyl group, a 2-adamantyl group, and the like; and the methyl group, the ethyl group, the n-propyl group, the isopropyl group, the n-butyl group, the isobutyl group, the sec-butyl group, the tert-butyl group, the n-pentyl group, the isopentyl group, the sec-pentyl group, the tert-pentyl group, the neopentyl group, the 2-methylbutyl group, the 1,2-dimethylpropyl group, the 1-ethylpropyl group, the n-hexyl group, the isohexyl group, the sec-hexyl group, the tert-hexyl group, the neohexyl group, the 2-methylpentyl group, the 1,2-dimethylbutyl group, the 2,3-dimethylbutyl group, the 1-ethylbutyl group, the n-heptyl group, the n-octyl group, the n-nonyl group, the n-decyl group, the n-undecyl group and the n-dodecyl group are preferable; and the methyl group, the ethyl group, the n-propyl group, the isopropyl group, the n-butyl group, the isobutyl group, the sec-butyl group, the tert-butyl group, the n-pentyl group, the isopentyl group and the n-hexyl group are more preferable; and the methyl group, the ethyl group, the n-propyl group, the isopropyl group, the n-butyl group, the isobutyl group, the sec-butyl group and the tert-butyl group are further preferable.

The alkoxy group having 1 to 20 carbon atoms, in R$_5$ of the general formula (1), may be any of the linear, branched and cyclic ones, and among them, the linear and branched ones are preferable. In addition, among the alkoxy group having 1 to 20 carbon atoms, the one having 1 to 12 carbon atoms is preferable, the one having 1 to 6 carbon atoms is more preferable, and the one having 1 to 4 carbon atoms is particularly preferable. It specifically includes, for example, a methoxy group, an ethoxy group, an n-propoxy group, an isopropoxy group, an n-butoxy group, an isobutoxy group, a sec-butoxy group, a tert-butoxy group, a cyclobutoxy group, an n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, an n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, an n-heptyloxy group, an isoheptyloxy group, a sec-heptyloxy group, a tert-heptyloxy group, a neoheptyloxy group, a cycloheptyloxy group, an n-octyloxy group, an isooctyloxy group, a sec-octyloxy group, a tertoctyloxy group, a neooctyloxy group, a 2-ethylhexyloxy group, a cyclooctyloxy group, an n-nonyloxy group, an isononyloxy group, a sec-nonyloxy group, a tert-nonyloxy group, a neononyloxy group, a cyclononyloxy group, an n-decyloxy group, an isodecyloxy group, a sec-decyloxy group, a tert-decyloxy group, a neodecyloxy group, a cyclodecyloxy group, an n-undecyloxy group, a cycloundecyloxy group, an n-dodecyloxy group, a cyclododecyloxy group, an n-tridecyloxy group, an isotridecyloxy group, an n-tetradecyloxy group, an isotetradecyloxy group, an n-pentadecyloxy group, an isopentadecyloxy group, an n-hexadecyloxy group, an isohexadecyloxy group, an n-heptadecyloxy group, an isoheptadecyloxy group, an n-octadecyloxy group, an isooctadecyloxy group, an n-nonadecyloxy group, an isononadecyloxy group, an n-icosyloxy group, an isoicosyloxy group, and the like; and the methoxy group, the ethoxy group, the n-propoxy group, the isopropoxy group, the n-butoxy group, the isobutoxy group, the sec-butoxy group, the tert-butoxy group, the n-pentyloxy group, the isopentyloxy group, the sec-pentyloxy group, the tert-pentyloxy group, the neopentyloxy group, the 2-methylbutoxy group, the 1,2-dimethylpropoxy group, the 1-ethylpropoxy group, the n-hexyloxy group, the isohexyloxy group, the sec-hexyloxy group, the tert-hexyloxy group, the neohexyloxy group, the 2-methylpentyloxy group, the 1,2-dimethylbutoxy group, the 2,3-dimethylbutoxy group and the 1-ethylbutoxy group are preferable; and the methoxy group, the ethoxy group, the n-propoxy group, the isopropoxy group, the n-butoxy group, the isobutoxy group, the sec-butoxy group and the tert-butoxy group are more preferable; and the methoxy group and the ethoxy group are further preferable.

The alkylthio group having 1 to 20 carbon atoms, in $R_5$ of the general formula (1), may be any of the linear, branched and cyclic ones, and among them, the linear and branched ones are preferable. In addition, among the alkylthio group having 1 to 20 carbon atoms, the one having 1 to 12 carbon atoms is preferable, the one having 1 to 6 carbon atoms is more preferable, and the one having 1 to 4 carbon atoms is particularly preferable. It specifically includes, for example, a methylthio group, an ethylthio group, an n-propylthio group, an isopropylthio group, an n-butylthio group, an isobutylthio group, a sec-butylthio group, a tert-butylthio group, a cyclobutylthio group, an n-pentylthio group, an isopentylthio group, a sec-pentylthio group, a tert-pentylthio group, a neopentylthio group, a 2-methylbutylthio group, a 1,2-dimethylpropylthio group, a 1-ethylpropylthio group, a cyclopentylthio group, an n-hexylthio group, an isohexylthio group, a sec-hexylthio group, a tert-hexylthio group, a neohexylthio group, a 2-methylpentylthio group, a 1,2-dimethylbutylthio group, a 2,3-dimethylbutylthio group, a 1-ethylbutylthio group, a cyclohexylthio group, an n-heptylthio group, an isoheptylthio group, a sec-heptylthio group, a tert-heptylthio group, a neoheptylthio group, a cycloheptylthio group, an n-octylthio group, an isooctylthio group, a sec-octylthio group, a tert-octylthio group, a neooctylthio group, a 2-ethylhexylthio group, a cyclooctylthio group, an n-nonylthio group, an isononylthio group, a sec-nonylthio group, a tert-nonylthio group, a neononylthio group, a cyclononylthio group, an n-decylthio group, an isodecylthio group, a sec-decylthio group, a tert-decylthio group, a neodecylthio group, a cyclodecylthio group, an n-undecylthio group, a cycloundecylthio group, an n-dodecylthio group, a cyclododecylthio group, an n-tridecylthio group, an isotridecylthio group, an n-tetradecylthio group, an isotetradecylthio group, an n-pentadecylthio group, an isopentadecylthio group, an n-hexadecylthio group, an isohexadecylthio group, an n-heptadecylthio group, an isoheptadecylthio group, an n-octadecylthio group, an isooctadecylthio group, an n-nonadecylthio group, an isononadecylthio group, an n-icosylthio group, an isoicosylthio group, and the like; and the methylthio group, the ethylthio group, the n-propylthio group, the isopropylthio group, the n-butylthio group, the isobutylthio group, the sec-butylthio group, the tert-butylthio group, the n-pentylthio group, the isopentylthio group, the sec-pentylthio group, the tert-pentylthio group, the neopentylthio group, the 2-methylbutylthio group, the 1,2-dimethylpropylthio group, the 1-ethylpropylthio group, the n-hexylthio group, the isohexylthio group, the sec-hexylthio group, the tert-hexylthio group, the neohexylthio group, the 2-methylpentylthio group, the 1,2-dimethylbutylthio group, the 2,3-dimethylbutylthio group and the 1-ethylbutylthio group are preferable; and the methylthio group, the ethylthio group, the n-propylthio group, the isopropylthio group, the n-butylthio group, the isobutylthio group, the sec-butylthio group and the tert-butylthio group are more preferable; and the methylthio group and the ethylthio group are further preferable.

The amino group having a substituent, in $R_5$ of the general formula (1), has one or two substituents. The substituent includes, for example, an alkyl group having 1 to 20 carbon atoms, a halogenated alkyl group having 1 to 20 carbon atoms, an aryl group having 6 to 10 carbon atoms, an arylalkyl group having 7 to 13 carbon atoms, and the like.

The alkyl group having 1 to 20 carbon atoms in the substituent of the amino group having a substituent, in $R_5$ of the general formula (1), includes the same one as the alkyl group having 1 to 20 carbon atoms, in $R_5$ of the general formula (1), and the preferable one is also the same.

The halogenated alkyl group having 1 to 20 carbon atoms in the substituent of the amino group having a substituent, in $R_5$ of the general formula (1), may be any of the linear, branched and cyclic ones, and among them, the linear and branched ones are preferable. In addition, among the halogenated alkyl group having 1 to 20 carbon atoms, the one having 1 to 12 carbon atoms is preferable, the one having 1 to 6 carbon atoms is more preferable, and the one having 1 to 3 carbon atoms is particularly preferable. It specifically includes, for example, a chloroalkyl group, such as a chloromethyl group, a trichloromethyl group, a 2-chloroethyl group, a 2,2,2-trichloroethyl group, a pentachloroethyl group, a 2-chloropropyl group, a 3-chloropropyl group, a 2-chloro-2-propyl group and a heptachloropropyl group; a bromoalkyl group, such as a bromomethyl group, a tribromomethyl group, a 2-bromoethyl group, a 2,2,2-tribromoethyl group, a pentabromoethyl group, a 2-bromopropyl group, a 3-bromopropyl group, a 2-bromo-2-propyl group and a heptabromopropyl group; an iodoalkyl group, such as an iodomethyl group, a triiodomethyl group, a 2-iodoethyl group, a 2,2,2-triiodoethyl group, a pentaiodoethyl group, a 2-iodopropyl group, a 3-iodopropyl group, a 2-iodo-2-propyl group and a heptaiodopropyl group; a fluoroalkyl group, such as a fluoromethyl group, a trifluoromethyl group, a 2-fluoroethyl group, a 2,2,2-trifluoroethyl group, a 1,1,2,2-tetrafluoroethyl group, a pentafluoroethyl group, a 3-fluoropropyl group, a 3,3,3-trifluoropropyl group, a 2,2,3,3-tetrafluoropropyl group and a heptafluoropropyl group. Among them, the perhalogenoalkyl group, such as the trichloromethyl group, the pentachloroethyl group, the heptachloropropyl group, the tribromomethyl group, the pentabromoethyl group, the heptabromopropyl group, the triiodomethyl group, the pentaiodoethyl group, the heptaiodopropyl group, the trifluoromethyl group, the pentafluoroethyl group, the heptafluoropropyl group, is preferable; the perfluoroalkyl group, such as the trifluoromethyl group, the pentafluoroethyl group, the heptafluoropropyl group, is more preferable; and the trifluoromethyl group is particularly preferable.

The aryl group having 6 to 10 carbon atoms in the substituent of the amino group having a substituent, in $R_5$ of the general formula (1), includes a phenyl group, a naphthyl group, and the like, and the phenyl group is preferable.

The arylalkyl group having 7 to 13 carbon atoms in the substituent of the amino group having a substituent, in $R_5$ of the general formula (1), includes a phenylalkyl group having 7 to 9 carbon atoms, a naphthylalkyl group having 11 to 13 carbon atoms, and the like, and the phenylalkyl group having 7 to 9 carbon atoms is preferable. It specifically includes, for example, a benzyl group, a phenethyl group (a 2-phenylethyl group), a 1-phenylethyl group, a hydrocinnamyl group (a 3-phenylpropyl group), a 2-phenylpropyl group, a 1-phenylpropyl group, a cumyl group (a 2-phenylpropane-2-yl group), a naphthylmethyl group, a 2-naphthylethyl group, a 3-naphthylpropyl group, and the like; the benzyl group, the phenethyl group, the 1-phenylethyl group, the hydrocinnamyl group, the 2-phenylpropyl group, the 1-phenylpropyl group and the cumyl group are preferable; the benzyl group, the phenethyl group and the hydrocinnamyl group are more preferable; and the benzyl group is further preferable.

As the amino group having a substituent or not having a substituent, in $R_5$ of the general formula (1), an amino group having a substituent is preferable; and an amino group having an alkyl group having 1 to 20 carbon atoms, a halogenated alkyl group having 1 to 20 carbon atoms, an aryl group having 6 to 10 carbon atoms, or an arylalkyl group having 7 to 13 carbon atoms is more preferable; and an amino group having an alkyl group having 1 to 6 carbon atoms, a phenyl group, or a phenylalkyl group having 7 to 9 carbon atoms is further preferable. It specifically includes, for example, a methylamino group, an ethylamino group, an n-propylamino group, an isopropylamino group, an n-butylamino group, an isobutylamino group, a sec-butylamino group, a tert-butylamino group, an n-pentylamino group, an isopentylamino group, an n-hexylamino group, a phenylamino group, a benzylamino group, a phenethylamino group, a hydrocinnamylamino group, a dimethylamino group, a diethylamino group, a di-n-propylamino group, a diisopropylamino group, a di-n-butylamino group, a diisobutylamino group, a di-sec-butylamino group, a di-tert-butylamino group, a di-n-pentylamino group, a diisopentylamino group, a di-n-hexylamino group, a diphenylamino group, a dibenzylamino group, a diphenethylamino group, a bis(hydrocinnamyl)amino group, and the like; and the methylamino group, the ethylamino group, the n-propylamino group, the isopropylamino group, the n-butylamino group, the isobutylamino group, the sec-butylamino group, the tert-butylamino group, the phenylamino group, the benzylamino group, the dimethylamino group, the diethylamino group, the di-n-propylamino group, the diisopropylamino group, the di-n-butylamino group, the diisobutylamino group, the di-sec-butylamino group, the di-tert-butylamino group, the diphenylamino group and the dibenzylamino group are preferable; and the methylamino group, the ethylamino group, the phenylamino group, the benzylamino group, the dimethylamino group, the diethylamino group, the diphenylamino group and the dibenzylamino group are more preferable.

The aryl group having 6 to 14 carbon atoms, in $R_5$ of the general formula (1), specifically includes, for example, a phenyl group, a naphthyl group, an anthracenyl group, and the like, and the phenyl group is preferable.

The aryloxy group having 6 to 14 carbon atoms, in $R_5$ of the general formula (1), specifically includes, for example, a phenoxy group, a naphthyloxy group, an anthracenyloxy group, and the like, and the phenoxy group is preferable.

The arylalkyl group having 7 to 20 carbon atoms, in $R_5$ of the general formula (1), includes a phenylalkyl group having 7 to 12 carbon atoms, a naphthylalkyl group having 11 to 16 carbon atoms, an anthracenylalkyl group having 15 to 20 carbon atoms, and the like; the phenylalkyl group having 7 to 12 carbon atoms is preferable; and an phenylalkyl group having 7 to 9 carbon atoms is more preferable. It specifically includes, for example, a benzyl group, a phenethyl group (a 2-phenylethyl group), a 1-phenylethyl group, a hydrocinnamyl group (a 3-phenylpropyl group), a 2-phenylpropyl group, a 1-phenylpropyl group, a cumyl group (a 2-phenylpropane-2-yl group), a 4-phenylbutyl group, a 3-phenylbutyl group, a 2-phenylbutyl group, a 1-phenylbutyl group, a 5-phenylpentyl group, a 4-phenylpentyl group, a 3-phenylpentyl group, a 2-phenylpentyl group, a 1-phenylpentyl group, a 6-phenylhexyl group, a 5-phenylhexyl group, a 4-phenylhexyl group, a 3-phenylhexyl group, a 2-phenylhexyl group, a 1-phenylhexyl group, a naphthylmethyl group, a 2-naphthylethyl group, a 3-naphthylpropyl group, a 4-naphthylbutyl group, a 5-naphthylpentyl group, a 6-naphthylhexyl group, a anthracenylmethyl group, a 2-anthracenylethyl group, a 3-anthracenylpropyl group, a 4-anthracenylbutyl group, a 5-anthracenylpentyl group, a 6-anthracenylhexyl group, and the like; and the benzyl group, the phenethyl group, the 1-phenylethyl group, the hydrocinnamyl group, the 2-phenylpropyl group, the 1-phenylpropyl group, the cumyl group, the 4-phenylbutyl group, the 3-phenylbutyl group, the 2-phenylbutyl group, the 1-phenylbutyl group, the 5-phenylpentyl group, the 4-phenylpentyl group, the 3-phenylpentyl group, the 2-phenylpentyl group, the 1-phenylpentyl group, the 6-phenylhexyl group, the 5-phenylhexyl group, the 4-phenylhexyl group, the 3-phenylhexyl group, the 2-phenylhexyl group and the 1-phenylhexyl group are preferable; and the benzyl group, the phenethyl group, the 1-phenylethyl group, the hydrocinnamyl group, the 2-phenylpropyl group, the 1-phenylpropyl group and the cumyl group are more preferable; and the benzyl group, the phenethyl group, the hydrocinnamyl group and the cumyl group are further preferable.

As $R_5$ of the general formula (1), a halogen atom; an alkyl group having 1 to 12 carbon atoms; an alkoxy group having 1 to 12 carbon atoms; an alkylthio group having 1 to 12 carbon atoms; an amino group having a halogen atom, an alkyl group having 1 to 20 carbon atoms, an aryl group having 6 to 10 carbon atoms, or an arylalkyl group having 7 to 13 carbon atoms; a hydroxy group; an aryl group having 6 to 14 carbon atoms; an aryloxy group having 6 to 14 carbon atoms; and an arylalkyl group having 7 to 20 carbon atoms are preferable; and the halogen atom; the alkyl group having 1 to 12 carbon atoms; the alkoxy group having 1 to 12 carbon atoms; the alkylthio group having 1 to 12 carbon atoms; an amino group having an alkyl group having 1 to 6 carbon atoms, a phenyl group, or a phenylalkyl group having 7 to 9 carbon atoms; the hydroxy group; a phenyl group; a phenoxy group; and a phenylalkyl group having 7 to 12 carbon atoms are more preferable; and the halogen atom; an alkyl group having 1 to 6 carbon atoms; an alkoxy group having 1 to 6 carbon atoms; an alkylthio group having 1 to 6 carbon atoms; the amino group having the alkyl group having 1 to 6 carbon atoms, the phenyl group, or the phenylalkyl group having 7 to 9 carbon atoms; the hydroxy group; the phenyl group; the phenoxy group; and a phenylalkyl group having 7 to 9 carbon atoms are further preferable. Specifically, a fluorine atom, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a methoxy group, an ethoxy group, an n-propoxy group, an isopropoxy group, an n-butoxy group, an isobutoxy group, a sec-butoxy group, a tert-butoxy group, a methylthio group, an ethylthio group, an n-propylthio group, an isopropylthio group, an n-butylthio group, an isobutylthio group, a sec-butylthio group, a tert-butylthio group, a methylamino group, an ethylamino group, an n-propylamino group, an isopropylamino group, an n-butylamino group, an isobutylamino group, a sec-butylamino group, a tert-butylamino group, a phenylamino group, a benzylamino group, a dimethylamino group, a diethylamino group, a di-n-propylamino group, a diisopropylamino group, a di-n-butylamino group, a diisobutylamino group, a di-sec-butylamino group, a di-tert-butylamino group, a diphenylamino group, a dibenzylamino group, a hydroxy group, a phenyl group, a phenoxy group, a benzyl group, a phenethyl group, a 1-phenylethyl group, a hydrocinnamyl group, a 2-phenylpropyl group, a 1-phenylpropyl group and a cumyl group are preferable; and the fluorine atom, the methyl group, the ethyl group, the n-propyl group, the isopropyl group, the n-butyl group, the isobutyl group, the sec-butyl group, the tert-butyl group, the methoxy group, the ethoxy group, the methylthio group, the ethylthio group, the methylamino group, the ethylamino group, the phenylamino group, the benzylamino group, the dimethylamino group, the diethylamino group, the diphenylamino group, the dibenzylamino group, the hydroxy group, the phenyl group, the phenoxy group, the benzyl group, the phenethyl group, the hydrocinnamyl group and the cumyl group are more preferable.

The group having the polymerizable unsaturated group, in $R_6$ of the general formula (1), may be the one having the polymerizable unsaturated group at the end of the functional group, and the polymerizable unsaturated group includes, for example, an acryloyl group, a methacryloyl group, a vinylaryl group, a vinyloxy group, an allyl group, and the like; and the acryloyl group and the methacryloyl group are preferable.

A preferable specific example, among the group having the polymerizable unsaturated group, in $R_6$ of the general formula (1), includes a group represented by the following general formula (2).

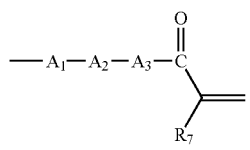

(2)

[wherein $R_7$ represents a hydrogen atom or a methyl group; $A_1$ represents —O—, or a group represented by the following general formula (2-1);

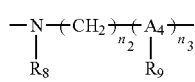

(2-1)

(wherein $R_8$ and $R_9$ each independently represent a hydrogen atom, or an alkyl group having 1 to 12 carbon atoms; $A_4$ represents a nitrogen atom, or a group represented by the following formula (2-2);

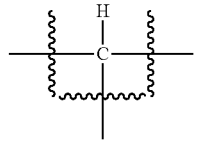

(2-2)

$n_2$ represents an integer of 0 to 3; $R_8$ and $R_9$ may form a ring structure of a 5 to 6-membered ring together with —N(CH$_2$)$_{n2}$-(A$_4$)$_{n3}$- bonding thereto; when the ring structure of the 5 to 6-membered ring is formed by $R_8$, $R_9$ and —N(CH$_2$)$_{n2}$-(A$_4$)$_{n3}$-, $n_3$ represents 1, and when the ring structure of the 5 to 6-membered ring is not formed, $n_3$ represents 0 or 1.);

$A_2$ represents an alkylene group having 1 to 21 carbon atoms which has at least one group selected from —O—, —OCO—, —COO—, —NHCO—, —CONH—, —NHCONH— and an arylene group in a chain; an alkylene group having 1 to 21 carbon atoms which has at least one group selected from —O—, —OCO—, —COO—, —NHCO—, —CONH—, —NHCONH— and an arylene group in a chain, and also has a hydroxy group as a substituent; an alkylene group having 1 to 21 carbon atoms which has a hydroxy group as a substituent; or an alkylene group having 1 to 21 carbon atoms; $A_3$ represents —NR$_{10}$— or —O—; and $R_{10}$ represents a hydrogen atom or an alkyl group having 1 to 12 carbon atoms.]

As $R_7$ of the general formula (2), a methyl group is preferable.

As $A_1$ of the general formula (2), —O— is preferable.

The alkyl group having 1 to 12 carbon atoms, in $R_8$ and $R_9$ of the general formula (2-1), may be any of the linear, branched and cyclic ones, and among them, the linear and branched ones are preferable. In addition, among the alkyl group having 1 to 12 carbon atoms, the one having 1 to 6 carbon atoms is preferable, and the one having 1 to 4 carbon atoms is more preferable. It specifically includes, for example, a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, an n-heptyl group, an isoheptyl group, a sec-heptyl group, a tert-heptyl group, a neoheptyl group, a cycloheptyl group, an n-octyl group, an isooctyl group, a sec-octyl group, a tert-octyl group, a neooctyl group, a 2-ethylhexyl group, a cyclooctyl group, an n-nonyl group, an isononyl group, a sec-nonyl group, a tert-nonyl group, a neononyl group, a cyclononyl group, an n-decyl group, an isodecyl group, a sec-decyl group, a tert-decyl group, a neodecyl group, a cyclodecyl group, an n-undecyl group, a cycloundecyl group, an n-dodecyl group, a cyclododecyl group, a cyclohexylmethyl group, a 1-cyclohexylethyl group, a 2-methylcyclohexyl group, a 3-methylcyclohexyl group, a 4-methylcyclohexyl group, a 2,6-dimethylcyclohexyl group, a 2,4-dimethylcyclohexyl group, a 3,5-dimethylcyclohexyl group, a 2,5-dimethylcyclohexyl group, a 2,3-dimethylcyclohexyl group, a 3,3,5-trimethylcyclohexyl group, a 4-tert-butylcyclohexyl group, a 1-adamantyl group, a 2-adamantyl group, and the like; and the methyl group, the ethyl group, the n-propyl group, the isopropyl group, the n-butyl group, the isobutyl group, the sec-butyl group, the tert-butyl group, the n-pentyl group, the isopentyl group, the sec-pentyl group, the tert-pentyl group, the neopentyl group, the 2-methylbutyl group, the 1,2-dimethylpropyl group, the 1-ethylpropyl group, the n-hexyl group, the isohexyl group, the sec-hexyl group, the tert-hexyl group, the neohexyl group, the 2-methylpentyl group, the 1,2-dimethylbutyl group, the 2,3-dimethylbutyl group, the 1-ethylbutyl group, the n-heptyl group, the n-octyl group, the n-nonyl group, the n-decyl group, the n-undecyl group and the n-dodecyl group are preferable; and the methyl group, the ethyl group, the n-propyl group, the isopropyl group, the n-butyl group, the isobutyl group, the sec-butyl group, the tert-butyl group, the n-pentyl group, the isopentyl group and the n-hexyl group are more preferable; and the methyl group, the ethyl group, the n-propyl group, the isopropyl group, the n-butyl group, the isobutyl group, the sec-butyl group and the tert-butyl group are further preferable.

As $R_8$ and $R_9$ of the general formula (2-1), a hydrogen atom and an alkyl group having 1 to 4 carbon atoms are preferable, and the hydrogen atom is more preferable. It specifically includes, for example, a hydrogen atom, a methyl group, an ethyl group, an n-propyl group, an isopropyl group, an n-butyl group, an isobutyl group, a sec-butyl group, a tert-butyl group, and the like; the hydrogen atom, the methyl group and the ethyl group are preferable; and the hydrogen atom are more preferable.

As $A_4$ of the general formula (2-1), the group represented by the formula (2-2) is preferable.

When $R_8$ and $R_9$ of the general formula (2-1) form a ring structure of a 5 to 6-membered ring together with —N—$(CH_2)_{n2}$-$(A_4)_{n3}$- bonding thereto, $n_3$ is 1, and the ring structure is the one represented by the following general formula (2-3).

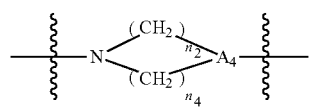
(2-3)

(wherein $n_4$ represents an integer of 0 to 4; and $A_4$ and $n_2$ are the same as described above; provided that $n_2+n_4$ is an integer of 3 to 4.)

When the ring structure represented by the general formula (2-3) is formed, $n_2$ of the general formula (2-1) is preferably 2, and when the ring structure represented by the general formula (2-3) is not formed, it is preferably 0.

When the ring structure represented by the general formula (2-3) is formed, $n_3$ of the general formula (2-1) represents 1, and when the ring structure represented by the general formula (2-3) is not formed, it is preferably 0.

As $n_4$ of the general formula (2-3), 2 is preferable.

The ring structure represented by the general formula (2-3) represents a 5 to 6-membered ring, and the 6-membered ring is preferable.

Specific examples of the ring structure represented by the general formula (2-3) include, for example, the following ones.

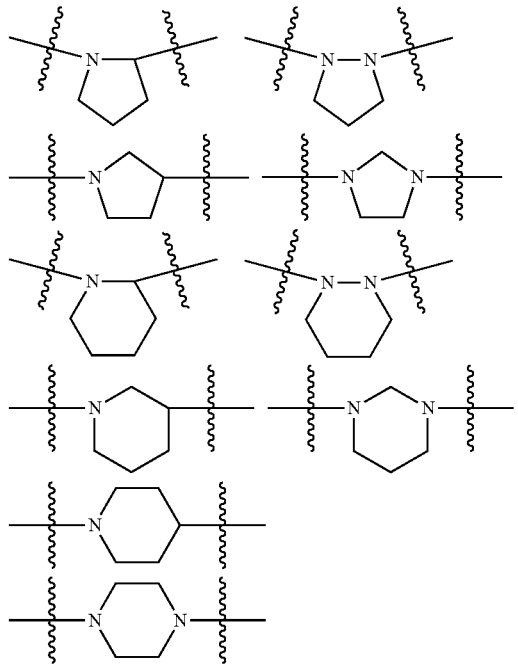

Among the specific examples, the following one is preferable.

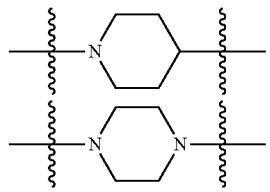

The alkylene group having 1 to 21 carbon atoms, in "an alkylene group having 1 to 21 carbon atoms which has at least one group selected from —O—, —OCO—, —COO—, —NHCO—, —CONH—, —NHCONH— and an arylene group in a chain", "an alkylene group having 1 to 21 carbon atoms which has at least one group selected from —O—, —OCO—, —COO— and an arylene group in a chain, and also has a hydroxy group as a substituent", "an alkylene group having 1 to 21 carbon atoms which has a hydroxy group as a substituent" and "an alkylene group having 1 to 21 carbon atoms", in $A_2$ of the general formula (2), may be any of the linear, branched and cyclic ones, and the one having 1 to 12 carbon atoms is preferable, and the one having 1 to 6 carbon atoms is more preferable, and the one having 1 to 3 carbon atoms is further preferable. It specifically includes, for example, a methylene group, an ethylene group, a trimethylene group, a propylene group, a tetramethylene group, a 1-methyltrimethylene group, a 2-methyltrimethylene group, a 1,2-dimethylethylene group, a 1,1-dimethylethylene group, an ethylethylene group, a pentamethylene group, a 1-methyltetramethylene group, a 2-methyltetramethylene group, a 1,2-dimethyltrimethylene group, a 1-ethyltrimethylene group, a hexamethylene group, a methylpentamethylene group, an n-heptylene group, an n-octylene group, an n-nonylene group, an n-decylene group, an n-undecylene group, an n-dodecylene group, an n-tridecylene group, an n-tetradecylene group, an n-pentadecylene group, an n-hexadecylene group, an n-heptadecylene group, an n-octadecylene group, an n-nonadecylene group, an n-icosylene, an n-henicosylene group, —C$_4$H$_6$—CH$_2$— group, —C$_5$H$_8$—CH$_2$— group, —C$_6$H$_{10}$—CH$_2$— group, —C$_6$H$_{10}$—C$_2$H$_4$— group, —C$_6$H$_{10}$—C$_3$H$_6$— group, —C$_7$H$_{12}$—CH$_2$— group, and the like; and the methylene group, the ethylene group, the trimethylene group, the tetramethylene group, the pentamethylene group, the hexamethylene group, —C$_6$H$_{10}$—CH$_2$— group, —C$_6$H$_{10}$—C$_2$H$_4$— group, —C$_6$H$_{10}$—C$_3$H$_6$— group, and the like, are preferable; and the methylene group, the ethylene group and the trimethylene group are more preferable; and the ethylene group is particularly preferable.

The arylene group in "an alkylene group having 1 to 21 carbon atoms which has at least one group selected from —O—, —OCO—, —COO—, —NHCO—, —CONH—, —NHCONH— and an arylene group in a chain" and "an alkylene group having 1 to 21 carbon atoms which has at least one group selected from —O—, —OCO—, —COO— and an arylene group in a chain, and also has a hydroxy group as a substituent", in A$_2$ of the general formula (2), includes the one having 6 to 10 carbon atoms, and specifically includes a phenylene group, a naphthylene group, and the like.

"An alkylene group having 1 to 21 carbon atoms which has at least one group selected from —O—, —OCO—, —COO—, —NHCO—, —CONH—, —NHCONH— and an arylene group in a chain" in A$_2$ of the general formula (2) includes, for example, groups represented by the following general formulae (21-1) to (21-5), and the like.

—(R$_{51}$—O—)$_{h1}$—R$_{52}$—  (21-1)

(wherein R$_{51}$ and R$_{52}$ each independently represent a linear or branched alkylene group having 1 to 4 carbon atoms; and h$_1$ represents an integer of 1 to 9; provided that total number of carbon atoms in the formula is 2 to 21.)

—(CH$_2$)$_{h2}$—OCO—(CH$_2$)$_{h3}$—  (21-2)

(wherein h$_2$ and h$_3$ each independently represent an integer of 1 to 10.)

—(CH$_2$)$_{h4}$—OCO—R$_{53}$—COO—(CH$_2$)$_{h5}$—  (21-3)

(wherein R$_{53}$ represents a phenylene group, or an alkylene group having 1 to 7 carbon atoms; and h$_4$ and h$_5$ each independently represent an integer of 1 to 3.)

—(CH$_2$)$_{h6}$-A$_5$-(CH$_2$)$_{h7}$—  (21-4)

(wherein A$_5$ represents —NHCO—, —CONH— or —NHCONH—; and h$_6$ and h$_7$ each independently represent an integer of 1 to 10.)

—(CH$_2$)$_{h8}$—O—CONH—(CH$_2$)$_{h9}$—  (21-5)

(wherein h$_8$ and h$_9$ each independently represent an integer of 1 to 10.)

The linear or branched alkylene group having 1 to 4 carbon atoms, in R$_{51}$ and R$_{52}$ of the general formula (21-1), specifically includes, for example, a methylene group, an ethylene group, a trimethylene group, a propylene group, a tetramethylene group, a 1-methyltrimethylene group, a 2-methyltrimethylene group, a 1,2-dimethylethylene group, a 1,1-dimethylethylene group, an ethylethylene group, and the like; and the ethylene group and the propylene group are preferable.

As h$_2$ of the general formula (21-2), an integer of 1 to 3 is preferable, and 2 is more preferable.

As h$_3$ of the general formula (21-2), 2 is preferable.

The alkylene group having 1 to 7 carbon atoms, in R$_{53}$ of the general formula (21-3), specifically includes, for example, a methylene group, an ethylene group, a trimethylene group, a tetramethylene group, a pentamethylene group, a hexamethylene group, an n-heptylene group, a cyclobutylene group, a cyclopentylene group, a cyclohexylene group, a cycloheptylene group, and the like.

As h$_4$ and h$_5$ of the general formula (21-3), the case where h$_4$ and h$_5$ are the same is preferable, and in addition, an integer of 1 to 3 is preferable, and 2 is more preferable.

As A$_5$ of the general formula (21-4), —NHCONH— is preferable.

As h$_6$ and h$_7$ of the general formula (21-4), the case where h$_6$ and h$_7$ are the same is preferable, and in addition, 2 is preferable.

As h$_8$ and h$_9$ of the general formula (21-5), the case where h$_8$ and h$_9$ are the same is preferable, and in addition, an integer of 1 to 4 is preferable.

The group represented by the general formula (21-1) specifically includes, for example,
—CH$_2$CH$_2$—O—CH$_2$CH$_2$—,
—(CH$_2$CH$_2$—O)$_2$—CH$_2$CH$_2$—,
—(CH$_2$CH$_2$—O)$_3$—CH$_2$CH$_2$—,
—(CH$_2$CH$_2$—O)$_4$—CH$_2$CH$_2$—,
—(CH$_2$CH$_2$—O)$_5$—CH$_2$CH$_2$—,
—(CH$_2$CH$_2$—O)$_6$—CH$_2$CH$_2$—,
—(CH$_2$CH$_2$—O)$_7$—CH$_2$CH$_2$—,
—(CH$_2$CH$_2$—O)$_8$—CH$_2$CH$_2$—,
—(CH$_2$CH$_2$—O)$_9$—CH$_2$CH$_2$—,
—CH$_2$CH(CH$_3$)—O—CH$_2$CH(CH$_3$)—,
—(CH$_2$CH(CH$_3$)—O)$_2$—CH$_2$CH(CH$_3$)—,
—(CH$_2$CH(CH$_3$)—O)$_3$—CH$_2$CH(CH$_3$)—,
—(CH$_2$CH(CH$_3$)—O)$_4$—CH$_2$CH(CH$_3$)—,
—(CH$_2$CH(CH$_3$)—O)$_5$—CH$_2$CH(CH$_3$)—,
—(CH$_2$CH(CH$_3$)—O)$_6$—CH$_2$CH(CH$_3$)—,
—CH(CH$_3$)CH$_2$—O—CH(CH$_3$)CH$_2$—,
—(CH(CH$_3$)CH$_2$—O)$_2$—CH(CH$_3$)CH$_2$—,
—(CH(CH$_3$)CH$_2$—O)$_3$—CH(CH$_3$)CH$_2$—,
—(CH(CH$_3$)CH$_2$—O)$_4$—CH(CH$_3$)CH$_2$—,
—(CH(CH$_3$)CH$_2$—O)$_5$—CH(CH$_3$)CH$_2$—,
—(CH(CH$_3$)CH$_2$—O)$_6$—CH(CH$_3$)CH$_2$—,
—CH(CH$_3$)CH$_2$—O—CH$_2$CH(CH$_3$)—, and the like.

The group represented by the general formula (21-2) specifically includes, for example,
—CH$_2$—O—CO—(CH$_2$)$_2$—,
—(CH$_2$)$_2$—O—CO—(CH$_2$)$_2$—,
—(CH$_2$)$_3$—O—CO—(CH$_2$)$_2$—, and the like.

The group represented by the general formula (21-3) specifically includes, for example,
—CH$_2$—O—CO—CH$_2$—CO—O—CH$_2$—,
—CH$_2$—O—CO—(CH$_2$)$_2$—CO—O—CH$_2$—,
—CH$_2$—O—CO—(CH$_2$)$_3$—CO—O—CH$_2$—,
—CH$_2$—O—CO—(CH$_2$)$_4$—CO—O—CH$_2$—,
—CH$_2$—O—CO—(CH$_2$)$_5$—CO—O—CH$_2$—,
—CH$_2$—O—CO—(CH$_2$)$_6$—CO—O—CH$_2$—,
—CH$_2$—O—CO—(CH$_2$)$_7$—CO—O—CH$_2$—,
—(CH$_2$)$_2$—O—CO—CH$_2$—CO—O—(CH$_2$)$_2$—,
—(CH$_2$)$_2$—O—CO—(CH$_2$)$_2$—CO—O—(CH$_2$)$_2$—,
—(CH$_2$)$_2$—O—CO—(CH$_2$)$_3$—CO—O—(CH$_2$)$_2$—,
—(CH$_2$)$_2$—O—CO—(CH$_2$)$_4$—CO—O—(CH$_2$)$_2$—,
—(CH$_2$)$_2$—O—CO—(CH$_2$)$_5$—CO—O—(CH$_2$)$_2$—,
—(CH$_2$)$_2$—O—CO—(CH$_2$)$_6$—CO—O—(CH$_2$)$_2$—,
—(CH$_2$)$_2$—O—CO—(CH$_2$)$_7$—CO—O—(CH$_2$)$_2$—,
—(CH$_2$)$_3$—O—CO—CH$_2$—CO—O—(CH$_2$)$_3$—,
—(CH$_2$)$_3$—O—CO—(CH$_2$)$_2$—CO—O—(CH$_2$)$_3$—,
—(CH$_2$)$_3$—O—CO—(CH$_2$)$_3$—CO—O—(CH$_2$)$_3$—,
—(CH$_2$)$_3$—O—CO—(CH$_2$)$_4$—CO—O—(CH$_2$)$_3$—,
—(CH$_2$)$_3$—O—CO—(CH$_2$)$_5$—CO—O—(CH$_2$)$_3$—,
—(CH$_2$)$_3$—O—CO—(CH$_2$)$_6$—CO—O—(CH$_2$)$_3$—, —$(CH_2)_3$—O—CO—$(CH_2)_7$—CO—O—$(CH_2)_3$—,
—$CH_2$—O—CO—$C_6H_4$—CO—O—$CH_2$—,
—$(CH_2)_2$—O—CO—$C_6H_4$—CO—O—$(CH_2)_2$—,
—$(CH_2)_3$—O—CO—$C_6H_4$—CO—O—$(CH_2)_3$—,
—$CH_2$—O—CO—$C_6H_{10}$—O—$CH_2$—,
—$(CH_2)_2$—O—CO—$C_6H_{10}$—CO—O—$(CH_2)_2$—,
—$(CH_2)_3$—O—CO—$C_6H_{10}$—CO—O—$(CH_2)_3$—, and the like; and among them,
—$CH_2$—O—CO—$CH_2$—CO—O—$CH_2$—,
—$CH_2$—O—CO—$(CH_2)_2$—CO—O—$CH_2$—,
—$CH_2$—O—CO—$(CH_2)_3$—CO—O—$CH_2$—,
—$CH_2$—O—CO—$(CH_2)_4$—CO—O—$CH_2$—,
—$CH_2$—O—CO—$(CH_2)_5$—CO—O—$CH_2$—,
—$CH_2$—O—CO—$(CH_2)_6$—CO—O—$CH_2$—,
—$CH_2$—O—CO—$(CH_2)_7$—CO—O—$CH_2$—,
—$(CH_2)_2$—O—CO—$CH_2$—CO—O—$(CH_2)_2$—,
—$(CH_2)_2$—O—CO—$(CH_2)_2$—CO—O—$(CH_2)_2$—,
—$(CH_2)_2$—O—CO—$(CH_2)_3$—CO—O—$(CH_2)_2$—,
—$(CH_2)_2$—O—CO—$(CH_2)_4$—CO—O—$(CH_2)_2$—,
—$(CH_2)_2$—O—CO—$(CH_2)_5$—CO—O—$(CH_2)_2$—,
—$(CH_2)_2$—O—CO—$(CH_2)_6$—CO—O—$(CH_2)_2$—,
—$(CH_2)_2$—O—CO—$(CH_2)_7$—CO—O—$(CH_2)_2$—,
—$(CH_2)_3$—O—CO—$CH_2$—CO—O—$(CH_2)_3$—,
—$(CH_2)_3$—O—CO—$(CH_2)_2$—CO—O—$(CH_2)_3$—,
—$(CH_2)_3$—O—CO—$(CH_2)_3$—CO—O—$(CH_2)_3$—,
—$(CH_2)_3$—O—CO—$(CH_2)_4$—CO—O—$(CH_2)_3$—,
—$(CH_2)_3$—O—CO—$(CH_2)_5$—CO—O—$(CH_2)_3$—,
—$(CH_2)_3$—O—CO—$(CH_2)_6$—CO—O—$(CH_2)_3$— and
—$(CH_2)_3$—O—CO—$(CH_2)_7$—CO—O—$(CH_2)_3$— are preferable; and
—$(CH_2)_2$—O—CO—$CH_2$—CO—O—$(CH_2)_2$—,
—$(CH_2)_2$—O—CO—$(CH_2)_2$—CO—O—$(CH_2)_2$—,
—$(CH_2)_2$—O—CO—$(CH_2)_3$—CO—O—$(CH_2)_2$—,
—$(CH_2)_2$—O—CO—$(CH_2)_4$—CO—O—$(CH_2)_2$—,
—$(CH_2)_2$—O—CO—$(CH_2)_5$—CO—O—$(CH_2)_2$—,
—$(CH_2)_2$—O—CO—$(CH_2)_6$—CO—O—$(CH_2)_2$— and
—$(CH_2)_2$—O—CO—$(CH_2)_7$—CO—O—$(CH_2)_2$— are more preferable; and
—$(CH_2)_2$—O—CO—$(CH_2)_2$—CO—O—$(CH_2)_2$— is particularly preferable.

The group represented by the general formula (21-4) specifically includes, for example,
—$CH_2$—NHCO—$CH_2$—,
—$(CH_2)_2$—NHCO—$(CH_2)_2$—,
—$(CH_2)_3$—NHCO—$(CH_2)_3$—,
$(CH_2)_4$—NHCO—$(CH_2)_4$—,
—$CH_2$—CONH—$CH_2$—,
—$(CH_2)_2$—CONH—$(CH_2)_2$—,
—$(CH_2)_3$—CONH—$(CH_2)_3$—,
$(CH_2)_4$—CONH—$(CH_2)_4$—,
—$CH_2$—NHCONH—$CH_2$—,
—$(CH_2)_2$—NHCONH—$(CH_2)_2$—,
—$(CH_2)_3$—NHCONH—$(CH_2)_3$—,
—$(CH_2)_4$—NHCONH—$(CH_2)_4$—,
—$(CH_2)_5$—NHCONH—$(CH_2)_5$—,
—$(CH_2)_6$—NHCONH—$(CH_2)_6$—,
—$(CH_2)_7$—NHCONH—$(CH_2)_7$—,
—$(CH_2)_8$—NHCONH—$(CH_2)_8$—,
—$(CH_2)_9$—NHCONH—$(CH_2)_9$—,
—$(CH_2)_{10}$—NHCONH—$(CH_2)_{10}$—, and the like; and among them,
—$CH_2$—NHCONH—$CH_2$—,
—$(CH_2)_2$—NHCONH—$(CH_2)_2$—,
—$(CH_2)_3$—NHCONH—$(CH_2)_3$—,
—$(CH_2)_4$—NHCONH—$(CH_2)_4$—,
—$(CH_2)_5$—NHCONH—$(CH_2)_5$—,
—$(CH_2)_6$—NHCONH—$(CH_2)_6$—,
—$(CH_2)_7$—NHCONH—$(CH_2)_7$—,
—$(CH_2)_8$—NHCONH—$(CH_2)_8$—,
—$(CH_2)_9$—NHCONH—$(CH_2)_9$— and
—$(CH_2)_{10}$—NHCONH—$(CH_2)_{10}$— are preferable; and
—$(CH_2)_2$—NHCONH—$(CH_2)_2$— is more preferable.

The group represented by the general formula (21-5) specifically includes, for example,
—$CH_2$—O—CONH—$CH_2$—,
—$(CH_2)_2$—O—CONH—$(CH_2)_2$—,
—$(CH_2)_3$—O—CONH—$(CH_2)_3$—,
—$(CH_2)_4$—O—CONH—$(CH_2)_4$—, and the like.

"An alkylene group having 1 to 21 carbon atoms which has at least one group selected from —O—, —OCO—, —COO—, —NHCO—, —CONH—, —NHCONH— and an arylene group in a chain, and also has a hydroxy group as a substituent" in $A_2$ of the general formula (2) includes, for example, groups represented by the following general formulae (22-1) to (22-2), and the like.

$$—R_{54}—(CH_2)_{h10}— \qquad (22\text{-}1)$$

(wherein $R_{54}$ represents an arylene group having 6 to 10 carbon atoms which has a hydroxy group as a substituent; and $h_{10}$ represents an integer of 1 to 4.)

$$—R_{55}\text{-}A_6\text{-}(CH_2)_{h11}— \qquad (22\text{-}2)$$

(wherein $R_{55}$ represents an alkylene group having 1 to 7 carbon atoms which has a hydroxy group as a substituent, or an arylene group having 6 to 10 carbon atoms which has a hydroxy group as a substituent; $A_6$ represents —O—, —OCO—, —COO—, —NHCO—, —CONH— or —NHCONH—; and $h_{11}$ represents an integer of 2 to 4.)

The arylene group having 6 to 10 carbon atoms which has a hydroxy group as a substituent, in $R_{54}$ of the general formula (22-1), includes a hydroxyphenylene group, a dihydroxyphenylene group, a hydroxynaphthylene group, a dihydroxynaphthylene group, and the like.

The alkylene group having 1 to 7 carbon atoms which has a hydroxy group as a substituent, in $R_{55}$ of the general formula (22-2), includes a hydroxymethylene group, a hydroxyethylene group, a hydroxytrimethylene group, a hydroxytetramethylene group, a hydroxypentamethylene group, a hydroxyhexamethylene group, a hydroxyheptylene group, a hydroxycyclobutylene group, a hydroxycyclopentylene group, a hydroxycyclohexylene group, a hydroxycycloheptylene group, and the like.

The arylene group having 6 to 10 carbon atoms which has a hydroxy group as a substituent, in $R_{55}$ of the general formula (22-2), includes the same one as the arylene group having 6 to 10 carbon atoms which has a hydroxy group as a substituent, in $R_{54}$ of the general formula (22-1).

Preferable specific examples of the group represented by the general formula (22-1) include, for example,
—$C_6H_3(OH)$—$CH_2$—, —$C_6H_3(OH)$—$(CH_2)_2$—,
—$C_6H_3(OH)$—$(CH_2)_3$—, —$C_6H_3(OH)$—$(CH_2)_4$—,
—$C_6H_2(OH)_2$—$CH_2$—, —$C_6H_2(OH)_2$—$(CH_2)_2$—,
—$C_6H_2(OH)_2$—$(CH_2)_3$—, —$C_6H_2(OH)_2$—$(CH_2)_4$—, and the like.

Preferable specific examples of the group represented by the general formula (22-2) include, for example,
—CH(OH)—$CH_2$—O—$(CH_2)_2$—,
—CH(OH)—$CH_2$—O—$(CH_2)_3$—,
—CH(OH)—$CH_2$—O—$(CH_2)_4$—,
—CH(OH)—$CH_2$—OCO—$(CH_2)_2$—,
—CH(OH)—$CH_2$—OCO—$(CH_2)_3$—,
—CH(OH)—$CH_2$—OCO—$(CH_2)_4$—,
—CH(OH)—$CH_2$—COO—$(CH_2)_2$—,
—CH(OH)—$CH_2$—COO—$(CH_2)_3$—, —CH(OH)—CH$_2$—COO—(CH$_2$)$_4$—,
—CH(OH)—CH$_2$—NHCO—(CH$_2$)$_2$—,
—CH(OH)—CH$_2$—NHCO—(CH$_2$)$_3$—,
—CH(OH)—CH$_2$—NHCO—(CH$_2$)$_4$—,
—CH(OH)—CH$_2$—CONH—(CH$_2$)$_2$—,
—CH(OH)—CH$_2$—CONH—(CH$_2$)$_3$—,
—CH(OH)—CH$_2$—CONH—(CH$_2$)$_4$—,
—CH(OH)—CH$_2$—NHCONH—(CH$_2$)$_2$—,
—CH(OH)—CH$_2$—NHCONH—(CH$_2$)$_3$—,
—CH(OH)—CH$_2$—NHCONH—(CH$_2$)$_4$—, and the like.

"An alkylene group having 1 to 21 carbon atoms which has a hydroxy group as a substituent" in A$_2$ of the general formula (2) includes, for example, a group represented by the following general formula (23-1), and the like.

$$-R_{56}-(CH_2)_{h12}-\tag{23-1}$$

(wherein R$_{56}$ represents an alkylene group having 1 to 7 carbon atoms which has a hydroxy group as a substituent; and h$_{12}$ represents an integer of 1 to 4.)

The alkylene group having 1 to 7 carbon atoms which has a hydroxy group as a substituent, in R$_{56}$ of the general formula (23-1), includes the same one as the alkylene group having 1 to 7 carbon atoms which has a hydroxy group as a substituent, in R$_{55}$ of the general formula (22-2).

The group represented by the general formula (23-1) specifically includes, for example,
—C$_6$H$_9$(OH)—CH$_2$—, —C$_6$H$_9$(OH)—(CH$_2$)$_2$—,
—C$_6$H$_9$(OH)—(CH$_2$)$_3$—, —C$_6$H$_9$(OH)—(CH$_2$)$_4$—,
—CH(OH)—CH$_2$—, —CH(OH)—(CH$_2$)$_2$—,
—CH(OH)—(CH$_2$)$_3$—, —CH(OH)—(CH$_2$)$_4$—, and the like.

When A$_1$ in the general formula (2) is —O—, A$_2$ in the general formula (2) is preferably the alkylene group having 1 to 21 carbon atoms. Among them, a methylene group, an ethylene group, a trimethylene group, a tetramethylene group, a pentamethylene group, a hexamethylene group, and the like, is preferable; and the methylene group, the ethylene group and the trimethylene group are more preferable; and the ethylene group is particularly preferable.

When A$_1$ in the general formula (2) is the group represented by the general formula (2-1), A$_2$ in the general formula (2) is preferably the alkylene group having 1 to 21 carbon atoms which has at least one group selected from —O—, —OCO—, —COO—, —NHCO—, —CONH—, —NHCONH— and an arylene group in a chain. Among them, the groups represented by the general formulae (21-3) and (21-4) are preferable, and more specifically,
—CH$_2$—O—CO—CH$_2$—CO—O—CH$_2$—,
—CH$_2$—O—CO—(CH$_2$)$_2$—CO—O—CH$_2$—,
—CH$_2$—O—CO—(CH$_2$)$_3$—CO—O—CH$_2$—,
—CH$_2$—O—CO—(CH$_2$)$_4$—CO—O—CH$_2$—,
—CH$_2$—O—CO—(CH$_2$)$_5$—CO—O—CH$_2$—,
—CH$_2$—O—CO—(CH$_2$)$_6$—CO—O—CH$_2$—,
—CH$_2$—O—CO—(CH$_2$)$_7$—CO—O—CH$_2$—,
—(CH$_2$)$_2$—O—CO—CH$_2$—CO—O—(CH$_2$)$_2$—,
—(CH$_2$)$_2$—O—CO—(CH$_2$)$_2$—CO—O—(CH$_2$)$_2$—,
—(CH$_2$)$_2$—O—CO—(CH$_2$)$_3$—CO—O—(CH$_2$)$_2$—,
—(CH$_2$)$_2$—O—CO—(CH$_2$)$_4$—CO—O—(CH$_2$)$_2$—,
—(CH$_2$)$_2$—O—CO—(CH$_2$)$_5$—CO—O—(CH$_2$)$_2$—,
—(CH$_2$)$_2$—O—CO—(CH$_2$)$_6$—CO—O—(CH$_2$)$_2$—,
—(CH$_2$)$_2$—O—CO—(CH$_2$)$_7$—CO—O—(CH$_2$)$_2$—,
—(CH$_2$)$_3$—O—CO—CH$_2$—CO—O—(CH$_2$)$_3$—,
—(CH$_2$)$_3$—O—CO—(CH$_2$)$_2$—CO—O—(CH$_2$)$_3$—,
—(CH$_2$)$_3$—O—CO—(CH$_2$)$_3$—CO—O—(CH$_2$)$_3$—,
—(CH$_2$)$_3$—O—CO—(CH$_2$)$_4$—CO—O—(CH$_2$)$_3$—,
—(CH$_2$)$_3$—O—CO—(CH$_2$)$_5$—CO—O—(CH$_2$)$_3$—,
—(CH$_2$)$_3$—O—CO—(CH$_2$)$_6$—CO—O—(CH$_2$)$_3$—,
—(CH$_2$)$_3$—O—CO—(CH$_2$)$_7$—CO—O—(CH$_2$)$_3$—,
—CH$_2$—NHCONH—CH$_2$—,
—(CH$_2$)$_2$—NHCONH—(CH$_2$)$_2$—,
—(CH$_2$)$_3$—NHCONH—(CH$_2$)$_3$—,
—(CH$_2$)$_4$—NHCONH—(CH$_2$)$_4$—,
—(CH$_2$)$_5$—NHCONH—(CH$_2$)$_5$—,
—(CH$_2$)$_6$—NHCONH—(CH$_2$)$_6$—,
—(CH$_2$)$_7$—NHCONH—(CH$_2$)$_7$—,
—(CH$_2$)$_8$—NHCONH—(CH$_2$)$_8$—,
—(CH$_2$)$_9$NHCONH—(CH$_2$)$_9$— and
—(CH$_2$)$_{10}$—NHCONH—(CH$_2$)$_{10}$—, are preferable; and
—(CH$_2$)$_2$—O—CO—CH$_2$—CO—O—(CH$_2$)$_2$—,
—(CH$_2$)$_2$—O—CO—(CH$_2$)$_2$—CO—O—(CH$_2$)$_2$—,
—(CH$_2$)$_2$—O—CO—(CH$_2$)$_3$—CO—O—(CH$_2$)$_2$—,
—(CH$_2$)$_2$—O—CO—(CH$_2$)$_4$—CO—O—(CH$_2$)$_2$—,
—(CH$_2$)$_2$—O—CO—(CH$_2$)$_5$—CO—O—(CH$_2$)$_2$—,
—(CH$_2$)$_2$—O—CO—(CH$_2$)$_6$—CO—O—(CH$_2$)$_2$—,
—(CH$_2$)$_2$—O—CO—(CH$_2$)$_7$—CO—O—(CH$_2$)$_2$—,
—CH$_2$—NHCONH—CH$_2$—,
—(CH$_2$)$_2$—NHCONH—(CH$_2$)$_2$—,
—(CH$_2$)$_3$—NHCONH—(CH$_2$)$_3$—,
—(CH$_2$)$_4$—NHCONH—(CH$_2$)$_4$—,
—(CH$_2$)$_5$—NHCONH—(CH$_2$)$_5$—,
—(CH$_2$)$_6$—NHCONH—(CH$_2$)$_6$—,
—(CH$_2$)$_7$—NHCONH—(CH$_2$)$_7$—,
—(CH$_2$)$_8$—NHCONH—(CH$_2$)$_8$—,
—(CH$_2$)$_9$—NHCONH—(CH$_2$)$_9$— and
—(CH$_2$)$_{10}$—NHCONH—(CH$_2$)$_{10}$— are more preferable; and
—(CH$_2$)$_2$—O—CO—(CH$_2$)$_2$—CO—O—(CH$_2$)$_2$— and
—(CH$_2$)$_2$—NHCONH—(CH$_2$)$_2$— are particularly preferable.

The alkyl group having 1 to 12 carbon atoms, in R$_{10}$ in A$_3$ of the general formula (2), includes the same one as the alkyl group having 1 to 12 carbon atoms, in R$_8$ and R$_9$ of the general formula (2-1), and the preferable one is also the same.

As R$_{10}$ in A$_3$ of the general formula (2), a hydrogen atom and an alkyl group having 1 to 4 carbon atoms are preferable, and the hydrogen atom is more preferable. It specifically includes a hydrogen atom, a methyl group, an ethyl group, an n-propyl group, an isopropyl group, an n-butyl group, an isobutyl group, a sec-butyl group, a tert-butyl group, and the like; and the hydrogen atom the methyl group, and the ethyl group are preferable; and the hydrogen atom is more preferable.

As A$_3$ in the general formula (2), —O— is preferable.

A preferable specific example among the group represented by the general formula (2) includes a group represented by the following general formula (2').

(wherein R$_7$, A$_1$ and A$_2$ are the same as described above.)

Preferable specific examples among the group represented by the general formula (2') include groups represented by the following general formula (2'a) and the following general formula (2'b).

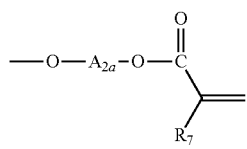
(2'a)

(wherein $A_{2a}$ represents an alkylene group having 1 to 21 carbon atoms; and $R_7$ is the same as described above.)

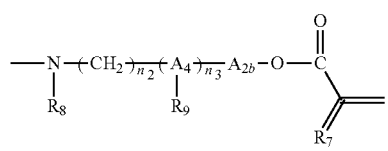
(2'b)

(wherein $A_{2b}$ represents an alkylene group having 1 to 21 carbon atoms which has at least one group selected from —O—, —OCO—, —COO—, —NHCO—, —CONH—, —NHCONH— and an arylene group in a chain; and $R_7$ to $R_9$, $A_4$, $n_2$ and $n_3$ are the same as described above.)

The alkylene group having 1 to 21 carbon atoms, in $A_{2a}$ of the general formula (2'a), includes the same one as the alkylene group having 1 to 21 carbon atoms, in $A_2$ of the general formula (2), and the preferable one is also the same.

The alkylene group having 1 to 21 carbon atoms which has at least one group selected from —O—, —OCO—, —COO—, —NHCO—, —CONH—, —NHCONH— and an arylene group in a chain, in $A_{2b}$ of the general formula (2'b), includes the same one as the alkylene group having 1 to 21 carbon atoms which has at least one group selected from —O—, —OCO—, —COO—, —NHCO—, —CONH—, —NHCONH— and an arylene group in a chain, in $A_2$ of the general formula (2), and the preferable one is also the same.

Preferable specific examples of the group represented by the general formula (2'a) include, for example, the following ones.

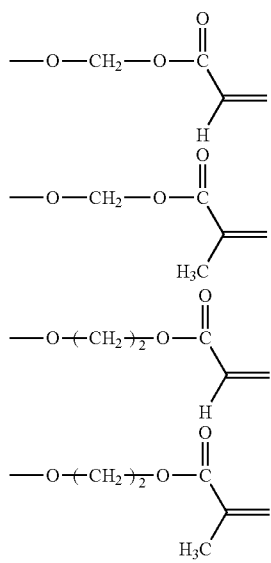

-continued

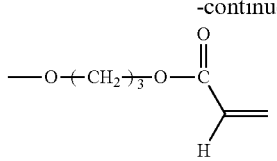
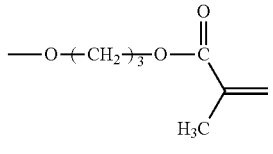
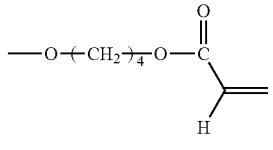
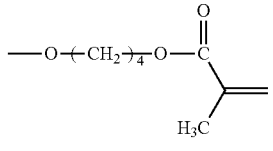
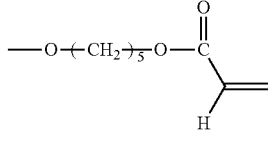
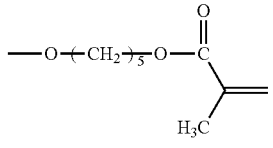
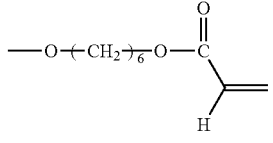
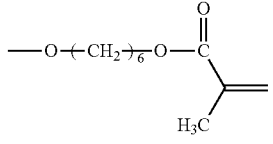

Among the specific examples, the following ones are preferable.

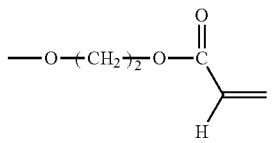
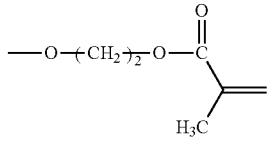

Preferable specific examples of the group represented by the general formula (2'b) include, for example, the following ones.

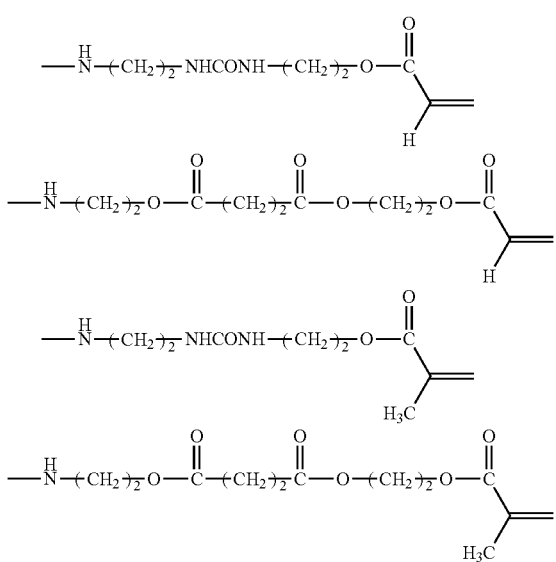

The alkoxy group having 1 to 20 carbon atoms, in $R_6$ of the general formula (1), includes the same one as the alkoxy group having 1 to 20 carbon atoms, in $R_5$ of the general formula (1), and the preferable one is also the same.

The amino group having a substituent, in $R_6$ of the general formula (1), has one or two substituents, and preferably two substituents. The substituent includes, for example, a halogenated alkyl group having 1 to 20 carbon atoms, an alkyl group having 1 to 20 carbon atoms, and the like.

The halogenated alkyl group having 1 to 20 carbon atoms in the substituent of the amino group having a substituent, in $R_6$ of the general formula (1), includes the same one as the halogenated alkyl group having 1 to 20 carbon atoms, in the substituent of the amino group having a substituent, in $R_5$ of the general formula (1), and the preferable one is also the same.

The alkyl group having 1 to 20 carbon atoms, in the substituent of the amino group having a substituent, in $R_6$ of the general formula (1), includes the same one as the alkyl group having 1 to 20 carbon atoms, in $R_5$ of the general formula (1), and the preferable one is also the same.

The amino group having a substituent or not having a substituent, in $R_6$ of the general formula (1), is preferably an amino group having a halogenated alkyl group having 1 to 20 carbon atoms, or an alkyl group having 1 to 20 carbon atoms, or not having a substituent; and it is more preferably an amino group having an alkyl group having 1 to 20 carbon atoms, or not having a substituent; and it is further preferably an amino group having an alkyl group having 1 to 6 carbon atoms, or not having a substituent; and it is particularly preferably an amino group having an alkyl group having 1 to 4 carbon atoms, or not having a substituent. It specifically includes, for example, an amino group, a methylamino group, an ethylamino group, an n-propylamino group, an isopropylamino group, an n-butylamino group, an isobutylamino group, a sec-butylamino group, a tert-butylamino group, a dimethylamino group, a diethylamino group, a di-n-propylamino group, a diisopropylamino group, a di-n-butylamino group, a diisobutylamino group, a di-sec-butylamino group, a di-tert-butylamino group, an N-ethylmethylamino group, an N-ethylpropylamino group, an N-methylpropylamino group, an N-butylmethylamino group, an N-butylethylamino group, an N-butylpropylamino group, and the like.

The heterocyclic amino group in $R_6$ of the general formula (1) includes a 5 to 7-membered heterocyclic amino group, and a 5-membered or 6-membered heterocyclic amino group is preferable. It specifically includes, for example, a pyrrolidino group, a 1-pyrrolyl group, a 1-pyrazolyl group, a 1-imidazolyl group, a 3-oxazolyl group, a 3-thiazolyl group, a piperidino group, a piperazino group, a morpholino group, a 1-pyridyl group, a 1-pyridazinyl group, a 1-pyrimidinyl group, a 1-pyrazinyl group, and the like; and the pyrrolidino group, the 1-pyrrolyl group, the piperidino group and the 1-pyridyl group are preferable; and the piperidino group is more preferable.

As $R_6$ of the general formula (1), a group having a polymerizable unsaturated group, a hydroxy group, an alkoxy group having 1 to 20 carbon atoms, an amino group having an alkyl group having 1 to 20 carbon atoms or not having a substituent, and a heterocyclic amino group are preferable; and a group having an acryloyl group or a methacryloyl group, the hydroxy group, an alkoxy group having 1 to 6 carbon atoms, an amino group having an alkyl group having 1 to 6 carbon atoms or not having a substituent, and a 5-membered or 6-membered heterocyclic amino group are more preferable; and the group represented by the general formula (2), the hydroxy group, an alkoxy group having 1 to 4 carbon atoms, an amino group having an alkyl group having 1 to 4 carbon atoms or not having a substituent, and a piperidino group are further preferable; and the group represented by the general formula (2) is particularly preferable.

A group represented by the following general formula (1-8), to be bond to a phenyl group in a fundamental skeleton, in the general formula (1), may be located at any of an ortho position, a meta position or a para position of the phenyl group, and the ortho position is preferable. Specifically, the group represented by the general formula (1-8) is preferably the one which is bonded to the phenyl group in a fundamental skeleton of Rhodamine, as a compound represented by the following general formula (1-9).

(1-8)

(wherein $R_6$ is the same as described above.)

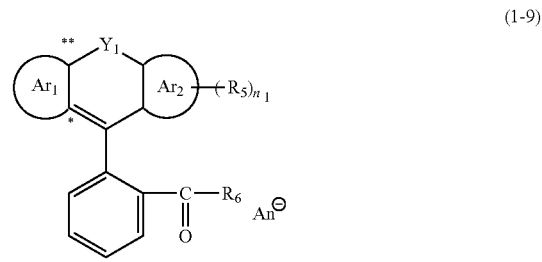

(1-9)

(wherein $n_1$ pieces of $R_5$, $R_6$, $Y_1$, $An^-$, $Ar_1$, $Ar_2$, $n_1$, * and ** are the same as described above.)

The alkyl group having 1 to 6 carbon atoms, in $R_{32}$ of $Y_1$ of the general formula (1), may be any of the linear, branched and cyclic ones, and among them, the linear and branched ones are preferable. In addition, among the alkyl group having 1 to 6 carbon atoms, the one having 1 to 4 carbon atoms is preferable. It specifically includes, for example, a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, and the like; and the methyl group, the ethyl group, the n-propyl group, the isopropyl group, the n-butyl group, the isobutyl group, the sec-butyl group and the tert-butyl group are preferable; and the methyl group and the ethyl group are more preferable.

As $Y_1$ of the general formula (1), an oxygen atom and $-NR_{32}-$ are preferable, and the oxygen atom is more preferable. It specifically includes, for example, an oxygen atom, a sulfur atom, $-NCH_3-$, $-NC_2H_5-$, $NC_3H_7-$, and the like; and the oxygen atom, the sulfur atom and $-NCH_3-$ are preferable; and the oxygen atom and $-NCH_3-$ are more preferable; and the oxygen atom is particularly preferable.

The alkyl group having 1 to 20 carbon atoms, in $R_2$ and $R_3$ of the general formula (1-1), includes the same one as the alkyl group having 1 to 20 carbon atoms, in $R_5$ of the general formula (1), and the preferable one is also the same.

The aryl group having 6 to 14 carbon atoms in "an aryl group having 6 to 14 carbon atoms which has a substituent or no substituent", in $R_2$ and $R_3$ of the general formula (1-1), includes a phenyl group, a naphthyl group, an anthracenyl group, and the like, and the phenyl group is preferable.

The aryl group having 6 to 14 carbon atoms which has a substituent, in $R_2$ and $R_3$ of the general formula (1-1), has usually one to five substituents, and preferably one to three substituents, and more preferably one substituent. The substituent includes, for example, an alkyl group having 1 to 20 carbon atoms.

The alkyl group having 1 to 20 carbon atoms in the substituent of "an aryl group having 6 to 14 carbon atoms which has the substituent", in $R_2$ and $R_3$ of the general formula (1-1), includes the same one as the alkyl group having 1 to 20 carbon atoms, in $R_5$ of the general formula (1), and the preferable one is also the same.

The aryl group having 6 to 14 carbon atoms which has a substituent, in $R_2$ and $R_3$ of the general formula (1-1), includes an aryl group having 6 to 14 carbon atoms which has an alkyl group having 1 to 20 carbon atoms, and the like; and a phenyl group which has an alkyl group having 1 to 20 carbon atoms, a naphthyl group and an anthracenyl group are preferable; and a phenyl group which has an alkyl group having 1 to 12 carbon atoms is more preferable; and a phenyl group which has an alkyl group having 1 to 6 carbon atoms is further preferable; and a phenyl group which has an alkyl group having 1 to 3 carbon atoms is particularly preferable. It specifically includes, for example, an o-tolyl group (a methylphenyl group), a m-tolyl group, a p-tolyl group, an o-ethylphenyl group, a m-ethylphenyl group, a p-ethylphenyl group, an o-propylphenyl group, a m-propylphenyl group, a p-propylphenyl group, an o-butylphenyl group, a m-butylphenyl group, a p-butylphenyl group, an o-pentylphenyl group, a m-pentylphenyl group, a p-pentylphenyl group, an o-hexylphenyl group, a m-hexylphenyl group, a p-hexylphenyl group, a 2,3-xylyl group (a 2,3-dimethylphenyl group), a 2,4-xylyl group, a 2,5-xylyl group, a 2,6-xylyl group, a 3,4-xylyl group, a 3,5-xylyl group, a mesityl group (a 2,4,6-trimethylphenyl group), and the like; and the p-tolyl group, the p-ethylphenyl group, the p-propylphenyl group, the p-butylphenyl group, the p-pentylphenyl group, the p-hexylphenyl group, the 2,4-xylyl group, the 2,6-xylyl group, the 3,5-xylyl group and the mesityl group are preferable; and the p-tolyl group, the p-ethylphenyl group and the p-propylphenyl group are more preferable. It should be noted that the alkyl group among the specific examples is not limited to a normal-form, and contains all of the branched forms, such as a sec-form, a tert-form, an iso-form and a neo-form.

When $R_1$ and $R_2$ of the general formula (1-1) form an alkylene group having 2 to 4 carbon atoms, and when $R_3$ and $R_4$ of the general formula (1-1) form an alkylene group having 2 to 4 carbon atoms, the alkylene group having 2 to 4 carbon atoms may be any of the linear or branched one, and the linear one is preferable. It specifically includes, for example, an ethylene group, a trimethylene group, a propylene group, a 1,1-dimethylmethylene group, a tetramethylene group, a 1-methyltrimethylene group, a 2-methyltrimethylene group, a 1,2-dimethylethylene group, a 1,1-dimethylethylene group, an ethylethylene group, and the like; and the ethylene group, the trimethylene group and the tetramethylene group are preferable; and the trimethylene group is more preferable.

When $R_1$ and $R_2$ form an alkylene group having 2 to 4 carbon atoms, and/or when $R_3$ and $R_4$ form an alkylene group having 2 to 4 carbon atoms, in the general formula (1-1), specific examples of the ring structure represented by the general formula (1-1) include, for example, the following ones.

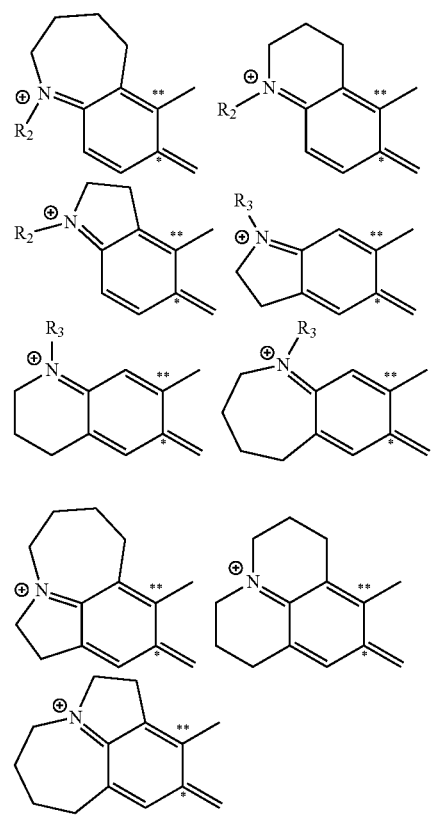

(wherein $R_2$, $R_3$, * and ** are the same as described above.)

Among the specific examples, the following ones are preferable.

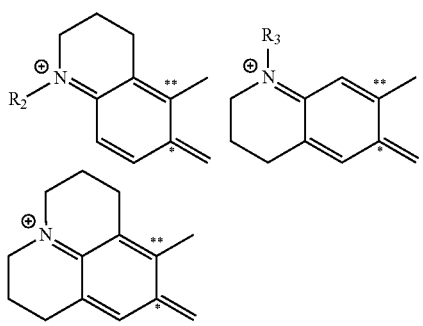

(wherein $R_2$, $R_3$, * and ** are the same as described above.)

Among the specific examples, the following one is more preferable.

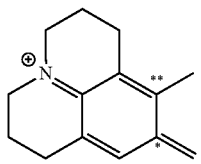

(wherein * and ** are the same as described above.)

As $R_1$ of the general formula (1-1), a hydrogen atom, and the one forming a linear alkylene group having 2 to 4 carbon atoms, by $R_1$ and $R_2$, are preferable. It specifically includes, for example, a hydrogen atom, the one forming an ethylene group by $R_1$ and $R_2$, the one forming a trimethylene group by $R_1$ and $R_2$, and the one forming a tetramethylene group by $R_1$ and $R_2$; and the hydrogen atom, and the one forming the trimethylene group by $R_1$ and $R_2$ are preferable.

As $R_2$ of the general formula (1-1), an alkyl group having 1 to 12 carbon atoms, a phenyl group which has an alkyl group having 1 to 6 carbon atoms or no substituent, and the one forming an alkylene group having 2 to 4 carbon atoms by $R_1$ and $R_2$ are preferable; and an alkyl group having 1 to 6 carbon atoms, a phenyl group which has an alkyl group having 1 to 3 carbon atoms or no substituent, and the one forming a linear alkylene group having 2 to 4 carbon atoms by $R_1$ and $R_2$ are more preferable. It specifically includes, for example, a methyl group, an ethyl group, a propyl group, a butyl group, a pentyl group, a hexyl group, a phenyl group, a p-tolyl group, a p-ethylphenyl group, a p-propylphenyl group, a p-butylphenyl group, a p-pentylphenyl group, a p-hexylphenyl group, a 2,4-xylyl group, a 2,6-xylyl group, a 3,5-xylyl group, a mesityl group, the one forming an ethylene group by $R_1$ and $R_2$, the one forming a trimethylene group by $R_1$ and $R_2$, the one forming a tetramethylene group by $R_1$ and $R_2$, and the like; and the methyl group, the ethyl group, the propyl group, the butyl group, the pentyl group, the hexyl group, the phenyl group, the p-tolyl group, the p-ethylphenyl group, the p-propylphenyl group, and the one forming the trimethylene group by $R_1$ and $R_2$ are preferable. It should be noted that the alkyl group among the specific examples is not limited to a normal-form, and contains all of the branched forms, such as a sec-form, a tert-form, an iso-form and a neo-form.

As $R_3$ of the general formula (1-1), an alkyl group having 1 to 12 carbon atoms, a phenyl group which has an alkyl group having 1 to 6 carbon atoms or no substituent, and the one forming an alkylene group having 2 to 4 carbon atoms by $R_3$ and $R_4$ are preferable; and an alkyl group having 1 to 6 carbon atoms, a phenyl group which has an alkyl group having 1 to 3 carbon atoms or no substituent, and the one forming a linear alkylene group having 2 to 4 carbon atoms by $R_3$ and $R_4$ are more preferable. It specifically includes, for example, a methyl group, an ethyl group, a propyl group, a butyl group, a pentyl group, a hexyl group, a phenyl group, a p-tolyl group, a p-ethylphenyl group, a p-propylphenyl group, a p-butylphenyl group, a p-pentylphenyl group, a p-hexylphenyl group, a 2,4-xylyl group, a 2,6-xylyl group, a 3,5-xylyl group, a mesityl group, the one forming an ethylene group by $R_3$ and $R_4$, the one forming a trimethylene group by $R_3$ and $R_4$, the one forming a tetramethylene group by $R_3$ and $R_4$, and the like; and the methyl group, the ethyl group, the propyl group, the butyl group, the pentyl group, the hexyl group, the phenyl group, the p-tolyl group, the p-ethylphenyl group, the p-propylphenyl group, and the one forming the trimethylene group by $R_3$ and $R_4$ are preferable. It should be noted that the alkyl group among the specific examples is not limited to a normal-form, and contains all of the branched forms, such as a sec-form, a tert-form, an iso-form and a neo-form.

As $R_4$ of the general formula (1-1), a hydrogen atom, and the one forming a linear alkylene group having 2 to 4 carbon atoms, by $R_3$ and $R_4$, are preferable. It specifically includes, for example, a hydrogen atom, the one forming an ethylene group by $R_3$ and $R_4$, the one forming a trimethylene group by $R_3$ and $R_4$, and the one forming a tetramethylene group by $R_3$ and $R_4$; and the hydrogen atom, and the one forming the trimethylene group by $R_3$ and $R_4$ are preferable.

The alkyl group having 1 to 20 carbon atoms, in $R_{31}$ of the general formulae (1-2) to (1-7), includes the same one as the alkyl group having 1 to 20 carbon atoms, in $R_5$ of the general formula (1), and the preferable one is also the same.

As $Ar_1$ of the general formula (1), the ring structure represented by the general formula (1-1) is preferable.

In the general formula (1), * and ** correspond to * and ** in the general formulae (1-1) to (1-7), and indicate that the groups represented by the general formulae (1-1) to (1-7) bind at the position represented by * and ** of the compound represented by the general formula (1). Specifically, they are represented by the following structures.

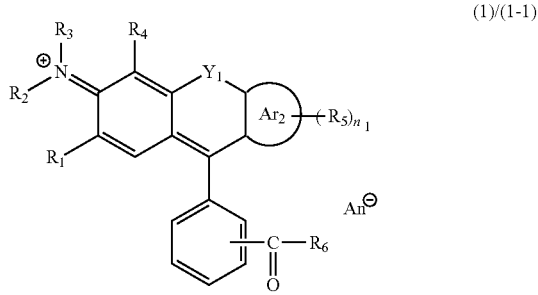

(1)/(1-1)

(1)/(1-2)
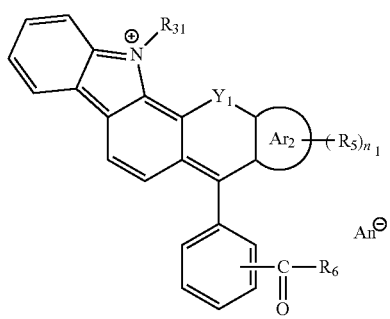

(1)/(1-3)
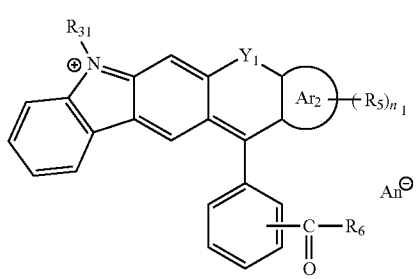

(1)/(1-4)
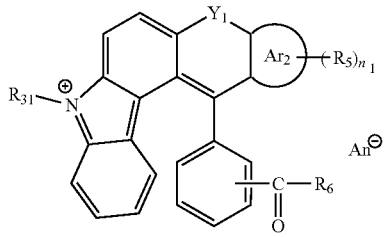

(1)/(1-5)
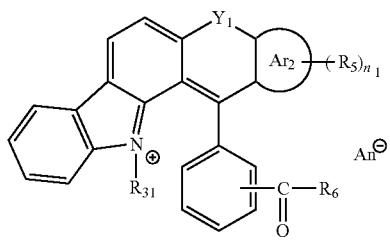

(1)/(1-6)
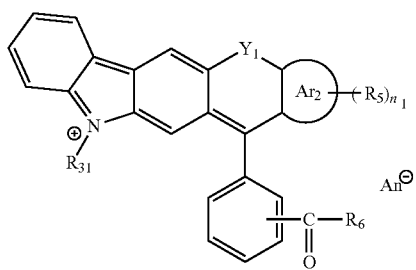

(1)/(1-7)
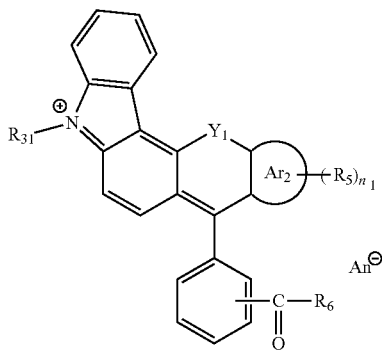

(wherein $R_1$ to $R_6$, $R_{31}$, $Y_1$, $An^-$, $Ar_2$ and $n_1$ are the same as described above.)

As $Ar_2$ of the general formula (1), a benzene ring and a naphthalene ring are preferable.

As $n_1$ of the general formula (1), when $Ar_2$ is a benzene ring, an integer of 0 to 3 is preferable, and 1 or 2 is more preferable; and when $Ar_2$ is a naphthalene ring or an anthracene ring, 0 or 1 is preferable, and 0 is more preferable.

When $Ar_2$ of the general formula (1) is a benzene ring, the general formula (1) is represented by the following general formulae (10-1) to (10-3).

(10-1)
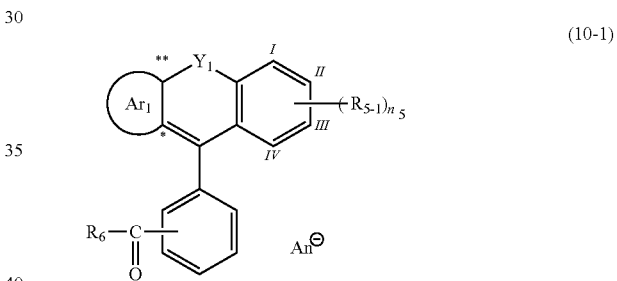

(10-2)
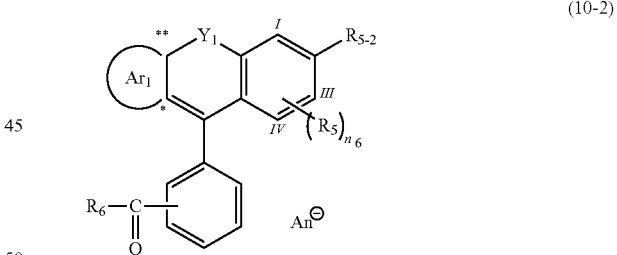

(10-3)
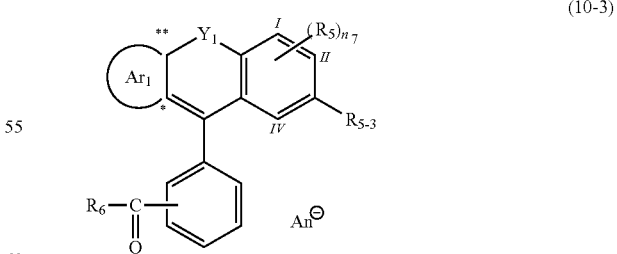

(wherein I to IV represent substitutable positions of $R_5$ and $R_{5-1}$; $R_5$, $R_6$, $Y_1$, $An^-$ and $Ar_1$ are the same as described above; $n_5$ pieces of $R_{5-1}$ each independently represent a halogen atom, an alkyl group having 1 to 20 carbon atoms, an alkoxy group having 1 to 20 carbon atoms, an alkylthio group having 1 to 20 carbon atoms, a hydroxy group, an aryl group having 6 to 14 carbon atoms, an aryloxy group having 6 to 14 carbon atoms, or an arylalkyl group having 7 to 20 carbon atoms; $R_{5-2}$ and $R_{5-3}$ each independently represent an amino group having a substituent or not having a substituent; $n_5$ represents an integer of 0 to 4; $n_6$ represents an integer of 1 to 3; and $n_7$ represents an integer of 0 to 3.)

Specific examples of the halogen atom, the alkyl group having 1 to 20 carbon atoms, the alkoxy group having 1 to 20 carbon atoms, the alkylthio group having 1 to 20 carbon atoms, the hydroxy group, the aryl group having 6 to 14 carbon atoms, the aryloxy group having 6 to 14 carbon atoms, and the arylalkyl group having 7 to 20 carbon atoms, in $R_{5-1}$ of the general formula (10-1), include the same one as those of $R_5$ in the general formula (1), and the preferable one is also the same.

As $R_{5-1}$ of the general formula (10-1), a halogen atom, an alkyl group having 1 to 12 carbon atoms, an alkoxy group having 1 to 12 carbon atoms, an alkylthio group having 1 to 12 carbon atoms, a hydroxy group, an aryl group having 6 to 14 carbon atoms, an aryloxy group having 6 to 14 carbon atoms, and an arylalkyl group having 7 to 20 carbon atoms are preferable; and the halogen atom, the alkyl group having 1 to 12 carbon atoms, the alkoxy group having 1 to 12 carbon atoms, the alkylthio group having 1 to 12 carbon atoms, the hydroxy group, a phenyl group, a phenoxy group, and a phenylalkyl group having 7 to 12 carbon atoms are more preferable; the halogen atom, an alkyl group having 1 to 6 carbon atoms, an alkoxy group having 1 to 6 carbon atoms, an alkylthio group having 1 to 6 carbon atoms, the phenyl group, the phenoxy group, and a phenylalkyl group having 7 to 9 carbon atoms are further preferable. Specifically, a fluorine atom, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a methoxy group, an ethoxy group, an n-propoxy group, an isopropoxy group, an n-butoxy group, an isobutoxy group, a sec-butoxy group, a tert-butoxy group, a methylthio group, an ethylthio group, an n-propylthio group, an isopropylthio group, an n-butylthio group, an isobutylthio group, a sec-butylthio group, a tert-butylthio group, a hydroxy group, a phenyl group, a phenoxy group, a benzyl group, a phenethyl group, a 1-phenylethyl group, a hydrocinnamyl group, a 2-phenylpropyl group, a 1-phenylpropyl group and a cumyl group are more preferable; and the fluorine atom, the methyl group, the ethyl group, the n-propyl group, the isopropyl group, the n-butyl group, the isobutyl group, the sec-butyl group, the tert-butyl group, the methoxy group, the ethoxy group, the methylthio group, the ethylthio group, the hydroxy group, the phenyl group, the phenoxy group, the benzyl group, the phenethyl group, the hydrocinnamyl group and the cumyl group are particularly preferable.

As $n_5$ of the general formula (10-1), an integer of 0 to 3 is preferable, and 1 or 2 is more preferable.

In the general formula (10-1), $n_5$ pieces of $R_{5-1}$ may be located at any of the I to IV positions of the benzene ring; and when $n_5$ is 1, it is preferable that $R_{5-1}$ is located at the II position or the III position; when $n_5$ is 2, it is preferable that $R_{5-1}$ is located at the II position and the III position, or the II position and the IV position; and when $n_5$ is 3, it is preferable that $R_{5-1}$ is located at the II position, the III position and the IV position.

The amino group having a substituent, in $R_{5-2}$ of the general formula (10-2) and $R_{5-3}$ of the general formula (10-3), includes the same one as the amino group having a substituent, in $R_5$ of the general formula (1), and the preferable one is also the same.

As $R_{5-2}$ of the general formula (10-2) and $R_{5-3}$ of the general formula (10-3), an amino group having a substituent is preferable; an amino group having a halogen atom, an alkyl group having 1 to 20 carbon atoms, an aryl group having 6 to 10 carbon atoms, or an arylalkyl group having 7 to 13 carbon atoms is more preferable; and an amino group having an alkyl group having 1 to 6 carbon atoms, a phenyl group, or a phenylalkyl group having 7 to 9 carbon atoms is further preferable. Specifically, a methylamino group, an ethylamino group, an n-propylamino group, an isopropylamino group, an n-butylamino group, an isobutylamino group, a sec-butylamino group, a tert-butylamino group, a phenylamino group, a benzylamino group, a dimethylamino group, a diethylamino group, a di-n-propylamino group, a diisopropylamino group, a di-n-butylamino group, a diisobutylamino group, a di-sec-butylamino group, a di-tert-butylamino group, a diphenylamino group and a dibenzylamino group are preferable; and the methylamino group, the ethylamino group, the phenylamino group, the benzylamino group, the dimethylamino group, the diethylamino group, the diphenylamino group and the dibenzylamino group are more preferable.

As $n_6$ of the general formula (10-2), 1 or 2 is preferable, and 1 is more preferable.

In the general formula (10-2), $n_6$ pieces of $R_5$ may be located at any of the I position, the III position or the IV position of the benzene ring; and when $n_6$ is 1, it is preferable that $R_5$ is located at the III position; and when $n_6$ is 2, it is preferable that $R_5$ is located at the III position and the IV position.

As $n_7$ of the general formula (10-3), an integer of 0 to 2 is preferable, and 0 or 1 is more preferable.

In the general formula (10-3), $n_7$ pieces of $R_5$ may be located at any of the I position, the II position or the IV position of a benzene ring; and when $n_6$ is 1, it is preferable that $R_5$ is located at the II position; and when $n_6$ is 2, it is preferable that $R_5$ is located at the II position and the IV position.

When $Ar_2$ of the general formula (1) is a naphthalene ring, the general formula (1) is represented by the following general formulae (10-4) to (10-6).

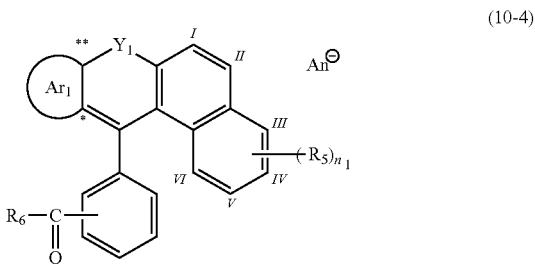

(10-4)

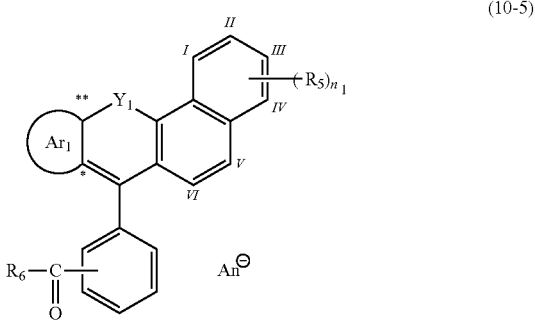

(10-5)

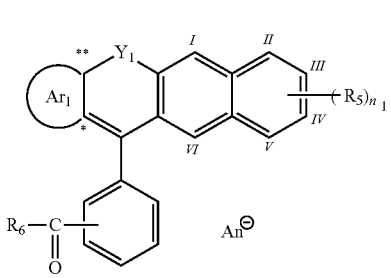

(10-6)

(wherein I to VI represent substitutable positions of $R_5$; and $n_1$ pieces of $R_5$, $R_6$, $Y_1$, $An^-$, $Ar_1$ and $n_1$ are the same as described above.)

In the general formula (10-4), $n_1$ pieces of $R_5$ may be located at any of the I to VI positions of the naphthalene ring, and it is preferable to be located at the IV position or the VI position.

In the general formula (10-5), $n_1$ pieces of $R_5$ may be located at any of the I to VI positions of the naphthalene ring, and it is preferable to be located at the III position.

In the general formula (10-6), $n_1$ pieces of $R_5$ may be located at any of the I to VI positions of the naphthalene ring, and it is preferable to be located at the II position or the IV position.

When $Ar_2$ of the general formula (1) is an anthracene ring, the general formula (1) is represented by the following general formulae (10-7) to (10-9).

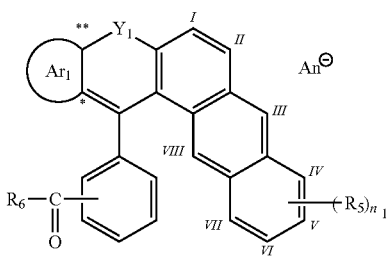

(10-7)

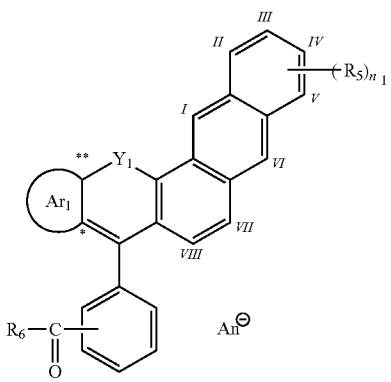

(10-8)

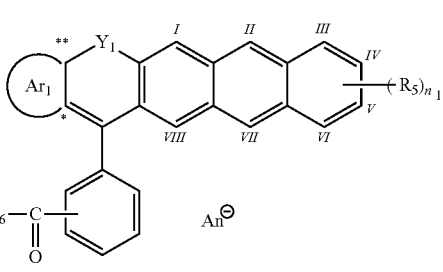

(10-9)

(wherein I to VIII represent substitutable positions of $R_5$; and $n_1$ pieces of $R_5$, $R_6$, $Y_1$, $An^-$, $Ar_1$ and $n_1$ are the same as described above.)

In the general formula (10-7), $n_1$ pieces of $R_5$ may be located at any of the I to VI positions of the anthracene ring, and it is preferable to be located at the I position, the V position or the VI position.

In the general formula (10-8), $n_1$ pieces of $R_5$ may be located at any of the I to VI positions of the anthracene ring, and it is preferable to be located at the II position, the V position or the VII position.

In the general formula (10-9), $n_1$ pieces of $R_5$ may be located at any of the I to VI positions of the anthracene ring, and it is preferable to be located at the IV position or the V position.

In the general formula (1), the following structure (1-10) is a left-right asymmetric structure.

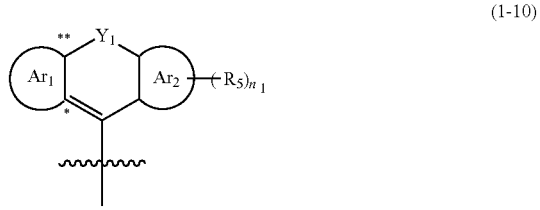

(1-10)

(wherein $n_1$ pieces of $R_5$, $Y_1$, $Ar_1$, $Ar_2$, $n_1$, * and ** are the same as described above.)

In other words, the compound represented by the general formula (1) does not include a compound represented by the following general formula (1-11).

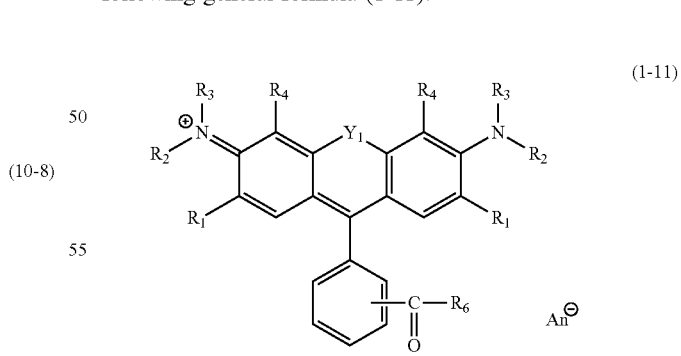

(1-11)

(wherein $R_1$ to $R_4$, $R_6$, $Y_1$ and $An^-$ are the same as described above, and two of $R_1$ to $R_4$ are the same.)

The quencher of the present invention exerts superior effect to be capable of sufficiently quenching fluorescence of a compound having fluorescent property, including the xanthene-based dye, because the structure (1-10) takes a left-right asymmetric structure.

An⁻ of the general formula (1) may be any anion, and specifically includes, for example, an anion containing an aryl group having an electron withdrawing substituent, a sulfonyl group having an electron withdrawing substituent, a halogenated alkyl group, or a halogeno group; a halogen oxoacid anion; or a sulfonate anion (hereinafter, it may be abbreviated as the anion pertaining to the present invention.).

An anion moiety in the anion containing the aryl group having the electron withdrawing substituent, the sulfonyl group having the electron withdrawing substituent, or the halogenated alkyl group, represented by An⁻ of the general formula (1), includes, for example, a sulfonate anion, a nitrogen anion (N⁻), a quaternary boron anion, a nitrate ion, a phosphate ion, and the like; and the sulfonate anion, the nitrogen anion and the quaternary boron anion are preferable; and the quaternary boron anion is more preferable.

An anion moiety in the anion containing the halogeno group, represented by An⁻ of the general formula (1), includes, for example, a quaternary boron anion, a phosphorus anion, an antimony anion, and the like; the phosphorus anion and the antimony anion are preferable; and the antimony anion is more preferable.

The electron withdrawing substituent in the aryl group having the electron withdrawing substituent, or the sulfonyl group having the electron withdrawing substituent, in the anion pertaining to the present invention, includes, for example, a halogenated alkyl group having 1 to 3 carbon atoms, a halogeno group, a nitro group, and the like; and among them, the halogenated alkyl group having 1 to 3 carbon atoms, and the halogeno group are preferable; and the halogeno group is particularly preferable.

The halogenated alkyl group having 1 to 3 carbon atoms, as the electron withdrawing substituent, includes, for example, a chloroalkyl group such as a chloromethyl group, a trichloromethyl group, a 2-chloroethyl group, a 2,2,2-trichloroethyl group, a pentachloroethyl group, a 2-chloropropyl group, a 3-chloropropyl group, a 2-chloro-2-propyl group and a heptachloropropyl group; a bromoalkyl group such as a bromomethyl group, a tribromomethyl group, a 2-bromoethyl group, a 2,2,2-tribromoethyl group, a pentabromoethyl group, a 2-bromopropyl group, a 3-bromopropyl group, a 2-bromo-2-propyl group and a heptabromopropyl group; an iodoalkyl group filtrated and an iodomethyl group, a triiodomethyl group, a 2-iodoethyl group, a 2,2,2-triiodoethyl group, a pentaiodoethyl group, a 2-iodopropyl group, a 3-iodopropyl group, a 2-iodo-2-propyl group and a heptaiodopropyl group; and a fluoroalkyl group such as a fluoromethyl group, a trifluoromethyl group, a 2-fluoroethyl group, a 2,2,2-trifluoroethyl group, a 1,1,2,2-tetrafluoroethyl group, a pentafluoroethyl group, a 3-fluoropropyl group, a 3,3,3-trifluoropropyl group, a 2,2,3,3-tetrafluoropropyl group and a heptafluoropropyl group. Among them, the perhalogeno alkyl group such as the trichloromethyl group, the pentachloroethyl group, the heptachloropropyl group, the tribromomethyl group, the pentabromoethyl group, the heptabromopropyl group, the triiodomethyl group, the pentaiodoethyl group, the heptaiodopropyl group, the trifluoromethyl group, the pentafluoroethyl group and the heptafluoropropyl group, is preferable; and the perfluoroalkyl group such as the trifluoromethyl group, the pentafluoroethyl group and the heptafluoropropyl group, is more preferable; and the trifluoromethyl group is particularly preferable.

The halogeno group as the electron withdrawing substituent includes a fluoro group, a chloro group, a bromo group and an iodo group, and the fluoro group is preferable.

As the electron withdrawing substituent in the aryl group having the electron withdrawing substituent in the anion pertaining to the present invention, among the specific examples, the one having strong electron withdrawing ability is preferable, and a trifluoromethyl group, a fluoro group and a nitro group are preferable, and the fluoro group is more preferable.

As the electron withdrawing substituent in the sulfonyl group having the electron withdrawing substituent in the anion pertaining to the present invention, among the specific examples, a trifluoromethyl group, a pentafluoroethyl group, a heptafluoropropyl group and a fluoro group are preferable.

The aryl group in the aryl group having the electron withdrawing substituent in the anion pertaining to the present invention includes, for example, a phenyl group, a naphthyl group, and the like, and the phenyl group is preferable.

Specific examples of the aryl group having the electron withdrawing substituent, in the anion pertaining to the present invention, include, for example, those represented by the following general formulae (11) and (12).

(11)

(wherein m represents an integer of 1 to 5; and m pieces of $R_{41}$ each independently represent a halogenated alkyl group having 1 to 3 carbon atoms, a halogen atom or a nitro group.)

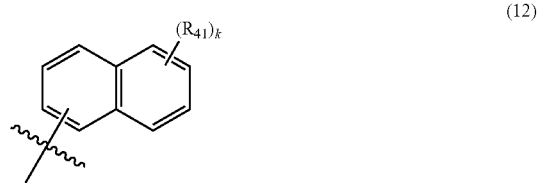

(12)

(wherein k represents an integer of 1 to 7; $R_{41}$ is the same as described above; and k pieces of $R_{41}$ may be the same or different.)

In the general formula (11), m is usually an integer of 1 to 5, and, when $R_{41}$ is a halogen atom, 2 to 5 is preferable, and 3 to 5 is more preferable, and 5 is further preferable. When $R_{41}$ is a nitro group, 1 to 3 is preferable, and 1 is more preferable. When $R_{41}$ is a halogenated alkyl group, 1 to 5 is preferable, and 1 to 3 is more preferable.

In the general formula (12), k is usually an integer of 1 to 7, and, when $R_{41}$ is a halogen atom, 2 to 7 is preferable. When $R_{41}$ is a nitro group, 1 to 3 is preferable, and 1 is more preferable. When $R_{41}$ is a halogenated alkyl group, 1 to 7 is preferable, and 1 to 3 is more preferable.

The halogenated alkyl group having 1 to 3 carbon atoms, in $R_{41}$ of the general formula (11) and the general formula (12), includes the same one as the halogenated alkyl group having 1 to 3 carbon atoms, as the electron withdrawing substituent in the anion pertaining to the present invention, and the preferable one is also the same.

The halogen atom in $R_{41}$ of the general formula (11) and the general formula (12) includes a fluorine atom, a chlorine atom, a bromine atom, an iodine atom, and the like, and among them, the fluorine atom is preferable.

Preferable specific examples of $R_{41}$ in the general formula (11) and the general formula (12) are the same as the preferable ones of the electron withdrawing substituent in the aryl group having the electron withdrawing substituent.

The group represented by the general formula (11) specifically includes, for example, a trifluoromethylphenyl group, a di(trifluoromethyl)phenyl group, a tri(trifluoromethyl)phenyl group, a monofluorophenyl group, a difluorophenyl group, a trifluorophenyl group, a perfluorophenyl group, a monochlorophenyl group, a dichlorophenyl group, a trichlorophenyl group, a perchlorophenyl group, a monobromophenyl group, a dibromophenyl group, a tribromophenyl group, a perbromophenyl group, a monoiodophenyl group, a diiodophenyl group, a triiodophenyl group, a periodophenyl group, a nitrophenyl group, a dinitrophenyl group, a trinitrophenyl group, and the like; and the difluorophenyl group, the trifluorophenyl group, the perfluorophenyl group, and the like, are preferable; and the perfluorophenyl group is more preferable.

The group represented by the general formula (12) specifically includes, for example, a trifluoromethylnaphthyl group, a di(trifluoromethyl) naphthyl group, a tri(trifluoromethyl)naphthyl group, a monofluoronaphthyl group, a difluoronaphthyl group, a trifluoronaphthyl group, a perfluoronaphthyl group, a monochloronaphthyl group, a dichloronaphthyl group, a trichloronaphthyl group, a perchloronaphthyl group, a monobromonaphthyl group, a dibromonaphthyl group, a tribromonaphthyl group, a perbromonaphthyl group, a monoiodonaphthyl group, a diiodonaphthyl group, a triiodonaphthyl group, a periodonaphthyl group, a nitronaphthyl group, a dinitronaphthyl group, a trinitronaphthyl group, and the like.

The aryl group having the electron withdrawing substituent in the anion pertaining to the present invention, among the specific examples, the group represented by the general formula (11) is preferable, and specifically, a trifluoromethylphenyl group, a nitrophenyl group, a dinitrophenyl group, a trinitrophenyl group, a monofluorophenyl group, a difluorophenyl group, a trifluorophenyl group and a perfluorophenyl group are preferable; and the difluorophenyl group, the trifluorophenyl group, the nitrophenyl group and the perfluorophenyl group are more preferable; and the perfluorophenyl group is further particularly preferable.

The sulfonyl group having the electron withdrawing substituent in the anion pertaining to the present invention includes, for example, $-SO_2-CF_3$, $-SO_2-C_2F_5$, $-SO_2-C_3F_7$, $-SO_2-F$, $-SO_2-Cl$, $-SO_2-Br$, $-SO_2-I$, and the like.

The halogenated alkyl group in the anion pertaining to the present invention includes a halogenated alkyl group having 1 to 3 carbon atoms; and among them, a perhalogenated alkyl group is preferable; and specifically includes, for example, a trifluoromethyl group, a pentafluoroethyl group, a heptafluoropropyl group, a trichloromethyl group, a pentachloroethyl group, a heptachloropropyl group, a tribromomethyl group, a pentabromoethyl group, a heptabromopropyl group, a triiodomethyl group, a pentaiodoethyl group, a heptaiodopropyl group, and the like; and the trifluoromethyl group, the pentafluoroethyl group and the heptafluoropropyl group are preferable.

The halogeno group in the anion pertaining to the present invention includes a fluoro group, a chloro group, a bromo group and an iodo group; and the fluoro group is preferable.

The anion containing the aryl group having the electron withdrawing substituent, the sulfonyl group having the electron withdrawing substituent, the halogenated alkyl group, or the halogeno group, pertaining to the present invention, specifically includes, for example, those represented by the following general formulae (13) to (19).

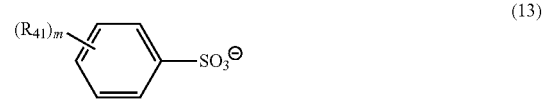

(wherein $R_{41}$ and m are the same as described above; and m pieces of $R_{41}$ may be the same or different.)

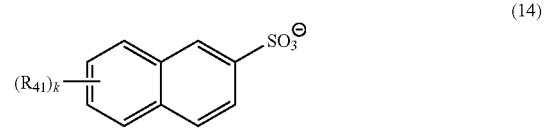

(wherein $R_{41}$ and k are the same as described above; and k pieces of $R_{41}$ may be the same or different.)

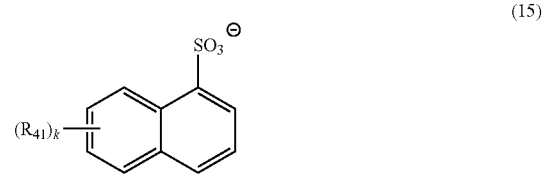

(wherein $R_{41}$ and k are the same as described above; and k pieces of $R_{41}$ may be the same or different.)

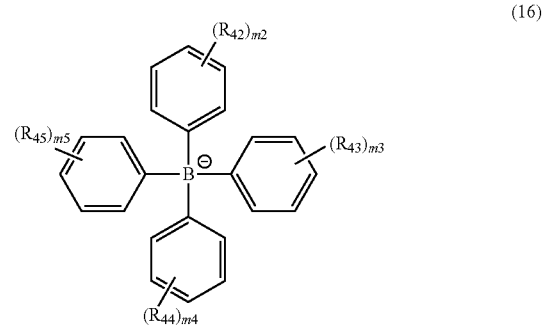

(wherein $R_{42}$ to $R_{45}$ each independently represent a halogenated alkyl group having 1 to 3 carbon atoms, a halogen atom, or a nitro group; $m_2$ to $m_5$ each independently represent an integer of 1 to 5; and $m_2$ pieces of $R_{42}$, $m_3$ pieces of $R_{43}$, $m_4$ pieces of $R_{44}$ and $m_5$ pieces of $R_{45}$ each independently may be the same or different.)

(wherein 4 pieces of $R_{46}$ each independently represent a halogenated alkyl group having 1 to 3 carbon atoms, or a halogen atom.)

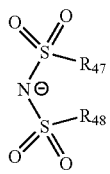
(18)

(wherein $R_{47}$ and $R_{48}$ each independently represent a halogenated alkyl group having 1 to 3 carbon atoms, or a halogen atom; and $R_{47}$ and $R_{48}$ may form a halogenated alkylene group having 2 to 3 carbon atoms.)

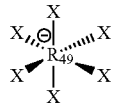
(19)

(wherein $R_{49}$ represents a phosphorus atom or an antimony atom; and 6 pieces of X all represent the same halogen atom.)

Combinations of $R_{41}$ and m in the general formula (13) include, for example, those described in the following table. It should be noted that m pieces of $R_{41}$ are each independent, and the case where they are the same is preferable.

| $R_{41}$ | m |
|---|---|
| trifluoromethyl group (—CF$_3$) | 1 to 3 |
| pentafluoroethyl group (—C$_2$F$_5$) | 1 to 3 |
| heptafluoropropyl group (—C$_3$F$_7$) | 1 to 3 |
| nitro group | 1 to 3 |
| fluorine atom | 1 to 5 |
| chlorine atom | 1 to 5 |
| bromine atom | 1 to 5 |
| iodine atom | 1 to 5 |

Preferable specific examples of the anion represented by the general formula (13) include, for example, the following ones.

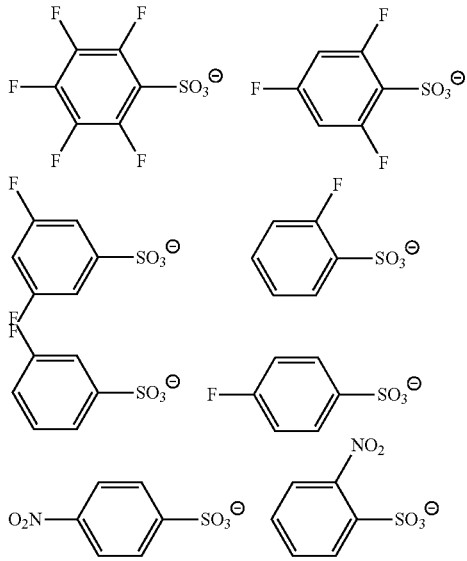

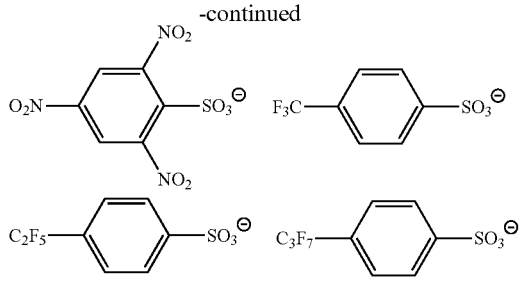

Combinations of $R_{41}$ and k in the general formulae (14) and (15) include, for example, those described in the following table. It should be noted that k pieces of $R_{41}$ are each independent, and the case where they are the same is preferable.

| $R_{41}$ | k |
|---|---|
| trifluoromethyl group (—CF$_3$) | 1 to 3 |
| pentafluoroethyl group (—C$_2$F$_5$) | 1 to 3 |
| heptafluoropropyl group (—C$_3$F$_7$) | 1 to 3 |
| nitro group | 1 to 3 |
| fluorine atom | 1 to 7 |
| chlorine atom | 1 to 7 |
| bromine atom | 1 to 7 |
| iodine atom | 1 to 7 |

Preferable specific examples of the anion represented by the general formulae (14) and (15) include, for example, the following ones.

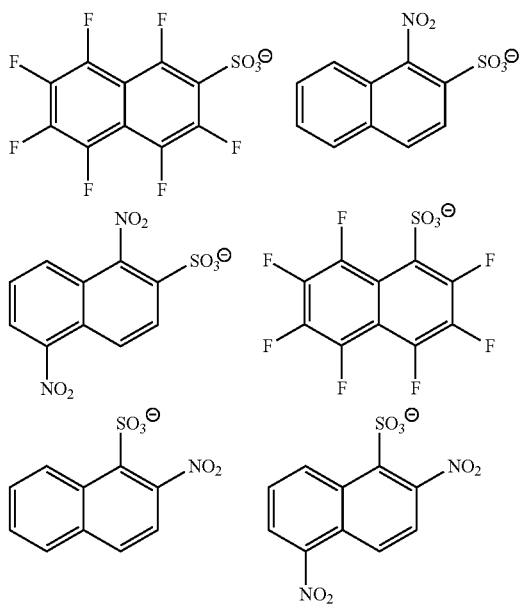

The halogenated alkyl group having 1 to 3 carbon atoms, in $R_{42}$ to $R_{45}$ of the general formula (16), includes the same one as the halogenated alkyl group having 1 to 3 carbon atoms, as the electron withdrawing substituent in the anion pertaining to the present invention, and the preferable one is also the same.

The halogen atom in $R_{42}$ to $R_{45}$ of the general formula (16) includes a fluorine atom, a chlorine atom, a bromine atom, an iodine atom, and the like, and among them, the fluorine atom is preferable.

Combinations of $R_{42}$ to $R_{45}$ and $m_2$ to $m_5$ in the general formula (16) include, for example, those described in the following table.

| $R_{42}$ | $m_2$ | $R_{43}$ | $m_3$ | $R_{44}$ | $m_4$ | $R_{45}$ | $m_5$ |
|---|---|---|---|---|---|---|---|
| —$CF_3$ | 1 to 3 | —$CF_3$ | 1 to 3 | —$CF_3$ | 1 to 3 | —$CF_3$ | 1 to 3 |
| —$C_2F_5$ | 1 to 3 | —$C_2F_5$ | 1 to 3 | —$C_2F_5$ | 1 to 3 | —$C_2F_5$ | 1 to 3 |
| —$C_3F_7$ | 1 to 3 | —$C_3F_7$ | 1 to 3 | —$C_3F_7$ | 1 to 3 | —$C_3F_7$ | 1 to 3 |
| nitro group | 1 to 3 | nitro group | 1 to 3 | nitro group | 1 to 3 | nitro group | 1 to 3 |
| fluorine | 1 to 5 | fluorine | 1 to 5 | fluorine | 1 to 5 | fluorine | 1 to 5 |
| chlorine | 1 to 5 | chlorine | 1 to 5 | chlorine | 1 to 5 | chlorine | 1 to 5 |
| bromine | 1 to 5 | bromine | 1 to 5 | bromine | 1 to 5 | bromine | 1 to 5 |
| iodine | 1 to 5 | iodine | 1 to 5 | iodine | 1 to 5 | iodine | 1 to 5 |
| nitro group | 1 to 3 | fluorine | 1 to 5 | fluorine | 1 to 5 | fluorine | 1 to 5 |
| nitro group | 1 to 3 | nitro group | 1 to 3 | fluorine | 1 to 5 | fluorine | 1 to 5 |
| nitro group | 1 to 3 | nitro group | 1 to 3 | nitro group | 1 to 3 | fluorine | 1 to 5 |

Preferable specific examples of the anion represented by the general formula (16) include, for example, the following ones.

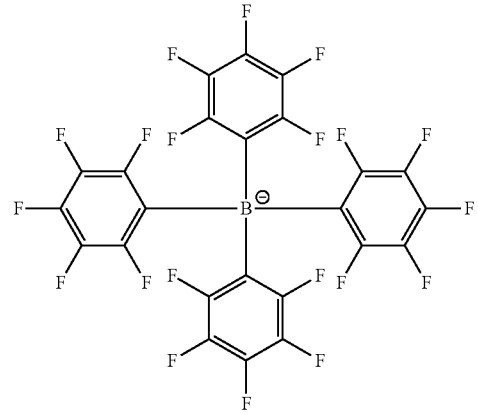

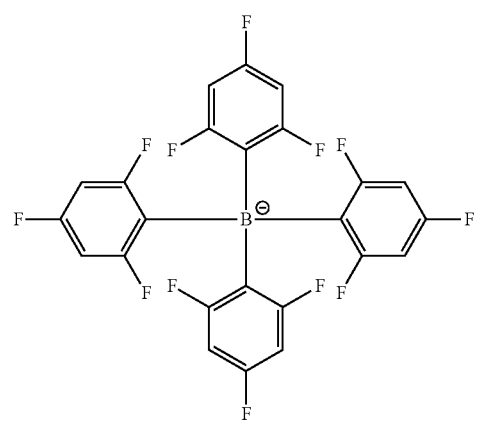

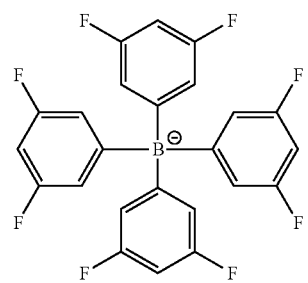

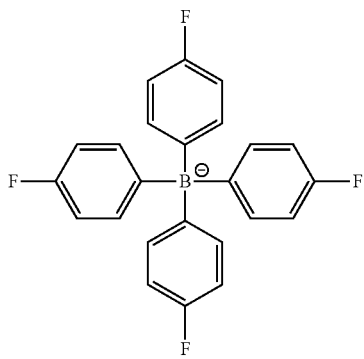

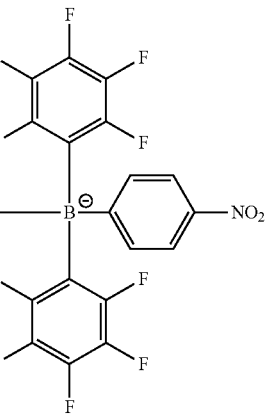

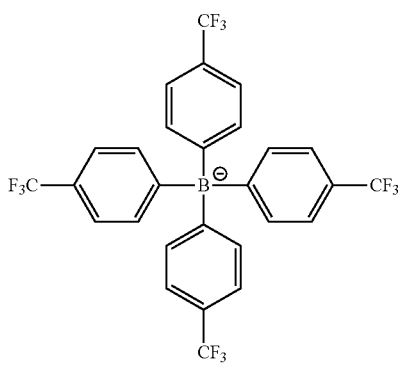

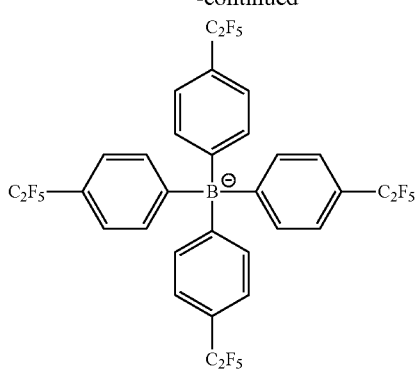

Among the specific examples, the following ones are more preferable.

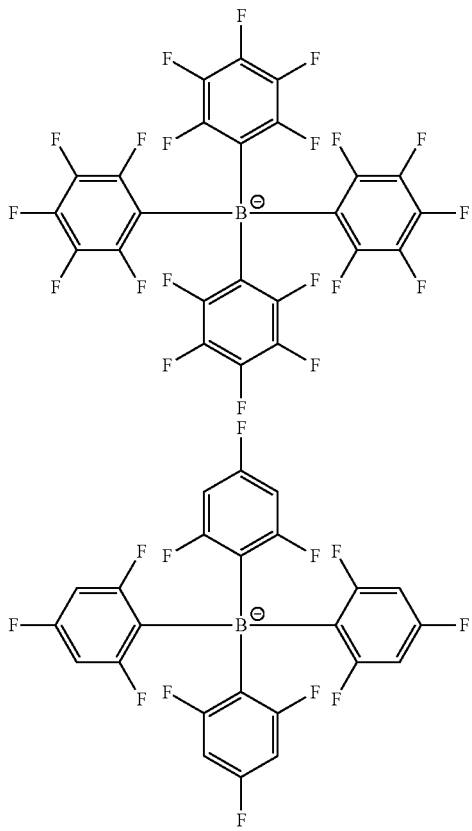

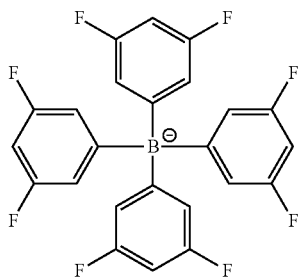

Among the specific examples, the following one is particularly preferable.

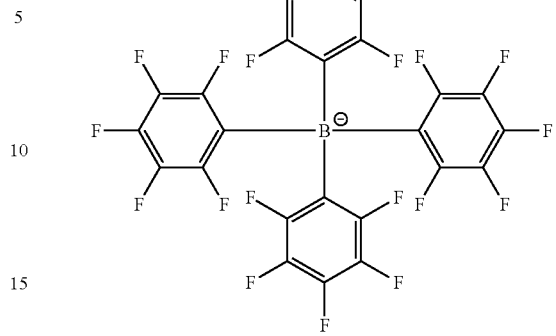

The halogenated alkyl group having 1 to 3 carbon atoms, in $R_{46}$ of the general formula (17), includes the same one as the halogenated alkyl group having 1 to 3 carbon atoms, as the electron withdrawing substituent in the anion pertaining to the present invention, and the preferable one is also the same.

The halogen atom in $R_{46}$ of the general formula (17) includes a fluorine atom, a chlorine atom, a bromine atom, an iodine atom, and the like, and among them, the fluorine atom is preferable.

Preferable specific examples of the anion represented by the general formula (17) include, for example, $BF_4^-$, $CF_3BF_3^-$, $C_2F_5BF_3^-$, $C_3F_7BF_3^-$, $(CF_3)_4B^-$, $(C_2F_5)_4B^-$, $(C_3F_7)_4B^-$, and the like.

The halogenated alkyl group having 1 to 3 carbon atoms, in $R_{47}$ and $R_{48}$ of the general formula (18), includes the same one as the halogenated alkyl group having 1 to 3 carbon atoms, as the electron withdrawing substituent in the anion pertaining to the present invention, and the preferable one is also the same.

The halogen atom in $R_{47}$ and $R_{48}$ of the general formula (18) includes a fluorine atom, a chlorine atom, a bromine atom, an iodine atom, and the like, and among them, the fluorine atom is preferable.

The halogenated alkylene group having 2 to 3 carbon atoms, formed by $R_{47}$ and $R_{48}$ of the general formula (18), includes, for example, a tetrafluoroethylene group, a hexafluoropropylene group, and the like, and the hexafluoropropylene group is preferable.

Preferable specific examples of the anion represented by the general formula (18) include, for example, the following ones.

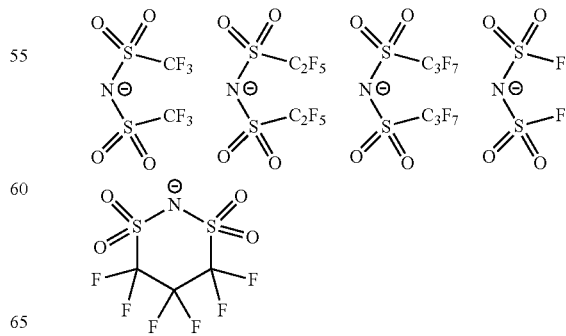

As $R_{49}$ of the general formula (19), an antimony atom is preferable.

The halogen atom in X of the general formula (19) includes a fluorine atom, a chlorine atom, a bromine atom, an iodine atom, and the like, and among them, the fluorine atom is preferable.

Preferable specific examples of the anion represented by the general formula (19) include, for example, the following ones.

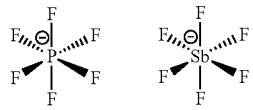

Specific examples of the halogen oxoacid anion in the anion pertaining to the present invention include, for example, a hypochlorite anion, a chlorite anion, a chlorate anion, a perchlorate anion, and the like, and the perchlorate anion is preferable.

Specific examples of the sulfonate anion in the anion pertaining to the present invention include, for example, an alkylsulfonate anion having 1 to 20 carbon atoms, such as a methane sulfonate anion; a halogenated alkylsulfonate anion having 1 to 20 carbon atoms, such as a trifluoromethane sulfonate anion; a benzene sulfonate anion having a substituent or not having a substituent, such as a benzene sulfonate anion and a toluene sulfonate anion.

As the anion represented by An⁻ of the general formula (1), the anion pertaining to the present invention is preferable; the anion containing the aryl group having the electron withdrawing substituent, the sulfonyl group having the electron withdrawing substituent, the halogenated alkyl group, or the halogeno group, is more preferable; and specifically, the one represented by the general formulae (16) to (19) is preferable; and the one represented by the general formula (16), the general formula (18) and the general formula (19) is more preferable; and the one represented by the general formula (16) and the general formula (18) is further preferable; and the one represented by the general formula (16) is particularly preferable.

As the anion represented by An⁻ of the general formula (1), among the specific examples, the following ones are preferable.

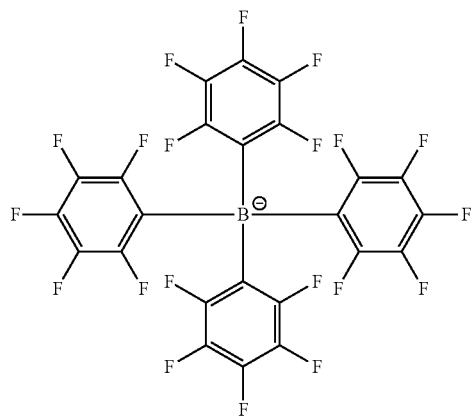

-continued

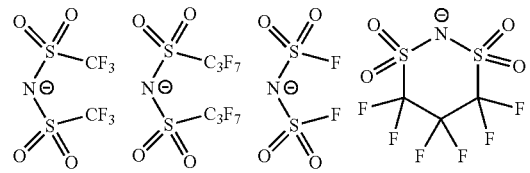

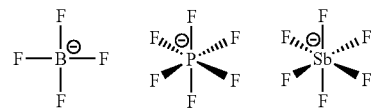

Among the specific examples, the following ones are more preferable.

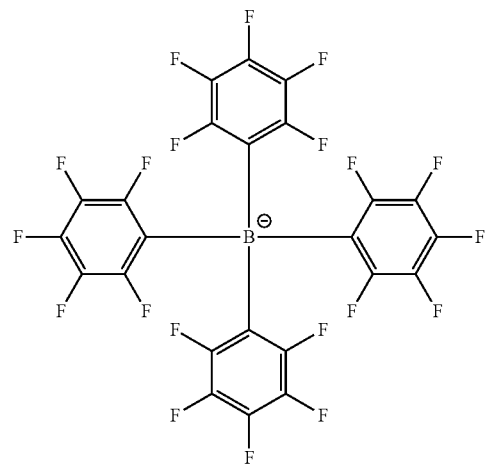 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

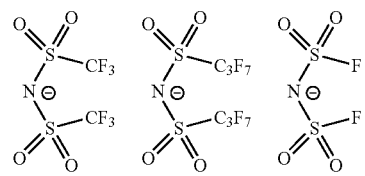

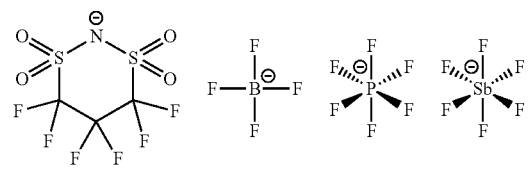

Among the specific examples, the following ones are further preferable.

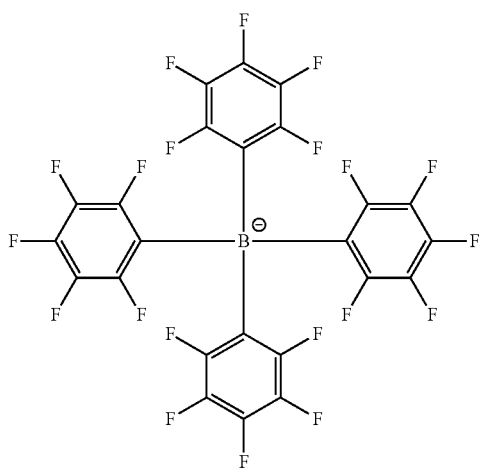

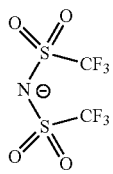

Among the specific examples, the following one is particularly preferable.

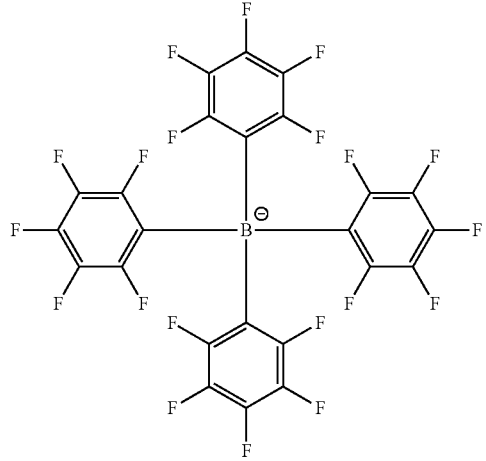

Preferable specific examples of the quencher of the present invention include the one comprising a compound represented by the following general formula (3).

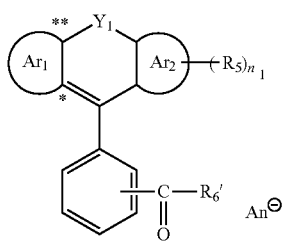 (3)

[wherein $R_6'$ represents a group having a polymerizable unsaturated group; $n_1$ pieces of $R_5$, $Y_1$, $An^-$, $Ar_1$, $Ar_2$, $n_1$, * and ** are the same as described above; and the following structure (1-10) in the general formula (3) is an asymmetric structure;

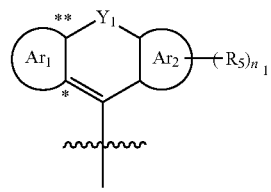 (1-10)

(wherein $n_1$ pieces of $R_5$, $Y_1$, $Ar_1$, $Ar_2$, $n_1$, * and ** are the same as described above.)]

The group having the polymerizable unsaturated group, in $R_6'$ of the general formula (3), includes the same one as the group having the polymerizable unsaturated group, in $R_6$ of the general formula (1), and the preferable one is also the same.

When $Ar_2$ of the general formula (3) is a benzene ring, the general formula (3) is represented by the following general formulae (30-1) to (30-3).

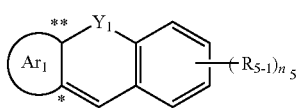 (30-1)

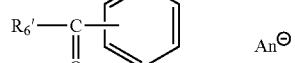

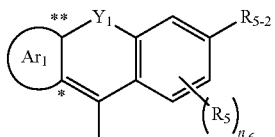 (30-2)

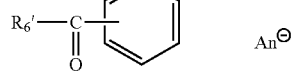

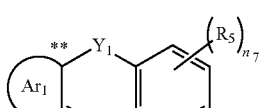 (30-3)

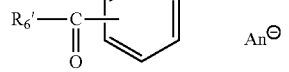

(wherein $R_5$, $R_{5-1}$, $R_{5-2}$, $R_{5-3}$, $R_6'$, $Y_1$, $An^-$, $Ar_1$, $n_5$, $n_6$, $n_7$, * and ** are the same as described above.)

When $Ar_2$ of the general formula (3) is a naphthalene ring, the general formula (3) is represented by the following general formulae (30-4) to (30-6).

(30-4)

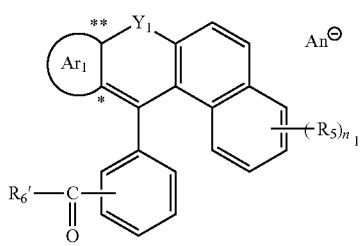

(30-5)

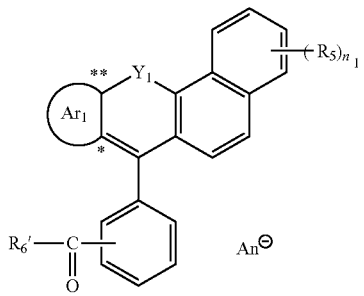

(30-6)

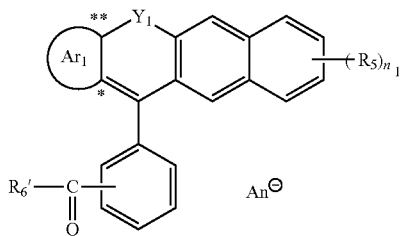

(wherein $R_5$, $R_6'$, $Y_1$, $An^-$, $Ar_1$, $n_1$, * and ** are the same as described above.)

When $Ar_2$ of the general formula (3) is an anthracene ring, the general formula (3) is represented by the following general formulae (30-7) to (30-9).

(30-7)

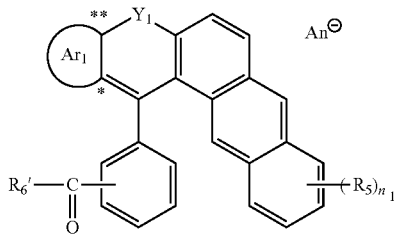

(30-8)

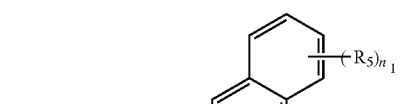
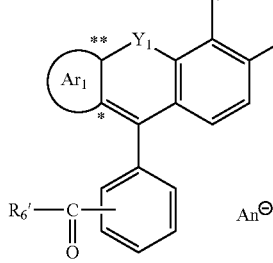

(30-9)

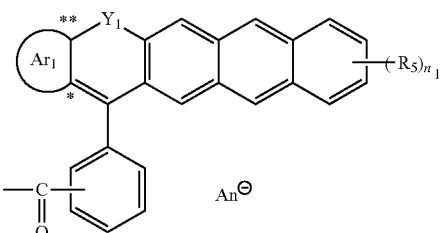

(wherein $R_5$, $R_6'$, $Y_1$, $An^-$, $Ar_1$, $n_1$, * and ** are the same as described above.)

The quencher comprising the compound represented by the general formula (3) is less fading caused by heating, and exerts high heat resistance effect, in addition to quenching effect on a compound having fluorescent property. Furthermore, the quencher comprising the polymer, having the monomer unit derived from the compound represented by the general formula (3), has high elution resistance and weather resistance.

Preferable specific examples, among the compound represented by the general formula (3), include a compound represented by the following general formula (3-1).

(3-1)

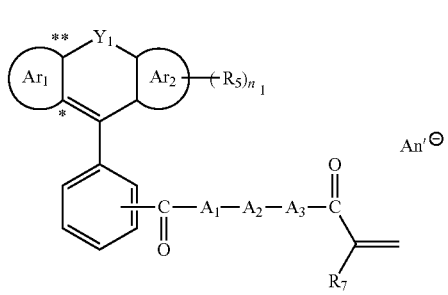

[wherein $An'^-$ represents an anion containing an aryl group having an electron withdrawing substituent, a sulfonyl group having an electron withdrawing substituent, a halogenated alkyl group, or a halogeno group; $n_1$ pieces of $R_5$, $R_7$, $Y_1$, $A_1$, $A_2$, $A_3$, $Ar_1$, $Ar_2$, $n_1$, * and ** are the same as described above; and the following structure (1-10) in the general formula (3-1) is an asymmetric structure;

(1-10)

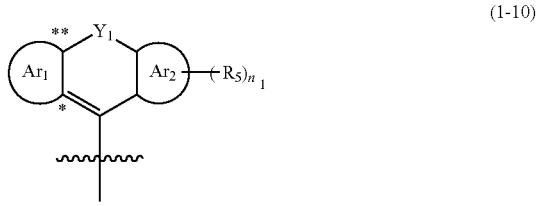

(wherein $n_1$ pieces of $R_5$, $Y_1$, $Ar_1$, $Ar_2$, $n_1$, * and ** are the same as described above.)]

The anion containing the aryl group having the electron withdrawing substituent, the sulfonyl group having the electron withdrawing substituent, the halogenated alkyl group, or the halogeno group, in $An'^-$ of the general formula (3-1), includes the same one as those of the anion pertaining to the present invention in the general formula (1), and the preferable one is also the same.

Preferable specific examples, among the compound represented by the general formula (3-1), include a compound represented by the following general formulae (3-2a) to (3-2c), and the compound represented by the general formula (3-2a) are more preferable.

(3-2a)

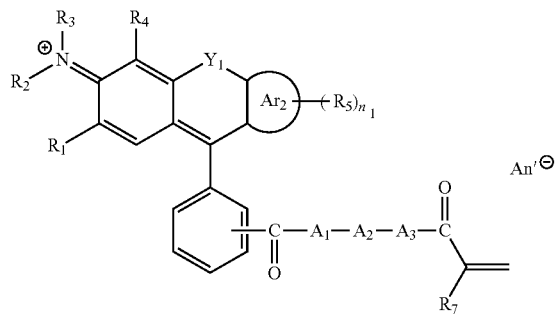

[wherein $R_1$ to $R_5$, $R_7$, $Y_1$, $An'^-$, $A_1$, $A_2$, $A_3$, $Ar_2$ and $n_1$ are the same as described above; and the following structure (1-12) in the general formula (3-2a) is an asymmetric structure;

(1-12)

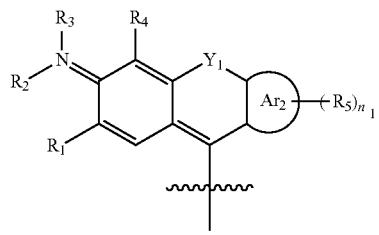

(wherein $R_1$ to $R_5$, $Y_1$, $Ar_2$ and $n_1$ are the same as described above.)]

(3-2b)

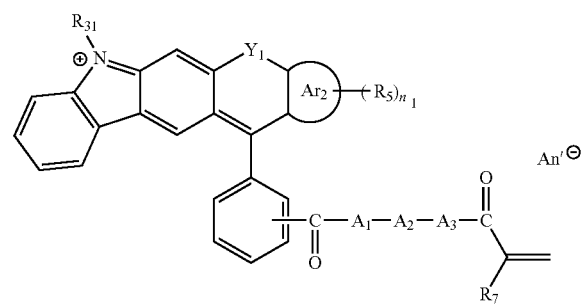

(wherein $R_5$, $R_7$, $R_{31}$, $Y_1$, $An'^-$, $A_1$, $A_2$, $A_3$, $Ar_2$ and $n_1$ are the same as described above.)

(3-2c)

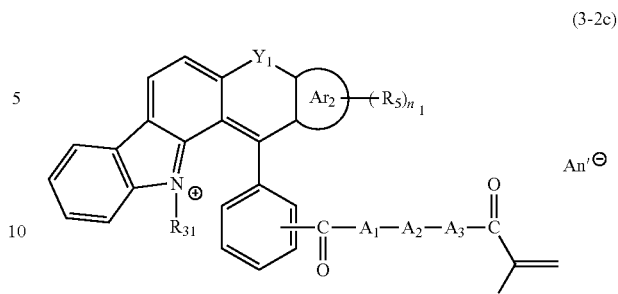

(wherein $R_5$, $R_7$, $R_{31}$, $Y_1$, $An'^-$, $A_1$, $A_2$, $A_3$, $Ar_2$ and $n_1$ are the same as described above.)

In the general formula (3-2a), the following structure (1-12) is a left-right asymmetric structure.

(1-12)

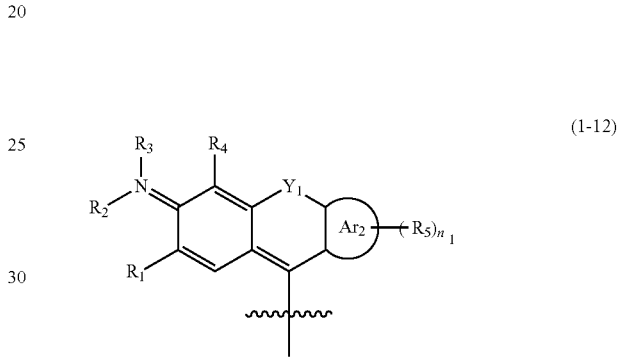

(wherein $R_1$ to $R_5$, $Y_1$, $Ar_2$ and $n_1$ are the same as described above.)

In other words, the compound represented by the general formula (3-2a) does not include a compound represented by the following general formula (1-13).

(1-13)

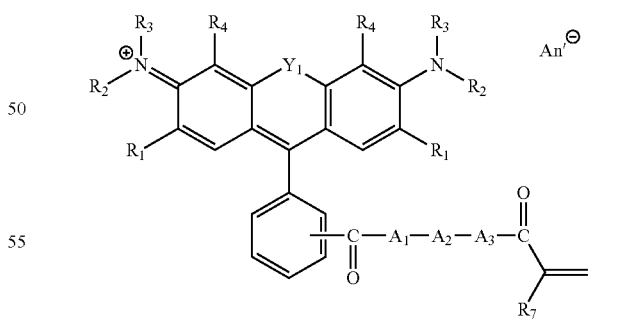

(wherein $R_1$ to $R_4$, $R_7$, $Y_1$, $An'^-$, $A_1$, $A_2$ and $A_3$ are the same as described above; and two of $R_1$ to $R_4$ are the same.)

Preferable specific examples, among the compound represented by the general formula (3-2a), include a compound represented by the following general formulae (3-3a) and the general formula (3-3b), and the compound represented by the general formula (3-3a) is preferable.

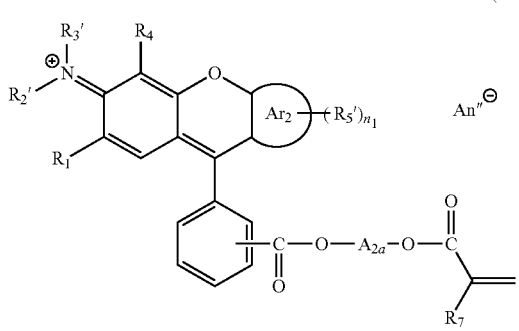

(3-3a)

[wherein $R_2'$ and $R_3'$ represent an alkyl group having 1 to 12 carbon atoms, or a phenyl group which has an alkyl group having 1 to 6 carbon atoms or no substituent; $R_1$ and $R_2'$ may form an alkylene group having 2 to 4 carbon atoms; $R_3'$ and $R_4$ may form an alkylene group having 2 to 4 carbon atoms; $R_5'$ represents a halogen atom; an alkyl group having 1 to 12 carbon atoms; an alkoxy group having 1 to 12 carbon atoms; an alkylthio group having 1 to 12 carbon atoms; an amino group having a halogen atom, an alkyl group having 1 to 20 carbon atoms, an aryl group having 6 to 10 carbon atoms, or an arylalkyl group having 7 to 13 carbon atoms; a hydroxy group; an aryl group having 6 to 14 carbon atoms; an aryloxy group having 6 to 14 carbon atoms; or an arylalkyl group having 7 to 20 carbon atoms; $An'''^-$ represents the anion represented by the general formulae (16) to (19); $R_1$, $R_4$, $R_7$, $A_{2a}$, $Ar_2$ and $n_1$ are the same as described above; and a structure (1-14) in the general formula (3-3a) is an asymmetric structure;

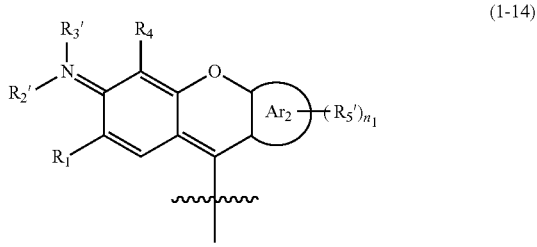

(1-14)

(wherein $R_1$, $R_2'$, $R_3'$, $R_4$, $R_5'$, $Ar_2$ and $n_1$ are the same as described above.)]

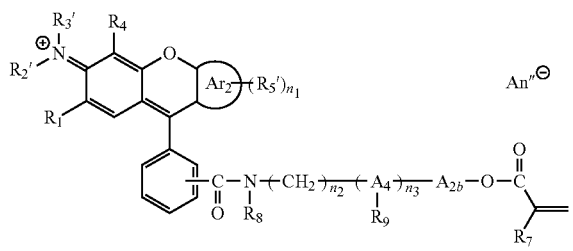

(3-3b)

[wherein $R_1$, $R_2'$, $R_3'$, $R_4$, $R_5'$, $R_7$ to $R_9$, $An'''^-$, $A_{2b}$, $A_4$, $Ar_2$ and $n_1$ to $n_3$ are the same as described above; and the following structure (1-14) in the general formula (3-3b) is an asymmetric structure;

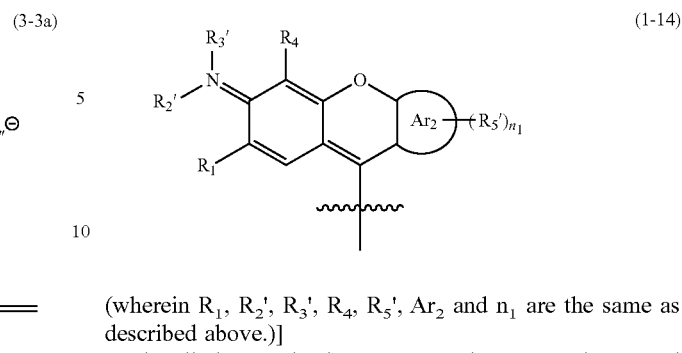

(1-14)

(wherein $R_1$, $R_2'$, $R_3'$, $R_4$, $R_5'$, $Ar_2$ and $n_1$ are the same as described above.)]

The alkyl group having 1 to 12 carbon atoms, in $R_2'$ and $R_3'$ of the general formula (3-3a), includes the same one as the alkyl group having 1 to 12 carbon atoms, in $R_8$ and $R_9$ of the general formula (2-1), and the preferable one is also the same.

The phenyl group which has the alkyl group having 1 to 6 carbon atoms, in $R_2'$ and $R_3'$ of the general formula (3-3a), has usually one to five pieces, and preferably one to three pieces, and more preferably one alkyl group. The alkyl group includes the same one as the alkyl group having 1 to 6 carbon atoms, in $R_{32}$ of the general formula (1), and the preferable one is also the same.

As the phenyl group which has the alkyl group having 1 to 6 carbon atoms, in $R_2'$ and $R_3'$ of the general formula (3-3a), a phenyl group which has an alkyl group having 1 to 3 carbon atoms is particularly preferable, and specifically includes, for example, an o-tolyl group (a methylphenyl group), a m-tolyl group, a p-tolyl group, an o-ethylphenyl group, a m-ethylphenyl group, a p-ethylphenyl group, an o-propylphenyl group, a m-propylphenyl group, a p-propylphenyl group, an o-butylphenyl group, a m-butylphenyl group, a p-butylphenyl group, an o-pentylphenyl group, a m-pentylphenyl group, a p-pentylphenyl group, an o-hexylphenyl group, a m-hexylphenyl group, a p-hexylphenyl group, a 2,3-xylyl group (a 2,3-dimethylphenyl group), a 2,4-xylyl group, a 2,5-xylyl group, a 2,6-xylyl group, a 3,4-xylyl group, a 3,5-xylyl group, a mesityl group (a 2,4,6-trimethylphenyl group), and the like; and the p-tolyl group, the p-ethylphenyl group, the p-propylphenyl group, the p-butylphenyl group, the p-pentylphenyl group, the p-hexylphenyl group, the 2,4-xylyl group, the 2,6-xylyl group, the 3,5-xylyl group and the mesityl group are preferable; and the p-tolyl group, the p-ethylphenyl group and the p-propylphenyl group are more preferable. It should be noted that the alkyl group among the specific examples is not limited to a normal-form, and contains all of the branched forms, such as a sec-form, a tert-form, an iso-form and a neo-form.

The alkylene group having 2 to 4 carbon atoms, when $R_1$ and $R_2'$ form the alkylene group having 2 to 4 carbon atoms, and when $R_3'$ and $R_4$ form the alkylene group having 2 to 4 carbon atoms, in the general formula (3-3a), includes the same one as the alkylene group having 2 to 4 carbon atoms, when $R_1$ and $R_2$ form the alkylene group having 2 to 4 carbon atoms, and when $R_3$ and $R_4$ form the alkylene group having 2 to 4 carbon atoms, in the general formula (1-1); and the preferable one is also the same.

Specific examples, when $R_1$ and $R_2'$ form the alkylene group having 2 to 4 carbon atoms, and/or when $R_3'$ and $R_4$ form the alkylene group having 2 to 4 carbon atoms, in the general formula (3-3a), include, for example, the following ones.

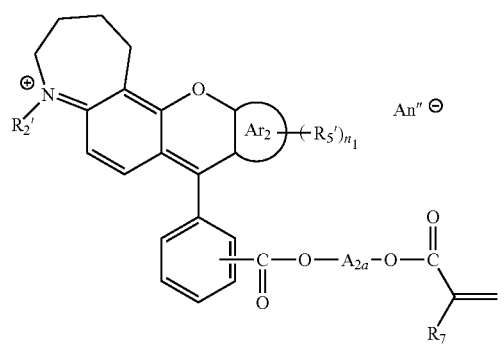
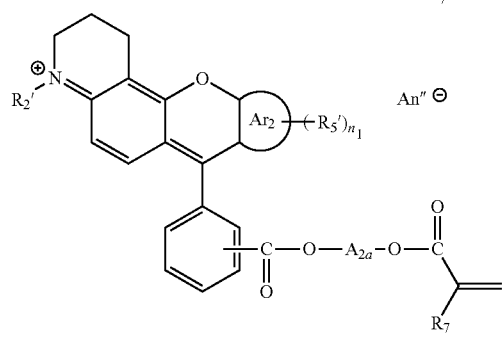
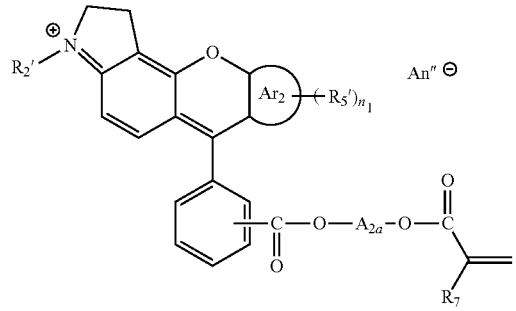
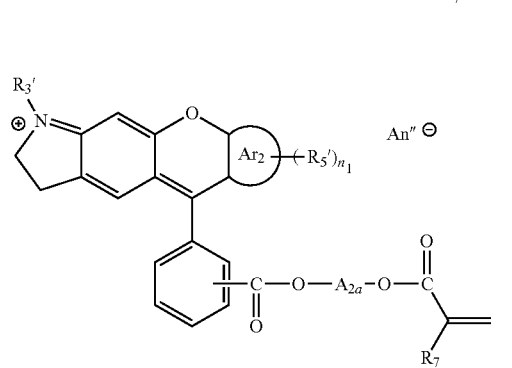
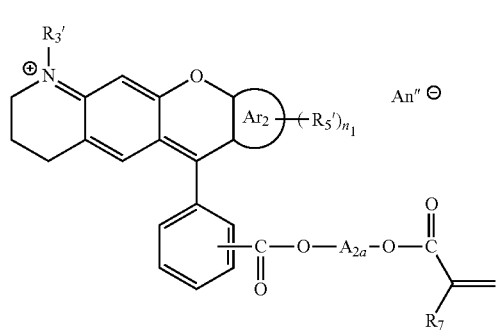
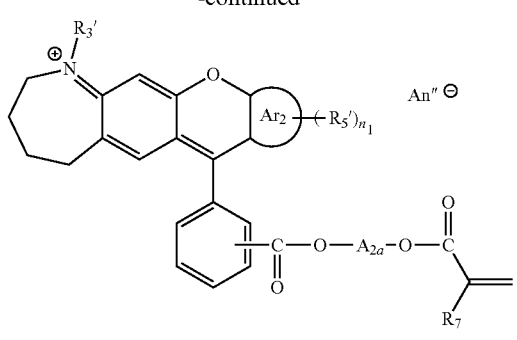
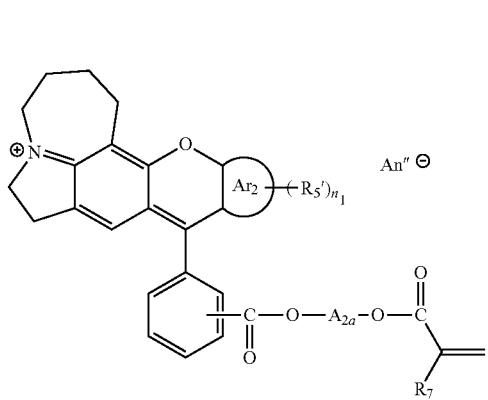
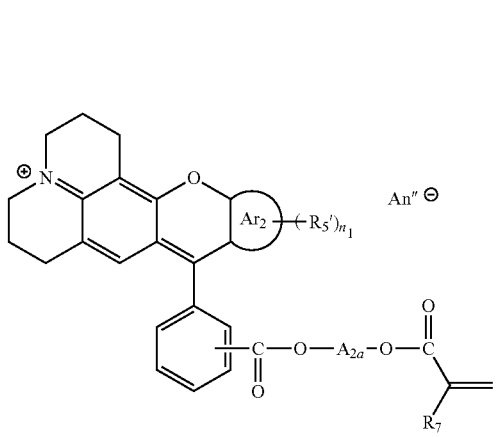
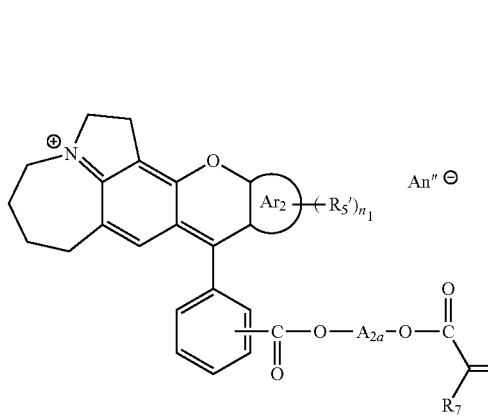
(wherein $R_2'$, $R_3'$, $R_5'$, $R_7$, $An''^-$, $A_{2a}$, $Ar_2$ and $n_1$ are the same as described above.)
Among the specific examples, the following ones are preferable.

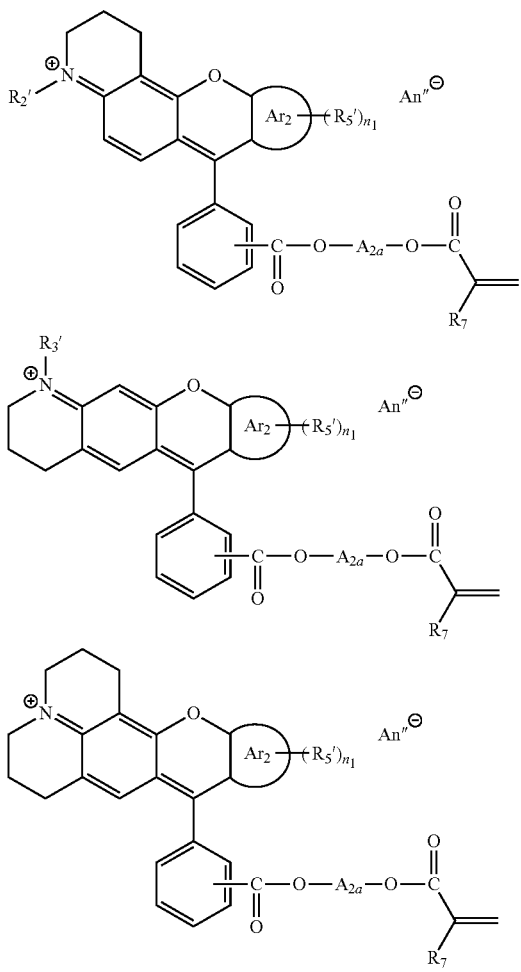

(wherein $R_2'$, $R_3'$, $R_5'$, $R_7$, $An'''^-$, $A_{2a}$, $Ar_2$ and $n_1$ are the same as described above.)

Among the specific examples, the following one is more preferable.

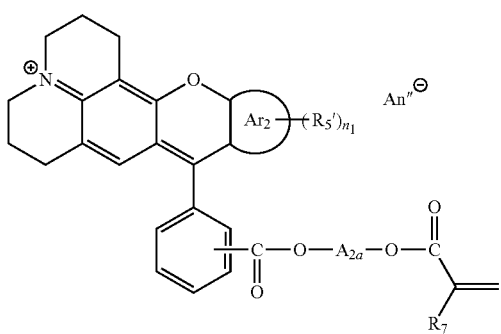

(wherein $R_5'$, $R_7$, $An'''^-$, $A_{2a}$, $Ar_2$ and $n_1$ are the same as described above.)

As $R_2'$ of the general formula (3-3a), an alkyl group having 1 to 6 carbon atoms, a phenyl group which has an alkyl group having 1 to 3 carbon atoms or no substituent, and the one forming a linear alkylene group having 2 to 4 carbon atoms by $R_1$ and $R_2'$ are preferable. It specifically includes, for example, a methyl group, an ethyl group, a propyl group, a butyl group, a pentyl group, a hexyl group, a phenyl group, a p-tolyl group, a p-ethylphenyl group, a p-propylphenyl group, a p-butylphenyl group, a p-pentylphenyl group, a p-hexylphenyl group, a 2,4-xylyl group, a 2,6-xylyl group, a 3,5-xylyl group, a mesityl group, the one forming an ethylene group by $R_1$ and $R_2'$, the one forming a trimethylene group by $R_1$ and $R_2'$, the one forming a tetramethylene group by $R_1$ and $R_2'$, and the like; and the methyl group, the ethyl group, the propyl group, the butyl group, the pentyl group, the hexyl group, the phenyl group, the p-tolyl group, the p-ethylphenyl group, the p-propylphenyl group, and the one forming the trimethylene group by $R_1$ and $R_2'$ are preferable. It should be noted that the alkyl group among the specific examples is not limited to a normal-form, and contains all of the branched forms, such as a sec-form, a tert-form, an iso-form and a neo-form.

As $R_3'$ of the general formula (3-3a), an alkyl group having 1 to 6 carbon atoms, a phenyl group which has an alkyl group having 1 to 3 carbon atoms or no substituent, and the one forming a linear alkylene group having 2 to 4 carbon atoms by $R_3'$ and $R_4$ are preferable. It specifically includes, for example, a methyl group, an ethyl group, a propyl group, a butyl group, a pentyl group, a hexyl group, a phenyl group, a p-tolyl group, a p-ethylphenyl group, a p-propylphenyl group, a p-butylphenyl group, a p-pentylphenyl group, a p-hexylphenyl group, a 2,4-xylyl group, a 2,6-xylyl group, a 3,5-xylyl group, a mesityl group, the one forming an ethylene group by $R_3'$ and $R_4$, the one forming a trimethylene group by $R_3'$ and $R_4$, the one forming a tetramethylene group by $R_3'$ and $R_4$, and the like; and the methyl group, the ethyl group, the propyl group, the butyl group, the pentyl group, the hexyl group, the phenyl group, the p-tolyl group, the p-ethylphenyl group, the p-propylphenyl group, and the one forming the trimethylene group by $R_3'$ and $R_4$ are preferable. It should be noted that the alkyl group among the specific examples is not limited to a normal-form, and contains all of the branched forms, such as a sec-form, a tert-form, an iso-form and a neo-form.

The halogen atom in $R_5'$ of the general formula (3-3a) includes, for example, a fluorine atom, a chlorine atom, a bromine atom, an iodine atom, and the like, and among them, the fluorine atom is preferable.

The alkyl group having 1 to 12 carbon atoms, in $R_5'$ of the general formula (3-3a), includes the same one as the alkyl group having 1 to 12 carbon atoms, in $R_8$ and $R_9$ of the general formula (2-1), and the preferable one is also the same.

The alkoxy group having 1 to 12 carbon atoms, in $R_5'$ of the general formula (3-3a), may be any of the linear, branched and cyclic ones, and among them, the linear and branched ones are preferable. In addition, the one having 1 to 6 carbon atoms is more preferable, and the one having 1 to 4 carbon atoms is particularly preferable. Specifically, a methoxy group, an ethoxy group, an n-propoxy group, an isopropoxy group, an n-butoxy group, an isobutoxy group, a sec-butoxy group, a tert-butoxy group, an n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, an n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group and a 1-ethylbutoxy group are preferable; and the methoxy group, the ethoxy group, the n-propoxy group, the isopropoxy group, the n-butoxy group, the isobutoxy group, the sec-butoxy group and the tert-butoxy group are more preferable; and the methoxy group and the ethoxy group are further preferable.

The alkylthio group having 1 to 12 carbon atoms, in $R_5'$ of the general formula (3-3a), may be any of the linear, branched and cyclic ones, and among them, the linear and branched ones are preferable. In addition, the one having 1 to 6 carbon atoms is more preferable, and the one having 1 to 4 carbon atoms is particularly preferable. Specifically, a methylthio group, an ethylthio group, an n-propylthio group, an isopropylthio group, an n-butylthio group, an isobutylthio group, a sec-butylthio group, a tert-butylthio group, an n-pentylthio group, an isopentylthio group, a sec-pentylthio group, a tert-pentylthio group, a neopentylthio group, a 2-methylbutylthio group, a 1,2-dimethylpropylthio group, a 1-ethylpropylthio group, an n-hexylthio group, an isohexylthio group, a sec-hexylthio group, a tert-hexylthio group, a neohexylthio group, a 2-methylpentylthio group, a 1,2-dimethylbutylthio group, a 2,3-dimethylbutylthio group and a 1-ethylbutylthio group are preferable; and the methylthio group, the ethylthio group, the n-propylthio group, the isopropylthio group, the n-butylthio group, the isobutylthio group, the sec-butylthio group and the tert-butylthio group are more preferable; and the methylthio group and the ethylthio group are further preferable.

Specific examples of the amino group having the halogen atom, the alkyl group having 1 to 20 carbon atoms, the aryl group having 6 to 10 carbon atoms, or the arylalkyl group having 7 to 13 carbon atoms in "an amino group having a halogen atom, an alkyl group having 1 to 20 carbon atoms, an aryl group having 6 to 10 carbon atoms, or an arylalkyl group having 7 to 13 carbon atoms", in $R_5'$ of the general formula (3-3a), include the same one as "an amino group having a substituent" in $R_5$ of the general formula (1), and the preferable one is also the same.

As the amino group having the halogen atom, the alkyl group having 1 to 20 carbon atoms, the aryl group having 6 to 10 carbon atoms, or the arylalkyl group having 7 to 13 carbon atoms, in $R_5'$ of the general formula (3-3a), an amino group having an alkyl group having 1 to 6 carbon atoms, a phenyl group, or a phenylalkyl group having 7 to 9 carbon atoms is preferable. It specifically includes, for example, a methylamino group, an ethylamino group, an n-propylamino group, an isopropylamino group, an n-butylamino group, an isobutylamino group, a sec-butylamino group, a tert-butylamino group, an n-pentylamino group, an isopentylamino group, an n-hexylamino group, a phenylamino group, a benzylamino group, a phenethylamino group, a hydrocinnamylamino group, a dimethylamino group, a diethylamino group, a di-n-propylamino group, a diisopropylamino group, a di-n-butylamino group, a diisobutylamino group, a di-sec-butylamino group, a di-tert-butylamino group, a di-n-pentylamino group, a diisopentylamino group, a di-n-hexylamino group, a diphenylamino group, a dibenzylamino group, a diphenethylamino group, a bis(hydrocinnamyl) amino group, and the like; and the methylamino group, the ethylamino group, the n-propylamino group, the isopropylamino group, the n-butylamino group, the isobutylamino group, the sec-butylamino group, the tert-butylamino group, the phenylamino group, the benzylamino group, the dimethylamino group, the diethylamino group, the di-n-propylamino group, the diisopropylamino group, the di-n-butylamino group, the diisobutylamino group, the di-sec-butylamino group, the di-tert-butylamino group, the diphenylamino group and the dibenzylamino group are preferable; and the methylamino group, the ethylamino group, the phenylamino group, the benzylamino group, the dimethylamino group, the diethylamino group, the diphenylamino group and the dibenzylamino group are more preferable.

Specific examples of the aryl group having 6 to 14 carbon atoms, the aryloxy group having 6 to 14 carbon atoms, and the arylalkyl group having 7 to 20 carbon atoms, in $R_5'$ of the general formula (3-3a), include the same one as those in $R_5$ of the general formula (1), and the preferable one is also the same.

As $R_5'$ of the general formula (3-3a), a halogen atom; an alkyl group having 1 to 12 carbon atoms; an alkoxy group having 1 to 12 carbon atoms; an alkylthio group having 1 to 12 carbon atoms; an amino group having an alkyl group having 1 to 6 carbon atoms, a phenyl group, or a phenylalkyl group having 7 to 9 carbon atoms; an hydroxy group; a phenyl group; a phenoxy group; and a phenylalkyl group having 7 to 12 carbon atoms are preferable; and the halogen atom; an alkyl group having 1 to 6 carbon atoms; an alkoxy group having 1 to 6 carbon atoms; an alkylthio group having 1 to 6 carbon atoms; the amino group having the alkyl group having 1 to 6 carbon atoms, the phenyl group, or the phenylalkyl group having 7 to 9 carbon atoms; the hydroxy group; the phenyl group; the phenoxy group; and a phenylalkyl group having 7 to 9 carbon atoms are more preferable. Specifically, a fluorine atom, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a methoxy group, an ethoxy group, an n-propoxy group, an isopropoxy group, an n-butoxy group, an isobutoxy group, a sec-butoxy group, a tert-butoxy group, a methylthio group, an ethylthio group, an n-propylthio group, an isopropylthio group, an n-butylthio group, an isobutylthio group, a sec-butylthio group, a tert-butylthio group, a methylamino group, an ethylamino group, an n-propylamino group, an isopropylamino group, an n-butylamino group, an isobutylamino group, a sec-butylamino group, a tert-butylamino group, a phenylamino group, a benzylamino group, a dimethylamino group, a diethylamino group, a di-n-propylamino group, a diisopropylamino group, a di-n-butylamino group, a diisobutylamino group, a di-sec-butylamino group, a di-tert-butylamino group, a diphenylamino group, a dibenzylamino group, a hydroxy group, a phenyl group, a phenoxy group, a benzyl group, a phenethyl group, a 1-phenylethyl group, a hydrocinnamyl group, a 2-phenylpropyl group, a 1-phenylpropyl group and a cumyl group are preferable; and the fluorine atom, the methyl group, the ethyl group, the n-propyl group, the isopropyl group, the n-butyl group, the isobutyl group, the sec-butyl group, the tert-butyl group, the methoxy group, the ethoxy group, the methylthio group, the ethylthio group, the methylamino group, the ethylamino group, the phenylamino group, the benzylamino group, the dimethylamino group, the diethylamino group, the diphenylamino group, the dibenzylamino group, the hydroxy group, the phenyl group, the phenoxy group, the benzyl group, the phenethyl group, the hydrocinnamyl group and the cumyl group are more preferable.

In the general formula (3-3a) and the general formula (3-3b), the following structure (1-14) is a left-right asymmetric structure.

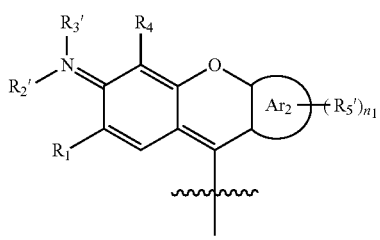

(1-14)

(wherein $R_1$, $R_2'$, $R_3'$, $R_4$, $R_5'$, $Ar_2$ and $n_1$ are the same as described above.)

In other words, the compound represented by the general formula (3-3a) does not include a compound represented by the following general formula (1-15).

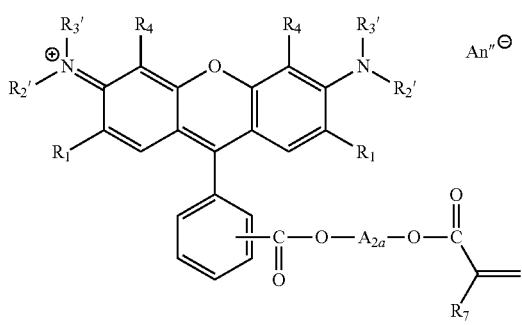

(1-15)

(wherein $R_1$, $R_2'$, $R_3'$, $R_4$, $R_7$, $An''^-$ and $A_{2a}$ are the same as described above; and two of $R_1$, $R_2'$, $R_3'$ and $R_4$ are the same.)

In addition, the compound represented by the general formula (3-3b) does not include a compound represented by the following general formula (1-16).

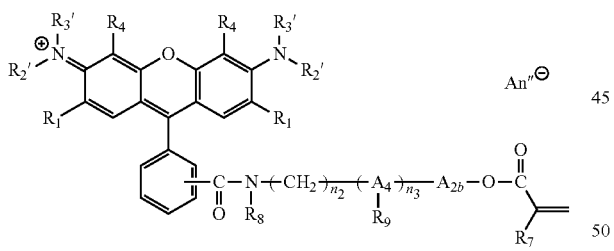

(1-16)

(wherein $R_1$, $R_2'$, $R_3'$, $R_4$, $R_7$ to $R_9$, $An''^-$, $A_{2b}$, $A_4$ and $n_1$ to $n_3$ are the same as described above; and two of $R_1$, $R_2'$, $R_3'$ and $R_4$ are the same.)

The anion represented by the general formulae (16) to (19), in $An''^-$ of the general formula (3-3a), includes the same one as the anion represented by the general formulae (16) to (19), in $An^-$ of the general formula (1), and the preferable one is also the same.

As the anion represented by $An''^-$ of the general formula (3-3a), the one represented by the general formula (16), the general formula (18), and the general formula (19) is preferable, and the one represented by the general formula (16), and the general formula (18) is more preferable, and the one represented by the general formula (16) is particularly preferable. Specifically, for example, the following ones are preferable.

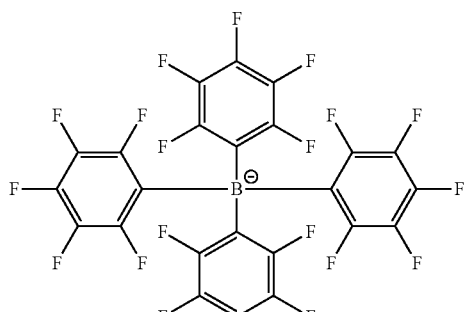

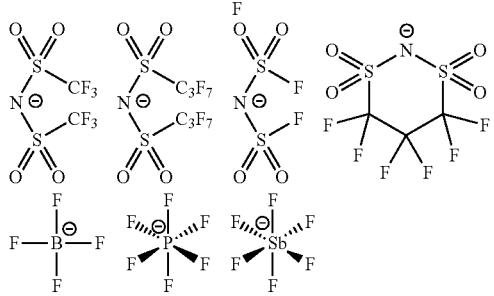

Among the specific examples, the following ones are more preferable.

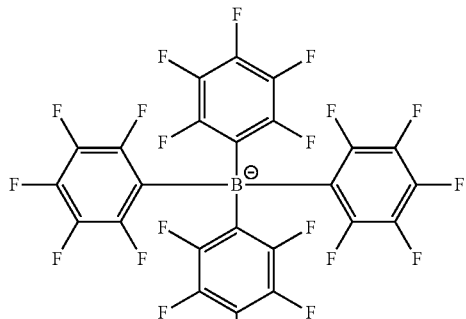

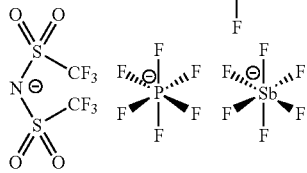

Among the specific examples, the following ones are further preferable.

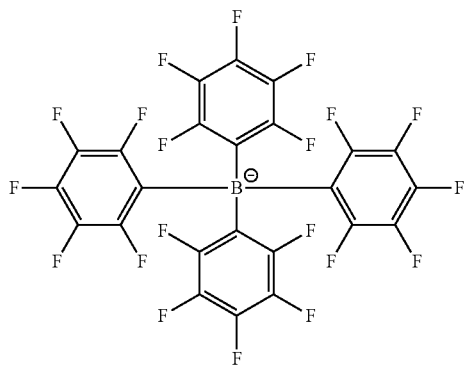 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

-continued

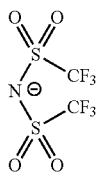

Among the specific examples, the following one is particularly preferable.

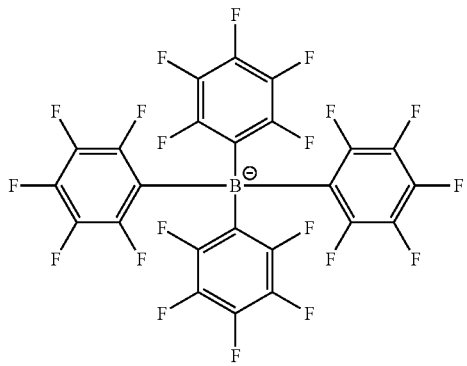

Preferable combinations of $R_1$, $R_2'$, $R_3'$, $R_4$, $R_5'$, $R_7$, $A_{2a}$, $Ar_2$ and $n_1$, in the general formula (3-3a), include, for example, those described in the following table. It should be noted that "alkyl groups A" in $R_2'$ column and $R_3'$ column, as well as "alkyl groups B", "alkoxy groups", "alkylthio groups" and "substituted amino groups" in $R_5'$ column each represent the group consisting of the following substituents.

Alkyl groups A: a methyl group, an ethyl group, an n-propyl group, an isopropyl group, an n-butyl group, an isobutyl group, a sec-butyl group, a tert-butyl group, an n-pentyl group, an isopentyl group, an n-hexyl group Alkyl groups B: a methyl group, an ethyl group, an n-propyl group, an isopropyl group, an n-butyl group, an isobutyl group, a sec-butyl group, a tert-butyl group Alkoxy groups: a methoxy group, an ethoxy group Alkylthio groups: a methylthio group, an ethylthio group Substituted amino group: a methylamino group, an ethylamino group, a phenylamino group, a benzylamino group, a dimethylamino group, a diethylamino group, a diphenylamino group, a dibenzylamino group

| $R_1$ | $R_2'$ | $R_3'$ | $R_4$ | $R_7$ | $A_{2a}$ | $Ar_2$ | $R_5'$ | $n_1$ |
|---|---|---|---|---|---|---|---|---|
| hydrogen atom | alkyl groups A, phenyl group, p-tolyl group, p-ethylphenyl group, p-(n-propyl)phenyl group, or p-isopropylphenyl group | alkyl groups A, phenyl group, p-tolyl group, p-ethylphenyl group, p-(n-propyl)phenyl group, or p-isopropylphenyl group | hydrogen atom | hydrogen atom or methyl group | ethylene group | benzene ring | fluorine atom | 1 |
| | | | | | | | alkyl groups B | 1 |
| | | | | | | | alkoxy groups | 1 |
| | | | | | | | alkylthio groups | 1 |
| | | | | | | | substituted amino groups | 1 |
| | | | | | | | hydroxy group | 1 |
| | | | | | | | phenyl group | 1 |
| | | | | | | | phenoxy group | 1 |
| | | | | | | | benzyl group | 1 |
| | | | | | | | cumyl group | 1 |
| | | | | | | | alkyl groups B | 2 |
| | | | | | | | combination of alkyl groups B and substituted amino groups | 2 |
| | | | | | | | alkyl groups B | 3 |
| | | | | | | | alkoxy groups | 3 |
| | | | | | | | alkylthio groups | 3 |
| | | | | | | | — | 0 |
| | | | | | | naphthalene ring | fluorine atom | 1 |
| | | | | | | | alkyl groups B | 1 |
| | | | | | | | alkoxy groups | 1 |
| | | | | | | | alkylthio groups | 1 |
| | | | | | | | substituted amino groups | 1 |
| | | | | | | | hydroxy group | 1 |
| | | | | | | | phenyl group | 1 |
| | | | | | | | phenoxy group | 1 |
| | | | | | | | benzyl group | 1 |
| | | | | | | | cumyl group | 1 |
| | | | | | | | — | 0 |
| | trimethylene group | trimethylene group | hydrogen atom or methyl group | | ethylene group | benzene ring | fluorine atom | 1 |
| | | | | | | | alkyl groups B | 1 |
| | | | | | | | alkoxy groups | 1 |
| | | | | | | | alkylthio groups | 1 |
| | | | | | | | substituted amino groups | 1 |
| | | | | | | | hydroxy group | 1 |
| | | | | | | | phenyl group | 1 |
| | | | | | | | phenoxy group | 1 |
| | | | | | | | benzyl group | 1 |
| | | | | | | | cumyl group | 1 |

| $R_1$ | $R_2'$ | $R_3'$ | $R_4$ | $R_7$ | $A_{2a}$ | $Ar_2$ | $R_5'$ | $n_1$ |
|---|---|---|---|---|---|---|---|---|
| | | | | | | naphthalene ring | fluorine atom | 1 |
| | | | | | | | alkyl groups B | 1 |
| | | | | | | | alkoxy groups | 1 |
| | | | | | | | alkylthio groups | 1 |
| | | | | | | | substituted amino groups | 1 |
| | | | | | | | hydroxy group | 1 |
| | | | | | | | phenyl group | 1 |
| | | | | | | | phenoxy group | 1 |
| | | | | | | | benzyl group | 1 |
| | | | | | | | cumyl group | 1 |
| | | | | | | | — | 0 |

In the general formula (3-3b), when $R_8$, $R_9$ and —N—$(CH_2)_{n2}$-$(A_4)_{n3}$- do not form a ring structure of a 5 to 6-membered ring, preferable combinations of $R_1$, $R_2'$, $R_3'$, $R_4$, $R_5'$, $R_7$ to $R_9$, $A_{2b}$, $A_4$, $Ar_2$ and $n_1$ to $n_3$ include those described in the following table. It should be noted that formulae (P) and (Q) in the $A_{2b}$ column represent groups represented by the following formulae. In addition, "alkyl groups A" in the $R_2'$ column, and "alkyl groups B", "alkoxy groups", "alkylthio groups" and "substituted amino groups" in the $R_5'$ column are the same as described above.

$$—(CH_2)_2—O—CO—(CH_2)_2—CO—O—(CH_2)_2— \quad (P)$$

$$—(CH_2)_2—NHCONH—(CH_2)_2— \quad (Q)$$

| $R_1$ | $R_2'$ | $R_3'$ | $R_4$ | $R_7$ | $R_8$ | $R_9$ | $A_4$ | $A_{2b}$ | $Ar_2$ | $R_5'$ | $n_1$ | $n_2$ | $n_3$ |
|---|---|---|---|---|---|---|---|---|---|---|---|---|---|
| hydrogen atom | alkyl groups A, phenyl group, p-tolyl group, p-ethylphenyl group, p-(n-propyl)phenyl group or p-isopropylphenyl group | alkyl groups A | hydrogen atom | hydrogen atom or methyl group | hydrogen atom | — | — | formula (P) or (Q) | benzene ring | fluorine atom | 1 | 0 | 0 |
| | | | | | | | | | | alkyl groups B | 1 | 0 | 0 |
| | | | | | | | | | | alkoxy groups | 1 | 0 | 0 |
| | | | | | | | | | | alkylthio groups | 1 | 0 | 0 |
| | | | | | | | | | | substituted amino groups | 1 | 0 | 0 |
| | | | | | | | | | | hydroxy group | 1 | 0 | 0 |
| | | | | | | | | | | phenyl group | 1 | 0 | 0 |
| | | | | | | | | | | phenoxy group | 1 | 0 | 0 |
| | | | | | | | | | | benzyl group | 1 | 0 | 0 |
| | | | | | | | | | | cumyl group | 1 | 0 | 0 |
| | | | | | | | | | | alkyl groups B | 2 | 0 | 0 |
| | | | | | | | | | | combination of alkyl groups B and substituted amino groups | 2 | 0 | 0 |
| | | | | | | | | | | alkyl groups B | 3 | 0 | 0 |
| | | | | | | | | | | alkoxy groups | 3 | 0 | 0 |
| | | | | | | | | | | alkylthio groups | 3 | 0 | 0 |
| | | | | | | | | | | — | 0 | 0 | 0 |
| | | | | | | | | | naphthalene ring | fluorine atom | 1 | 0 | 0 |
| | | | | | | | | | | alkyl groups B | 1 | 0 | 0 |
| | | | | | | | | | | alkoxy groups | 1 | 0 | 0 |
| | | | | | | | | | | alkylthio groups | 1 | 0 | 0 |
| | | | | | | | | | | substituted amino groups | 1 | 0 | 0 |
| | | | | | | | | | | hydroxy group | 1 | 0 | 0 |
| | | | | | | | | | | phenyl group | 1 | 0 | 0 |
| | | | | | | | | | | phenoxy group | 1 | 0 | 0 |
| | | | | | | | | | | benzyl group | 1 | 0 | 0 |
| | | | | | | | | | | cumyl group | 1 | 0 | 0 |
| | | | | | | | | | | — | 0 | 0 | 0 |

In the general formula (3-3b), when $R_8$, $R_9$ and $—N—(CH_2)_{n2}-(A_4)_{n3}-$ form a ring structure of a 5 to 6-membered ring, preferable combinations of $R_1$, $R_2'$, $R_3'$, $R_4$, $R_5'$, $R_7$ to $R_9$, $A_{2b}$, $A_4$, $Ar_2$ and $n_1$ to $n_3$ include, for example, those described in the following table. It should be noted that "alkyl groups A" in the $R_2'$ column, "alkyl groups B", "alkoxy groups", "alkylthio groups" and "substituted amino groups" in the $R_5'$ column are the same as described above.

| $R_1$ | $R_2'$ | $R_3'$ | $R_4$ | $R_7$ | $R_8$ | $R_9$ | $A_4$ | $A_{2b}$ | $Ar_2$ | $R_5'$ | $n_1$ | $n_2$ | $n_3$ |
|---|---|---|---|---|---|---|---|---|---|---|---|---|---|
| hydrogen atom | alkyl groups A, phenyl group, p-tolyl group, p-ethylphenyl group, p-(n-propyl)phenyl group, or p-isopropylphenyl group | alkyl groups A | hydrogen atom | hydrogen atom or methyl group | trimethylene group | | nitrogen atom or formula (2-2) | methyl group, ethyl group or n-isopropyl group | benzene ring | fluorine atom | 1 | 0 | 0 |
| | | | | | | | | | | alkyl groups B | 1 | 0 | 0 |
| | | | | | | | | | | alkoxy groups | 1 | 0 | 0 |
| | | | | | | | | | | alkylthio groups | 1 | 0 | 0 |
| | | | | | | | | | | substituted amino groups | 1 | 0 | 0 |
| | | | | | | | | | | hydroxy group | 1 | 0 | 0 |
| | | | | | | | | | | phenyl group | 1 | 0 | 0 |
| | | | | | | | | | | phenoxy group | 1 | 0 | 0 |
| | | | | | | | | | | benzyl group | 1 | 0 | 0 |
| | | | | | | | | | | cumyl group | 1 | 0 | 0 |
| | | | | | | | | | | alkyl groups B | 2 | 0 | 0 |
| | | | | | | | | | | combination of alkyl groups B and substituted amino groups | 2 | 0 | 0 |
| | | | | | | | | | | alkyl groups B | 3 | 0 | 0 |
| | | | | | | | | | | alkoxy groups | 3 | 0 | 0 |
| | | | | | | | | | | alkylthio groups | 3 | 0 | 0 |
| | | | | | | | | | | — | 0 | 0 | 0 |
| | | | | | | | | | naphthalene ring | fluorine atom | 1 | 0 | 0 |
| | | | | | | | | | | alkyl groups B | 1 | 0 | 0 |
| | | | | | | | | | | alkoxy groups | 1 | 0 | 0 |
| | | | | | | | | | | alkylthio groups | 1 | 0 | 0 |
| | | | | | | | | | | substituted amino groups | 1 | 0 | 0 |
| | | | | | | | | | | hydroxy group | 1 | 0 | 0 |
| | | | | | | | | | | phenyl group | 1 | 0 | 0 |
| | | | | | | | | | | phenoxy group | 1 | 0 | 0 |
| | | | | | | | | | | benzyl group | 1 | 0 | 0 |
| | | | | | | | | | | cumyl group | 1 | 0 | 0 |
| | | | | | | | | | | — | 0 | 0 | 0 |

In addition, $An^{n''-}$ to be used together with the combinations described in the table includes the following ones.

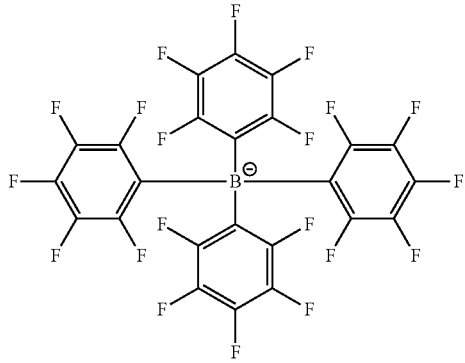

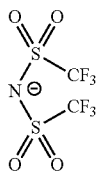

Among the specific examples, the following one is preferable.

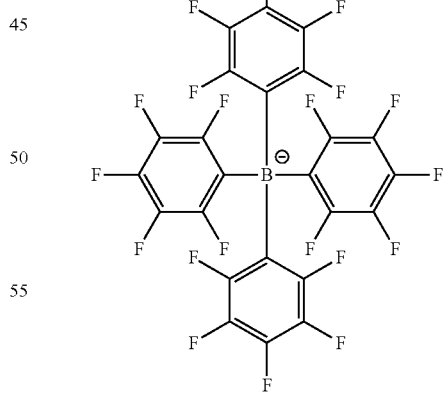

The quencher of the present invention is the one capable of quenching fluorescence emitted by a compound having fluorescent property.

A object of quenching by the quencher of the present invention (hereinafter it may be abbreviated as the object compound of quenching) may be any compound having fluorescent property; and specifically includes, for example, a compound having fluorescent property such as a compound having an anthracene skeleton, a compound having a xanthene skeleton, a compound having a coumarin skeleton, a compound having a stilbene skeleton, a compound having a naphthalimide skeleton, a compound having a perylene skeleton, a compound having a pyridine skeleton, a compound having an oxazine skeleton, a compound having a cyanine skeleton, a compound having an olefin skeleton, a compound having an azole skeleton, a thiazine-type dye, a phthalocyanine-type dye, an anthraquinone-type dye, an acridone-type dye, a quinacridone-type dye, an isoindolinone-type dye, a thioflavin-type dye, a thioindigo-type dye, a fluorene-type dye, an azo-type dye, a di- and triphenylmethane-type dye, a terphenyl-type dye, a chrysene-type dye and a pyrene-type dye.

The compound having the anthracene skeleton includes, for example, an anthracene-type dye such as anthracene, 9,10-bis(phenylethynyl)anthracene and 1-chloro-9,10-bis(phenylethynyl)anthracene, and the like.

The compound having the xanthene skeleton includes, for example, a Rhodamine-type dye such as Rhodamine B, Rhodamine 6G, Rhodamine 3B, Rhodamine 101, Rhodamine 110, Basic violet 11, Sulforhodamine 101, Basic violet 11 and Basic red 2; an Eosin-type dye such as Eosin Y and Eosin B; a fluorescein-type dye such as fluorescein, fluorescein isothiocyanate; and the like.

The compound having the coumarin skeleton includes, for example, a coumarin-type dye such as coumarin 6, coumarin 7, coumarin 153, coumarin 314, coumarin 334, coumarin 545, coumarin 545T, coumarin 545P and 7-hydroxy-4-methylcoumarin, and the like.

The compound having the stilbene skeleton includes, for example, a stilbene-type dye such as 1,4-bis(2-methylstyryl)benzene and trans-4,4'-diphenylstyrylbenzene, and the like.

The compound having the naphthalimide skeleton includes, for example, a naphthalimide-type dye such as Basic Yellow 51, Solvent Yellow 11, Solvent Yellow 98, Solvent Yellow 116, Solvent Yellow 43 and Solvent Yellow 44, and the like.

The compound having the perylene skeleton includes, for example, a perylene-type dye such as perylene, Lumogen Yellow, Lumogen Green, Lumogen Orange, Lumogen Pink, Lumogen Red, Solvent Orange 5 and Solvent Green 5, and the like.

The compound having the pyridine skeleton includes, for example, a pyridine-type dye such as 1-ethyl-2-[4-(p-dimethylaminophenyl)-1,3-butadienyl]-pyridinium-perchlorate (pyridine 1), an acridine-type dye, and the like.

The compound having the oxazine skeleton includes, for example, an oxazine-type dye such as Cresyl Violet Acetate, a dioxazine-type dye, and the like.

The compound having the cyanine skeleton includes, for example, a cyanine-type dye such as 4-dicyanomethylene-2-methyl-6-(p-dimethylaminostyryl)-4H-pyran, and the like.

The compound having the olefin skeleton includes, for example, an ethene-type dye, a butadiene-type dye, a hexatriene-type dye, and the like.

The compound having the azole skeleton includes, for example, an oxazole-type dye, a thiazole-type dye, and the like.

Among the object compound of quenching, a compound having an anthracene skeleton, a xanthene skeleton, a coumarin skeleton or an oxazine skeleton is preferable; a compound having a xanthene skeleton is more preferable; and the Rhodamine-type dye is particularly preferable. Specifically, for example, anthracene, 9,10-bis(phenylethynyl)anthracene, 1-chloro-9,10-bis(phenylethynyl)anthracene, Rhodamine B, Rhodamine 6G, Rhodamine 3B, Rhodamine 101, Rhodamine 110, Sulforhodamine, Basic Violet 11, Basic Red 2, Eosin Y, Eosin B, fluorescein, fluorescein isothiocyanate, coumarin 6, coumarin 7, coumarin 153, coumarin 314, coumarin 334, coumarin 545, coumarin 545T, coumarin 545P and 7-hydroxy-4-methylcoumarin are preferable; and Rhodamine B, Rhodamine 6G, Rhodamine 3B, Rhodamine 101, Rhodamine 110, Sulforhodamine, Basic violet 11, Basic red 2, Eosin Y, Eosin B, fluorescein, fluorescein isothiocyanate are more preferable; and Rhodamine B, Rhodamine 6G, Rhodamin 3B, Rhodamine 101, Rhodamine 110, Sulforhodamine, Basic violet 11 and Basic red 2 are particularly preferable.

In addition, the object compound of quenching includes the object compound of quenching, having a polymerizable group; that is, a monomer having fluorescent property, as well as having a polymerizable unsaturated group (hereinafter, it may be abbreviated as the polymerizable object compound of quenching); and also a polymer thereof.

The polymerizable unsaturated group in the polymerizable object compound of quenching includes, for example, an acryloyl group, a methacryloyl group, a vinylaryl group, a vinyloxy group, an allyl group, and the like.

The polymer of the polymerizable object compound of quenching is the one having a monomer unit derived from the polymerizable object compound of quenching, as a composition components, and having fluorescent property.

Specific examples of the polymerizable object compound of quenching or the polymer thereof may be those described in JP-A-05-271567, JP-A-09-272814, JP-A-2001-011336, JP-A-2013-045088, WO2014/126167, WO2015/098999, WO2015/133578, WO2015/147285, WO2015/182680, and the like, or commercially available ones.

As the object compound of quenching, the polymerizable object compound of quenching, or the polymer thereof is preferable; and the polymerizable object compound of quenching is more preferable.

To quench fluorescence emitted by the object compound of quenching, using the quencher of the present invention; the quencher of the present invention may be used, for example, in a solvent to be used usually in this field, in usually 0.5 to 300 equivalents, preferably 100 to 200 equivalents, relative to mole number of the object compound of quenching. Reaction condition in this quenching reaction, such as use amount of the solvent, temperature and pressure, may be selected as appropriate, in consideration of technical common sense in an organic chemistry field.

[Production Method for the Quencher of the Present Invention]

Among the quencher of the present invention, for example, the one where $Y_1$ is an oxygen atom, and $R_6$ is a hydroxy group, in the general formula (1) (a compound represented by the following general formula (36)), can be produced by a series of methods represented by the next reactions [I] to [III].

That is, firstly, a compound represented by the following general formula (32) is obtained, by a reaction between a compound represented by the following general formula (31) and phthalic anhydride (the reaction [I]). Next, a compound represented by the following general formula (34) is obtained, by a reaction between the resulting compound represented by the general formula (32) and a compound represented by the following general formula (33) (the reaction [II]). After that, the resulting compound represented by the general formula (34) and a compound represented by the following general formula (35) may be subjected to a reaction, as needed, and a salt formation reaction may be carried out (the reaction [III]).

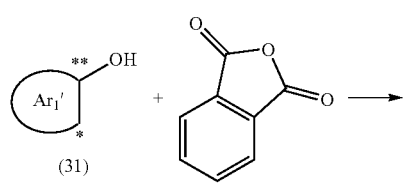

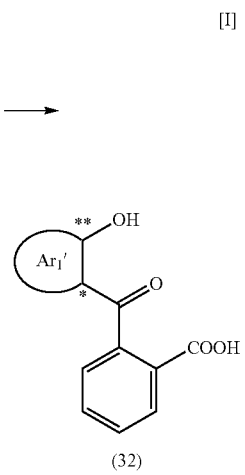

[wherein Ar₁' represents a ring structure represented by the following general formula (1-1') and the following formulae (1-2') to (1-7');

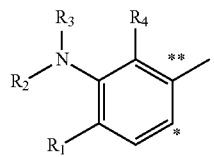

(wherein R₁ to R₄ are the same as described above.),

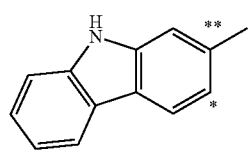

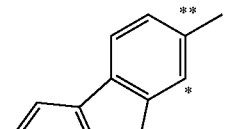

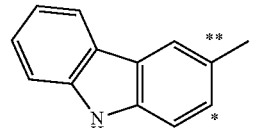

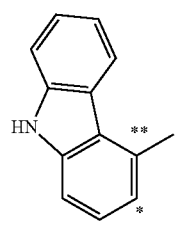

and * and ** are the same as described above.]

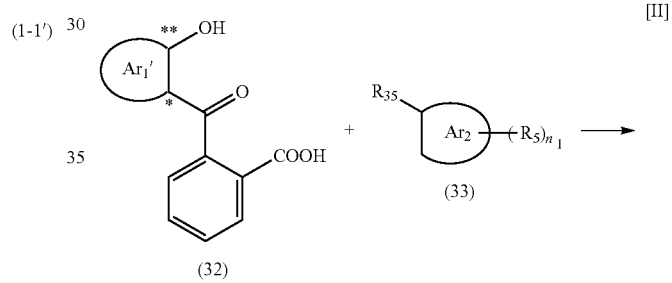

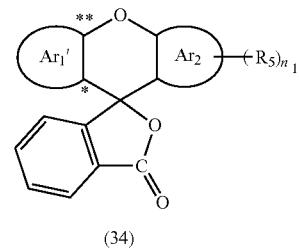

(wherein R₃₅ represents a hydroxy group or a methoxy group; and n₁ pieces of R₅, Ar₁', Ar₂, n₁, * and ** are the same as described above.)

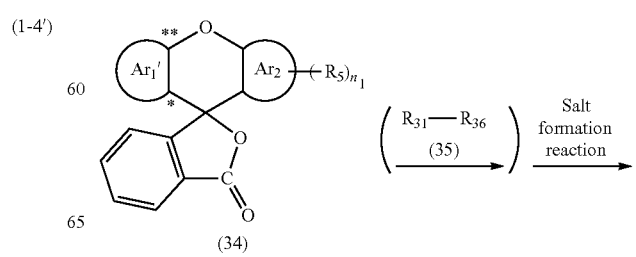

-continued

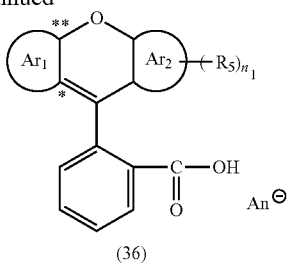

(36)

[wherein $R_{36}$ represents a halogen atom, a trifluoromethylsulfonyloxy group, a mesyloxy group (a methylsulfonyloxy group) or a tosyloxy group (a p-toluenesulfonyloxy group); and $n_1$ pieces of $R_5$, $R_{31}$, $An^-$, $Ar_1$, $Ar_1'$, $Ar_2$, $n_1$, * and ** are the same as described above.]

As $Ar_1'$ of the general formula (31), the ring structure represented by the general formula (1-1') is preferable.

As $R_{35}$ of the general formula (33), a hydroxy group is preferable.

The halogen atom in $R_{36}$ of the general formula (35) includes, for example, a fluorine atom, a chlorine atom, a bromine atom, an iodine atom, and the like, and among them, the iodine atom is preferable.

As $R_{36}$ of the general formula (35), a halogen atom is preferable, and an iodine atom is more preferable.

In the reaction [I], the compound represented by the general formula (31) and phthalic anhydride may be subjected to a reaction in a solvent, usually at 80 to 160° C., preferably at 90 to 120° C., usually for 1 to 24 hours, and preferably for 3 to 10 hours.

The solvent includes ethers, for example, diethyl ether, diisopropyl ether, ethyl methyl ether, tetrahydrofuran, 1,4-dioxane, dimethoxyethane, and the like; ketones, for example, acetone, dimethyl ketone, methyl ethyl ketone, diethyl ketone, 2-hexanone, tert-butyl methyl ketone, cyclopentanone, cyclohexanone, and the like; halogenated hydrocarbons, for example, chloromethane, chloroform, dichloromethane, dichloroethane, trichloroethane, carbon tetrachloride, chlorobenzene, and the like; hydrocarbons, for example, n-hexane, benzene, toluene, xylene, and the like; esters, for example, ethyl acetate, butyl acetate, methyl propionate, and the like; nitriles, for example, acetonitrile, and the like; and amides, for example, N,N-dimethylformamide, and the like. Among them, hydrocarbons are preferable, and toluene is more preferable. These may be used singly, or in combination of two or more kinds thereof as appropriate. Use amount of the reaction solvent is usually 1 to 50 times, and preferably 5 to 10 times, relative to the total weight of the compound represented by the general formula (31) and phthalic anhydride.

Use amount of phthalic anhydride is usually 1 to 2 equivalents, and preferably 1 to 1.5 equivalents, relative to mole number of the compound represented by the general formula (31).

Specific examples of the compound represented by the general formula (31) include, for example, the following ones.

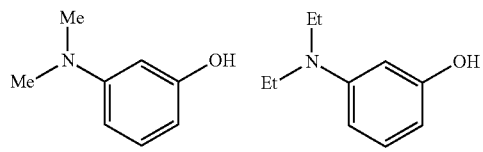

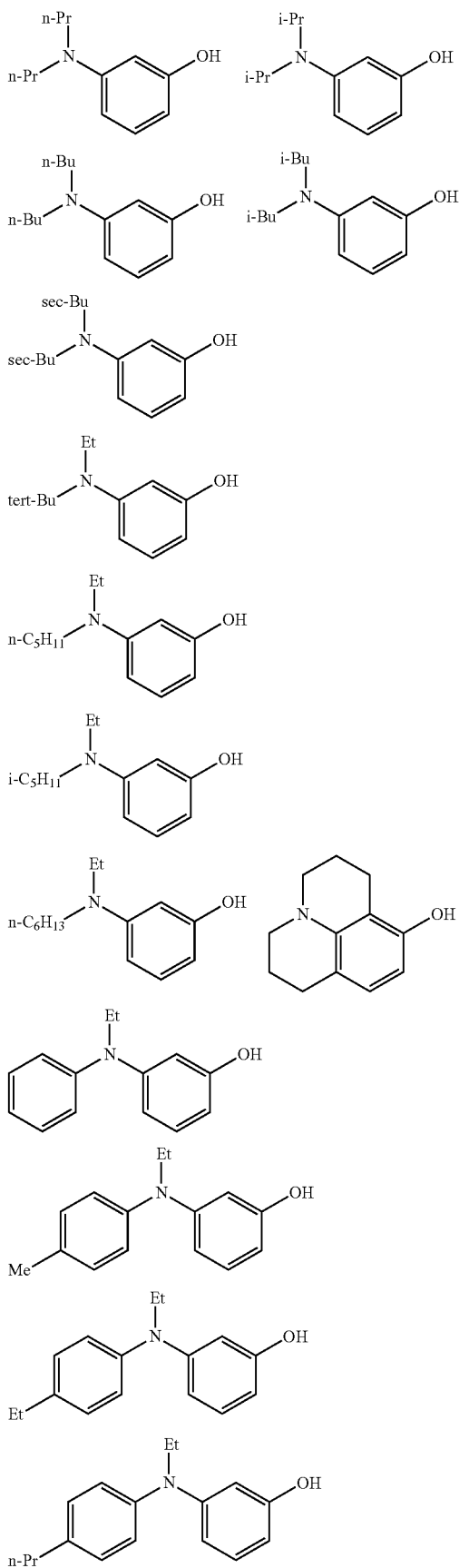

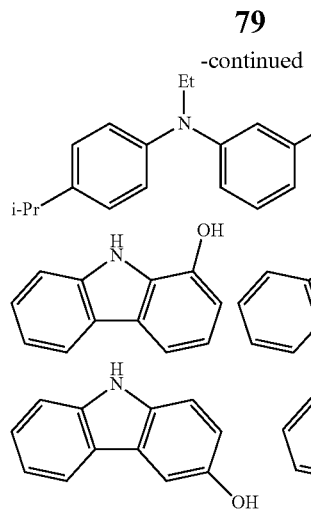

In the reaction [II], the compound represented by the general formula (32) obtained in the reaction [I], and the compound represented by the general formula (33) may be subjected to a reaction, in the presence of an acid catalyst, usually at 70 to 140° C., preferably at 80 to 120° C., usually for 1 to 24 hours, and preferably for 3 to 10 hours.

The acid catalyst includes sulfuric acid, methane sulfonic acid, trifluoromethane sulfonic acid, p-toluene sulfonic acid, camphor sulfonic acid, and the like, and methane sulfonic acid is preferable. Use amount of the acid catalyst is usually 1 to 50 times, and preferably 3 to 10 times, relative to total weight of the compound represented by the general formula (32) and the compound represented by the general formula (33).

Use amount of the compound represented by the general formula (33) is usually 1 to 2 equivalents, and preferably 1 to 1.5 equivalents, relative to mole number of the compound represented by the general formula (32).

Specific examples of the compound represented by the general formula (33) include, for example, the following ones.

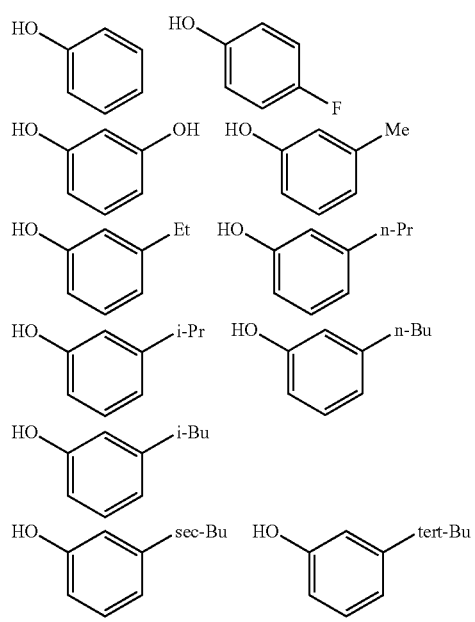

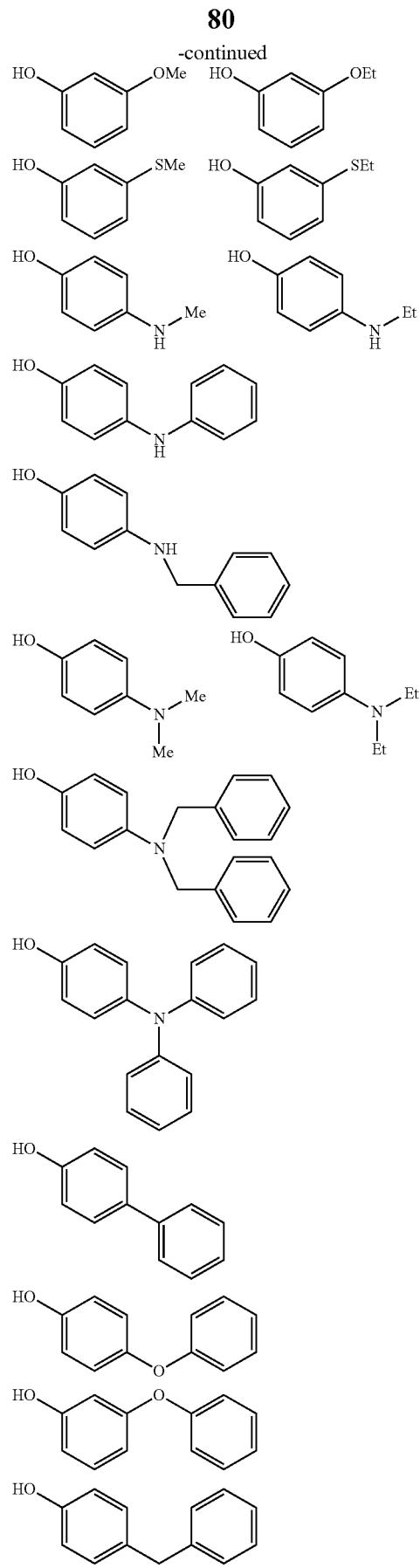

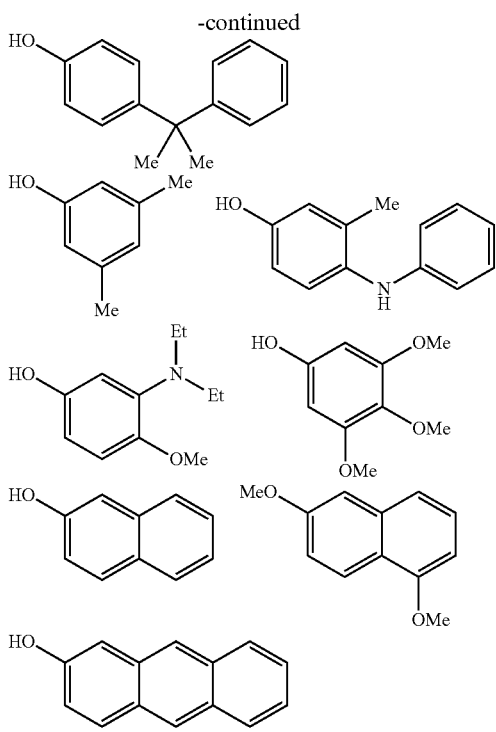

In the reaction [III], (a) when $Ar_1'$ of the compound represented by the general formula (34) is the ring structure represented by the general formula (1-1'), the compound represented by the general formula (34) may be subjected to the salt formation reaction, and (b) when $Ar_1'$ of the compound represented by the general formula (34) is the ring structure represented by the formulae (1-2') to (1-7'), after carrying out a reaction between the compound represented by the general formula (34) and the compound represented by the general formula (35), the resulting compound may be subjected to the salt formation reaction.

The salt formation reaction in (a) of the reaction [III] is carried out by making a salt of the anion represented by $An^-$ contacted with the compound represented by the general formula (34), in a solvent.

The salt formation reaction is carried out usually at 0 to 80° C., preferably at 10 to 50° C., usually for 1 to 24 hours, and preferably for 2 to 10 hours.

The solvent in the salt forming reaction includes an organic solvent, such as methanol, ethanol, isopropyl alcohol (IPA), tetrahydrofuran (THF), dioxane, N,N-dimethylformamide (DMF), dichloromethane, dichloroethane and ethyl acetate, and among them, ethanol, dichloromethane and ethyl acetate are preferable. These may be used singly, or in combination of two or more kinds thereof as appropriate. Use amount of the reaction solvent is usually 1 to 50 times, and preferably 1 to 15 times, relative to total weight of the compound represented by the general formula (34) and the salt of the anion represented by $An^-$.

The salt of the anion represented by $An^-$ in the salt formation reaction includes an alkali metal salt of the anion represented by $An^-$, or an inorganic acid.

The alkali metal salt of the anion represented by $An^-$ includes a salt composed of the anion represented by An, and an alkali metal, such as sodium, potassium and lithium; and a salt composed of the anion represented by $An^-$, and potassium or lithium is preferable. Use amount of the alkali metal salt of the anion represented by $An^-$ is usually 1 to 2 equivalents, and preferably 1 to 1.5 equivalents, relative to mole number of the compound represented by the general formula (34).

The inorganic acid includes hydrochloric acid, hydrogen bromide, hydrogen iodide, hypochlorous acid, chlorous acid, chloric acid, perchloric acid, hexafluorophosphoric acid, hexafluoroantimonic acid, and the like, and hydrochloric acid, perchloric acid, hexafluorophosphoric acid, and hexafluoroantimonic acid are preferable. Use amount of the inorganic acid is usually 1 to 50 equivalents, and preferably 1 to 10 equivalents, relative to mole number of the compound of the general formula (34).

When the salt of the anion represented by $An^-$ in the salt formation reaction is the alkali metal salt of the anion represented by $An^-$, it is preferable that the compound represented by the general formula (34) and the alkali metal salt of the anion represented by $An^-$ may be subjected to a reaction in a solvent in the coexistence with hydrochloric acid, and via a chloro salt. Use amount of the hydrochloric acid is usually 1 to 50 equivalents, and preferably 1 to 10 equivalents, relative to mole number of the compound represented by the general formula (34).

In addition, when the salt of the anion represented by $An^-$ in the salt formation reaction is the inorganic acid, the compound represented by the general formula (34) and the inorganic acid may be subjected to a reaction, in a solvent.

The reaction between the compound represented by the general formula (34) and the compound represented by the general formula (35), in (b) of the reaction [III], may be carried out in a solvent, in the presence of a base catalyst, usually at 0 to 80° C., preferably at 10 to 50° C., usually for 1 to 24 hours, and preferably for 2 to 10 hours.

The base catalyst includes an alkali metal, such as potassium and sodium; a hydroxide of an alkali metal or an alkaline-earth metal, such as lithium hydroxide, potassium hydroxide, sodium hydroxide, calcium hydroxide and barium hydroxide; amines, such as triethylene diamine, piperidine, ethylene diamine, diethylene triamine, pyrrolidone and tetrahydroquinoline; and the like. These may be used singly, or in combination of two or more kinds. Use amount of the basic catalyst is usually 1 to 50 times, and preferably 3 to 10 times, relative to total weight of the compound represented by the general formula (34) and the compound represented by the general formula (35).

The solvent includes an organic solvent, such as methanol, ethanol, isopropyl alcohol (IPA), tetrahydrofuran (THF), dioxane, N,N-dimethylformamide (DMF), dichloromethane, dichloroethane and ethyl acetate; and among them, ethanol, dichloromethane and ethyl acetate are preferable. These may be used singly, or in combination of two or more kinds thereof as appropriate. Use amount of the reaction solvent is usually 1 to 50 times, and preferably 1 to 15 times, relative to total weight of the compound represented by the general formula (34) and the compound represented by the general formula (35).

Use amount of the compound represented by the general formula (35) is usually 1 to 2 equivalents, and preferably 1 to 1.5 equivalents, relative to mole number of the compound represented by the general formula (34).

Specific examples of the compound represented by the general formula (35) include, for example, fluoromethane, fluoroethane, 1-fluoropropane, 2-fluoropropane, chloromethane, chloroethane, 1-chloropropane, 2-chloropropane, bromomethane, bromoethane, 1-bromopropane, 2-bromopropane, iodomethane, iodoethane, 1-iodopropane, 2-iodopropane, methyl trifluoromethane sulfonate, ethyl trifluoromethane sulfonate, propyl trifluoromethane sulfonate, methyl mesylate, ethyl mesylate, n-propyl mesylate, isopropyl mesylate, methyl tosylate, ethyl tosylate, n-propyl tosylate, isopropyl tosylate, and the like; and fluoromethane, chloromethane, bromomethane, iodomethane, methyl trifluoromethane sulfonate, methyl mesylate and methyl tosylate are preferable; and iodomethane is more preferable.

The salt formation reaction, in (b) of the reaction [III], may be carried out under reaction conditions (a reaction solvent, a reaction temperature, reaction time, each use amount) similar to those in the salt formation reaction, in (a) of the reaction [III], except for using the resulting compound by the reaction between the compound represented by the general formula (34) and the compound represented by the general formula (35), instead of the compound represented by the general formula (34), in the salt formation reaction in (a) of the reaction [III].

Among the quencher of the present invention, for example, the one where $Y_1$ is an oxygen atom, and $R_6$ is an alkoxy group having 1 to 20 carbon atoms, in the general formula (1) (a compound represented by the following general formula (38-1)) can be produced by a method represented by the next reaction [IV-I]. That is, a compound represented by the following general formula (38-1) can be obtained, by a reaction between the compound represented by the general formula (36) obtained in the reaction [III], and a compound represented by the following general formula (37-1).

In addition, among the quencher of the present invention, for example, the one where $Y_1$ is an oxygen atom, and $R_6$ is an amino group having a substituent or not having a substituent, in the general formula (1) (a compound represented by the following general formula (38-2)) can be produced by a method represented by the next reaction [IV-II]. That is, a compound represented by the following general formula (38-2) can be obtained, by a reaction between the compound represented by the general formula (36) obtained in the reaction [III], and a compound represented by the following general formula (37-2).

In addition, among the quencher of the present invention, for example, the one where $Y_1$ is an oxygen atom, and $R_6$ is a heterocyclic amino group, in the general formula (1) (a compound represented by the following general formula (38-3)) can be produced by a method represented by the next reaction [IV-III]. That is, a compound represented by the following general formula (38-3) can be obtained, by a reaction between the compound represented by the general formula (36) obtained in the reaction [III], and a compound represented by the following general formula (37-3).

In addition, among the quencher of the present invention, for example, the one where $Y_1$ is an oxygen atom, and $R_6$ is a group having the polymerizable unsaturated group represented by the general formula (2), in the general formula (1) (a compound represented by the following general formula (38-4)) can be produced by a method represented by the next reaction [IV-IV]. That is, a compound represented by the following general formula (38-4) can be obtained, by a reaction between the compound represented by the general formula (36) obtained in the reaction [III], and a compound represented by the following general formula (37-4).

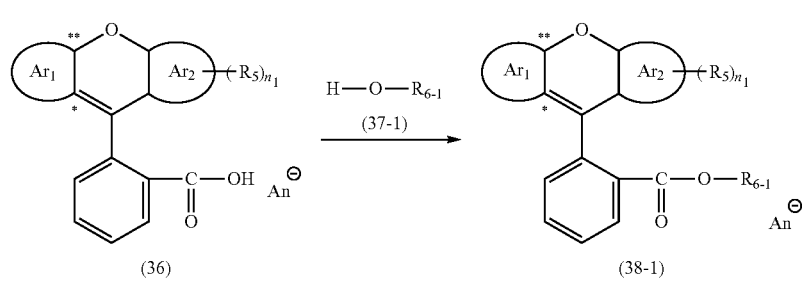

[IV-I]

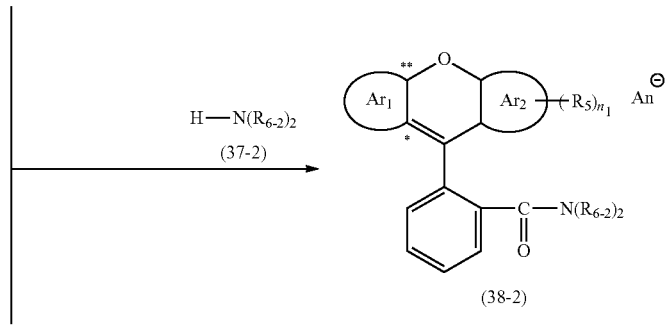

[IV-II]

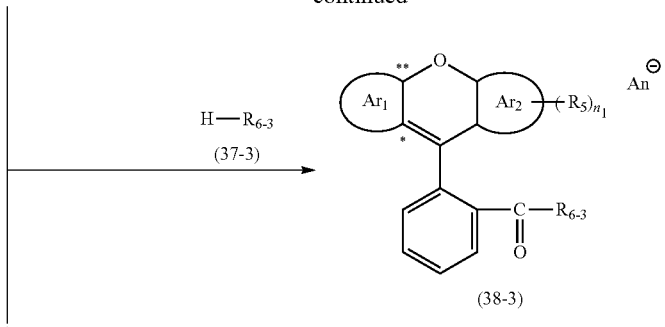

(37-3)

(38-3) [IV-III]

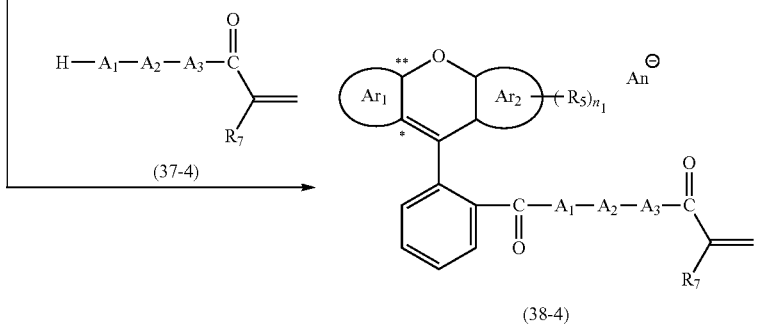

(37-4)

(38-4) [IV-IV]

(wherein $R_{6-1}$ represents an alkyl group having 1 to 20 carbon atoms; two pieces of $R_6$-2 each independently represent a hydrogen atom, a halogenated alkyl group having 1 to 20 carbon atoms, or an alkyl group having 1 to 20 carbon atoms; $R_6$-3 represents a heterocyclic amino group; and $n_1$ pieces of $R_5$, $R_7$, $A_1$, $A_2$, $A_3$, $An^-$, $Ar_1$, $Ar_2$, $n_1$, * and ** are the same as described above.)

The alkyl group having 1 to 20 carbon atoms, in $R_{6-1}$ of the general formula (37-1), includes the same one as the alkyl group having 1 to 20 carbon atoms, in $R_5$ of the general formula (1), and the preferable one is also the same.

The halogenated alkyl group having 1 to 20 carbon atoms, in $R_6$-2 of the general formula (37-2), includes the same one as the halogenated alkyl group having 1 to 20 carbon atoms, in the substituent of the amino group having the substituent, in $R_5$ of the general formula (1), and the preferable one is also the same.

The alkyl group having 1 to 20 carbon atoms, in $R_{6-2}$ of the general formula (37-2), includes the same one as the alkyl group having 1 to 20 carbon atoms, in $R_5$ of the general formula (1), and the preferable one is also the same.

As $R_6$-2 of the general formula (37-2), a hydrogen atom and an alkyl group having 1 to 20 carbon atoms are preferable, and the hydrogen atom and an alkyl group having 1 to 12 carbon atoms are more preferable, and an alkyl group having 1 to 6 carbon atoms is further preferable, and an alkyl group having 1 to 3 carbon atoms is particularly preferable. It specifically includes, for example, a methyl group, an ethyl group, an n-propyl group, an isopropyl group, and the like.

The heterocyclic amino group in $R_{6-3}$ of the general formula (37-3) includes the same one as the heterocyclic amino group in $R_6$ of the general formula (1), and the preferable one is also the same.

In the reaction [IV-I], the compound represented by the general formula (36) and the compound represented by the general formula (37-1) may be subjected to a reaction in a solvent, in the presence of a dehydration condensation agent, usually at 30 to 100° C., preferably at 50 to 80° C., usually for 1 to 50 hours, and preferably for 20 to 40 hours.

The solvent includes ethers, for example, diethyl ether, diisopropyl ether, ethyl methyl ether, tetrahydrofuran, 1,4-dioxane, dimethoxyethane, and the like; ketones, for example, acetone, dimethyl ketone, methyl ethyl ketone, diethyl ketone, 2-hexanone, tert-butyl methyl ketone, cyclopentanone, cyclohexanone, and the like; halogenated hydrocarbons, for example, chloromethane, chloroform, dichloromethane, dichloroethane, trichloroethane, carbon tetrachloride, chlorobenzene, and the like; hydrocarbons, for example, n-hexane, benzene, toluene, xylene, and the like; esters, for example, ethyl acetate, butyl acetate, methyl propionate, and the like; nitriles, for example, acetonitrile, and the like; and amides, for example, N,N-dimethylformamide, and the like. Among them, the ethers, the halogenated hydrocarbons and the hydrocarbons are preferable; and tetrahydrofuran, dichloromethane and toluene are more preferable. These may be used singly, or in combination of two or more kinds thereof as appropriate. Use amount of the reaction solvent is usually 1 to 50 times, and preferably 5 to 15 times, relative to total weight of the compound represented by the general formula (36) and the compound represented by the general formula (37-1).

The dehydration condensation agent may be any one generally used as a dehydration condensation agent; and includes inorganic dehydration agents, for example, diphosphorus pentaoxide, anhydrous zinc chloride, and the like; carbodiimides, for example, dicyclohexylcarbodiimide, diisopropylcarbodiimide, 1-ethyl-3-(3-dimethylaminopropyl)carbodiimide hydrochloride, and the like; for example, polyphosphoric acid; acetic anhydride; sulfuric acid; carbonyldiimidazole; p-toluenesulfonic acid; and the like; and the carbodiimides are preferable. Use amount of the dehydration condensation agent is usually 1 to 20 equivalents, and preferably 1 to 10 equivalents, relative to mole number of the compound represented by the general formula (36). A catalyst, such as dimethylaminopyridine, may be used to enhance efficiency of the dehydration condensation agent in the reaction [IV-I]. Use amount of the catalyst is usually 0.1 to 10 equivalents, relative to mole number of the compound represented by the general formula (36).

Use amount of the compound represented by the general formula (37-1) is usually 1 to 50 times, and preferably 5 to 15 times, relative to weight of the compound represented by the general formula (36).

Specific examples of the compound represented by the general formula (37-1) include, for example, methanol, ethanol, 1-propanol, 2-propanol, and the like.

In the reaction [IV-II], the compound represented by the general formula (36) and the compound represented by the general formula (37-2) may be subjected to a reaction in a solvent, in the presence of a dehydration condensation agent, usually at 0 to 80° C., preferably at 10 to 50° C., usually for 1 to 24 hours, and preferably for 3 to 18 hours.

The solvent includes ethers, for example, diethyl ether, diisopropyl ether, ethyl methyl ether, tetrahydrofuran, 1,4-dioxane, dimethoxyethane, and the like; ketones, for example, acetone, dimethyl ketone, methyl ethyl ketone, diethyl ketone, 2-hexanone, tert-butyl methyl ketone, cyclopentanone, cyclohexanone, and the like; halogenated hydrocarbons, for example, chloromethane, chloroform, dichloromethane, dichloroethane, trichloroethane, carbon tetrachloride, chlorobenzene, and the like; hydrocarbons, for example, n-hexane, benzene, toluene, xylene, and the like; esters, for example, ethyl acetate, butyl acetate, methyl propionate, and the like; nitriles, for example, acetonitrile, and the like; and amides, for example, N,N-dimethylformamide, and the like. Among them, the ethers, the halogenated hydrocarbons and the hydrocarbons are preferable; and tetrahydrofuran, dichloromethane and toluene are more preferable. These may be used singly, or in combination of two or more kinds thereof as appropriate. Use amount of the reaction solvent is usually 1 to 50 times, and preferably 5 to 15 times, relative to total weight of the compound represented by the general formula (36) and the compound represented by the general formula (37-2).

The dehydration condensation agent may be any one generally used as a dehydration condensation agent; and includes inorganic dehydration agents, for example, diphosphorus pentaoxide, anhydrous zinc chloride, and the like; carbodiimides, for example, dicyclohexylcarbodiimide, diisopropylcarbodiimide, 1-ethyl-3-(3-dimethylaminopropyl)carbodiimide hydrochloride, and the like; for example, polyphosphoric acid; acetic anhydride; sulfuric acid; carbonyldiimidazole; p-toluenesulfonic acid; and the like; and the carbodiimides are preferable. Use amount of the dehydration condensation agent is usually 1 to 20 equivalents, and preferably 1 to 10 equivalents, relative to mole number of the compound represented by the general formula (36). A catalyst, such as dimethylaminopyridine, may be used to enhance efficiency of the dehydration condensation agent in the reaction [IV-II]. Use amount of the catalyst is usually 0.1 to 10 equivalents, relative to mole number of the compound represented by the general formula (36).

Use amount of the compound represented by the general formula (37-2) is usually 1 to 2 equivalents, and preferably 1 to 1.5 equivalents, relative to mole number of the compound represented by the general formula (36).

Specific examples of the compound represented by the general formula (37-2) include, for example, ammonia, trifluoromethylamine, pentafluoroethylamine, heptafluoropropylamine, methylamine, ethylamine, n-propylamine, isopropylamine, dimethylamine, diethylamine, di(n-propyl) amine, N-ethylmethylamine, N-ethylpropylamine, N-methylpropylamine, and the like.

In the reaction [IV-III], the compound represented by the general formula (36) and the compound represented by the general formula (37-3) may be subjected to a reaction in a solvent, in the presence of a dehydration condensation agent, usually at 0 to 80° C., preferably at 10 to 50° C., usually for 1 to 24 hours, and preferably for 3 to 18 hours.

The solvent includes ethers, for example, diethyl ether, diisopropyl ether, ethyl methyl ether, tetrahydrofuran, 1,4-dioxane, dimethoxyethane, and the like; ketones, for example, acetone, dimethyl ketone, methyl ethyl ketone, diethyl ketone, 2-hexanone, tert-butyl methyl ketone, cyclopentanone, cyclohexanone, and the like; halogenated hydrocarbons, for example, chloromethane, chloroform, dichloromethane, dichloroethane, trichloroethane, carbon tetrachloride, chlorobenzene, and the like; hydrocarbons, for example, n-hexane, benzene, toluene, xylene, and the like; esters, for example, ethyl acetate, butyl acetate, methyl propionate, and the like; nitriles, for example, acetonitrile, and the like; and amides, for example, N,N-dimethylformamide, and the like. Among them, the ethers, the halogenated hydrocarbons and the hydrocarbons are preferable; and tetrahydrofuran, dichloromethane and toluene are more preferable. These may be used singly, or in combination of two or more kinds thereof as appropriate. Use amount of the reaction solvent is usually 1 to 50 times, and preferably 5 to 15 times, relative to total weight of the compound represented by the general formula (36) and the compound represented by the general formula (37-3).

The dehydration condensation agent may be any one generally used as a dehydration condensation agent; and includes inorganic dehydration agents, for example, diphosphorus pentaoxide, anhydrous zinc chloride, and the like; carbodiimides, for example, dicyclohexylcarbodiimide, diisopropylcarbodiimide, 1-ethyl-3-(3-dimethylaminopropyl)carbodiimide hydrochloride, and the like; for example, polyphosphoric acid; acetic anhydride; sulfuric acid; carbonyldiimidazole; p-toluenesulfonic acid; and the like; and the carbodiimides are preferable. Use amount of the dehydration condensation agent is usually 1 to 20 equivalents, and preferably 1 to 10 equivalents, relative to mole number of the compound represented by the general formula (36). A catalyst, such as dimethylaminopyridine, may be used to enhance efficiency of the dehydration condensation agent in the reaction [IV-III]. Use amount of the catalyst is usually 0.1 to 10 equivalents, relative to mole number of the compound represented by the general formula (36).

Use amount of the compound represented by the general formula (37-3) is usually 1 to 3 equivalents, and preferably 1 to 2 equivalents, relative to mole number of the compound represented by the general formula (36).

Specific examples of the compound represented by the general formula (37-3) include, for example, pyrrolidine, pyrrole, pyrazole, imidazole, oxazole, thiazole, piperidine, piperazine, morpholine, pyridine, pyridazine, pyrimidine, pyrazine, and the like; and pyrrolidine, pyrrole, piperidine and pyridine are preferable; and piperidine is more preferable.

In the reaction [IV-IV], the compound represented by the general formula (36) and the compound represented by the general formula (37-4) may be subjected to a reaction in a solvent, in the presence of a dehydration condensation agent, usually at 0 to 80° C., preferably at 10 to 50° C., usually for 1 to 24 hours, and preferably for 3 to 18 hours.

The solvent includes ethers, for example, diethyl ether, diisopropyl ether, ethyl methyl ether, tetrahydrofuran, 1,4- dioxane, dimethoxyethane, and the like; ketones, for example, acetone, dimethyl ketone, methyl ethyl ketone, diethyl ketone, 2-hexanone, tert-butyl methyl ketone, cyclopentanone, cyclohexanone, and the like; halogenated hydrocarbons, for example, chloromethane, chloroform, dichloromethane, dichloroethane, trichloroethane, carbon tetrachloride, chlorobenzene, and the like; hydrocarbons, for example, n-hexane, benzene, toluene, xylene, and the like; esters, for example, ethyl acetate, butyl acetate, methyl propionate, and the like; nitriles, for example, acetonitrile, and the like; amides, for example, N,N-dimethylformamide, and the like. Among them, the ethers, the halogenated hydrocarbons and the hydrocarbons are preferable; and tetrahydrofuran, dichloromethane and toluene are more preferable. These may be used singly, or in combination of two or more kinds thereof as appropriate. Use amount of the reaction solvent is usually 1 to 50 times, and preferably 5 to 15 times, relative to total weight of the compound represented by the general formula (36) and the compound represented by the general formula (37-4).

The dehydration condensation agent may be any one generally used as a dehydration condensation agent, and includes inorganic dehydration agents, for example, diphosphorus pentaoxide, anhydrous zinc chloride, and the like; carbodiimides, for example, dicyclohexylcarbodiimide, diisopropylcarbodiimide, 1-ethyl-3-(3-dimethylaminopropyl)carbodiimide hydrochloride, and the like; for example, polyphosphoric acid; acetic anhydride; sulfuric acid; carbonyldiimidazole; p-toluenesulfonic acid; and the like; and the carbodiimides are preferable. Use amount of the dehydration condensation agent is usually 1 to 20 equivalents, and preferably 1 to 10 equivalents, relative to mole number of the compound represented by the general formula (36). A catalyst, such as dimethylaminopyridine, may be used to enhance efficiency of the dehydration condensation agent in the reaction [IV-IV]. Use amount of the catalyst is usually 0.1 to 10 equivalents, relative to mole number of the compound represented by the general formula (36).

Use amount of the compound represented by the general formula (37-4) is usually 1 to 2 equivalents, and preferably 1 to 1.5 equivalents, relative to mole number of the compound represented by the general formula (36).

Specific examples of the compound represented by the general formula (37-4) include, for example, the following ones.

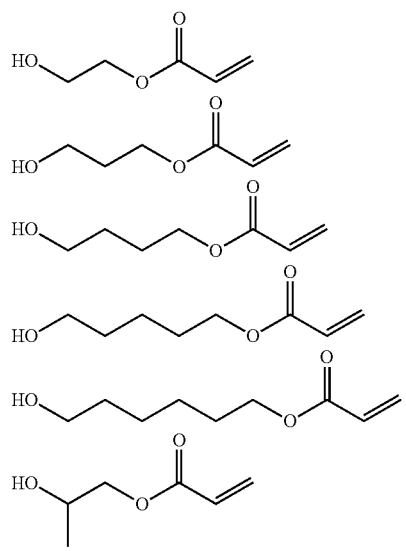

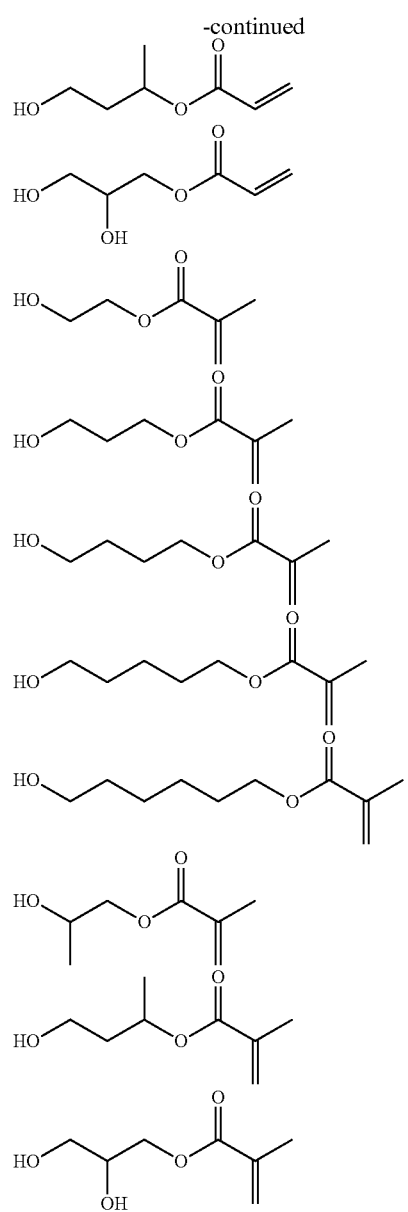

Among the quencher of the present invention, for example, the one where $Y_1$ is a sulfur atom or $-NR_{32}-$, and $R_6$ is a hydroxy group, in the general formula (1) (a compound represented by the following general formula (43)) can be produced by a series of methods represented by the next reactions [V] and [VI].

That is, firstly, a compound represented by the following general formula (39) and a compound represented by the following general formula (40) are subjected to a reaction, in the presence of a compound represented by the following general formula (41), and next, by a reaction between the resulting compound and phthalic anhydride, a compound represented by the following general formula (42) is obtained (the reaction [V]). After that, the resulting compound represented by the general formula (42) and a compound represented by the following general formula (35) may be subjected to a reaction, as needed, and a salt formation reaction may be carried out (the reaction [VI]).

In addition, among the quencher of the present invention, for example, the one where $Y_1$ is a sulfur atom or $-NR_{32}-$, and $R_6$ is an alkoxy group having 1 to 20 carbon atoms, in the general formula (1) (a compound represented by the following general formula (44-1)) can be produced by a method represented by the next reaction [VII-I]. That is, a compound represented by the following general formula (44-1) can be obtained, by a reaction between the compound represented by the general formula (43) obtained in the reaction [VI], and a compound represented by the following general formula (37-1).

In addition, among the quencher of the present invention, for example, the one where $Y_1$ is a sulfur atom or $-NR_{32}-$, and $R_6$ is an amino group having a substituent or not having a substituent, in the general formula (1) (a compound represented by the following general formula (44-2)) can be produced by a method represented by the next reaction [VII-II]. That is, a compound represented by the following general formula (44-2) can be obtained, by a reaction between the compound represented by the general formula (43) obtained in the reaction [VI], and a compound represented by the following general formula (37-2).

In addition, among the quencher of the present invention, for example, the one where $Y_1$ is a sulfur atom or $-NR_{32}-$, and $R_6$ is a heterocyclic amino group, in the general formula (1) (a compound represented by the following general formula (44-3)) can be produced by a method represented by the next reaction [VII-III]. That is, a compound represented by the following general formula (44-3) can be obtained, by a reaction between the compound represented by the general formula (43) obtained in the reaction [VI], and a compound represented by the following general formula (37-3).

In addition, among the quencher of the present invention, for example, the one where $Y_1$ is a sulfur atom or $-NR_{32}-$, and $R_6$ is a group having the polymerizable unsaturated group represented by the general formula (2), in the general formula (1) (a compound represented by the following general formula (44-4)) can be produced by a method represented by the next reaction [VII-IV]. That is, a compound represented by the following general formula (44-4) can be obtained, by a reaction between the compound represented by the general formula (43) obtained in the reaction [VI], and a compound represented by the following general formula (37-4).

[V]

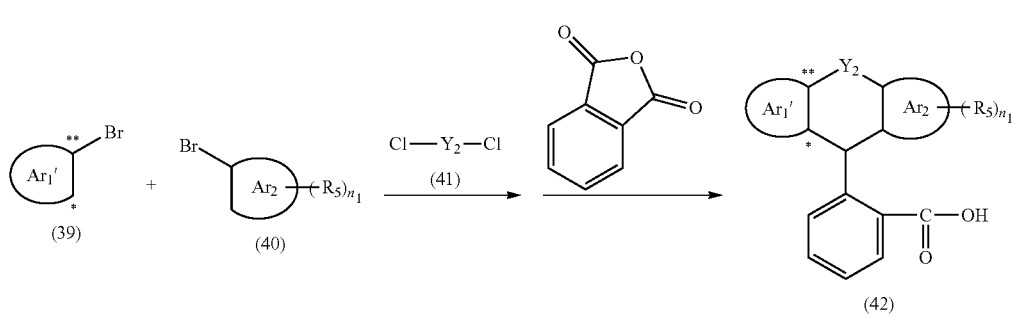

(wherein $Y_2$ represents a sulfur atom or $-NR_{32}-$; and $n_1$ pieces of $R_5$, $R_{32}$, $Ar_1'$, $Ar_2$, $n_1$, * and ** are the same as described above.)

[VI]

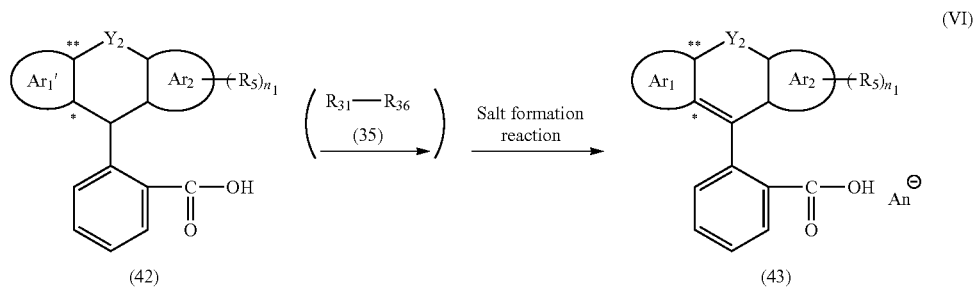

(wherein $n_1$ pieces of $R_5$, $R_{31}$, $R_{36}$, $Y_2$, An, $Ar_1$, $Ar_1'$, $Ar_2$, $n_1$, * and ** are the same as described above.)

[VII-I]

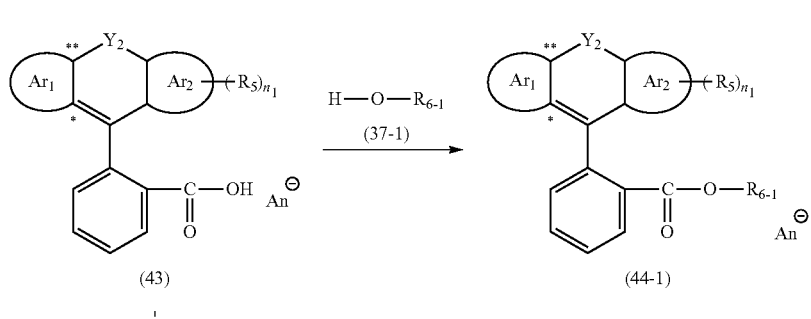

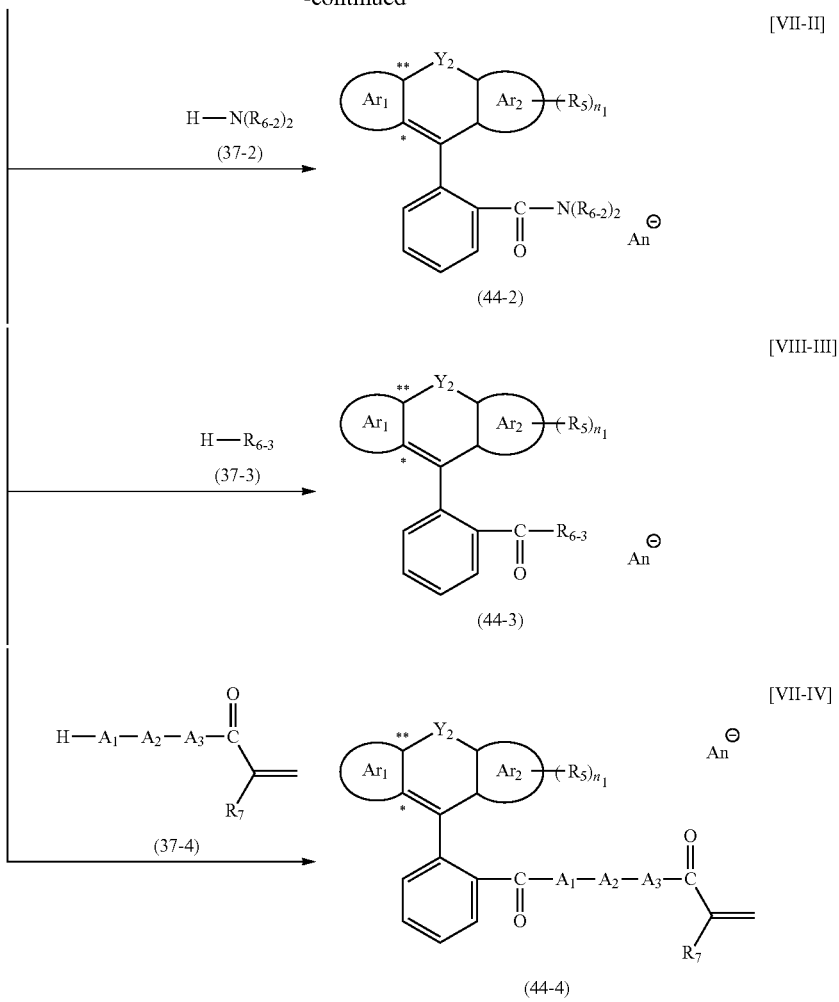

(wherein $n_1$ pieces of $R_5$, $R_{6-1}$, two pieces of $R_{6-2}$, $R_{6-3}$, $R_7$, $Y_2$, $A_1$, $A_2$, $A_3$, $An^-$, $Ar_1$, $Ar_2$, $n_1$, * and ** are the same as described above.)

As $Y_2$, —$NR_{32}$— is preferable. It specifically includes, for example, a sulfur atom, —$NCH_3$—, —$NC_2H_5$—, —$NC_3H_7$—, and the like, and the sulfur atom and —$NCH_3$— are preferable, and —$NCH_3$— is more preferable.

In the reaction [V], the compound represented by the general formula (39) and the compound represented by the general formula (40) may be subjected to a reaction in a solvent, in the presence of the compound represented by the general formula (41), usually at 80 to 160° C., preferably at 90 to 120° C., usually for 1 to 24 hours, and preferably for 3 to 10 hours; and next, the resulting compound and phthalic anhydride may be subjected to a reaction, usually at 80 to 160° C., preferably at 90 to 120° C., usually for 1 to 24 hours, and preferably for 3 to 10 hours.

The solvent includes ethers, for example, diethyl ether, diisopropyl ether, ethyl methyl ether, tetrahydrofuran, 1,4-dioxane, dimethoxyethane, and the like; ketones, for example, acetone, dimethyl ketone, methyl ethyl ketone, diethyl ketone, 2-hexanone, tert-butyl methyl ketone, cyclopentanone, cyclohexanone, and the like; halogenated hydrocarbons, for example, chloromethane, chloroform, dichloromethane, dichloroethane, trichloroethane, carbon tetrachloride, chlorobenzene, and the like; hydrocarbons, for example, n-hexane, benzene, toluene, xylene, and the like; esters, for example, ethyl acetate, butyl acetate, methyl propionate, and the like; nitriles, for example, acetonitrile, and the like; and amides, for example, N,N-dimethylformamide, and the like. Among them, hydrocarbons are preferable, and toluene is more preferable. These may be used singly, or in combination of two or more kinds thereof as appropriate. Use amount of the reaction solvent is usually 1 to 50 times, and preferably 5 to 10 times, relative to weight of the compound represented by the general formula (39).

Specific examples of the compound represented by the general formula (39) include, for example, the following ones.

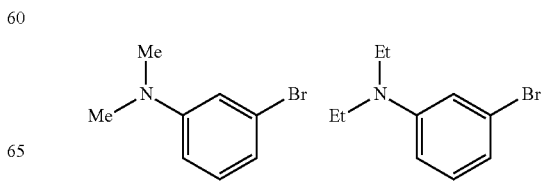

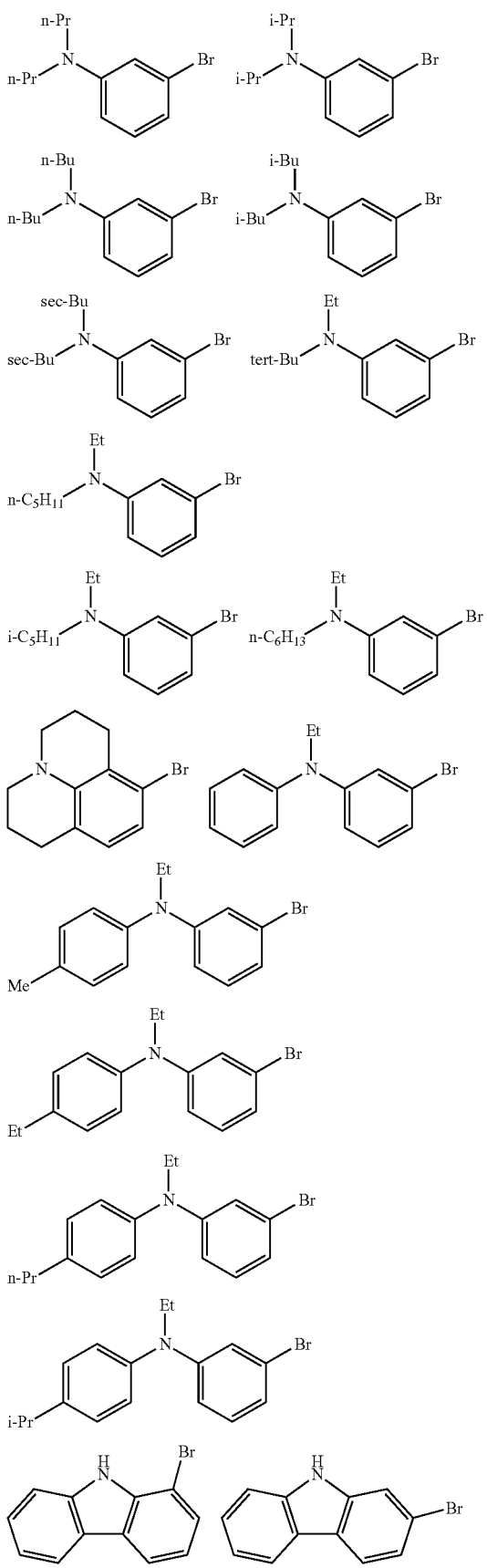
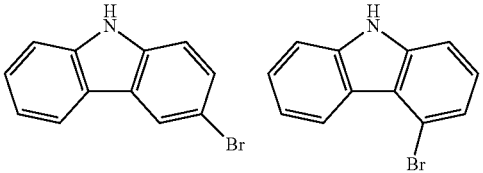
Use amount of the compound represented by the general formula (40) is usually 1 to 2 equivalents, and preferably 1 to 1.5 equivalents, relative to mole number of the compound represented by the general formula (39).
Specific examples of the compound represented by the general formula (40) include, for example, the following ones.
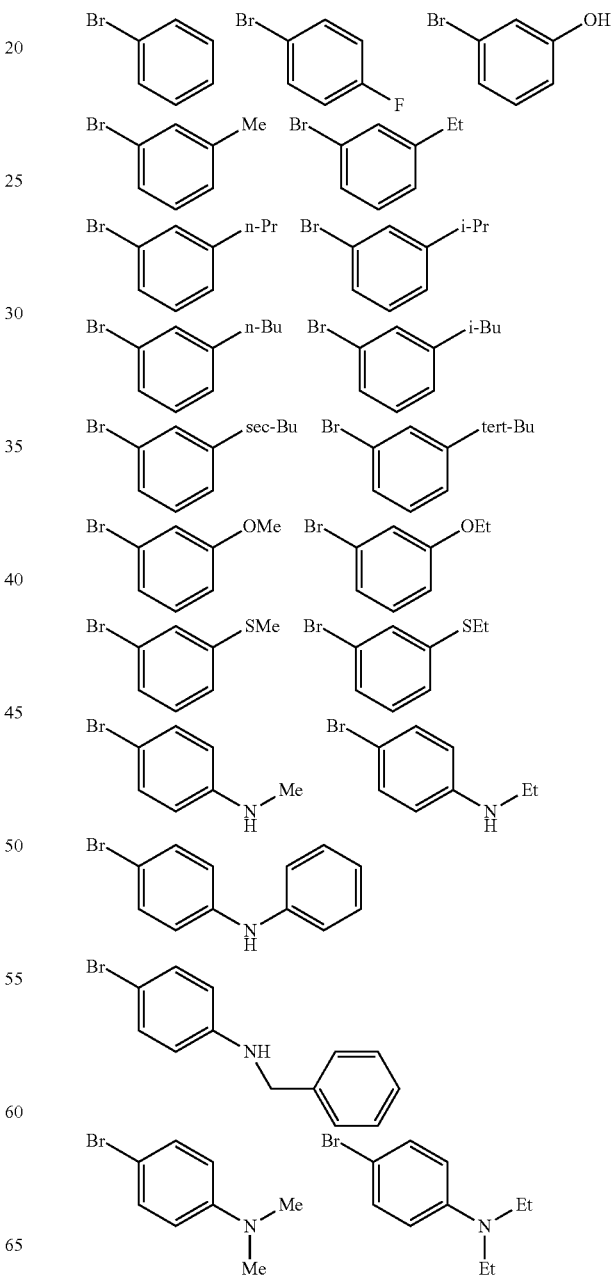

-continued

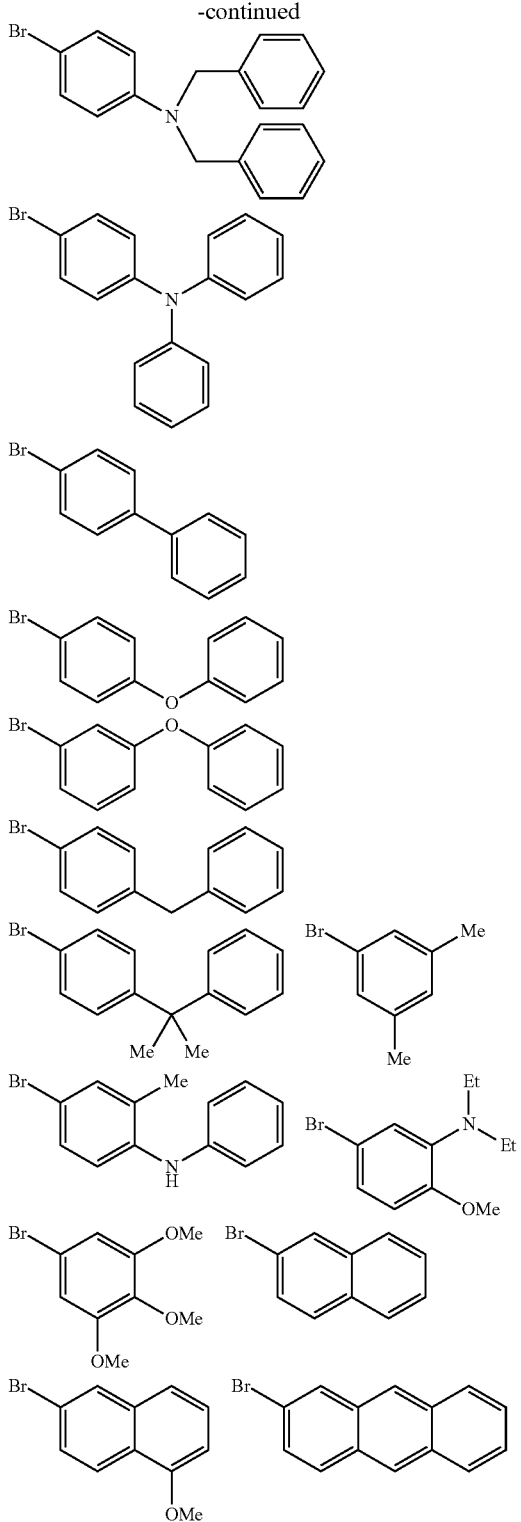

Use amount of the compound represented by the general formula (41) is usually 1 to 2 equivalents, and preferably 1 to 1.5 equivalents, relative to mole number of the compound represented by the general formula (39).

Specific examples of the compound represented by the general formula (41) include, for example, $SCl_2$, $CH_3NCl_2$, $C_2H_5NCl_2$, $C_3H_7NCl_2$, and the like.

Use amount of phthalic anhydride is usually 1 to 2 equivalents, and preferably 1 to 1.5 equivalents, relative to mole number of the compound represented by the general formula (39).

In the reaction [VI], (a) when $Ar_1'$ of the compound represented by the general formula (42) is the ring structure represented by the general formula (1-1'), the compound represented by the general formula (42) may be subjected to the salt formation reaction, and (b) when $Ar_1'$ of the compound represented by the general formula (42) is the ring structure represented by the formulae (1-2') to (1-7'), after carrying out a reaction between the compound represented by the general formula (42) and the compound represented by the general formula (35), the resulting compound may be subjected to the salt formation reaction.

The salt formation reaction, in (a) of the reaction [VI], may be carried out similarly to the salt formation reaction, in (a) of the reaction [III].

The reaction between the compound represented by the general formula (42) and the compound represented by the general formula (35), in (b) of the reaction [VI], may be carried out under reaction conditions (a reaction solvent, a reaction temperature, reaction time, each use amount) similar to those in the reaction with the compound represented by the general formula (35), in (b) of the reaction [III]; except for using the compound represented by the general formula (42), instead of the compound represented by the general formula (34), in the reaction of the compound represented by the general formula (34) and the compound represented by the general formula (35), in (b) of the reaction [III].

The salt formation reaction, in (b) of the reaction [VI], may be carried out under reaction conditions (a reaction solvent, a reaction temperature, reaction time, each use amount) similar to those in the salt formation reaction in (a) of the reaction [III], except for using the resulting compound by the reaction between the compound represented by the general formula (42) and the compound represented by the general formula (35), instead of the compound represented by the general formula (34), in the salt formation reaction in (a) of the reaction [III].

In the reaction [VII-I], the compound represented by the general formula (43) obtained in the reaction [VI], and the compound represented by the general formula (37-1) may be subjected to a reaction under reaction conditions (a reaction solvent, an acid catalyst, a reaction temperature, reaction time, each use amount) similar to those in the reaction [IV-I].

In the reaction [VII-II], the compound represented by the general formula (43) obtained in the reaction [VI], and the compound represented by the general formula (37-2) may be subjected to a reaction under reaction conditions (a reaction solvent, an acid catalyst, a reaction temperature, reaction time, each use amount) similar to those in the reaction [IV-II].

In the reaction [VII-III], the compound represented by the general formula (43) obtained in the reaction [VI], and the compound represented by the general formula (37-3) may be subjected to a reaction under reaction conditions (a reaction solvent, an acid catalyst, a reaction temperature, reaction time, each use amount) similar to those in the reaction [IV-III].

In the reaction [VII-IV], the compound represented by the general formula (43) obtained in the reaction [VI], and the compound represented by the general formula (37-4) may be subjected to a reaction under reaction conditions (a reaction solvent, an acid catalyst, a reaction temperature, reaction time, each use amount) similar to those in the reaction [IV-IV].

Pressure in the reactions [I] to [VII-IV] is not especially limited, as long as a series of the reactions is carried out without delay, and the reactions may be carried out, for example, under normal pressure.

The resulting reactants and products after the reactions [I] to [VII-IV] may be isolated, as needed, by a general post-treatment operation and purification operation usually carried out in this field. Specifically, for example, the resulting reactants and products may be isolated by filtration, washing, extraction, concentration under reduced pressure, recrystallization, distillation, column chromatography, or the like.

[Compound of the Present Invention]

The compound of the present invention is a compound represented by the general formula (3). Specific examples and preferable ranges thereof include the same ones as described as the compound represented by the general formula (3), in the quencher of the present invention.

The compound of the present invention is less fading caused by heating, and exerts high heat resistance effect, in addition to quenching effect on a compound having fluorescent property. Therefore, the compound of the present invention can be used not only in a quencher application, but also as a dye by the compound itself.

In addition, among the compound represented by the general formula (3), the one where $Ar_1$ is the general formula (1-1), $Ar_2$ is a benzene ring, and one piece of $R_5$ is a phenylamino group (a compound represented by the following general formula (50)) are useful as a black dye having higher heat resistance effect among the compound of the present invention.

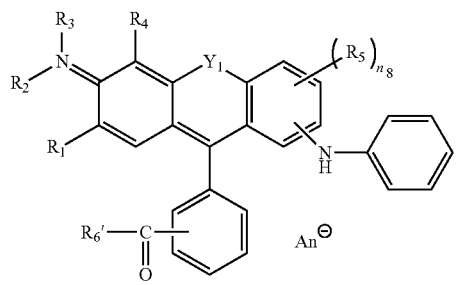

(50)

(wherein $R_1$ to $R_5$, $R_6'$, $Y_1$, and $An^-$ are the same as described above; and $n_8$ represents an integer of 0 to 3.)

As $n_8$ of the general formula (3), 0 or 1 is preferable, and 1 is more preferable.

Preferable specific examples, among the compound represented by the general formula (50), include a compound represented by the following general formula (51).

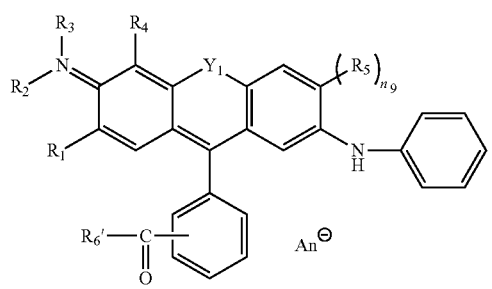

(51)

(wherein $R_1$ to $R_5$, $R_6'$, $Y_1$, and $An^-$ are the same as described above; and $n_9$ represents 0 or 1.)

As $n_9$ of the general formula (3), 1 is more preferable.

Preferable combinations of $R_1$ to $R_5$, $R_6'$, $Y_1$ and $n_9$, in the general formula (51), includes, for example, those described in the following table. It should be noted that "alkyl groups A" in $R_2$ column and $R_3$ column, "alkyl groups B", "alkoxy groups", "alkylthio groups" in $R_5'$ column, as well as "polymerizable groups" in $R_6'$ column are each represent the group consisting of the following functional groups.

Alkyl groups A: a methyl group, an ethyl group, an n-propyl group, an isopropyl group, an n-butyl group, an isobutyl group, a sec-butyl group, a tert-butyl group, an n-pentyl group, an isopentyl group, an n-hexyl group Alkyl groups B: a methyl group, an ethyl group, an n-propyl group, an isopropyl group, an n-butyl group, an isobutyl group, a sec-butyl group, a tert-butyl group Alkoxy groups: a methoxy group, an ethoxy group Alkylthio groups: a methylthio group, an ethylthio group Substituted amino groups; a methylamino group, an ethylamino group, a phenylamino group, a benzylamino group, a dimethylamino group, a diethylamino group, a diphenylamino group, a dibenzylamino group Polymerizable Groups:

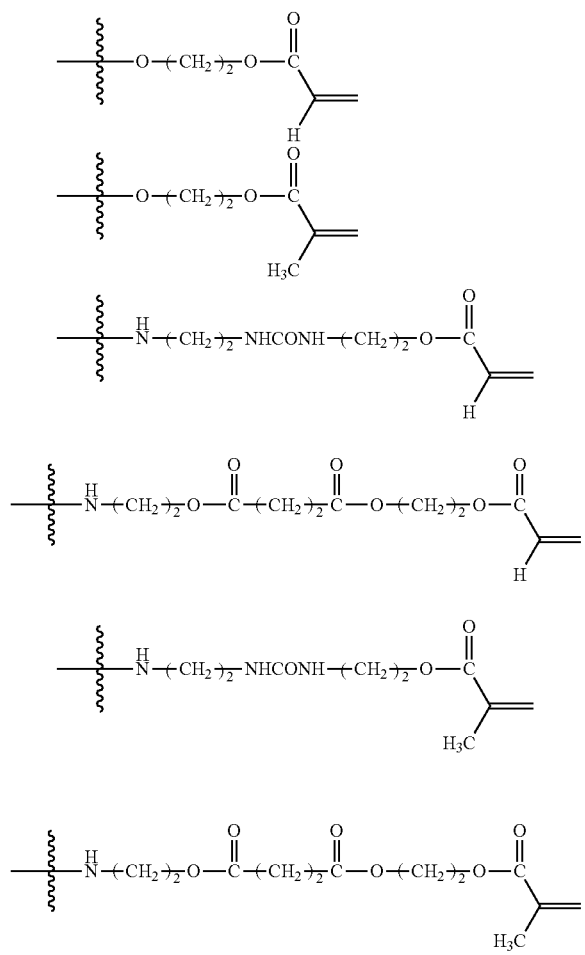

| $R_1$ | $R_2'$ | $R_3'$ | $R_4$ | $R_6'$ | $Y_1$ | $R_5$ | $n_9$ |
|---|---|---|---|---|---|---|---|
| hydrogen atom | alkyl groups A, phenyl group, p-tolyl group, p-ethylphenyl group, p-(n-propyl)phenyl group, or p-isopropylphenyl group | alkyl groups A, phenyl group, p-tolyl group, p-ethylphenyl group, p-(n-propyl)phenyl group, or p-isopropylphenyl group | hydrogen atom | polymerizable groups | oxygen atom | fluorine atom | 1 |
| | | | | | | alkyl groups B | 1 |
| | | | | | | alkoxy groups | 1 |
| | | | | | | alkylthio groups | 1 |
| | | | | | | substituted amino groups | 1 |
| | | | | | | hydroxy group | 1 |
| | | | | | | phenyl group | 1 |
| | | | | | | phenoxy group | 1 |
| | | | | | | benzyl group | 1 |
| | | | | | | cumyl group | 1 |
| | | | | | | — | 0 |
| | trimethylene group | | trimethylene group | | | fluorine atom | 1 |
| | | | | | | alkyl groups B | 1 |
| | | | | | | alkoxy groups | 1 |
| | | | | | | alkylthio groups | 1 |
| | | | | | | substituted amino groups | 1 |
| | | | | | | hydroxy group | 1 |
| | | | | | | phenyl group | 1 |
| | | | | | | phenoxy group | 1 |
| | | | | | | benzyl group | 1 |
| | | | | | | cumyl group | 1 |
| | | | | | | — | 0 |

In addition, $An^-$ to be used together with the combinations in the table includes the following ones.

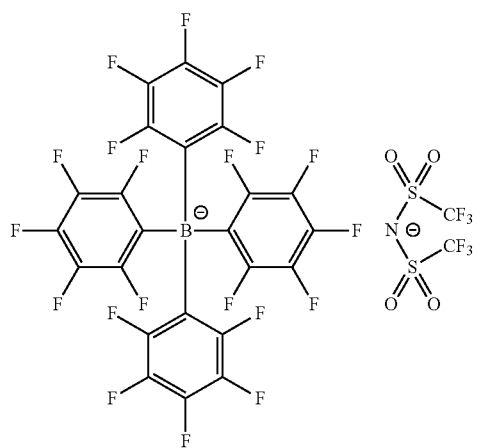 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F ; O=S(=O)([N-]S(=O)(=O)C(F)(F)F)C(F)(F)F]

Among the specific examples, the following one is preferable.

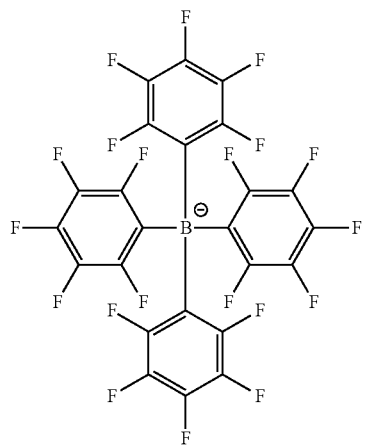 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

[Production Method for the Compound of the Present Invention]

Among the compound of the present invention, for example, the one where $Y_1$ is an oxygen atom, and $R_6$ is a group having the polymerizable unsaturated group, represented by the general formula (2), in the general formula (3) (the compound represented by the general formula (38-4)) can be produced by a method similar to a series of the methods represented by the reactions [I] to [III] and [IV-IV], in the production method for the quencher of the present invention.

In addition, among the compound of the present invention, for example, the one where $Y_1$ is a sulfur atom or $-NR_{32}-$, and $R_6$ is a group having the polymerizable unsaturated group represented by the general formula (2), in the general formula (3) (the compound represented by the general formula (44-4)) can be produced by a method similar to a series of the methods represented by the reactions [V], [VI] and [VII-IV], in the production method for the quencher of the present invention.

[Polymer of the Present Invention]

The polymer of the present invention is a polymer having a monomer unit derived from the compound of the present invention.

Weight average molecular weight (Mw) of the polymer of the present invention is usually 2,000 to 100,000, and preferably 2,000 to 50,000, and more preferably 2,000 to 30,000. In addition, distribution degree (Mw/Mn) thereof is usually 1.00 to 5.00, and preferably 1.00 to 3.00.

The polymer of the present invention may be a homopolymer or a copolymer, as long as it is the one having the monomer unit derived from the compound of the present invention, and the copolymer is preferable because of having high heat resistance effect.

The copolymer includes, for example, the one having a monomer unit derived from a fluorescent dye which has a polymerizable unsaturated group, and/or one or two kinds of monomer units derived from a compound represented by the following general formula (4), the general formula (5), the general formula (6) or the general formula (7); and a monomer unit derived from the compound represented by the general formula (3); as composition components (hereinafter it may be abbreviated as the copolymer of the present invention).

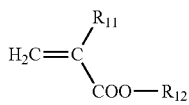

(4)

[wherein $R_{11}$ represents a hydrogen atom or a methyl group; and $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 12 carbon atoms which has an oxygen atom or no oxygen atom, a dialkylaminoalkyl group having 3 to 9 carbon atoms, a fluoroalkyl group having 1 to 18 carbon atoms, an N-alkylenephthalimide group having 9 to 14 carbon atoms, a group represented by the following general formula (4-1);

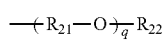

(4-1)

(wherein $R_{21}$ represents an alkylene group having 1 to 3 carbon atoms which has a hydroxy group as a substituent or no substituent; $R_{22}$ represents a phenyl group having a hydroxy group as a substituent or not having a substituent, or an alkyl group having 1 to 3 carbon atoms; and q represents an integer of 1 to 3), a group represented by the following general formula (4-2);

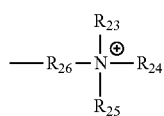

(4-2)

(wherein $R_{23}$ to $R_{25}$ represent an alkyl group having 1 to 3 carbon atoms; and $R_{26}$ represents an alkylene group having 1 to 3 carbon atoms.), or a group represented by the following general formula (4-3);

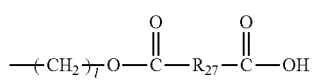

(4-3)

(wherein l represents an integer of 1 to 6; and $R_{27}$ represents a phenylene group or a cyclohexylene group.).],

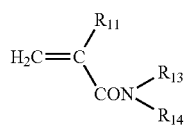

(5)

(wherein $R_{11}$ is the same as describe above; $R_{13}$ represents a hydrogen atom, or an alkyl group having 1 to 3 carbon atoms; $R_{14}$ represents a hydrogen atom, an alkyl group having 1 to 3 carbon atoms, a dialkylaminoalkyl group having 3 to 9 carbon atoms, or a hydroxyalkyl group having 1 to 6 carbon atoms; and $R_{13}$ and $R_{14}$ may form a morpholino group together with a nitrogen atom adjacent thereto.),

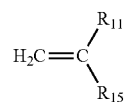

(6)

(wherein $R_{15}$ represents a phenyl group or a pyrrolidino group; and $R_{11}$ is the same as described above.),

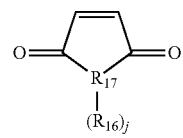

(7)

(wherein $R_{17}$ represents a nitrogen atom or an oxygen atom; when $R_{17}$ is the oxygen atom, j represents 0, and when $R_{17}$ is the nitrogen atom, j represents 1; and $R_{16}$ represents a hydrogen atom, an alkyl group having 1 to 20 carbon atoms, a hydroxyalkyl group having 1 to 10 carbon atoms, a halogenated alkyl group having 1 to 10 carbon atoms, an alkylcycloalkyl group having 6 to 10 carbon atoms, a halogenated cycloalkyl group having 6 to 7 carbon atoms, an aryl group having 6 to 10 carbon atoms, an aryl group having 6 to 10 carbon atoms which has an alkyl group having 1 to 6 carbon atoms as a substituent, or a halogenated aryl group having 6 to 10 carbon atoms.).

The monomer unit derived from the fluorescent dye which has the polymerizable unsaturated group may be the one having a monomer unit derived from the polymerizable object compound of quenching, that is, the compound having the polymerizable unsaturated group, as well as having fluorescent property, and the one capable of forming a copolymer by polymerization with the compound represented by the general formula (3).

Specific examples of the polymerizable unsaturated group include, for example, an acryloyl group, a methacryloyl group, a vinylaryl group, a vinyloxy group, an allyl group, and the like.

The fluorescent dye which has the polymerizable unsaturated group includes the same one as included as the polymerizable object compound of quenching, and the preferable one is also the same.

Specific examples of the fluorescent dye which has the polymerizable unsaturated group may be those described in JP-A-05-271567, JP-A-09-272814, JP-A-2001-011336, JP-A-2013-045088, WO2014/126167, WO2015/098999, WO2015/133578, WO2015/147285, WO2015/182680, and the like, or commercially available ones.

As $R_{11}$ in the general formula (4), a methyl group is preferable.

The alkyl group having 1 to 18 carbon atoms, in $R_{12}$ of the general formula (4), may be any of the linear, branched and cyclic ones, and specifically includes, for example, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a 3-methylpentyl group, a 2-methylpentyl group, a 1,2-dimethylbutyl group, an n-heptyl group, an isoheptyl group, a sec-heptyl group, an n-octyl group, an isooctyl group, a sec-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a cyclopropyl group, a cyclopentyl group, a cyclohexyl group, a cycloheptyl group, a cyclooctyl group, a cyclodecyl group, a cycloundecyl group, a cyclododecyl group, a cyclotetradecyl group, a cyclooctadecyl group, and the like; and the methyl group and the ethyl group are preferable.

The hydroxyalkyl group having 1 to 10 carbon atoms, in $R_{12}$ of the general formula (4), includes, for example, a hydroxymethyl group, a hydroxyethyl group, a hydroxypropyl group, a hydroxybutyl group, a hydroxypentyl group, a hydroxyhexyl group, a hydroxyheptyl group, a hydroxyoctyl group, a hydroxynonyl group, a hydroxydecyl group, and the like.

The aryl group having 6 to 10 carbon atoms, in $R_{12}$ of the general formula (4), includes a phenyl group, a naphthyl group, and the like.

The arylalkyl group having 7 to 13 carbon atoms, in $R_{12}$ of the general formula (4), includes, for example, a benzyl group, a phenylethyl group, a phenylpropyl group, a naphthylmethyl group, a naphthylethyl group, a naphthylpropyl group, and the like; and the benzyl group is preferable.

The alkoxyalkyl group having 2 to 9 carbon atoms, in $R_{12}$ of the general formula (4), includes, for example, a methoxymethyl group, a methoxyethyl group, a methoxypropyl group, a methoxybutyl group, a methoxypentyl group, a methoxyhexyl group, a methoxyheptyl group, a methoxyoctyl group, an ethoxymethyl group, an ethoxyethyl group, an ethoxypropyl group, an ethoxybutyl group, an ethoxypentyl group, an ethoxyhexyl group, an ethoxyheptyl group, a propoxymethyl group, a propoxyethyl group, a propoxypropyl group, a propoxybutyl group, a propoxypentyl group, a propoxyhexyl group, and the like.

The alkoxyalkoxyalkyl group having 3 to 9 carbon atoms, in $R_{12}$ of the general formula (4), includes, for example, a methoxymethoxymethyl group, a methoxymethoxyethyl group, a methoxymethoxypropyl group, an ethoxymethoxymethyl group, an ethoxymethoxyethyl group, an ethoxymethoxypropyl group, a propoxymethoxymethyl group, a propoxymethoxyethyl group, a propoxymethoxypropyl group, an ethoxyethoxymethyl group, an ethoxyethoxyethyl group, an ethoxyethoxypropyl group, a propoxyethoxymethyl group, a propoxyethoxyethyl group, a propoxyethoxypropyl group, a propoxypropoxymethyl group, a propoxypropoxyethyl group, a propoxypropoxypropyl group, and the like.

The aryloxyalkyl group having 7 to 13 carbon atoms, in $R_{12}$ of the general formula (4), includes, for example, a phenoxymethyl group, a phenoxyethyl group, a phenoxypropyl group, a naphthyloxymethyl group, a naphthyloxyethyl group, a naphthyloxypropyl group, and the like.

The morpholinoalkyl group having 5 to 7 carbon atoms, in $R_{12}$ of the general formula (4), includes, for example, a morpholinomethyl group, a morpholinoethyl group, a morpholinopropyl group, and the like.

The trialkylsilyl group having 3 to 9 carbon atoms, in $R_{12}$ of the general formula (4), includes, for example, a trimethylsilyl group, a triethylsilyl group, a tripropylsilyl group, a dimethylethylsilyl group, a diethylmethylsilyl group, and the like.

The alicyclic hydrocarbon group having 6 to 12 carbon atoms which has an oxygen atom, in $R_{12}$ of the general formula (4), includes, for example, a dicyclopentenyloxyethyl group, and the like.

The alicyclic hydrocarbon group having 6 to 12 carbon atoms which has no oxygen atom, in $R_{12}$ of the general formula (4), includes, for example, a cyclohexyl group, an isobornyl group, a dicyclopentanyl group, and the like.

The dialkylaminoalkyl group having 3 to 9 carbon atoms, in $R_{12}$ of the general formula (4), includes, for example, a dimethylaminomethyl group, a dimethylaminoethyl group, a dimethylaminopropyl group, a diethylaminomethyl group, a diethylaminoethyl group, a diethylaminopropyl group, a dipropylaminomethyl group, a dipropylaminoethyl group, a dipropylaminopropyl group, and the like.

The fluoroalkyl group having 1 to 18 carbon atoms, in $R_{12}$ of the general formula (4), includes, for example, a 2,2,2-trifluoroethyl group, a 2,2,3,3-tetrafluoropropyl group, a 2,2,3,3,4,4-hexafluorobutyl group, a 2,2,3,3,4,4,5,5-octafluoropentyl group, a 3,3,4,4,5,5,6,6,7,7,8,8,9,9,10,10,10-heptadecafluorodecyl, a 2-(heptadecafluorooctyl)ethyl group, and the like.

The N-alkylenephthalimide group having 9 to 14 carbon atoms, in $R_{12}$ of the general formula (4), includes, for example, a 2-phthalimideethyl group, a 2-tetrahydrophthalimideethyl group, and the like.

The alkylene group having 1 to 3 carbon atoms which has a hydroxy group as a substituent or no substituent, in $R_{21}$ of the general formula (4-1), includes a methylene group, an ethylene group, a propylene group, a hydroxymethylene group, a hydroxyethylene group, a 1-hydroxypropylene group, a 2-hydroxypropylene group, and the like; and the ethylene group, the propylene group and the 2-hydroxypropylene group are preferable.

The phenyl group having a hydroxy group as a substituent or not having a substituent, in $R_{22}$ of the general formula (4-1), includes a hydroxyphenyl group, a phenyl group, and the like.

The alkyl group having 1 to 3 carbon atoms, in $R_{22}$ of the general formula (4-1), includes a methyl group, an ethyl group, a propyl group, and the like.

Specific examples of the group represented by the general formula (4-1) include a (4-hydroxyphenoxy)methyl group, a (4-hydroxyphenoxy)ethyl group, a (4-hydroxyphenoxy)propyl group, a 1-hydroxy-1-phenoxymethyl group, a 1-hydroxy-2-phenoxyethyl group, a 2-hydroxy-3-phenoxypropyl group, a methyltrimethylene glycol group, a methyltriethylene glycol group, a methyltripropylene glycol group, and the like; and among them, the (4-hydroxyphenoxy)propyl group, the 2-hydroxy-3-phenoxypropyl group, the methyltripropylene glycol group, a methyltriethylene glycol group, and the like, are preferable.

The alkyl group having 1 to 3 carbon atoms, in $R_{23}$ to $R_{25}$ of the general formula (4-2), includes a methyl group, an ethyl group, a propyl group, and the like; and the methyl group is preferable.

The alkylene group having 1 to 3 carbon atoms, in $R_{26}$ of the general formula (4-2), includes a methylene group, an ethylene group, a propylene group, and the like.

Specific examples of the group represented by the general formula (4-2) include a trimethylammoniummethyl group, a trimethylammoniumethyl group, a triethylammoniummethyl group, a triethylammoniumethyl group, and the like.

Preferable specific examples of the group represented by the general formula (4-3) include, for example, the following ones.

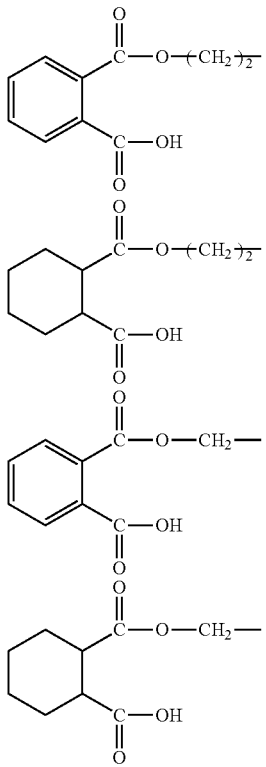

As $R_{12}$ in the general formula (4), a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an aryloxyalkyl group having 7 to 13 carbon atoms, the group represented by the general formula (4-1), and the group represented by the general formula (4-3) are preferable; and among them, the hydrogen atom, the alkyl group having 1 to 18 carbon atoms, the hydroxyalkyl group having 1 to 10 carbon atoms, the aryl group having 6 to 10 carbon atoms, the arylalkyl group having 7 to 13 carbon atoms, and the alkoxyalkyl group having 2 to 9 carbon atoms are more preferable; and the hydrogen atom and the arylalkyl group having 7 to 13 carbon atoms are particularly preferable.

Preferable specific examples of the general formula (4) include acrylic acid, benzyl acrylate, methacrylic acid, benzyl methacrylate, hydroxyethyl methacrylate, methyl methacrylate, and the like; and among them, acrylic acid, benzyl acrylate, methacrylic acid and benzyl methacrylate are preferable; and methacrylic acid and benzyl methacrylate are more preferable.

The alkyl group having 1 to 3 carbon atoms, in $R_{13}$ and $R_{14}$ of the general formula (5), includes a methyl group, an ethyl group, a propyl group, and the like.

The dialkylaminoalkyl group having 3 to 9 carbon atoms, in $R_{14}$ of the general formula (5), includes a dimethylaminomethyl group, a dimethylaminoethyl group, a dimethylaminopropyl group, a diethylaminomethyl group, a diethylaminoethyl group, a diethylaminopropyl group, a dipropylaminomethyl group, a dipropylaminoethyl group, a dipropylaminopropyl group, and the like.

The hydroxyalkyl group having 1 to 6 carbon atoms, in $R_{14}$ of the general formula (5), includes a hydroxymethyl group, a hydroxyethyl group, a hydroxypropyl group, a hydroxybutyl group, a hydroxypentyl group, a hydroxyhexyl group, and the like; and the hydroxyethyl group is preferable.

Preferable specific examples of the general formula (5) include (meth)acrylamide, N,N-dimethylacrylamide, N,N-diethylacrylamide, hydroxyethyl(meth)acrylamide, 4-acryloylmorpholine, and the like; and among them, (meth)acrylamide, N,N-dimethylacrylamide and N,N-diethylacrylamide are preferable; and N,N-diethylacrylamide is particularly preferable.

Preferable specific examples of the general formula (6) include styrene, α-methylstyrene, N-vinylpyrrolidone, and the like; and among them, styrene and α-methylstyrene are preferable; and styrene is particularly preferable.

The alkyl group having 1 to 20 carbon atoms, in $R_{16}$ of the general formula (7), may be any of the linear, branched and cyclic ones, and specifically includes, for example, a methyl group, an ethyl group, an n-propyl group, an isopropyl group, an n-butyl group, an isobutyl group, a tert-butyl group, a 1-methylpropyl group, an n-pentyl group, an isopentyl group, a tert-pentyl group, a neopentyl group, a 1-methylbutyl group, an n-hexyl group, an isohexyl group, a tert-hexyl group, a 3-methylpentyl group, a 2-methylpentyl group, a 1-methylpentyl group, a 1,2-dimethylbutyl group, a cyclohexyl group, an n-heptyl group, an isoheptyl group, a 1-methylhexyl group, an n-octyl group, an isooctyl group, a 1-methylheptyl group, a 2-ethylhexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a nonadecyl group, an icosyl group, and the like.

The hydroxyalkyl group having 1 to 10 carbon atoms, in $R_{16}$ of the general formula (7), includes, for example, a hydroxymethyl group, a hydroxyethyl group, a hydroxypropyl group, a hydroxybutyl group, a hydroxypentyl group, a hydroxyhexyl group, a hydroxyheptyl group, a hydroxyoctyl group, a hydroxynonyl group, a hydroxydecyl group, and the like.

The halogenated alkyl group having 1 to 10 carbon atoms, in $R_{16}$ of the general formula (7), includes, for example, a chloromethyl group, a chloroethyl group, a chloro-n-propyl group, a chloroisopropyl group, a chloro-n-butyl group, a chloro-tert-butyl group, a chloro-n-pentyl group, a chloro-n-hexyl group, a chloro-n-heptyl group, a chloro-n-octyl group, a chloro-n-nonyl group, a chloro-n-decyl group, a fluoromethyl group, a fluoroethyl group, a fluoro-n-propyl group, a fluoroisopropyl group, a fluoro-n-butyl group, a fluoro-tert-butyl group, a fluoro-n-pentyl group, a fluoro-n-hexyl group, a fluoro-n-heptyl group, a fluoro-n-octyl group, a fluoro-n-nonyl group, a fluoro-n-decyl group, and the like.

The alkylcycloalkyl group having 6 to 10 carbon atoms, in $R_{16}$ of the general formula (7), includes, for example, a methylcyclopentyl group, an ethylcyclopentyl group, a propylcyclopentyl group, a methylcyclohexyl group, an ethylcyclohexyl group, a propylcyclohexyl group, a butylcyclohexyl group, a methylcycloheptyl group, an ethylcycloheptyl group, a propylcycloheptyl group, a methylcyclooctyl group, an ethylcyclooctyl group, and the like.

The halogenated cycloalkyl group having 6 to 7 carbon atoms, in $R_{16}$ of the general formula (7), includes, for example, a chlorocyclohexyl group, a fluorocyclohexyl group, a bromocyclohexyl group, a chlorocycloheptyl group, a fluorocycloheptyl group, a bromocycloheptyl group, and the like.

The aryl group having 6 to 10 carbon atoms, in $R_{16}$ of the general formula (7), includes a phenyl group, a naphthyl group, and the like.

The aryl group having 6 to 10 carbon atoms which has the alkyl group having 1 to 6 carbon atoms as a substituent, in $R_{16}$ of the general formula (7), includes, for example, a methylphenyl group, an ethylphenyl group, an n-propylphenyl group, an n-butylphenyl group, an n-pentylphenyl group, an n-hexylphenyl group, a methylnaphthyl group, an ethylnaphthyl group, a n-propylnaphthyl group, and the like.

The halogenated aryl group having 6 to 10 carbon atoms, in $R_{16}$ of the general formula (7), includes, for example, a chlorophenyl group, a fluorophenyl group, a chloronaphthyl group, a fluoronaphthyl group, and the like.

Preferable specific examples of the general formula (7) include maleic anhydride, maleimide, N-methylmaleimide, N-ethylmaleimide, N-butylmaleimide, N-octylmaleimide, N-dodecylmaleimide, N-(2-ethylhexyl)maleimide, N-(2-hydroxyethyl)maleimide, N-(2-chlorohexyl)maleimide, N-cyclohexylmaleimide, N-(2-methylcyclohexyl)maleimide, N-(2-ethylcyclohexyl)maleimide, N-(2-chlorocyclohexyl)maleimide, N-phenylmaleimide, N-(2-methylphenyl)maleimide, N-(2-ethylphenyl)maleimide, N-(2-chlorophenyl)maleimide, and the like; and among them, N-phenylmaleimide is preferable.

The copolymer of the present invention may contain a monomer unit derived from various kinds of dyes, besides the above monomer unit. However, the dyes are different from the compound represented by the general formula (3) and the fluorescent dye which has the polymerizable unsaturated group.

The copolymer of the present invention specifically includes combinations of the monomer units described in the following table, and among them, the combinations 1, 2 and 6 to 12 are preferable, the combinations 1, 2 and 6 to 9 are more preferable, and the combinations 1, 2 and 6 are particularly preferable. In addition, among the following combinations 2 and 6, the combination comprising the compound represented by the general formula (3), and two kinds of the compounds represented by the general formula (4) is preferable.

| | Compound from which monomer unit is derived | |
|---|---|---|
| Combination 1 | General formula (3) | Fluorescent dye having polymerizable unsaturated group | — |
| Combination 2 | | General formula (4) | — |
| Combination 3 | | General formula (5) | — |
| Combination 4 | | General formula (6) | — |
| Combination 5 | | General formula (7) | — |
| Combination 6 | | Fluorescent dye having polymerizable unsaturated group | General formula (4) |
| Combination 7 | | Fluorescent dye having polymerizable unsaturated group | General formula (5) |
| Combination 8 | | Fluorescent dye having polymerizable unsaturated group | General formula (6) |
| Combination 9 | | Fluorescent dye having polymerizable unsaturated group | General formula (7) |
| Combination 10 | | General formula (4) | General formula (5) |
| Combination 11 | | General formula (4) | General formula (6) |
| Combination 12 | | General formula (4) | General formula (7) |

Weight ratio of the monomer unit derived from the compound represented by the general formula (3), and the monomer unit derived from the fluorescent dye which has the polymerizable unsaturated group, and/or the monomer unit derived from the compound represented by the general formula (4), the general formula (5), the general formula (6) or the general formula (7) may be set as appropriate, depending on kinds of the monomer units to be used, however, the monomer unit derived from the compound represented by the general formula (3) is usually 1 to 90% by weight, and preferably 5 to 85% by weight, relative to total weight of the resulting polymer.

Preferable specific examples of the copolymer of the present invention include a polymer containing the monomer unit derived from the compound represented by the general formula (3), the monomer unit derived from the fluorescent dye which has the polymerizable unsaturated group, and/or one or two kinds of monomer units derived from a compound represented by the following general formula (4').

(wherein $R'_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, or an alkoxyalkyl group having 2 to 9 carbon atoms; and $R_{11}$ is the same as described above.)

Specific examples of the alkyl group having 1 to 18 carbon atoms, the hydroxyalkyl group having 1 to 10 carbon atoms, the aryl group having 6 to 10 carbon atoms, the arylalkyl group having 7 to 13 carbon atoms, and the alkoxyalkyl group having 2 to 9 carbon atoms, in $R'_{12}$ of the general formula (4'), include the same one as those of $R_{12}$ in the general formula (4).

As $R'_{12}$ in the general formula (4'), a hydrogen atom, an alkyl group having 1 to 18 carbon atoms, and an arylalkyl group having 7 to 13 carbon atoms are preferable; and the hydrogen atom, and the arylalkyl group having 7 to 13 carbon atoms are more preferable.

Preferable specific examples of the general formula (4') include acrylic acid, benzyl acrylate, methacrylic acid, benzyl methacrylate, and the like; and among them, methacrylic acid and benzyl methacrylate are preferable.

The polymer of the present invention is less fading caused by heating, and exerts high heat resistance effect, in addition to quenching effect on a compound having fluorescent property. In addition, the polymer of the present invention is superior also in elution resistance and weather resistance. Therefore, the polymer of the present invention can be used not only in a quencher application, but also as a dye by the polymer itself.

In addition, when the polymer of the present invention is the one comprising the monomer unit derived from the fluorescent dye which has the polymerizable unsaturated group, the compound (monomer) of the present invention contained in the polymer is capable of suppressing fluorescence emitted by the fluorescent dye contained in the polymer, inside the polymer molecule. That is, the polymer can be used more suitably as a dye, because fluorescence emission is more suppressed, as compared with a polymer comprising only the fluorescent dye having the polymerizable unsaturated group.

The polymer of the present invention comprising the fluorescent dye which has the polymerizable unsaturated group is capable, by one kind of the polymer itself, of obtaining effect which can be obtained by blending a polymer comprising the monomer unit derived from the compound of the present invention (a polymer 1), and a polymer comprising the monomer unit derived from the fluorescent dye which has the polymerizable unsaturated group (a polymer 2). That is, for example, when a colored pixel, such as a color filter, is formed from the polymer 2, it is necessary to form a two-layered filter layer by two kinds of polymers, the polymer 1 and the polymer 2, to suppress fluorescence emission by the polymer 2. In contrast, in the case of using the polymer of the present invention comprising the fluorescent dye which has the polymerizable unsaturated group, for formation of a colored pixel, the colored pixel, suppressed fluorescence similar to the two-layered filter layer formed by the polymer 1 and the polymer 2, can be formed by a one-layered filter layer, and then it also enables to reduce total thickness of the filter layer.

It should be noted that in the case of using the polymer of the present invention as a quencher, the object compound of quenching includes the same one as described in the item of the quencher of the present invention; and also use amount, use method thereof, or the like, may be in accordance with the amount, the method, or the like, described in the item of the quencher of the present invention.

[Production Method for the Polymer of the Present Invention]

The polymer of the present invention is produced, for example, as follows. That is, the polymer of the present invention can be obtained by subjecting the compound of the present invention obtained as described above to a polymerization reaction known per se. When the polymer of the present invention is a copolymer, in the polymerization reaction, after mixing the compound represented by the general formula (3), the fluorescent dye which has the polymerizable unsaturated group, and/or one or two kinds of the compound represented by the general formula (4), the general formula (5), the general formula (6) or the general formula (7), so as to attain ratio of the monomer unit derived from each monomer in the finally obtained polymer, as described above, polymerization may be carried out.

The polymerization reaction is carried out, for example, as follows. That is, the compound represented by the general formula (3), or the compound represented by the general formula (3), and the fluorescent dye which has the polymerizable unsaturated group and/or one or two kinds of the compound represented by the general formula (4), the general formula (5), the general formula (6) or the general formula (7) are dissolved in 1 to 10 times volume of an appropriate solvent, such as toluene, 1,4-dioxane, tetrahydrofuran, isopropanol, methyl ethyl ketone and propylene glycol monomethyl ether acetate, relative to total volume thereof. Next, a reaction may be carried out at 50 to 150° C., for 1 to 48 hours, in the presence of 0.01 to 30% by weight of a polymerization initiator, such as azobisisobutyronitrile, 2,2'-azobis(2,4-dimethylvaleronitrile), 2,2'-azobis(2-methylpropionate), 2,2'-azobis(2-methylbutyronitrile), benzoyl peroxide and lauroyl peroxide, relative to total amount of the dissolved compound. After the reaction, it may be treated according to a conventional method for polymer acquisition.

[Colored Composition 1]

As described above, the compound or the polymer of the present invention can be used not only as a quenching application but also as a dye by the compound or the polymer itself. Therefore, the colored composition containing at least one kind of the compound or the polymer of the present invention (hereinafter it may be abbreviated as the colored composition 1 of the present invention) is a colored composition having less fading caused by heating, and still more, it is capable of forming a superior colored cured film having heat resistance. Therefore, the colored composition 1 of the present invention can be used in an application of formation of a colored pixel such as a color filter, to be used in a liquid crystal display device (LCD) or a solid-state imaging element (CCD, CMOS, or the like), or in applications of printing ink, inkjet ink, paint, and the like; and it is particularly suitable for the color filter of the liquid crystal display device. Still more, the colored composition 1 of the present invention can be used also as a colored resin molded articles by molding to sheets, films, bottles, cups, or the like, by a conventionally known molding method. Accordingly, it can be used also in applications of spectacles, color contact lenses, or the like; and can be used similarly by making a multi-layered structure with a known resin. In addition, it can be used also in applications of, for example, optical films, hair coloring agents, labeling substances for compounds or biomaterials, materials of organic solar cells, or the like. The colored composition 1 of the present invention may contain an additive, and the like, usually used in this field, besides the compound or the polymer of the present invention.

For example, when the colored composition 1 of the present invention is used as a colored resin application, the colored composition 1 of the present invention is preferably the one which contains at least one or more kinds of the compound or the polymer of the present invention, as well as is mixed with other resins, and more preferably the one which contains one or more kinds of the polymer of the present invention and is mixed with other resins. The other resins are not especially limited, and include, for example, a polyolefin resin, a polystyrene resin, a polyester resin, a polyamide resin, a polyurethane resin, a polycarbonate resin, an epoxy resin, an acrylic resin, an acrylonitrile resin, and the like. As more specific examples of other resins, a homopolymer derived from one kind of the fluorescent dye which has the polymerizable unsaturated group, the compound represented by the general formula (4), the compound represented by the general formula (5), the compound represented by the general formula (6), and the compound represented by the general formula (7), or the copolymer derived from two or more kinds selected from these is preferable, and the homopolymer is more preferable. As the homopolymer, a homopolymer derived from the fluorescent dye which has the polymerizable unsaturated group, and a homopolymer derived from the compound represented by the general formula (4) are preferable, and the homopolymer derived from the fluorescent dye which has the polymerizable unsaturated group, and a homopolymer derived from the compound represented by the general formula (4') are more preferable. In addition, when the other resins are mixed, mixing ratio thereof may be set as appropriate depending on required color of the colored resin. When the colored composition 1 of the present invention is used as the colored resin, it may be used after molding it by a molding method known per se. Further, the colored composition 1 of the present invention may contain an additive usually used in this field, such as a lubricant, an antistatic agent, a UV inhibitor, an antioxidant, a light stabilizer, a dispersing agent, a processing stabilizer, a processing aid, an impact modifier, fillers, a reinforcing agent, a flame-proofing agent, a plasticizer and a foaming agent; besides the compound or the polymer of the present invention and, if necessary, the other resins; within a range not interfering with the object and effect of the present invention. The colored composition 1 of the present invention has less elution of a dye even in contact with a solvent, and excellent weather resistance, when it is used as the colored resin application.

For example, when the colored composition 1 of the present invention is used in a colored pixel formation application, the colored composition 1 of the present invention is preferably the one containing, at least one or more kinds of the compound or the polymer of the present invention, as well as a polymerization initiator, a binder resin and a radically polymerizable monomer or oligomer, and as needed, may contain a pigment, a solvent, a silane coupling agent, a cross-linking agent, and the like. The colored composition 1 of the present invention contains 1 to 50%, and preferably 5 to 30% of the compound or the polymer of the present invention, relative to weight of the colored composition 1 of the present invention. It should be noted that, weight of the colored composition 1 of the present invention referred to herein means weight of solid components excluding a solvent, and means the same hereafter in the present application.

As the polymerization initiator, a known thermal polymerization initiator and a photo-polymerization initiator can be used, and the photo-polymerization initiator is preferable. It specifically includes an acetophenone-type, such as diethoxyacetophenone, 2-hydroxy-2-methyl-1-phenylpropane-1-one, benzyldimethylketal, 1-(4-isopropylphenyl)-2-hydroxy-2-methylpropane-1-one, 4-(2-hydroxyethoxy)phenyl-(2-hydroxy-2-propyl)ketone, 1-hydroxycyclohexyl-phenylketone, 2-methyl-2-morpholino(4-thiomethylphenyl) propane-1-one and 2-benzyl-2-dimethylamino-1-(4-morpholinophenyl)-butanone; a benzoin-type, such as benzoin, benzoin isopropyl ether and benzoin isobutyl ether; an acylphosphine oxide-type, such as 2,4,6-trimethylbenzoyl diphenylphosphine oxide; benzyl, a methylphenylglyoxy ester-type; a benzophenone-type, such as benzophenone, methyl o-benzoylbenzoate, 4-phenylbenzophenone, 4,4'-dichlorobenzophenone, hydroxybenzophenone, 4-benzoyl-4'-methyl-diphenylsulfide, acrylated benzophenone, 3,3',4,4'-tetra(tert-butylperoxycarbonyl)benzophenone and 3,3'-dimethyl-4-methoxybenzophenone; a thioxanthone-type, such as 2-isopropylthioxanthone, 2,4-dimethylthioxanthone, 2,4-diethylthioxanthone and 2,4-dichlorothioxanthone; an aminobenzophenone-type, such as Michler's ketone and 4,4'-diethylaminobenzophenone; an oxime ester-type, such as 1-[4-(phenylthio)phenyl]-1,2-octanedione-2-(o-benzoyloxime) and 1-[6-(2-methylbenzoyl)-9-ethyl-9H-carbazole-3-yl]ethanone-o-acetyloxime; 10-butyl-2-chloroacridone, 2-ethylanthraquinone, 9,10-phenanthrenequinone, camphor quinone; and the like.

The polymerization initiator may be contained singly, or in two or more kinds. Content thereof is 1 to 50% by weight, and preferably 5 to 30% by weight, relative to weight of the colored composition 1 of the present invention.

The binder resin includes, for example, an ethylenically unsaturated monomer having at least one of a carboxy group or a hydroxy group; a copolymer of the ethylenically unsaturated monomer, and an ethylenically unsaturated monomer having an aromatic hydrocarbon group or an aliphatic hydrocarbon group; the one having an epoxy group at the side chain or the terminal, or the like, of the copolymer; the one to which an acrylate is added; and the like. They may be used singly, or in combination of two or more kinds.

Specific examples of the ethylenically unsaturated monomer having the carboxy group include unsaturated mono carboxylic acids such as acrylic acid, methacrylic acid, benzyl methacrylate, crotonic acid, α-chloroacrylic acid, ethacrylic acid and cinnamic acid; unsaturated dicarboxylic acids (anhydrides) such as maleic acid, maleic anhydride, fumaric acid, itaconic acid, itaconic anhydride, citraconic acid, citraconic anhydride and mesaconic acid; tri or more polyvalent unsaturated carboxylic acids (anhydrides), 2-(meth)acryloyloxyethyl hexahydrophthalate, 2-methacryloyloxyethyl 2-hydroxypropyl phthalate, 2-acryloyloxyethyl 2-hydroxyethyl phthalate, and the like.

Content of the binder resin is 10 to 50% by weight, and preferably 20 to 50% by weight, relative to weight of the colored composition 1 of the present invention.

As an example, the radically polymerizable monomer or oligomer includes polyethylene glycol diacrylate (the one having 2 to 14 ethylene groups), polyethylene glycol dimethacrylate (the one having 2 to 14 ethylene groups), trimethylolpropane diacrylate, trimethylolpropane dimethacrylate, trimethylolpropane triacrylate, trimethylolpropane trimethacrylate, trimethylolpropane ethoxytriacrylate, trimethylolpropane ethoxytrimethacrylate, trimethylolpropane propoxytriacrylate, trimethylolpropane propoxytrimethacrylate, tetramethylolmethane triacrylate, tetramethylolmethane trimethacrylate, tetramethylolmethane tetraacrylate, tetramethylolmethane tetramethacrylate, polypropylene glycol diacrylate (the one having 2 to 14 propylene groups), polypropylene glycol dimethacrylate (the one having 2 to 14 propylene groups), dipentaerythritol pentaacrylate, dipentaerythritol pentamethacrylate, dipentaerythritol hexaacrylate, dipentaerythritol hexamethacrylate, ethoxylated pentaerythritol tetraacrylate (the one having 40 or less ethoxy groups), propoxylated pentaerythritol tetraacrylate (the one having 40 or less propoxy groups), ethoxylated trimethylolpropane triacrylate (the one having 40 or less ethoxy groups), propoxylated trimethylolpropane triacrylate (the one having 40 or less propoxy groups), bisphenol A polyoxyethylene diacrylate, bisphenol A polyoxyethylene dimethacrylate, bisphenol A dioxyethylene diacrylate, bisphenol A dioxyethylene dimethacrylate, bisphenol A trioxyethylene diacrylate, bisphenol A trioxyethylene dimethacrylate, bisphenol A decaoxyethylene diacrylate, bisphenol A decaoxyethylene dimethacrylate, isocyanuric acid ethoxy modified triacrylate, an esterified product with a polyvalent carboxylic acid (phthalic anhydride, and the like) and a compound having a hydroxy group and a ethylenically unsaturated group (β-hydroxyethyl acrylate, β-hydroxyethyl methacrylate, and the like), an alkyl ester of acrylic acid or methacrylic acid (methyl acrylate, methyl methacrylate, ethyl acrylate, ethyl methacrylate, butyl acrylate, butyl methacrylate, 2-ethylhexyl acrylate, 2-ethylhexyl methacrylate, and the like), 2-hydroxyethyl acrylate, 2-hydroxyethyl methacrylate, phenoxyethyl acrylate, phenoxyethyl methacrylate, N,N-dimethylacrylamide, N,N-dimethylaminoethyl acrylate, a quaternary chloride of N,N-dimethylaminoethyl acrylate by methyl chloride, a quaternary chloride of N,N-dimethylaminopropyl acrylamide by methyl chloride, acryloylmorpholine, N-isopropylacrylamide, N,N-diethylacrylamide, and the like. Among them, dipentaerythritol pentaacrylate, dipentaerythritol pentamethacrylate, dipentaerythritol hexaacrylate and dipentaerythritol hexamethacrylate are preferable; and dipentaerythritol pentaacrylate and dipentaerythritol hexaacrylate are more preferable.

The pigment may be any pigment which is used to prepare a colored pattern of red color, blue color or green color, and includes, for example, a phthalocyanine-type pigment, and the like. The phthalocyanine-type pigment includes the one containing magnesium, titanium, iron, cobalt, nickel, copper, zinc or aluminum in central metal; and specifically includes C.I. Pigment Red 1, C.I. Pigment Red 2, C.I. Pigment Red 5, C.I. Pigment Red 17, C.I. Pigment Red 31, C.I. Pigment Red 32, C.I. Pigment Red 41, C.I. Pigment Red 122, C.I. Pigment Red, 123, C.I. Pigment Red 144, C.I. Pigment Red 149, C.I. Pigment Red 166, C.I. Pigment Red 168, C.I. Pigment Red 170, C.I. Pigment Red 171, C.I. Pigment Red 175, C.I. Pigment Red 176, C.I. Pigment Red 177, C.I. Pigment Red 178, C.I. Pigment Red 179, C.I. Pigment Red 180, C.I. Pigment Red 185, C.I. Pigment Red 187, C.I. Pigment Red 202, C.I. Pigment Red 206, C.I. Pigment Red 207, C.I. Pigment Red 209, C.I. Pigment Red 214, C.I. Pigment Red 220, C.I. Pigment Red 221, C.I. Pigment Red 224, C.I. Pigment Red 242, C.I. Pigment Red 243, C.I. Pigment Red 254, C.I. Pigment Red 255, C.I. Pigment Red 262, C.I. Pigment Red 264, C.I. Pigment Red 272, C.I. Pigment Blue 15, C.I. Pigment Blue 15:1, C.I. Pigment Blue 15:2, C.I. Pigment Blue 15:3, C.I. Pigment Blue 15:4, C.I. Pigment Blue 15:5, C.I. Pigment Blue 15:6, C.I. Pigment Blue 16, C.I. Pigment Blue 17:1, C.I. Pigment Blue 75, C.I. Pigment Blue 79, C.I. Pigment Green 7, C.I. Pigment Green 36, C.I. Pigment Green 37, C.I. Pigment Green 58, chloroaluminum phthalocyanine, hydroxyaluminum phthalocyanine, aluminum phthalocyanine oxide, and zinc phthalocyanine.

Content of the pigment is 10 to 50% by weight, and preferably 10 to 30% by weight, relative to weight of the colored composition 1 of the present invention.

When the colored composition 1 of the present invention contains the pigment, it is preferable to contain a pigment dispersant. The pigment dispersant includes, for example, polyamide amine and a salt thereof, polycarboxylic acid and a salt thereof, a high molecular weight unsaturated acid ester, modified polyurethane, modified polyester, modified poly(meth)acrylate, a (meth)acrylic copolymer, a naphthalene sulfonic acid/formalin condensate, a polyoxyethylene alkylphosphoric acid ester, a polyoxyethylene alkylamine, an alkanol amine, and the like. The pigment dispersant may be used singly, or in combination of two or more kinds. Content thereof is usually 1 to 80% by weight, and preferably 10 to 60% by weight, relative to weight of the pigment.

The solvent may be appropriately selected depending on the components contained in the colored composition 1 of the present invention. It specifically includes, for example, ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, methyl oxyacetate, ethyl oxyacetate, butyl oxyacetate, methyl methoxyacetate, ethyl methoxyacetate, butyl methoxyacetate, methyl ethoxyacetate, ethyl ethoxyacetate, methyl 3-oxypropionate, ethyl 3-oxypropionate, methyl 3-methoxypropionate, ethyl 3-methoxypropionate, methyl 3-ethoxypropionate, ethyl 3-ethoxypropionate, methyl 2-oxypropionate, ethyl 2-oxypropionate, propyl 2-oxypropionate, methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, methyl 2-methoxy-2-methylpropionate, ethyl 2-ethoxy-2-methylpropionate, methyl pyruvate, ethyl pyruvate, propyl pyruvate, methyl acetoacetate, ethyl acetoacetate, methyl 2-oxobutanoate, ethyl 2-oxobutanoate, diethylene glycol dimethyl ether, tetrahydrofuran, ethylene glycol monomethyl ether, ethylene glycol monoethyl ether, methylcellosolve acetate, ethylcellosolve acetate, diethylene glycol monomethyl ether, diethylene glycol monoethyl ether, diethylene glycol monobutyl ether, propylene glycol monomethyl ether, propylene glycol monoethyl ether acetate, propylene glycol monoethyl ether acetate, propylene glycol monopropyl ether acetate, methyl ethyl ketone, cyclohexanone, 2-heptanone, 3-heptanone, and the like. Amount of the solvent is an amount that attains a concentration of the colored composition 1 of the present invention of 10 to 80% by weight in the solvent.

The silane coupling agent is used in the case of bonding to a substrate, such as glass. As the silane coupling agent, the a conventionally known one usually used in this field can be used, and it includes a silane coupling agent having, for example, an epoxy group, a thiol group, a hydroxy group, an amino group, an ureido group, a vinyl group, an acryloyl group, and the like, as a reactive functional group. It specifically includes β-(3,4-epoxycyclohexyl)ethyltrimethoxysilane, γ-glycidooxypropyltrimethoxysilane, γ-mercaptopropyltrimethoxysilane, γ-aminopropyltriethoxysilane, N-β-(aminoethyl)-γ-aminopropyltrimethoxysilane, γ-ureidopropyltriethoxysilane, vinyltriethoxysilane, vinyltris(β-methoxyethoxy) silane, and γ-methacryloxypropyltrimethoxysilane. The silane coupling agent may be used in an amount of usually 0.1 to 10% by weight, and preferably 1 to 5% by weight, in a reaction solution.

The cross-linking agent is not especially limited, as long as it is capable of carrying out film curing by a cross-linking reaction, and includes, for example, (a) an epoxy resin; (b) a melamine compound, a guanamine compound, a glycoluril compound or an urea compound, substituted with at least one substituent selected from a methylol group, an alkoxymethyl group and an acyloxymethyl group; and (c) a phenol compound, a naphthol compound or a hydroxyanthracene compound, substituted with at least one substituent selected from a methylol group, an alkoxymethyl group and an acyloxymethyl group; and among them, a polyfunctional epoxy resin is preferable.

Content of the cross-linking agent is 10 to 50% by weight, and preferably 20 to 50% by weight, relative to weight of the colored composition 1 of the present invention.

The colored composition 1 of the present invention may contain a polymerization inhibitor, a surfactant, an additive, or the like, in addition to those as described above, and they are not especially limited, as long as they are those known per se, and the use amount is also not limited, as long as it is the amount usually used in this field.

The colored composition 1 of the present invention is prepared by mixing the above components.

[Colored Composition 2]

The quencher of the present invention is capable of forming the colored composition containing at least one kind of the quencher, and at least one kind of the object compound of quenching (hereinafter it may be abbreviated as the colored composition 2 of the present invention). The colored composition 2 of the present invention suppresses fluorescence emitted by the object compound of quenching, and when it is used, for example, as a color filter, it is capable of forming a superior colored cured film having high contrast. Therefore, the colored composition 2 of the present invention can be used in an application of formation of a colored pixel such as a color filter, to be used in a liquid crystal display device (LCD) or a solid-state imaging element (CCD, CMOS, or the like), or in applications of printing ink, inkjet ink, paint, and the like; and it is particularly suitable for the color filter of the liquid crystal display device. Still more, the colored composition 2 of the present invention can be used also as a colored resin molded articles by molding to sheets, films, bottles, cups, or the like, by a conventionally known molding method. Accordingly, it can be used also in applications of spectacles, color contact lenses, or the like; and can be used similarly by making a multi-layered structure with a known resin. In addition, it can be used also in applications of, for example, optical films, hair coloring agents, labeling substances for compounds or biomaterials, materials of organic solar cells, or the like.

The colored composition 2 of the present invention is preferably the one containing, at least one or more kinds of the quencher of the present invention, and at least one or more kinds of the object compounds of quenching, as well as a polymerization initiator, a binder resin, and a radically polymerizable monomer or oligomer, and as needed, may contain a pigment, a solvent, a silane coupling agent, a cross-linking agent, and the like. The colored composition 2 of the present invention contains 1 to 80% by weight, and preferably 10 to 50% by weight of the quencher of the present invention, relative to weight of the colored composition 2 of the present invention. It should be noted that, weight of the colored composition 2 of the present invention referred to herein means weight of solid components excluding a solvent.

The object compound of quenching includes the same one as described in the item of the quencher of the present invention.

Content of the object compound of quenching is 1 to 50% by weight, and preferably 5 to 30% by weight, relative to weight of the colored composition 2 of the present invention.

The polymerization initiator, the binder resin, the radically polymerizable monomer or oligomer, the pigment, the solvent, the silane coupling agent, and the cross-linking agent, in the colored composition 2 of the present invention, include the same one as those in the colored composition 1 of the present invention, and each content is also the same.

The present invention is described below in further detail by Examples, however, the present invention should not be limited to these Examples.

EXAMPLES

Example 1 Synthesis of a Carboxylic Acid Derivative (Compound 2)

Into a round-bottom flask equipped with a stirring apparatus, 2.5 g (6.0 mmol) of 6'-(diethylamino)-1',2'-benzofluoran (Compound 1: produced by Tokyo Chemical Industry Co., Ltd.), 0.6 g (6.0 mmol) of concentrated hydrochloric acid (produced by Wako Pure Chemical Industries, Ltd.), and 50 mL of ethanol were added, and the reaction was carried out at 40° C. for 3 hours. The solvent was removed from the reaction solution by concentration under reduced pressure to obtain 2.7 g (yield: 100%) of a reddish-brown solid carboxylic acid derivative having a chloride ion (Compound 2).

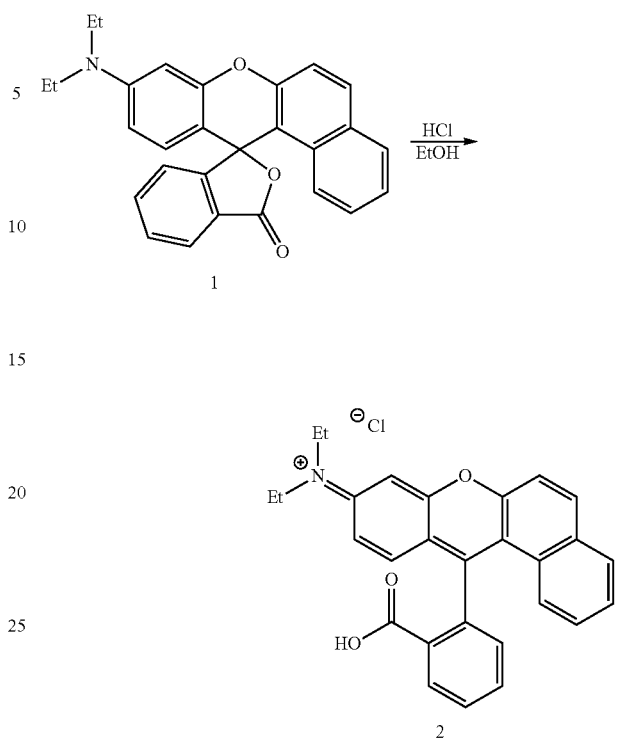

Example 2 Synthesis of a Carboxylic Acid Derivative (Compound 3)

Into a round-bottom flask equipped with a stirring apparatus, 4.2 g (9.9 mmol) of 6'-(diethylamino)-1',2'-benzofluoran (Compound 1: produced by Tokyo Chemical Industry Co., Ltd.), 30 mL (30 mmol) of 1 mol/L aqueous solution of hydrochloric acid (produced by Wako Pure Chemical Industries, Ltd.), 7.4 g (9.9 mmol) of a lithium tetrakis(pentafluorophenyl)borate (IV) (LiFABA) (produced by Tosoh Finechem Corp.), and 83 mL of ethanol were added, and the reaction was carried out at 40° C. for 4 hours. After dilution of the reaction solution with dichloromethane, it was washed with water. The solvent was removed from the reaction solution by concentration under reduced pressure to obtain 10.9 g (yield: 100%) of a reddish-brown solid carboxylic acid derivative having a tetrakis(pentafluorophenyl)borate (IV) anion (Compound 3).

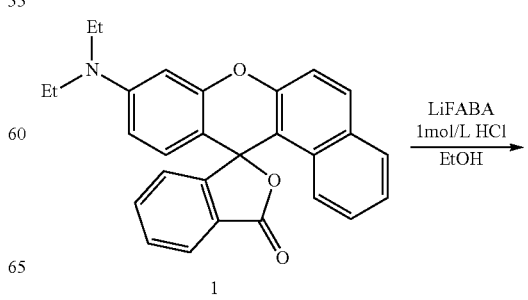

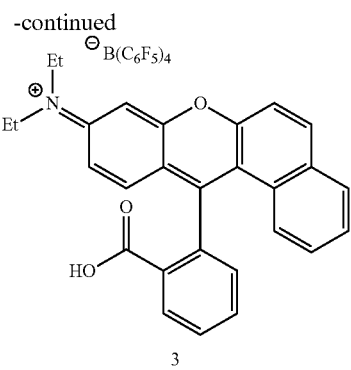

3

Example 3 Synthesis of a Carboxylic Acid Derivative (Compound 4)

Into a round-bottom flask equipped with a stirring apparatus, 5.0 g (12.0 mmol) of 6'-(diethylamino)-1',2'-benzofluoran (Compound 1: produced by Tokyo Chemical Industry Co., Ltd.), 36 mL (36.0 mmol) of 1 mol/L aqueous solution of hydrochloric acid (produced by Wako Pure Chemical Industries, Ltd.), 3.4 g (12.0 mmol) of lithium bis(trifluoromethanesulfonyl) imide (LiN(SO$_2$CF$_3$)$_2$) (produced by Wako Pure Chemical Industries, Ltd.), and 100 mL of ethanol were added, and the reaction was carried out at 60° C. for 3 hours. After dilution of the reaction solution with dichloromethane, it was washed with water. The solvent was removed from the reaction solution by concentration under reduced pressure to obtain 7.8 g (yield: 93%) of a reddish-brown solid carboxylic acid derivative having a bis(trifluoromethanesulfonyl)imide anion (Compound 4).

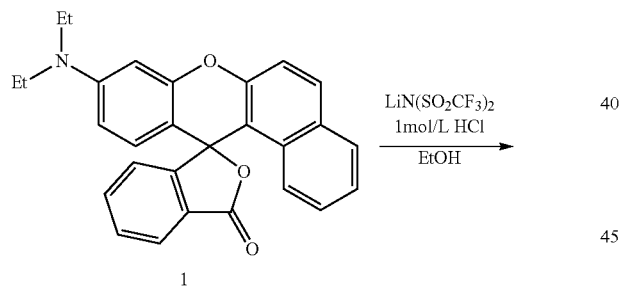

Example 4 Synthesis of a Carboxylic Acid Derivative (Compound 6)

Into a round-bottom flask equipped with a stirring apparatus, 3.2 g (8.0 mmol) of 6'-(diethylamino)-1',3'-dimethylfluoran (Compound 5: produced by Tokyo Chemical Industry Co., Ltd.), 24 mL (24.0 mmol) of 1 mol/L aqueous solution of hydrochloric acid (produced by Wako Pure Chemical Industries, Ltd.), 6.0 g (8.0 mmol) of LiFABA (produced by Tosoh Finechem Corp.), 60 mL of ethanol, and 10 mL of dichloromethane were added, and the reaction was carried out at room temperature for 4 hours. After dilution of the reaction solution with dichloromethane, it was washed with water. The solvent was removed from the reaction solution by concentration under reduced pressure to obtain 8.6 g (yield: 100%) of a red solid carboxylic acid derivative having a tetrakis(pentafluorophenyl)borate (IV) anion (Compound 6).

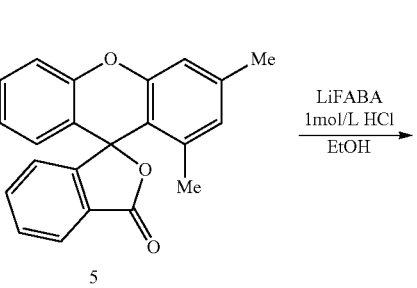

5

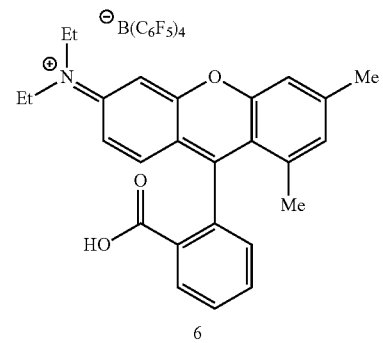

6

Example 5 Synthesis of a Carboxylic Acid Derivative (Compound 8)

Into a round-bottom flask equipped with a stirring apparatus, 5.1 g (9.0 mmol) of 2'-(dibenzylamino)-6'-(diethylamino)fluoran (Compound 7: produced by Tokyo Chemical Industry Co., Ltd.), 27 mL (27.0 mmol) of 1 mol/L aqueous solution of hydrochloric acid (produced by Wako Pure Chemical Industries, Ltd.), 6.7 g (9.0 mmol) of LiFABA (produced by Tosoh Finechem Corp.), 100 mL of ethanol, and 15 mL of dichloromethane were added, and the reaction was carried out at room temperature for 5 hours. After dilution of the reaction solution with dichloromethane, it was washed with water. The solvent was removed from the reaction solution by concentration under reduced pressure to obtain 11.2 g (yield: 100%) of a dark green solid carboxylic acid derivative having a tetrakis(pentafluorophenyl)borate (IV) anion (Compound 8).

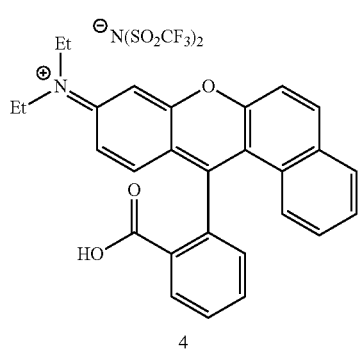

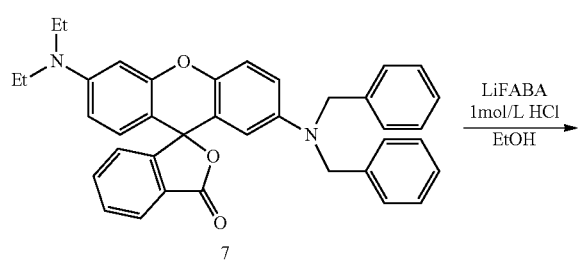

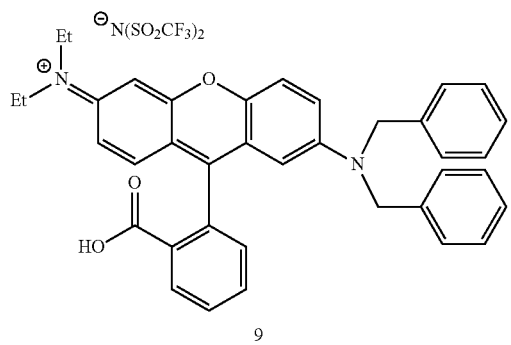

Example 7 Synthesis of a Carboxylic Acid Derivative (Compound 13)

(1) Synthesis of a Lactone Derivative (Compound 12)

Into a round-bottom flask equipped with a stirring apparatus, 54.8 g (175.0 mmol) of 2-(4-diethylamino-2-hydroxybenzoyl) benzoic acid (Compound 10: produced by Tokyo Chemical Industry Co., Ltd.), 25.6 g (210.0 mmol) of p-fluorophenol (Compound 11: produced by Wako Pure Chemical Industries, Ltd.), and 160 mL of methanesulfonic acid (produced by Wako Pure Chemical Industries, Ltd.) were added, and the reaction was carried out at 90° C. for 6 hours. After completion of the reaction, dichloromethane and water were added, and then a 25% aqueous sodium hydroxide was added for neutralization, and a reaction was carried out at room temperature for 1 hour. An organic layer, obtained by solution separation from the resulting reaction solution, was washed with water, and then the solvent was removed from the reaction solution by concentration under reduced pressure, and dried to obtain 63.8 g (yield: 94%) of a white solid lactone derivative (Compound 12).

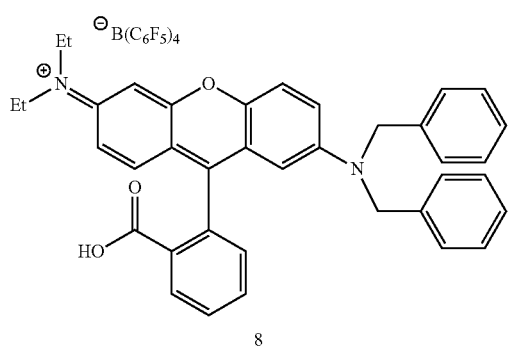

Example 6 Synthesis of a Carboxylic Acid Derivative (Compound 9)

Into a round-bottom flask equipped with a stirring apparatus, 8.5 g (15.0 mmol) of 2'-(dibenzylamino)-6'-(diethylamino)fluoran (Compound 7: produced by Tokyo Chemical Industry Co., Ltd.), 45 mL (45.0 mmol) of 1 mol/L aqueous solution of hydrochloric acid (produced by Wako Pure Chemical Industries, Ltd.), 4.3 g (15.0 mmol) of LiN(SO$_2$CF$_3$)$_2$ (produced by Wako Pure Chemical Industries, Ltd.), 150 mL of ethanol, and 15 mL of dichloromethane were added, and the reaction was carried out at room temperature for 5 hours. After dilution of the reaction solution with dichloromethane, it was washed with water. The solvent was removed from the reaction solution by concentration under reduced pressure to obtain 12.5 g (yield: 98%) of a dark green solid carboxylic acid derivative having a bis(trifluoromethanesulfonyl)imide anion (Compound 9).

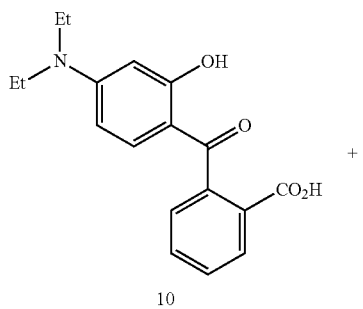

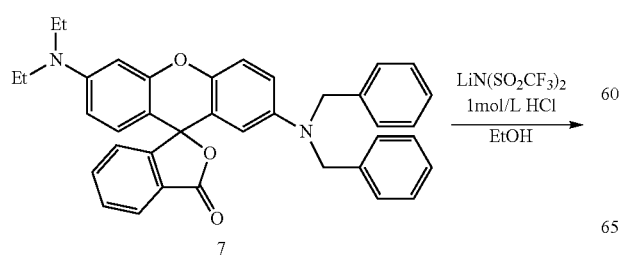

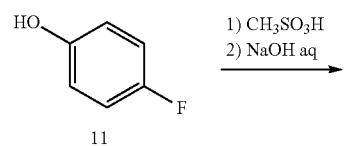

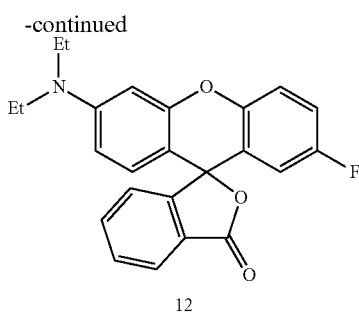

12

(2) Synthesis of a Carboxylic Acid Derivative (Compound 13)

Into a round-bottom flask equipped with a stirring apparatus, 31.2 g (80.0 mmol) of the lactone derivative (Compound 12) obtained in the (1), 200 mL (200.0 mmol) of 1 mol/L aqueous solution of hydrochloric acid (produced by Wako Pure Chemical Industries, Ltd.), 59.7 g (80.0 mmol) of LiFABA (produced by Tosoh Finechem Corp.), 500 mL of ethanol, and 100 mL of dichloromethane were added, and the reaction was carried out at room temperature for 3 hours. After dilution of the reaction solution with dichloromethane, it was washed with water. The solvent was removed from the reaction solution by concentration under reduced pressure to obtain 85.5 g (yield: 100%) of a red solid carboxylic acid derivative having a tetrakis(pentafluorophenyl)borate (IV) anion (Compound 13).

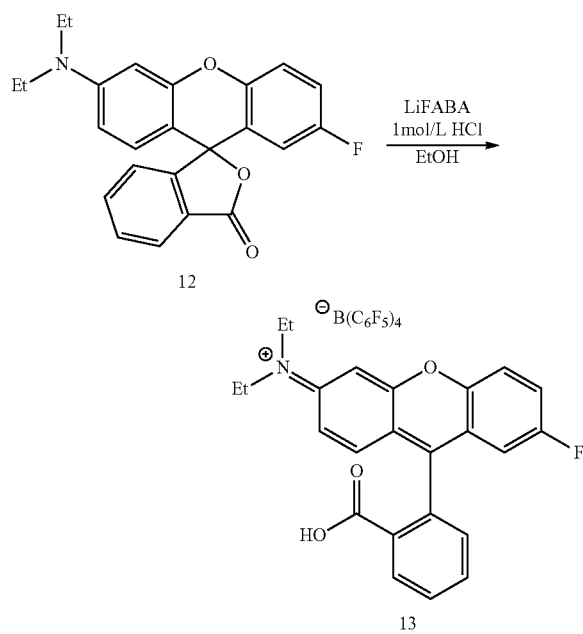

Example 8 Synthesis of a Methyl Ester Derivative (Compound 15)

(1) Synthesis of a Methyl Ester Derivative (Compound 14)

Into a round-bottom flask equipped with a stirring apparatus, 1.5 g (3.6 mmol) of 6'-(diethylamino)-1',2'-benzofluoran (Compound 1: produced by Tokyo Chemical Industry Co., Ltd.), 1 mL of concentrated sulfuric acid (produced by Wako Pure Chemical Industries, Ltd.), and 20 mL of methanol were added, and the reaction was carried out at 60° C. for 30 hours. After dilution of the reaction solution with dichloromethane, it was washed with water. The solvent was removed from the reaction solution by concentration under reduced pressure to obtain a reddish-brown solid. The solid was purified by a silica gel column to obtain 1.6 g (yield: 83%) of a reddish-brown solid methyl ester derivative (Compound 14).

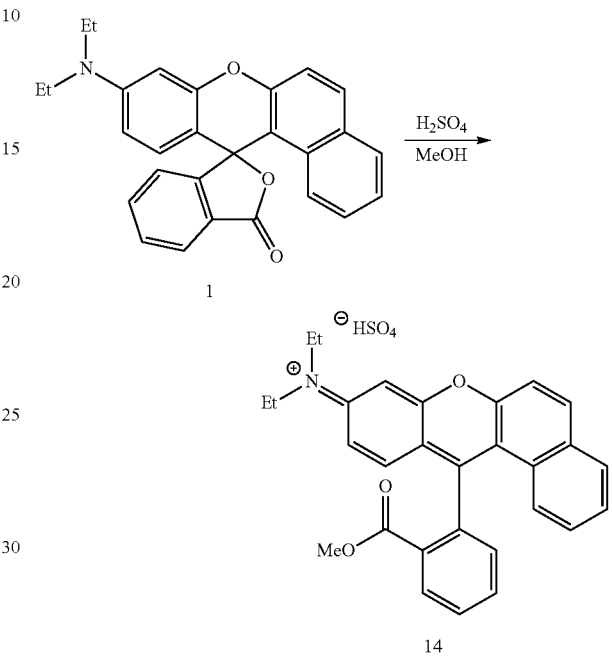

(2) Synthesis of a Methyl Ester Derivative (Compound 15)

Into a round-bottom flask equipped with a stirring apparatus, 0.5 g (1.0 mmol) of the methyl ester derivative (Compound 14) obtained in the (1), 3 mL (3.0 mmol) of 1 mol/L aqueous solution of hydrochloric acid (produced by Wako Pure Chemical Industries, Ltd.), 0.7 g (1.0 mmol) of LiFABA (produced by Tosoh Finechem Corp.), and 10 mL of ethanol were added, and the reaction was carried out at room temperature for 3 hours. After dilution of the reaction solution with dichloromethane, it was washed with water. The solvent was removed by concentration under reduced pressure from an organic layer, obtained by solution separation from the resulting reaction solution, to obtain 1.1 g (yield: 96%) of a reddish-brown solid methyl ester derivative having a tetrakis(pentafluorophenyl)borate (IV) anion (Compound 15).

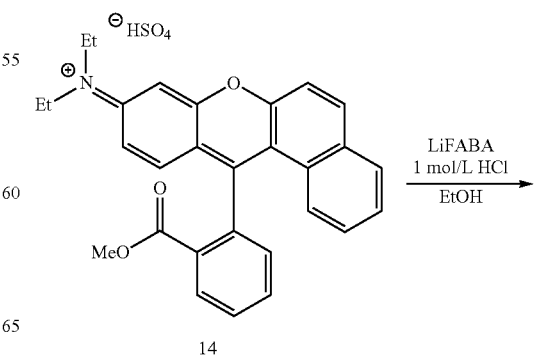

14

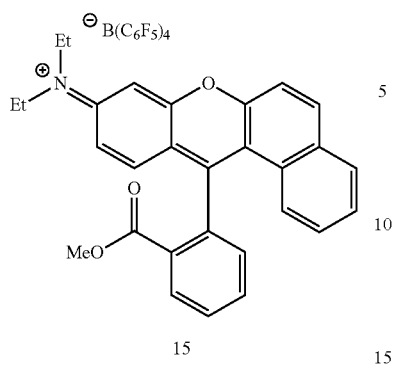

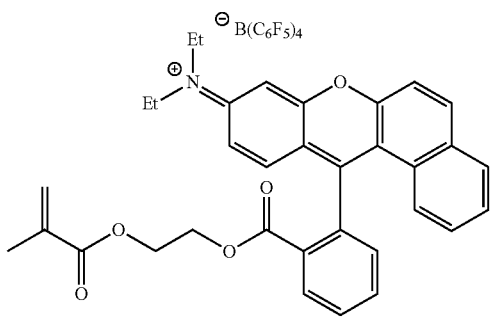

Example 9 Synthesis of a Monomer (Compound 17)

Into a round-bottom flask equipped with a stirring apparatus, 11.4 g (10.3 mmol) of the carboxylic acid derivative (Compound 3) obtained in Example 2, and 100 mL of dichloromethane were added for dissolution, and 1.6 g (12.4 mmol) of 2-hydroxyethyl methacrylate (Compound 16: produced by Wako Pure Chemical Industries, Ltd.), 0.4 g (3.1 mmol) of 4-dimethylaminopyridine (DMAP) (produced by Wako Pure Chemical Industries, Ltd.), and 3.4 g (17.5 mmol) of a 1-ethyl-3-(3-dimethylaminopropyl)carbodiimide hydrochloride (WSC) (produced by Toyobo Co., Ltd.) were added, and the reaction was carried out at 40° C. for 6 hours. After washing the reaction solution with water, the solvent was removed from the reaction solution by concentration under reduced pressure to obtain a reddish-brown solid. The solid was purified by a silica gel column to obtain 4.2 g (yield: 33%) of a reddish-brown solid monomer (Compound 17).

Example 10 Synthesis of a Monomer (Compound 18)

Into a round-bottom flask equipped with a stirring apparatus, 9.0 g (8.3 mmol) of the carboxylic acid derivative (Compound 6) obtained in Example 4, and 81 mL of dichloromethane were added for dissolution, and further 1.3 g (10.0 mmol) of 2-hydroxyethyl methacrylate (Compound 16: produced by Wako Pure Chemical Industries, Ltd.), 0.3 g (2.5 mmol) of DMAP (produced by Wako Pure Chemical Industries, Ltd.), and 2.7 g (14.2 mmol) of WSC (produced by Toyobo Co., Ltd.) were added, and the reaction was carried out at room temperature for 5 hours. After washing the reaction solution with water, the solvent was removed from the reaction solution by concentration under reduced pressure to obtain a red solid. The solid was purified by a silica gel column to obtain 4.6 g (yield: 46%) of a red solid monomer (Compound 18).

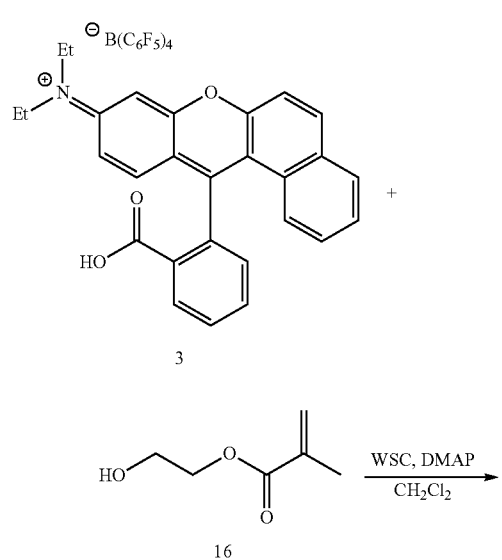

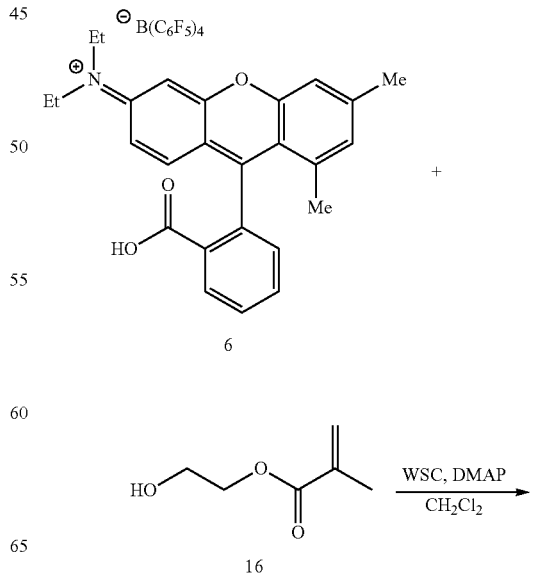

-continued

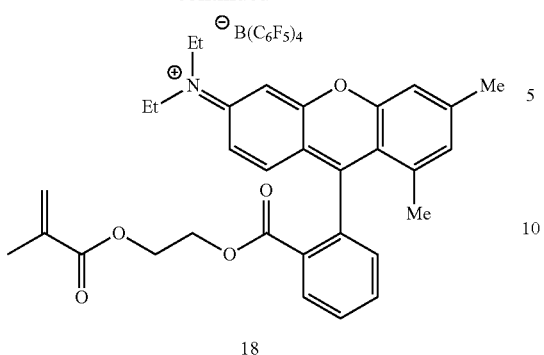

18

Example 11 Synthesis of a Monomer (Compound 19)

Into a round-bottom flask equipped with a stirring apparatus, 11.4 g (9.2 mmol) of the carboxylic acid derivative (Compound 8) obtained in Example 5, and 100 mL of dichloromethane were added for dissolution, and further 1.4 g (11.0 mmol) of 2-hydroxyethyl methacrylate (Compound 16: produced by Wako Pure Chemical Industries, Ltd.), 0.3 g (2.8 mmol) of DMAP (produced by Wako Pure Chemical Industries, Ltd.), and 3.0 g (15.6 mmol) of WSC (produced by Toyobo Co., Ltd.) were added, and the reaction was carried out at room temperature for 8 hours. After washing the reaction solution with water, the solvent was removed from the reaction solution by concentration under reduced pressure to obtain a deep green solid. The solid was purified by a silica gel column to obtain 8.7 g (yield: 70%) of a deep green solid monomer (Compound 19).

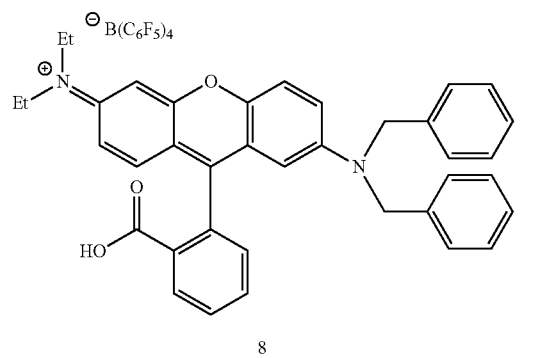

8

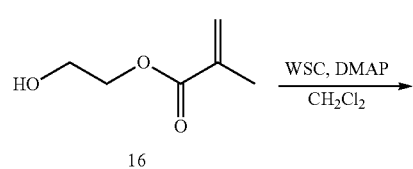

16

-continued

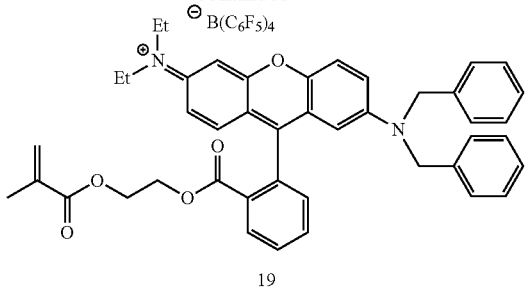

19

Example 12 Synthesis of a Monomer (Compound 20)

Into a round-bottom flask equipped with a stirring apparatus, 8.5 g (10.0 mmol) of the carboxylic acid derivative (Compound 9) obtained in Example 6, and 60 mL of dichloromethane were added for dissolution, and further 1.6 g (12.0 mmol) of 2-hydroxyethyl methacrylate (Compound 16: produced by Wako Pure Chemical Industries, Ltd.), 0.4 g (3.0 mmol) of DMAP (produced by Wako Pure Chemical Industries, Ltd.), and 3.3 g (17.0 mmol) of WSC (produced by Toyobo Co., Ltd.) were added, and the reaction was carried out at room temperature for 6 hours. After washing the reaction solution with water, the solvent was removed from the reaction solution by concentration under reduced pressure to obtain a deep green solid. The solid was purified by a silica gel column to obtain 6.4 g (yield: 67%) of a deep green solid monomer (Compound 20).

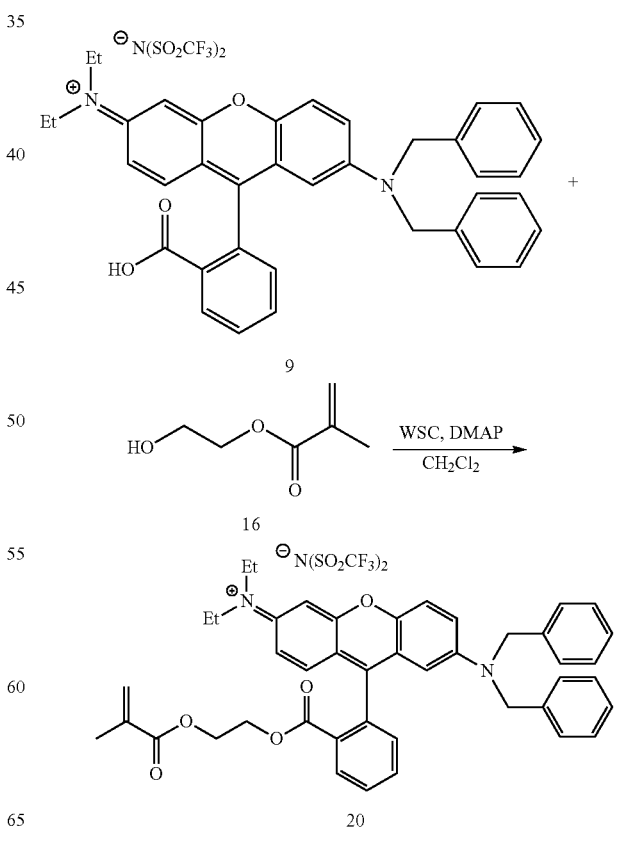

Example 13 Synthesis of a Monomer (Compound 21)

Into a round-bottom flask equipped with a stirring apparatus, 82.9 g (77.5 mmol) of the carboxylic acid derivative (Compound 13) obtained in Example 7, and 580 mL of dichloromethane were added for dissolution, and further 12.1 g (93.0 mmol) of 2-hydroxyethyl methacrylate (Compound 16: produced by Wako Pure Chemical Industries, Ltd.), 2.8 g (23.3 mmol) of DMAP (produced by Wako Pure Chemical Industries, Ltd.), and 25.3 g (131.8 mmol) of WSC (produced by Toyobo Co., Ltd.) were added, and the reaction was carried out at room temperature for 6 hours. After washing the reaction solution with water, the solvent was removed from the reaction solution by concentration under reduced pressure to obtain a red solid. The solid was purified by a silica gel column to obtain 32.7 g (yield: 36%) of a red solid monomer (Compound 21).

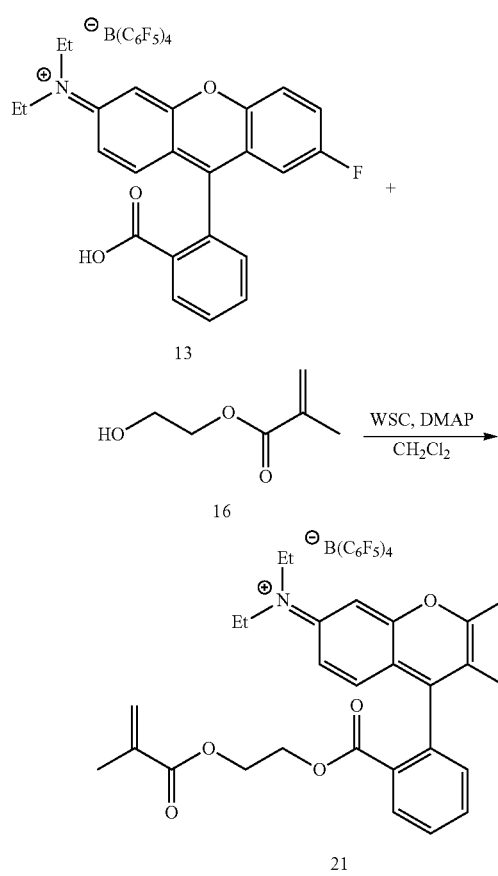

Example 14 Synthesis of a Carboxylic Acid Derivative (Compound 27)

(1) Synthesis of a Benzoic Acid Derivative (Compound 24)

Into a round-bottom flask equipped with a stirring apparatus, 1.9 g (9.8 mmol) of 2,3,6,7-tetrahydro-1,5-benzo[ij]quinolidine-8-ol (Compound 22: produced by Wako Pure Chemical Industries, Ltd.), 1.6 g (9.8 mmol) of phthalic anhydride (Compound 23: produced by Wako Pure Chemical Industries, Ltd.), and 30 mL of toluene were added, and the reaction was carried out at 100° C. for 6 hours. After completion of the reaction, the crystal precipitated by cooling to room temperature was filtrated, and washed with methanol, and dried to obtain 2.3 g (yield: 70%) of a white solid benzoic acid derivative (Compound 24).

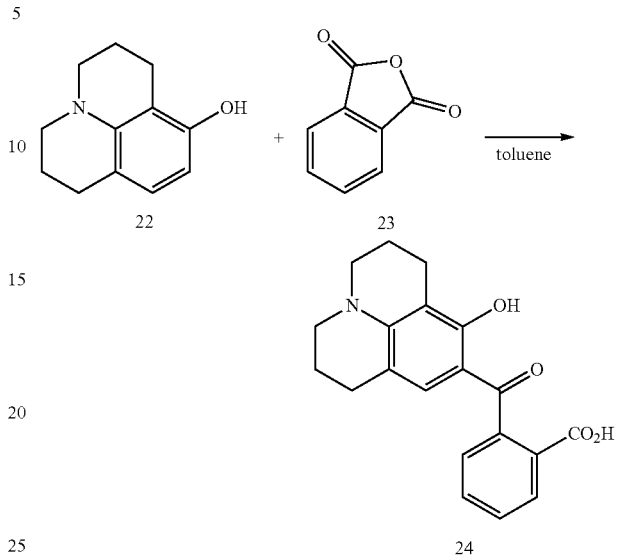

(2) Synthesis of a Lactone Derivative (Compound 26)

Into a round-bottom flask equipped with a stirring apparatus, 1.2 g (3.6 mmol) of the benzoic acid derivative (Compound 24) obtained in the (1), 0.6 g (3.9 mmol) of 2-naphthol (Compound 25: produced by Wako Pure Chemical Industries, Ltd.), and 5 mL of methanesulfonic acid (produced by Wako Pure Chemical Industries, Ltd.) were added, and the reaction was carried out at 90° C. for 6 hours. After completion of the reaction, dichloromethane and water were added to the resulting reaction solution, and then a 25% aqueous sodium hydroxide was added for neutralization, and a reaction was carried out at room temperature for 1 hour. An organic layer, obtained by solution separation from the resulting reaction solution, was washed with water, and the solvent was removed from the reaction solution by concentration under reduced pressure to obtain a white solid. The solid was purified by a silica gel column to obtain 1.0 g (yield: 63%) of a white solid lactone derivative (Compound 26).

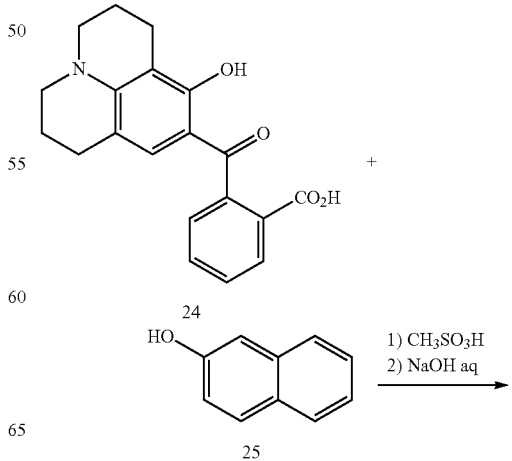

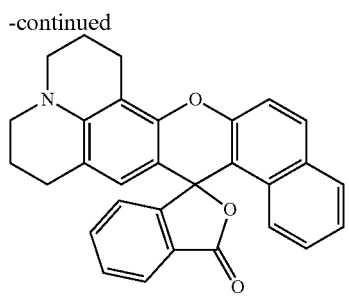

26

(3) Synthesis of a Carboxylic Acid Derivative (Compound 27)

Into a round-bottom flask equipped with a stirring apparatus, 0.8 g (1.7 mmol) of the lactone derivative (Compound 26) obtained in the (2), 5.1 mL (5.1 mmol) of 1 mol/L aqueous solution of hydrochloric acid (produced by Wako Pure Chemical Industries, Ltd.), 1.3 g (1.7 mmol) of LiFABA (produced by Tosoh Finechem Corp.), 15 mL of ethanol, and 15 mL of dichloromethane were added, and the reaction was carried out at 35° C. for 4 hours. After dilution of the reaction solution with methylene chloride, it was washed with water. The solvent was removed from the reaction solution by concentration under reduced pressure to obtain 1.9 g (yield: 100%) of a brown solid carboxylic acid derivative having a tetrakis(pentafluorophenyl)borate (IV) anion as a counter anion (Compound 27).

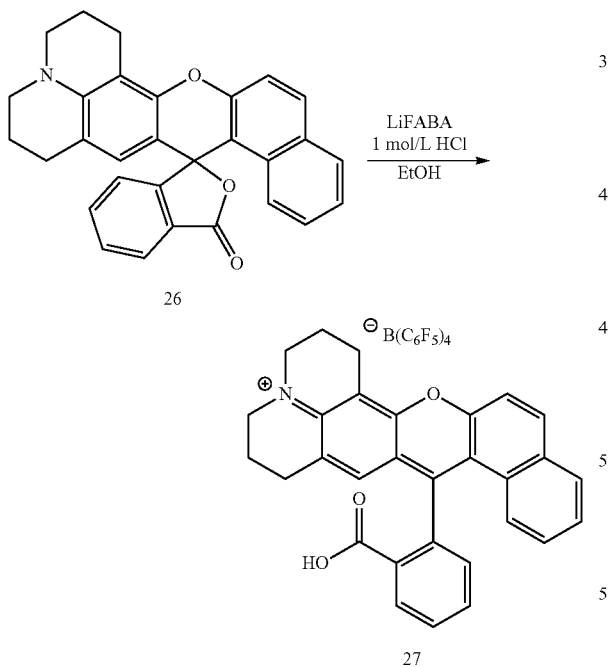

Example 15 Synthesis of a Monomer (Compound 28)

Into a round-bottom flask equipped with a stirring apparatus, 1.5 g (1.3 mmol) of the carboxylic acid derivative (Compound 27) obtained in Example 14, and 13 mL of dichloromethane were added for dissolution, and further 0.2 g (1.7 mmol) of 2-hydroxyethyl methacrylate (Compound 16: produced by Wako Pure Chemical Industries, Ltd.), 0.1 g (0.4 mmol) of DMAP (produced by Wako Pure Chemical Industries, Ltd.), and 0.4 g (2.3 mmol) of WSC (produced by Toyobo Co., Ltd.) were added, and the reaction was carried out at room temperature for 5 hours. An organic layer of the resulting reaction solution was washed with water, and the solvent was removed from the reaction solution by concentration under reduced pressure to obtain a reddish-brown solid. The solid was purified by a silica gel column to obtain 1.1 g (yield: 64%) of a reddish-brown solid monomer (Compound 28).

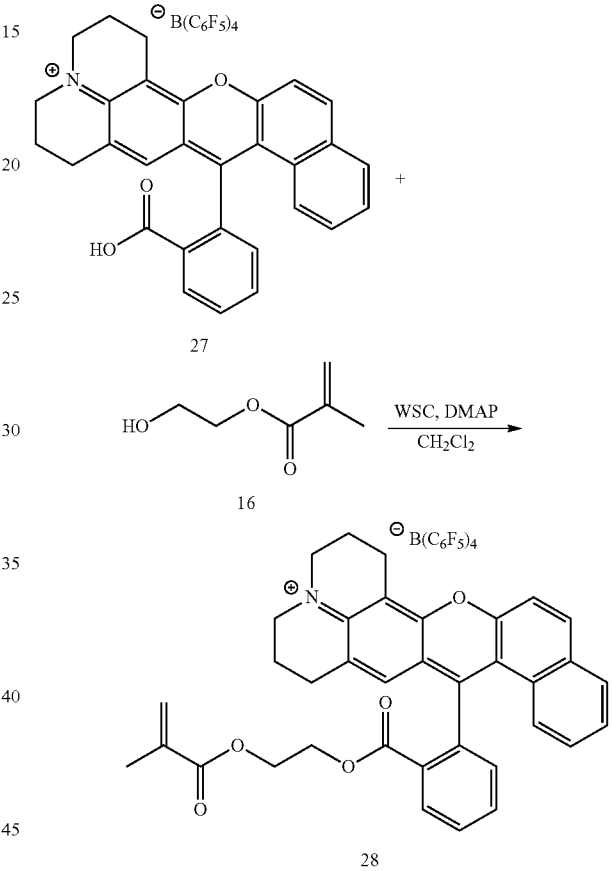

Example 16 Synthesis of a Monomer (Compound 30)

Into a round-bottom flask equipped with a stirring apparatus, 3.2 g (2.9 mmol) of the carboxylic acid derivative (Compound 3) obtained in Example 2, and 15 mL of tetrahydrofuran were added for dissolution, and further 0.4 g (3.5 mmol) of 2-hydroxyethyl acrylate (Compound 29: produced by Wako Pure Chemical Industries, Ltd.), 0.1 g (0.9 mmol) of DMAP (produced by Wako Pure Chemical Industries, Ltd.), and 0.9 g (4.9 mmol) of WSC (produced by Toyobo Co., Ltd.) were added, and the reaction was carried out at room temperature for 5 hours. An organic layer of the resulting reaction solution was washed with water, and the solvent was removed from the reaction solution by concentration under reduced pressure to obtain a reddish-brown solid. The solid was purified by a silica gel column to obtain 0.9 g (yield: 26%) of a reddish-brown solid monomer (Compound 30).

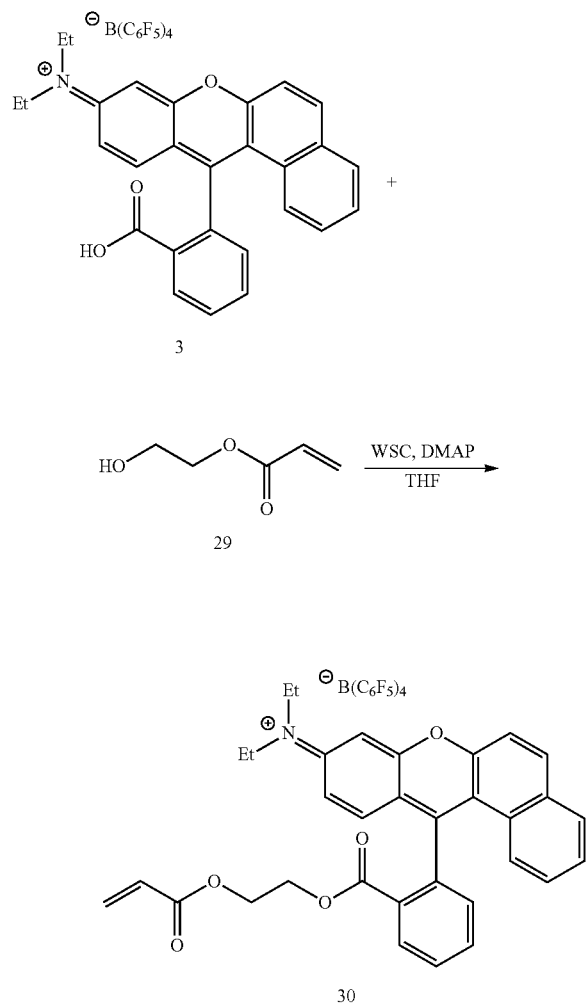

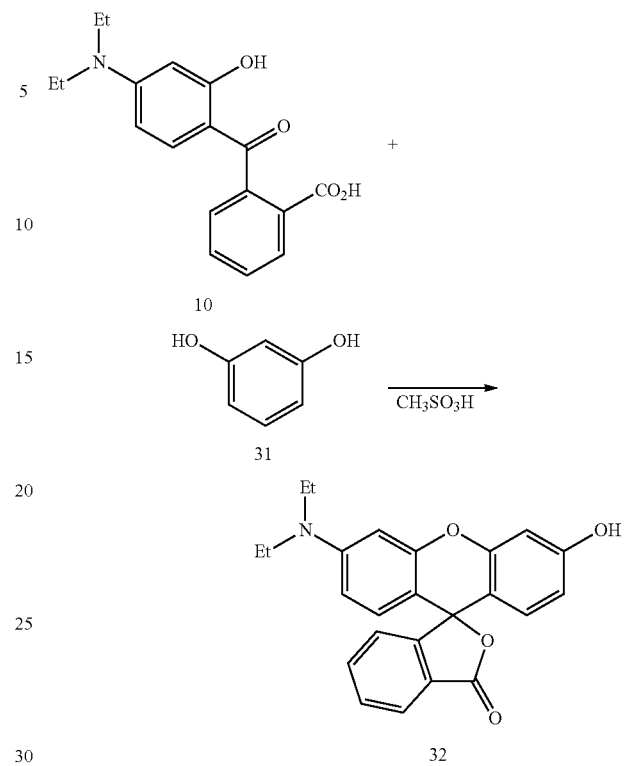

Example 17 Synthesis of a Carboxylic Acid Derivative (Compound 33)

(1) Synthesis of a Lactone Derivative (Compound 32)

Into a round-bottom flask equipped with a stirring apparatus, 2.1 g (5.0 mmol) of 2-(4-diethylamino-2-hydroxybenzoyl) benzoic acid (Compound 10: produced by Tokyo Chemical Industry Co., Ltd.), 0.7 g (6.0 mmol) of resorcinol (Compound 31: produced by Wako Pure Chemical Industries, Ltd.), and 6 mL of methanesulfonic acid (produced by Wako Pure Chemical Industries, Ltd.) were added, and the reaction was carried out at 90° C. for 8 hours. After completion of the reaction, dichloromethane and water were added, and an organic layer was obtained by solution separation, and then the solvent was removed from the reaction solution by concentration under reduced pressure. Ethyl acetate was added to the resulting black solid and stirred, and the precipitated solid was dried to obtain 1.8 g (yield: 94%) of a black solid lactone derivative (Compound 32).

(2) Synthesis of a Carboxylic Acid Derivative (Compound 33)

Into a round-bottom flask equipped with a stirring apparatus, 1.2 g (3.0 mmol) of the lactone derivative (Compound 32) obtained in the (1), and 19 mL of dichloromethane were added for dissolution, and further 0.2 g (6.0 mmol) of concentrated hydrochloric acid (produced by Wako Pure Chemical Industries, Ltd.), and 2.3 g (3.0 mmol) of LiFABA (produced by Tosoh Finechem Corp.) were added, and the reaction was carried out at room temperature for 2 hours. After dilution of the reaction solution with dichloromethane, it was washed with water. The solvent was removed from the reaction solution by concentration under reduced pressure to obtain 2.7 g (yield: 84%) of a black solid carboxylic acid derivative having a tetrakis(pentafluorophenyl)borate (IV) anion as a counter anion (Compound 33).

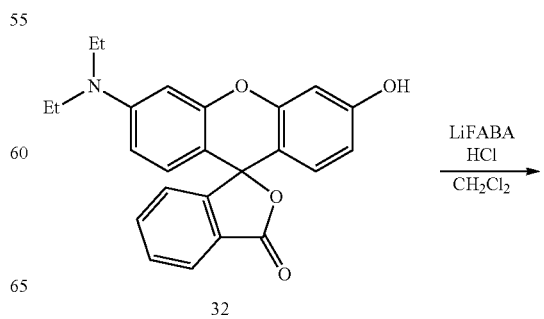

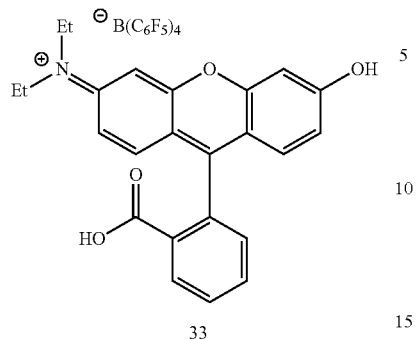

33

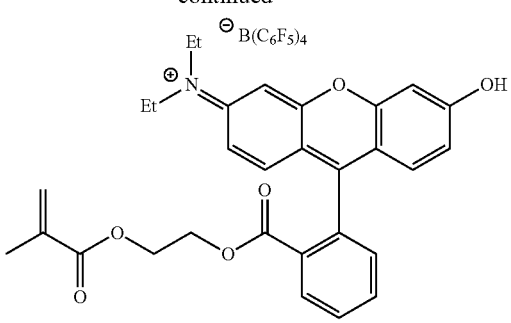

34

Example 18 Synthesis of a Monomer (Compound 34)

Into a round-bottom flask equipped with a stirring apparatus, 1.5 g (1.4 mmol) of the carboxylic acid derivative (Compound 33) obtained in Example 17, and 6 mL of dichloromethane were added for dissolution, and further 0.2 g (1.7 mmol) of 2-hydroxyethyl methacrylate (Compound 16: produced by Wako Pure Chemical Industries, Ltd.), 0.1 g (0.4 mmol) of DMAP (produced by Wako Pure Chemical Industries, Ltd.), and 0.5 g (2.4 mmol) of WSC (produced by Toyobo Co., Ltd.) were added, and the reaction was carried out at room temperature for 8 hours. The reaction solution was washed with water, and the solvent was removed from the reaction solution by concentration under reduced pressure to obtain a reddish-brown solid. The solid was purified by a silica gel column to obtain 0.2 g (yield: 10%) of a reddish-brown solid monomer (Compound 34).

Example 19 Synthesis of a Carboxylic Acid Derivative (Compound 37)

(1) Synthesis of a Lactone Derivative (Compound 36)

Into a round-bottom flask equipped with a stirring apparatus, 3.1 g (10.0 mmol) of 2-(4-diethylamino-2-hydroxybenzoyl) benzoic acid (Compound 10: produced by Tokyo Chemical Industry Co., Ltd.), 1.8 g (10.0 mmol) of 3,4,5-trimethoxyphenol (Compound 35: produced by Wako Pure Chemical Industries, Ltd.), and 10 mL of methanesulfonic acid (produced by Wako Pure Chemical Industries, Ltd.) were added, and the reaction was carried out at 80° C. for 3 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 4.0 g (yield: 87%) of a reddish-brown solid lactone derivative (Compound 36).

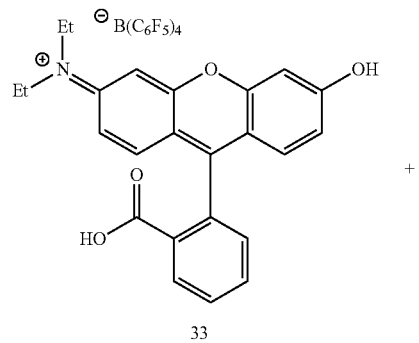

33

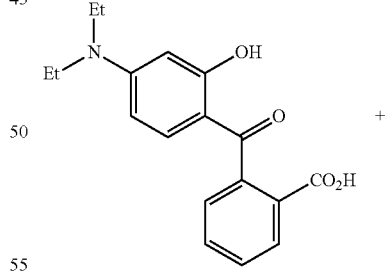

10

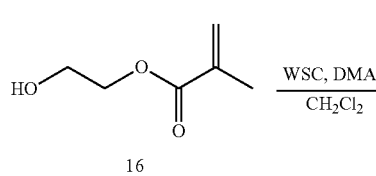

16

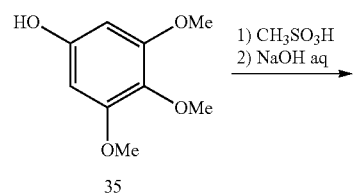

35

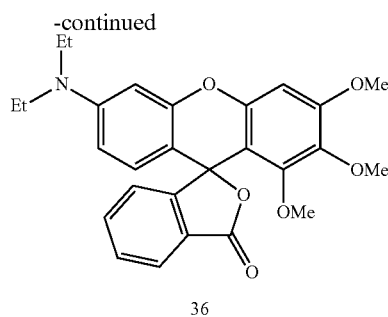

36

(2) Synthesis of a Carboxylic Acid Derivative (Compound 37)

Into a round-bottom flask equipped with a stirring apparatus, 1.0 g (2.2 mmol) of the lactone derivative (Compound 36) obtained in the (1), 0.5 g (4.5 mmol) of concentrated hydrochloric acid (produced by Wako Pure Chemical Industries, Ltd.), 1.7 g (2.2 mmol) of LiFABA (produced by Tosoh Finechem Corp.), and 10 mL of dichloromethane were added, and the reaction was carried out at room temperature for 5 hours. After dilution of the reaction solution with dichloromethane, it was washed with water. The solvent was removed from the reaction solution by concentration under reduced pressure to obtain 2.5 g (yield: 100%) of a red solid carboxylic acid derivative having a tetrakis(pentafluorophenyl)borate (IV) anion as a counter anion (Compound 37).

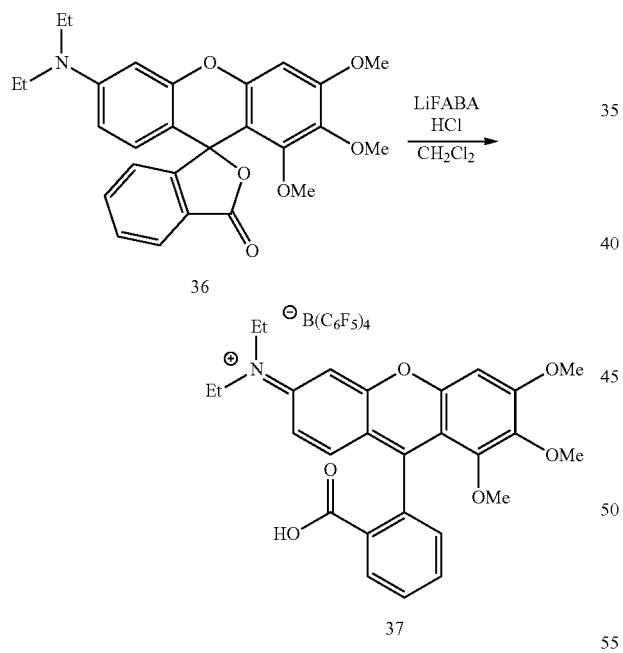

Example 20 Synthesis of a Monomer (Compound 38)

Into a round-bottom flask equipped with a stirring apparatus, 2.0 g (1.8 mmol) of the carboxylic acid derivative (Compound 37) obtained in Example 19, and 20 mL of dichloromethane were added for dissolution, and further 0.3 g (2.1 mmol) of 2-hydroxyethyl methacrylate (Compound 16: produced by Wako Pure Chemical Industries, Ltd.), 0.1 g (0.5 mmol) of DMAP (produced by Wako Pure Chemical Industries, Ltd.), and 0.6 g (3.0 mmol) of WSC (produced by Toyobo Co., Ltd.) were added, and the reaction was carried out at room temperature for 4 days. The reaction solution was washed with water, and the solvent was removed from the reaction solution by concentration under reduced pressure to obtain a red solid. The solid was purified by a silica gel column to obtain 0.8 g (yield: 37%) of a red solid monomer (Compound 38).

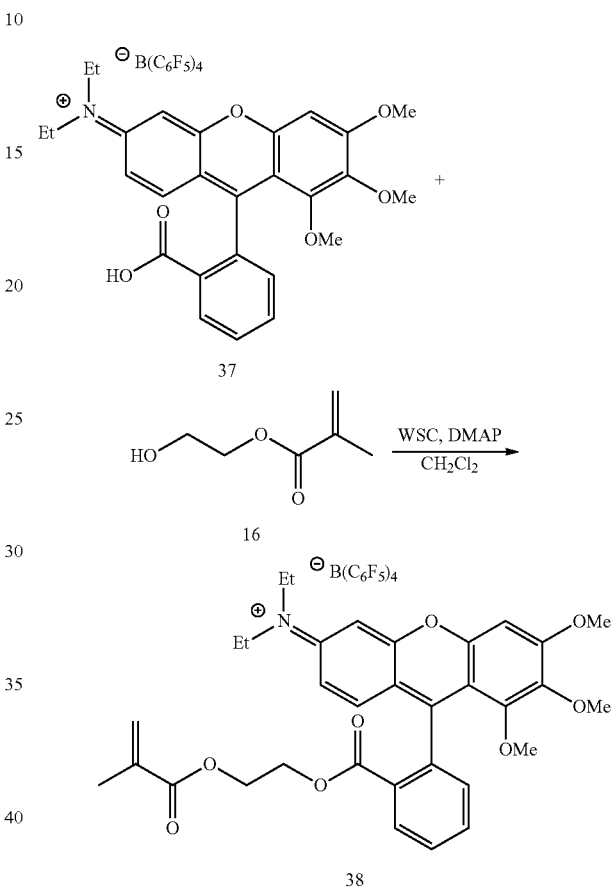

Example 21 Synthesis of a Carboxylic Acid Derivative (Compound 42)

(1) Synthesis of a Methyl Derivative (Compound 40)

Into a round-bottom flask equipped with a stirring apparatus, 1.6 g (10.0 mmol) of 1,6-dihydroxynaphthalene (Compound 39: produced by Tokyo Chemical Industry Co., Ltd.), and 15 mL of N,N-dimethylformamide (DMF) were added for dissolution, and further 14.2 g (100.0 mmol) of methyl iodide (produced by Wako Pure Chemical Industries, Ltd.), and 13.8 g (100.0 mmol) of potassium carbonate (produced by Wako Pure Chemical Industries, Ltd.) were added, and the reaction was carried out at room temperature for 2 hours. After completion of the reaction, dichloromethane and water were added, and then an organic layer, obtained by solution separation, was washed with water, and the solvent was removed from the reaction solution by concentration under reduced pressure to obtain 1.7 g (yield: 90%) of a colorless liquid methyl derivative (Compound 40).

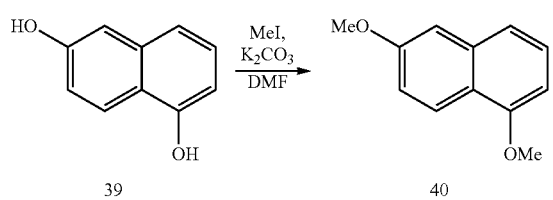

(2) Synthesis of a Lactone Derivative (Compound 41)

Into a round-bottom flask equipped with a stirring apparatus, 2.7 g (8.5 mmol) of 2-(4-diethylamino-2-hydroxybenzoyl) benzoic acid (Compound 10: produced by Tokyo Chemical Industry Co., Ltd.), 1.8 g (9.4 mmol) of the methyl derivative (Compound 40) obtained in the (1), and 10 mL of methanesulfonic acid (produced by Wako Pure Chemical Industries, Ltd.) were added, and the reaction was carried out at 90° C. for 3 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 1.7 g (yield: 44%) of a reddish-brown solid lactone derivative (Compound 41).

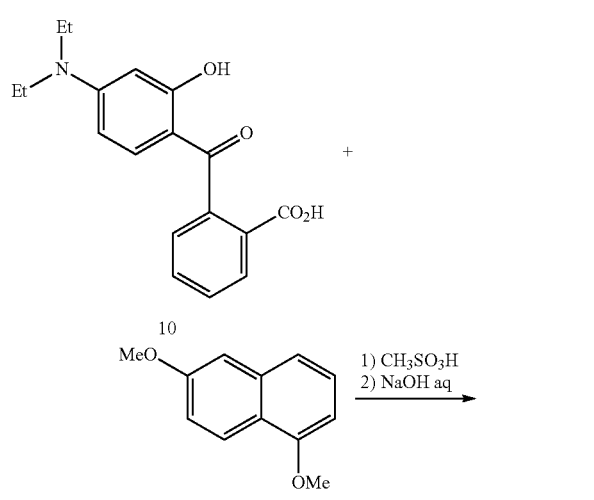

(3) Synthesis of a Carboxylic Acid Derivative (Compound 42)

Into a round-bottom flask equipped with a stirring apparatus, 0.5 g (1.0 mmol) of the lactone derivative (Compound 41) obtained in the (2), 0.2 g (2.0 mmol) of concentrated hydrochloric acid (produced by Wako Pure Chemical Industries, Ltd.), 0.8 g (1.0 mmol) of LiFABA (produced by Tosoh Finechem Corp.), and 10 mL of dichloromethane were added, and the reaction was carried out at room temperature for 4.5 hours. After dilution of the reaction solution with dichloromethane, it was washed with water. The solvent was removed from the reaction solution by concentration under reduced pressure to obtain 1.1 g (yield: 96%) of a reddish-brown solid carboxylic acid derivative having a tetrakis (pentafluorophenyl)borate (IV) anion as a counter anion (Compound 42).

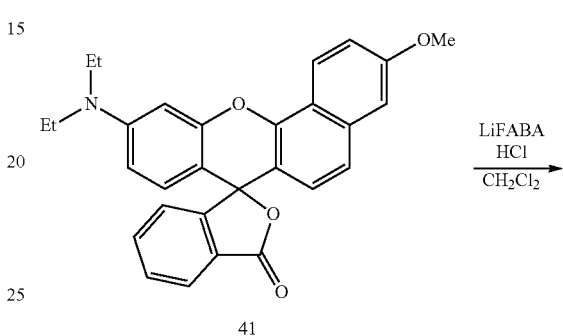

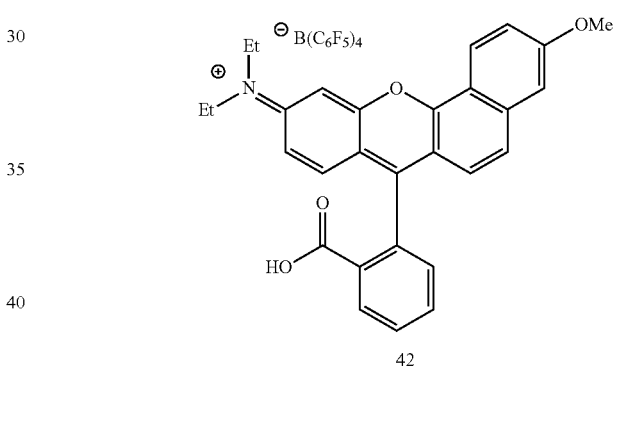

Example 22 Synthesis of a Monomer (Compound 43)

Into a round-bottom flask equipped with a stirring apparatus, 0.9 g (0.8 mmol) of the carboxylic acid derivative (Compound 42) obtained in Example 21, and 10 mL of dichloromethane were added for dissolution, and 0.1 g (0.9 mmol) of 2-hydroxyethyl methacrylate (Compound 16: produced by Wako Pure Chemical Industries, Ltd.), 0.1 g (0.9 mmol) of N,N'-diisopropylcarbodiimide (DIC) (Compound 16, produced by Wako Pure Chemical Industries, Ltd.), and 0.1 g (0.9 mmol) of DMAP (produced by Wako Pure Chemical Industries, Ltd.) were added, and the reaction was carried out at room temperature for 4 days. The reaction solution was washed with water, and the solvent was removed from the reaction solution by concentration under reduced pressure to obtain a reddish-brown solid. The solid was purified by a silica gel column to obtain 0.5 g (yield: 50%) of a reddish-brown solid monomer (Compound 43).

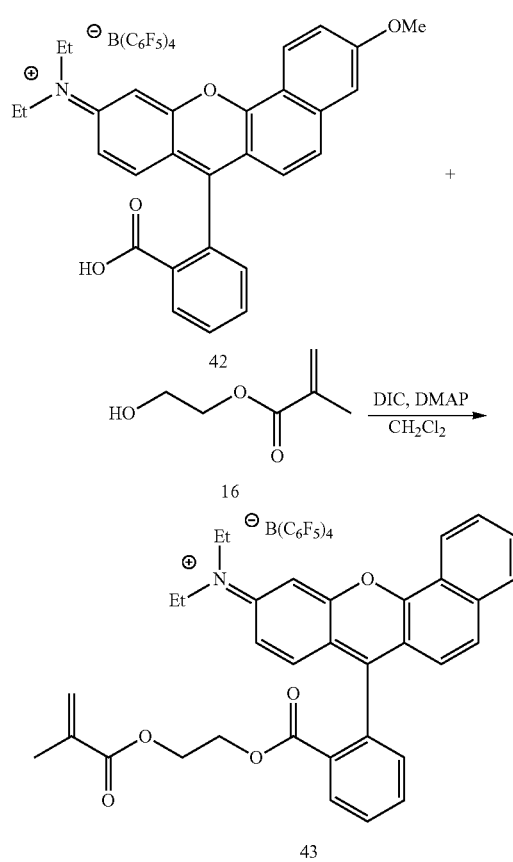

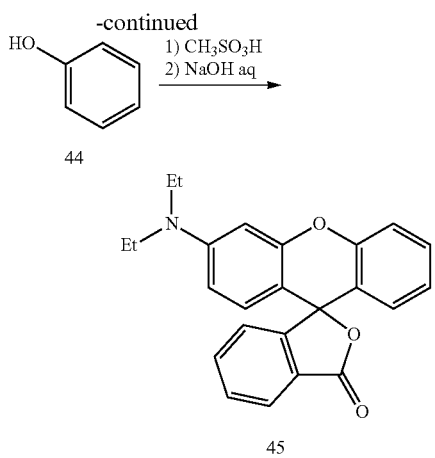

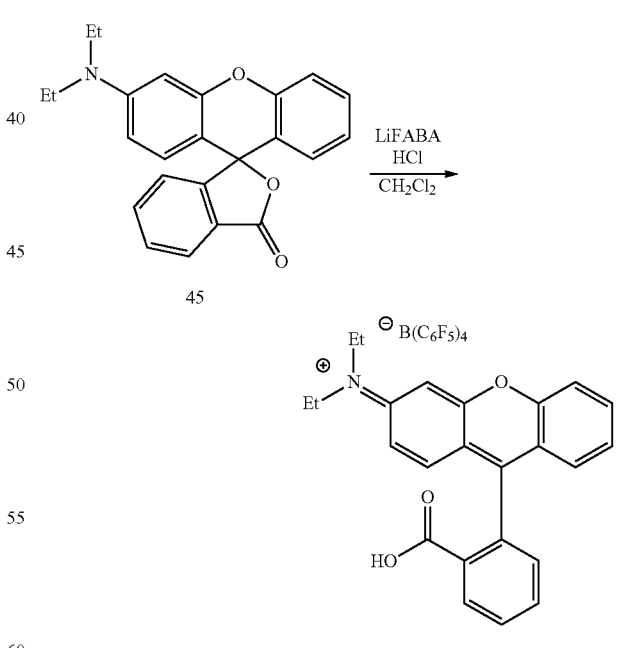

(2) Synthesis of a Carboxylic Acid Derivative (Compound 46)

Into a round-bottom flask equipped with a stirring apparatus, 0.8 g (2.1 mmol) of the lactone derivative (Compound 45) obtained in the (1), and 20 mL of dichloromethane were added for dissolution, and 0.4 g (4.2 mmol) of concentrated hydrochloric acid (produced by Wako Pure Chemical Industries, Ltd.), and 1.6 g (2.1 mmol) of LiFABA (produced by Tosoh Finechem Corp.) were added, and the reaction was carried out at room temperature for 2 hours. After dilution of the reaction solution with dichloromethane, it was washed with water. The solvent was removed from the reaction solution by concentration under reduced pressure to obtain 2.2 g (yield: 100%) of a black solid carboxylic acid derivative having a tetrakis(pentafluorophenyl)borate (IV) anion as a counter anion (Compound 46).

Example 23 Synthesis of a Carboxylic Acid Derivative (Compound 46)

(1) Synthesis of a Lactone Derivative (Compound 45)

Into a round-bottom flask equipped with a stirring apparatus, 4.7 g (15.0 mmol) of 2-(4-diethylamino-2-hydroxybenzoyl) benzoic acid (Compound 10: produced by Tokyo Chemical Industry Co., Ltd.), 1.6 g (15.8 mmol) of phenol (Compound 44: produced by Wako Pure Chemical Industries, Ltd.), and 15 mL of methanesulfonic acid (produced by Wako Pure Chemical Industries, Ltd.) were added, and the reaction was carried out at 90° C. for 3 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 1.7 g (yield: 28%) of a red solid lactone derivative (Compound 45).

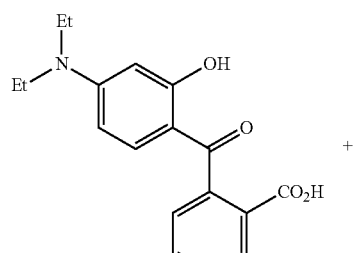

Example 24 Synthesis of a Monomer (Compound 47)

Into a round-bottom flask equipped with a stirring apparatus, 1.6 g (1.5 mmol) of the carboxylic acid derivative (Compound 46) obtained in Example 23, and 5 mL of dichloromethane were added for dissolution, and 0.2 g (1.7 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.5 g (2.6 mmol) of WSC (produced by Toyobo Co., Ltd.) were added, and the reaction was carried out at room temperature for 12 hours. The reaction solution was washed with water, and the solvent was removed from the reaction solution by concentration under reduced pressure to obtain a reddish-brown solid. The solid was purified by a silica gel column to obtain 0.3 g (yield: 18%) of a red solid monomer (Compound 47).

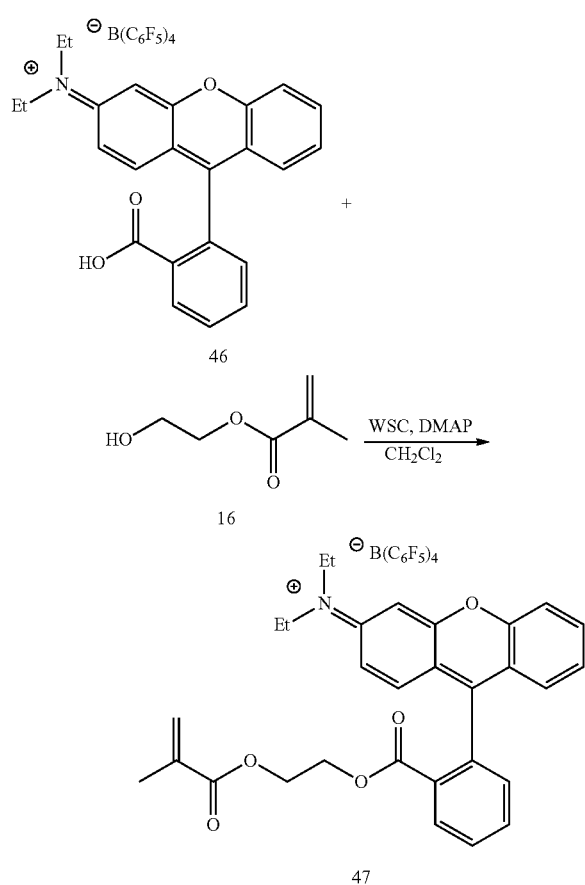

Example 25 Synthesis of a Carboxylic Acid Derivative (Compound 50)

(1) Synthesis of a Lactone Derivative (Compound 49)

Into a round-bottom flask equipped with a stirring apparatus, 4.7 g (15.0 mmol) of 2-(4-diethylamino-2-hydroxybenzoyl) benzoic acid (Compound 10: produced by Tokyo Chemical Industry Co., Ltd.), 2.4 g (15.8 mmol) of p-tert-butylphenol (Compound 48: produced by Wako Pure Chemical Industries, Ltd.), and 15 mL of methanesulfonic acid (produced by Wako Pure Chemical Industries, Ltd.) were added, and the reaction was carried out at 90° C. for 3 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 6.3 g (yield: 99%) of a red solid lactone derivative (Compound 49).

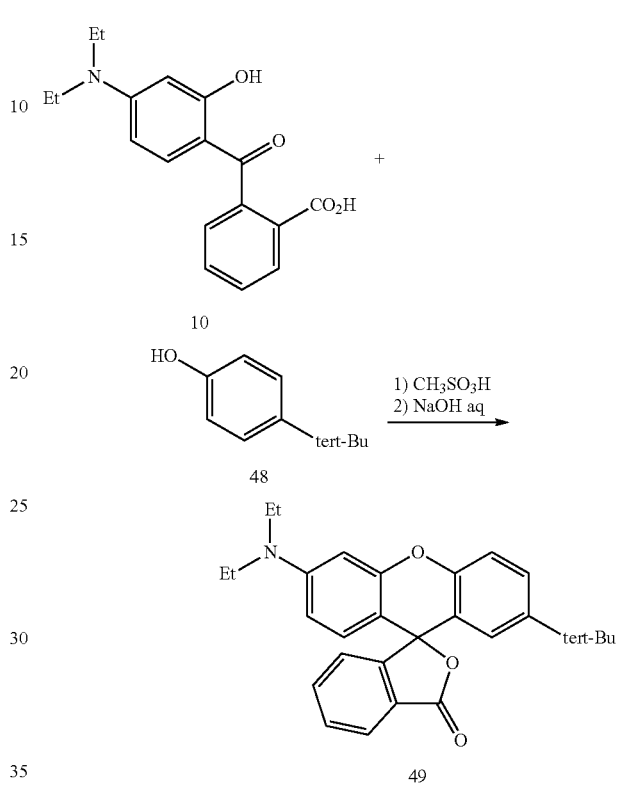

(2) Synthesis of a Carboxylic Acid Derivative (Compound 50)

Into a round-bottom flask equipped with a stirring apparatus, 1.2 g (2.8 mmol) of the lactone derivative (Compound 49) obtained in the (1), 0.6 g (5.6 mmol) of concentrated hydrochloric acid (produced by Wako Pure Chemical Industries, Ltd.), 2.1 g (2.8 mmol) of LiFABA (produced by Tosoh Finechem Corp.), and 25 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 3.1 g (yield: 100%) of a red solid carboxylic acid derivative having a tetrakis(pentafluorophenyl)borate (IV) anion as a counter anion (Compound 50).

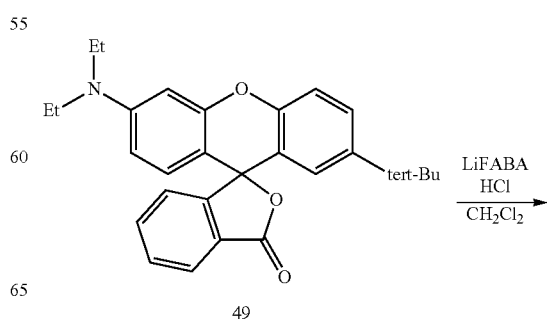

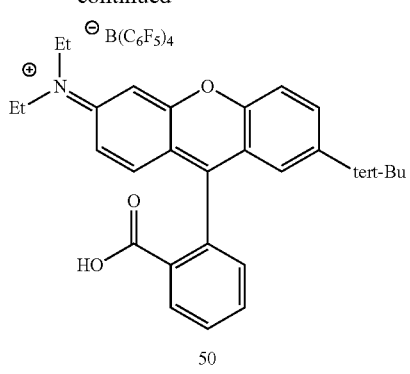

50

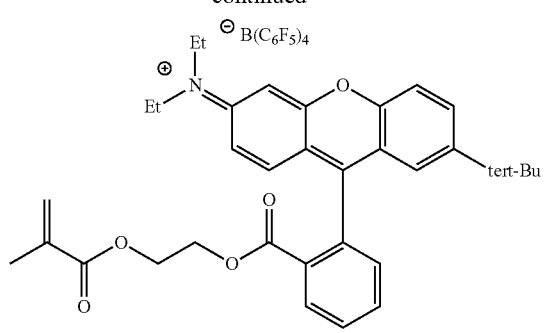

51

Example 26 Synthesis of a Monomer (Compound 51)

Into a round-bottom flask equipped with a stirring apparatus, 2.2 g (2.0 mmol) of the carboxylic acid derivative (Compound 50) obtained in Example 25, and 7 mL of dichloromethane were added for dissolution, and 0.3 g (2.2 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.7 g (3.4 mmol) of WSC (produced by Toyobo Co., Ltd.) were added, and the reaction was carried out at room temperature for 8 hours. The reaction solution was washed with water, and the solvent was removed from the reaction solution by concentration under reduced pressure to obtain a red solid. The solid was purified by a silica gel column to obtain 0.9 g (yield: 35%) of a red solid monomer (Compound 51).

Example 27 Synthesis of a Carboxylic Acid Derivative (Compound 54)

(1) Synthesis of a Lactone Derivative (Compound 53)

Into a round-bottom flask equipped with a stirring apparatus, 4.7 g (15.0 mmol) of 2-(4-di ethylamino-2-hydroxybenzoyl) benzoic acid (Compound 10: produced by Tokyo Chemical Industry Co., Ltd.), 2.7 g (15.8 mmol) of p-phenylphenol (Compound 52, produced by Wako Pure Chemical Industries, Ltd.), and 15 mL of methanesulfonic acid (produced by Wako Pure Chemical Industries, Ltd.) were added, and the reaction was carried out at 90° C. for 3 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 6.4 g (yield: 96%) of a red solid lactone derivative (Compound 53).

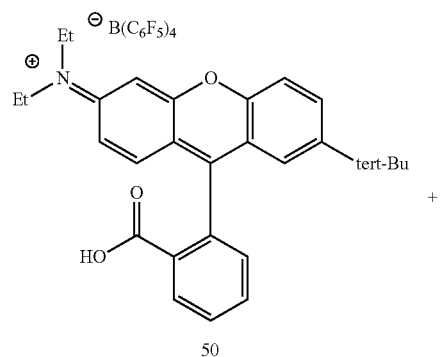

50

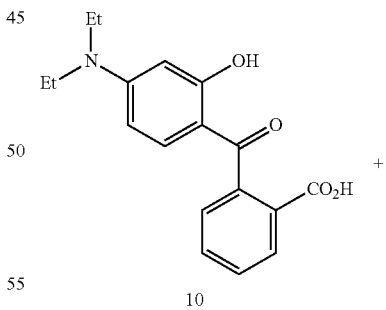

10

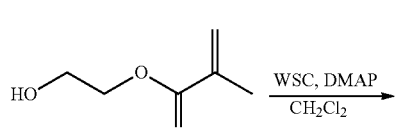

16

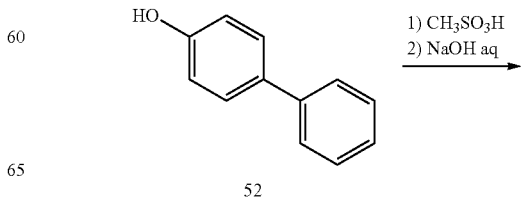

52

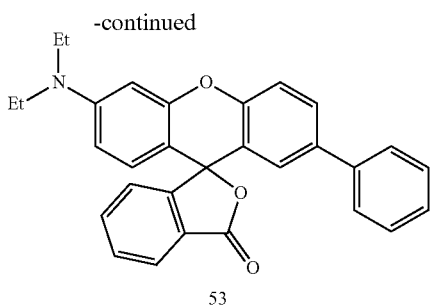

53

(2) Synthesis of a Carboxylic Acid Derivative (Compound 54)

Into a round-bottom flask equipped with a stirring apparatus, 1.4 g (3.1 mmol) of the lactone derivative (Compound 53) obtained in the (1), 0.7 g (6.2 mmol) of concentrated hydrochloric acid (produced by Wako Pure Chemical Industries, Ltd.), 2.4 g (3.1 mmol) of LiFABA (produced by Tosoh Finechem Corp.), and 30 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 3.5 g (yield: 100%) of a red solid carboxylic acid derivative having a tetrakis(pentafluorophenyl)borate (IV) anion as a counter anion (Compound 54).

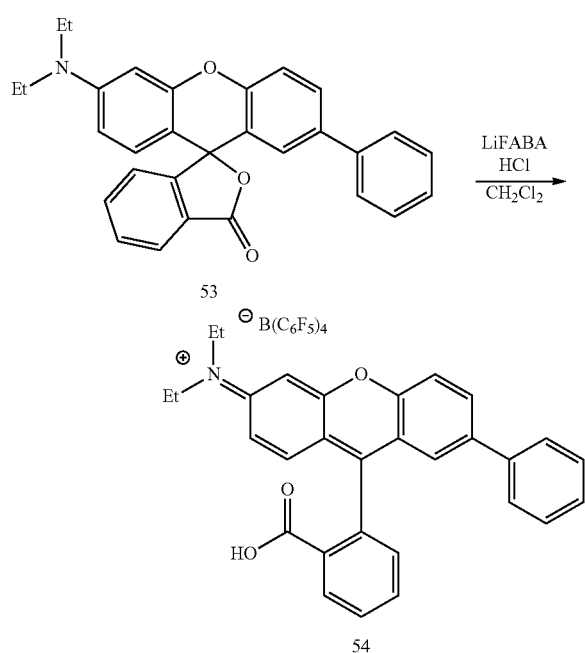

Example 28 Synthesis of a Monomer (Compound 55)

Into a round-bottom flask equipped with a stirring apparatus, 2.3 g (2.0 mmol) of the carboxylic acid derivative (Compound 54) obtained in Example 27, and 7 mL of dichloromethane were added for dissolution, and 0.3 g (2.2 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.7 g (3.4 mmol) of WSC (produced by Wako Pure Chemical Industries, Ltd.) were added, and the reaction was carried out at room temperature for 5 hours. The reaction solution was washed with water, and the solvent was removed from the reaction solution by concentration under reduced pressure to obtain a reddish-brown solid. The solid was purified by a silica gel column to obtain 0.8 g (yield: 31%) of a red solid monomer (Compound 55).

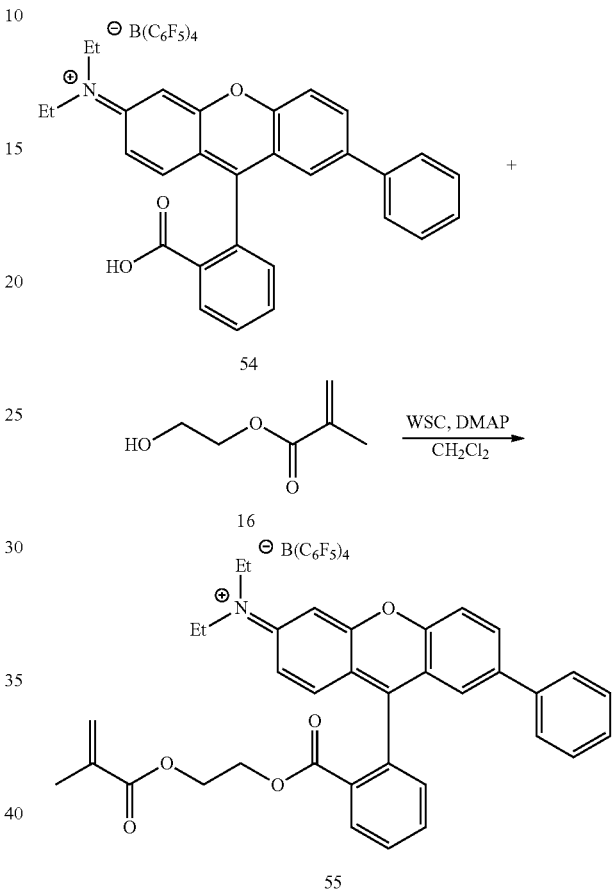

Example 29 Synthesis of a Carboxylic Acid Derivative (Compound 58)

(1) Synthesis of a Lactone Derivative (Compound 57)

Into a round-bottom flask equipped with a stirring apparatus, 4.7 g (15.0 mmol) of 2-(4-diethylamino-2-hydroxybenzoyl) benzoic acid (Compound 10: produced by Tokyo Chemical Industry Co., Ltd.), 3.6 g (15.8 mmol) of p-cumylphenol (Compound 56: produced by Wako Pure Chemical Industries, Ltd.), and 15 mL of methanesulfonic acid (produced by Wako Pure Chemical Industries, Ltd.) were added, and the reaction was carried out at 90° C. for 5 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain a reddish-brown solid. The solid was purified by a silica gel column to obtain 5.1 g (yield: 69%) of a white solid lactone derivative (Compound 57).

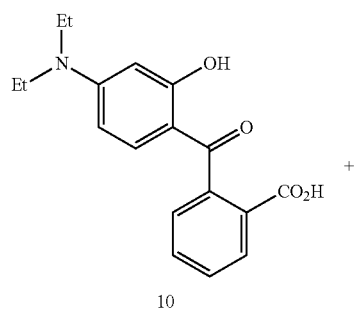

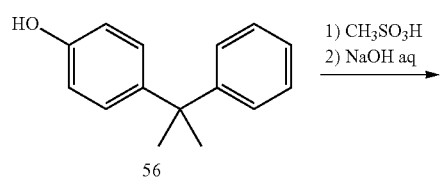

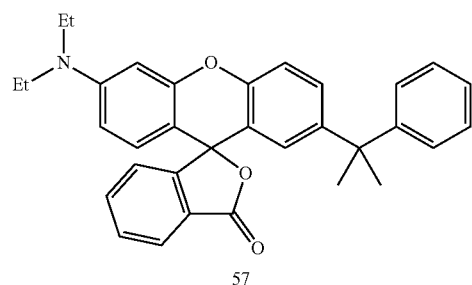

(2) Synthesis of a Carboxylic Acid Derivative (Compound 58)

Into a round-bottom flask equipped with a stirring apparatus, 0.9 g (1.8 mmol) of the lactone derivative (Compound 57) obtained in the (1), 0.4 g (3.6 mmol) of concentrated hydrochloric acid (produced by Wako Pure Chemical Industries, Ltd.), 1.4 g (1.8 mmol) of LiFABA (produced by Tosoh Finechem Corp.), and 20 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 2.1 g (yield: 100%) of a reddish-brown solid carboxylic acid derivative having a tetrakis(pentafluorophenyl)borate (IV) anion as a counter anion (Compound 58).

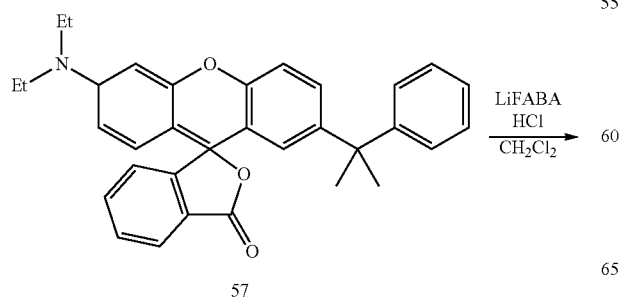

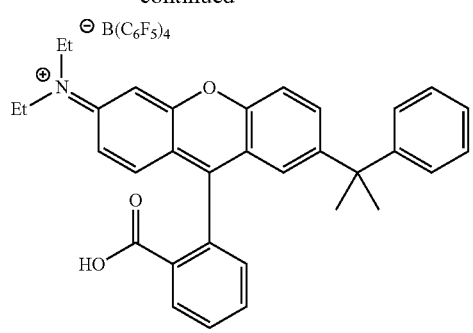

Example 30 Synthesis of a Monomer (Compound 59)

Into a round-bottom flask equipped with a stirring apparatus, 1.8 g (1.5 mmol) of the carboxylic acid derivative (Compound 58) obtained in Example 29, and 5 mL of dichloromethane were added for dissolution, and 0.2 g (1.7 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.5 mg (2.6 mmol) of WSC (produced by Wako Pure Chemical Industries, Ltd.) were added, and the reaction was carried out at room temperature for 8 hours. The reaction solution was washed with water, and the solvent was removed from the reaction solution by concentration under reduced pressure to obtain a red solid. The solid was purified by a silica gel column to obtain 0.4 g (yield 19%) of a red solid monomer (Compound 59).

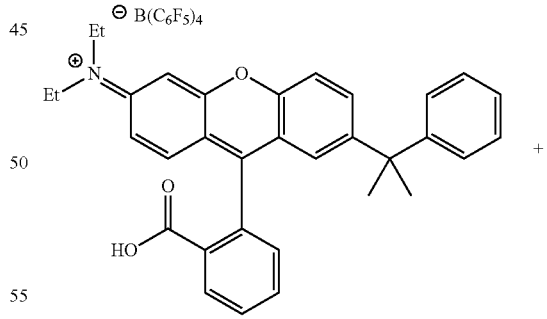

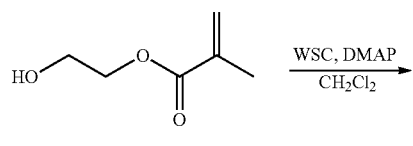

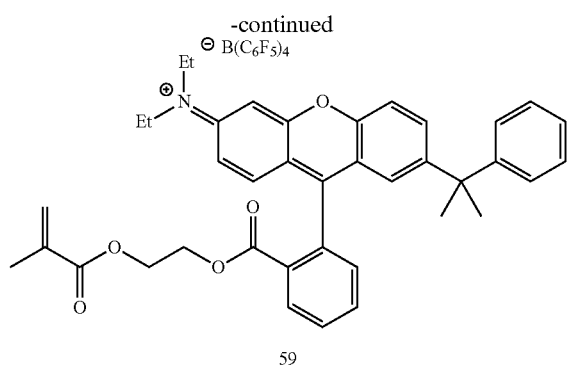

59

Example 31 Synthesis of a Carboxylic Acid Derivative (Compound 62)

(1) Synthesis of a Lactone Derivative (Compound 61)

Into a round-bottom flask equipped with a stirring apparatus, 4.7 g (15.0 mmol) of 2-(4-diethylamino-2-hydroxybenzoyl) benzoic acid (Compound 10: produced by Tokyo Chemical Industry Co., Ltd.), 2.9 g (15.8 mmol) of 4-phenoxyphenol (Compound 60: produced by Tokyo Chemical Industry Co., Ltd.), and 15 mL of methanesulfonic acid (produced by Wako Pure Chemical Industries, Ltd.) were added, and the reaction was carried out at 90° C. for 3 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 6.2 g (yield: 89%) of a purple solid lactone derivative (Compound 61).

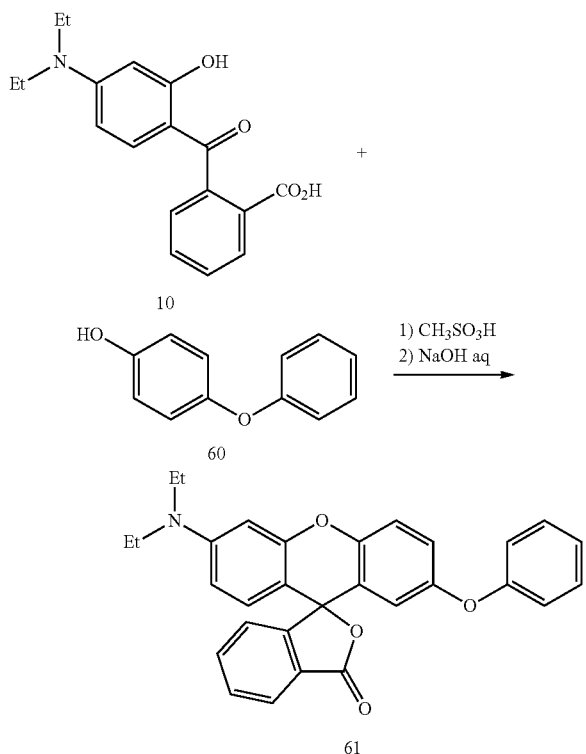

(2) Synthesis of a Carboxylic Acid Derivative (Compound 62)

Into a round-bottom flask equipped with a stirring apparatus, 1.5 g (3.2 mmol) of the lactone derivative (Compound 61) obtained in the (1), 0.7 g (6.5 mmol) of concentrated hydrochloric acid (produced by Wako Pure Chemical Industries, Ltd.), 2.5 g (3.2 mmol) of LiFABA (produced by Tosoh Finechem Corp.), and 30 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 3.7 g (yield: 100%) of a reddish-brown solid carboxylic acid derivative having a tetrakis (pentafluorophenyl)borate (IV) anion as a counter anion (Compound 62).

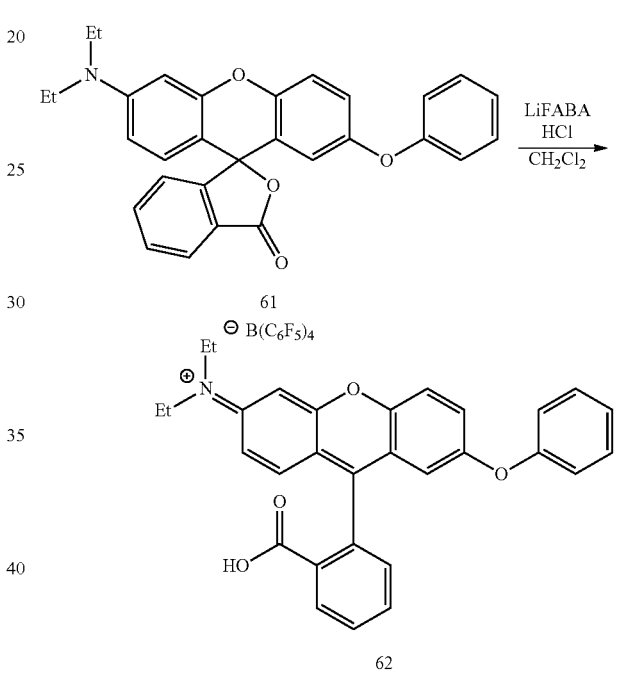

Example 32 Synthesis of a Monomer (Compound 63)

Into a round-bottom flask equipped with a stirring apparatus, 2.3 g (2.0 mmol) of the carboxylic acid derivative (Compound 62) obtained in Example 31, and 7 mL of dichloromethane were added for dissolution, and 0.3 g (2.2 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.7 g (3.4 mmol) of WSC (produced by Wako Pure Chemical Industries, Ltd.) were added, and the reaction was carried out at room temperature for 5 hours. The reaction solution was washed with water, and the solvent was removed from the reaction solution by concentration under reduced pressure to obtain a reddish-brown solid. The solid was purified by a silica gel column to obtain 0.4 g (yield: 14%) of a red solid monomer (Compound 63).

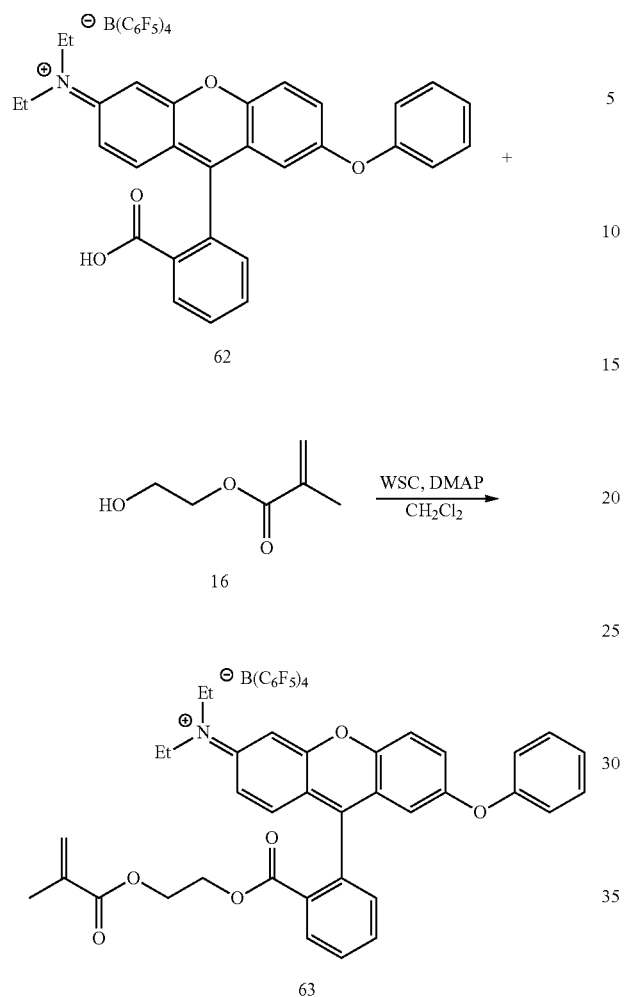

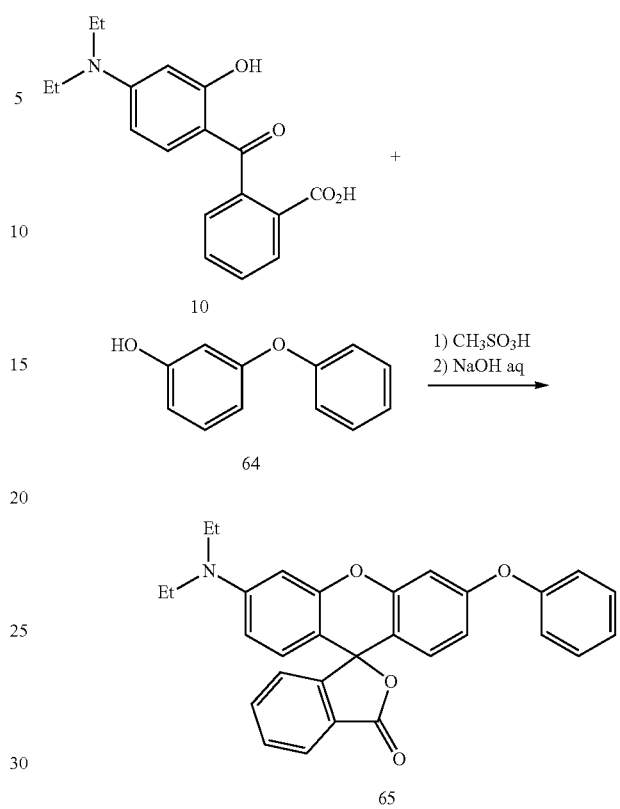

Example 33 Synthesis of a Carboxylic Acid Derivative (Compound 66)

(1) Synthesis of a Lactone Derivative (Compound 65)

Into a round-bottom flask equipped with a stirring apparatus, 4.7 g (15.0 mmol) of 2-(4-diethylamino-2-hydroxybenzoyl) benzoic acid (Compound 10: produced by Tokyo Chemical Industry Co., Ltd.), 2.9 g (15.8 mmol) of m-phenoxyphenol (Compound 64: produced by Wako Pure Chemical Industries, Ltd.), and 15 mL of methanesulfonic acid (produced by Wako Pure Chemical Industries, Ltd.) were added, and the reaction was carried out at 100° C. for 5 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain a reddish-brown solid. The solid was purified by a silica gel column to obtain 4.3 g (yield: 62%) of a reddish-brown solid lactone derivative (Compound 65).

(2) Synthesis of a Carboxylic Acid Derivative (Compound 66)

Into a round-bottom flask equipped with a stirring apparatus, 2.3 g (4.9 mmol) of the lactone derivative (Compound 65) obtained in the (1), 1.0 g (9.8 mmol) of concentrated hydrochloric acid (produced by Wako Pure Chemical Industries, Ltd.), 3.7 g (4.9 mmol) of LiFABA (produced by Tosoh Finechem Corp.), and 30 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 5.6 g (yield: 100%) of a reddish-brown solid carboxylic acid derivative having a tetrakis (pentafluorophenyl)borate (IV) anion as a counter anion (Compound 66).

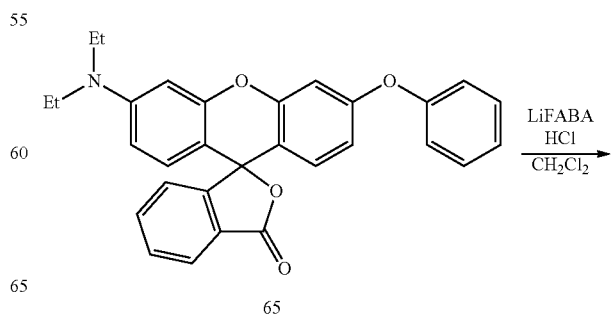

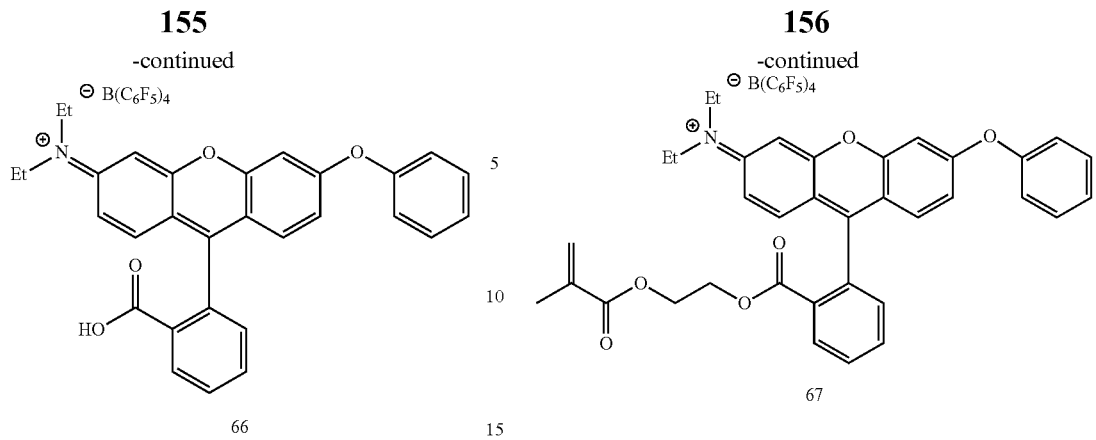

Example 34 Synthesis of a Monomer (Compound 67)

Into a round-bottom flask equipped with a stirring apparatus, 2.3 g (2.0 mmol) of the carboxylic acid derivative (Compound 66) obtained in Example 33, and 7 mL of dichloromethane were added for dissolution, and 0.3 g (2.2 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.7 g (3.4 mmol) of WSC (produced by Wako Pure Chemical Industries, Ltd.) were added, and the reaction was carried out at room temperature for 10 hours. The reaction solution was washed with water, and the solvent was removed from the reaction solution by concentration under reduced pressure to obtain a reddish-brown solid. The solid was purified by a silica gel column to obtain 0.6 g (yield: 22%) of a red solid monomer (Compound 67).

Example 35 Synthesis of a Carboxylic Acid Derivative (Compound 70)

(1) Synthesis of a Lactone Derivative (Compound 69)

Into a round-bottom flask equipped with a stirring apparatus, 4.7 g (15.0 mmol) of 2-(4-diethylamino-2-hydroxybenzoyl) benzoic acid (Compound 10: produced by Tokyo Chemical Industry Co., Ltd.), 2.0 g (15.8 mmol) of p-methoxythioanisole (Compound 68: produced by Wako Pure Chemical Industries, Ltd.), and 15 mL of methanesulfonic acid (produced by Wako Pure Chemical Industries, Ltd.) were added, and the reaction was carried out at 90° C. for 4 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain a reddish-brown solid. The solid was purified by a silica gel column to obtain 3.0 g (yield: 49%) of a red solid lactone derivative (Compound 69).

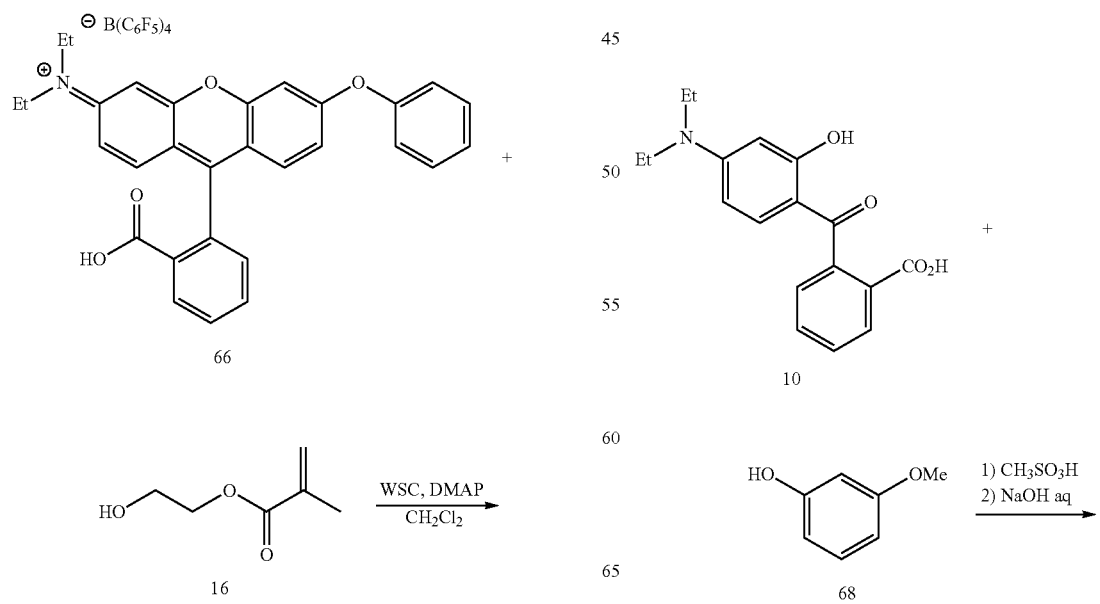

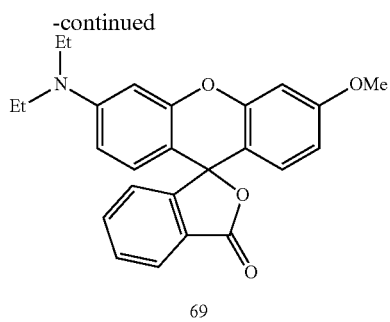

69

(2) Synthesis of a Carboxylic Acid Derivative (Compound 70)

Into a round-bottom flask equipped with a stirring apparatus, 2.3 g (5.8 mmol) of the lactone derivative (Compound 69) obtained in the (1), 0.2 g (2.0 mmol) of concentrated hydrochloric acid (produced by Wako Pure Chemical Industries, Ltd.), 1.2 g (11.6 mmol) of LiFABA (produced by Tosoh Finechem Corp.), and 30 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 6.3 g (yield: 100%) of a reddish-brown solid carboxylic acid derivative having a tetrakis(pentafluorophenyl)borate (IV) anion as a counter anion (Compound 70).

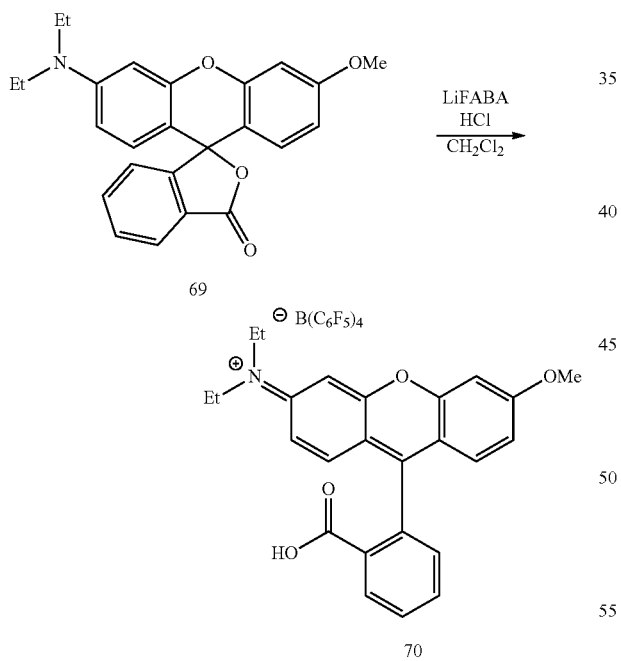

Example 36 Synthesis of a Monomer (Compound 71)

Into a round-bottom flask equipped with a stirring apparatus, 2.2 g (2.0 mmol) of the carboxylic acid derivative (Compound 70) obtained in Example 35, and 7 mL of dichloromethane were added for dissolution, and 0.3 g (2.2 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.7 g (3.4 mmol) of WSC (produced by Wako Pure Chemical Industries, Ltd.) were added, and the reaction was carried out at room temperature for 10 hours. The reaction solution was washed with water, and the solvent was removed from the reaction solution by concentration under reduced pressure to obtain a reddish-brown solid. The solid was purified by a silica gel column to obtain 0.6 g (yield: 25%) of a reddish-brown solid monomer (Compound 71).

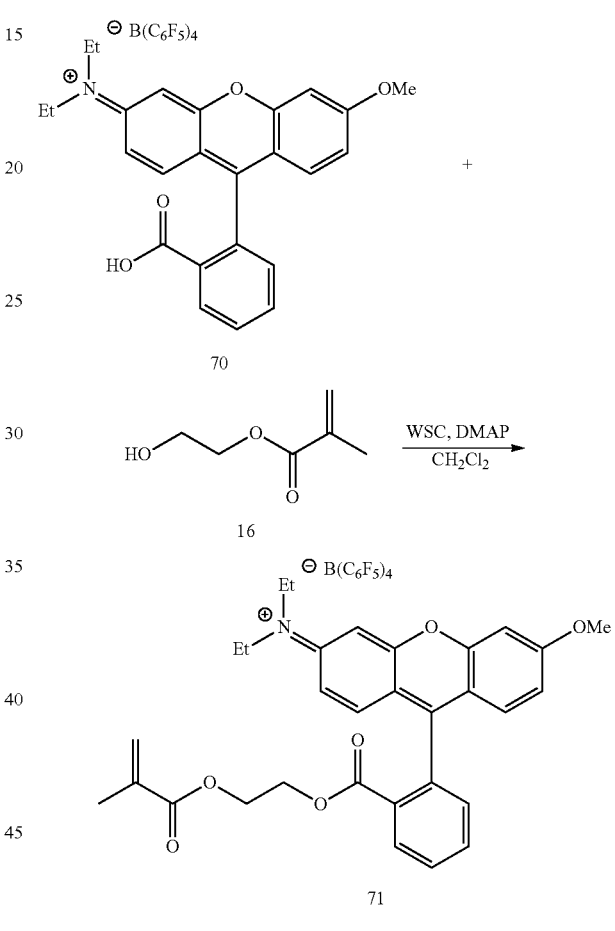

Example 37 Synthesis of a Carboxylic Acid Derivative (Compound 75)

(1) Synthesis of a Benzoic Acid Derivative (Compound 73)

Into a round-bottom flask equipped with a stirring apparatus, 4.4 g (20.0 mmol) of N,N-dibutyl-m-aminophenol (Compound 72: produced by Wako Pure Chemical Industries, Ltd.), 3.2 g (20.0 mmol) of phthalic anhydride (Compound 23: produced by Wako Pure Chemical Industries, Ltd.), and 50 mL of toluene were added, and the reaction was carried out at 100° C. for 30 hours. After completion of the reaction, the crystal precipitated by cooling to room temperature was filtrated, and washed with ethyl acetate, and dried to obtain 3.0 g (yield: 41%) of a purple solid benzoic acid derivative (Compound 73).

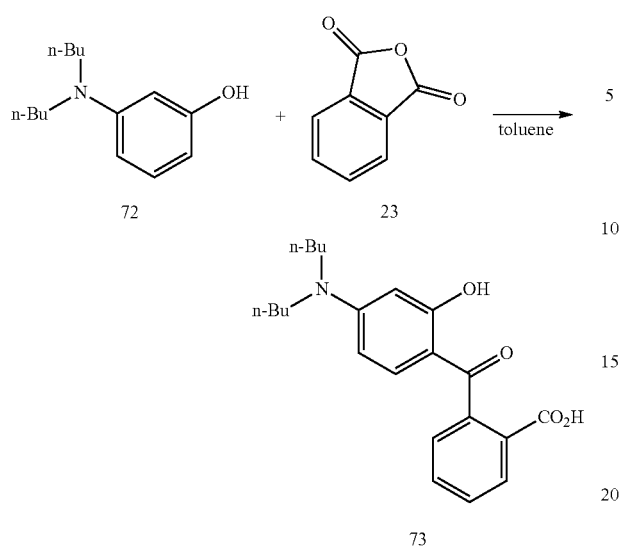

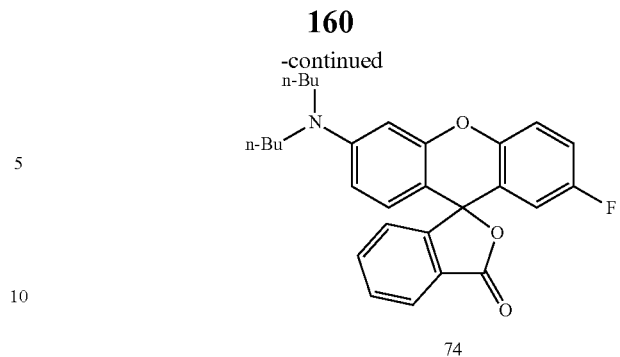

(2) Synthesis of a Lactone Derivative (Compound 74)

Into a round-bottom flask equipped with a stirring apparatus, 1.5 g (4.0 mmol) of the benzoic acid derivative (Compound 73) obtained in the (1), 0.6 g (4.4 mmol) of p-fluorophenol (Compound 11: produced by Tokyo Chemical Industry Co., Ltd.), and 4 mL of methanesulfonic acid (produced by Wako Pure Chemical Industries, Ltd.) were added, and the reaction was carried out at 90° C. for 5 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 1.5 g (yield: 86%) of a reddish-brown solid lactone derivative (Compound 74).

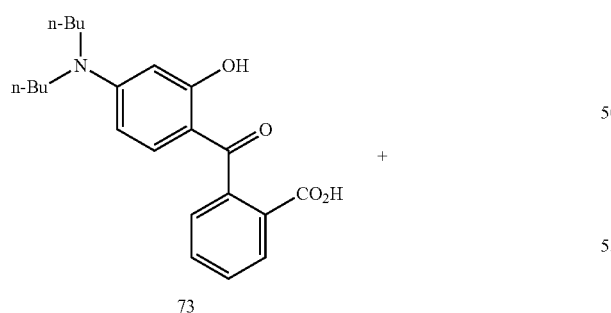

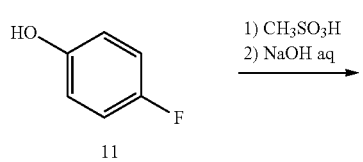

(3) Synthesis of a Carboxylic Acid Derivative (Compound 75)

Into a round-bottom flask equipped with a stirring apparatus, 1.1 g (2.5 mmol) of the lactone derivative (Compound 74) obtained in the (2), 0.5 g (5.0 mmol) of concentrated hydrochloric acid (produced by Wako Pure Chemical Industries, Ltd.), 1.9 g (2.5 mmol) of LiFABA (produced by Tosoh Finechem Corp.), and 25 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 2.8 g (yield: 100%) of a reddish-brown solid carboxylic acid derivative having a tetrakis (pentafluorophenyl)borate (IV) anion as a counter anion (Compound 75).

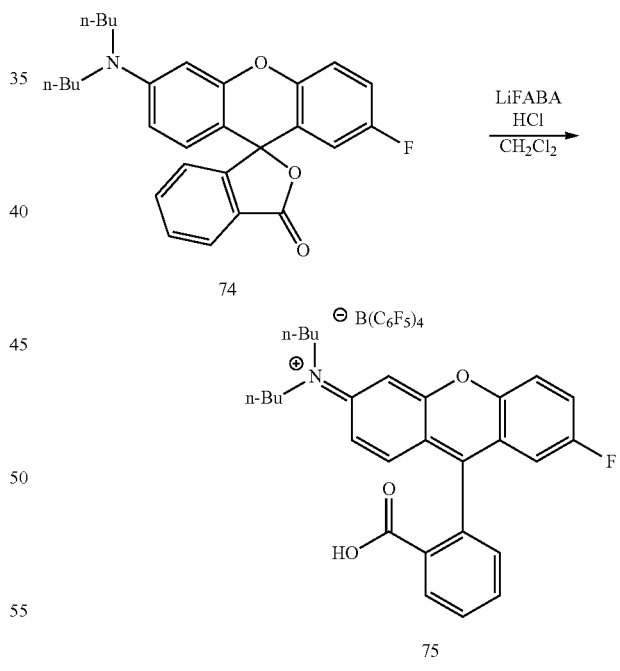

Example 38 Synthesis of a Monomer (Compound 76)

Into a round-bottom flask equipped with a stirring apparatus, 2.3 g (2.0 mmol) of the carboxylic acid derivative (Compound 75) obtained in Example 37, and 7 mL of dichloromethane were added for dissolution, and 0.3 g (2.2 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.7 g (3.4 mmol) of WSC (produced by Toyobo Co., Ltd.) were added, and the reaction was carried out at room temperature for 13 hours. An organic layer, obtained by solution separation, was washed with water, and the solvent was removed from the reaction solution by concentration under reduced pressure to obtain a reddish-brown solid. The solid was purified by a silica gel column to obtain 0.9 g (yield: 34%) of a reddish-brown solid monomer (Compound 76).

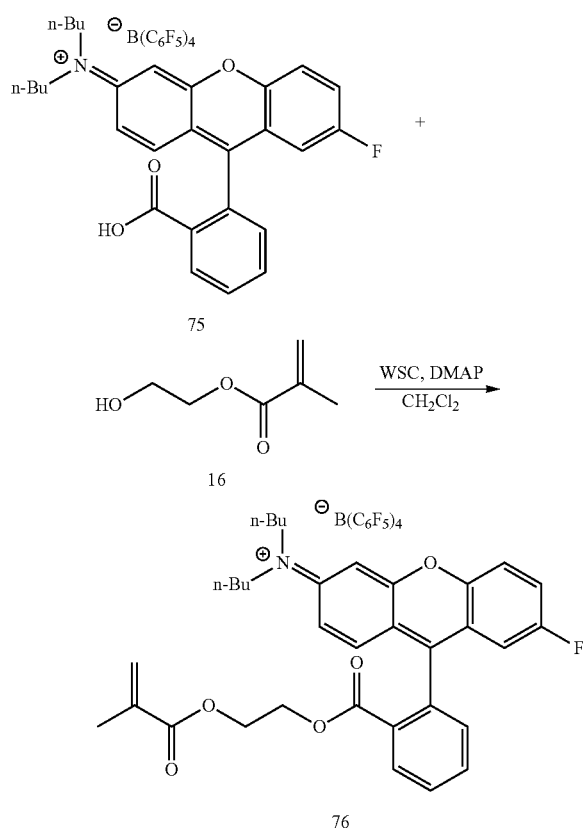

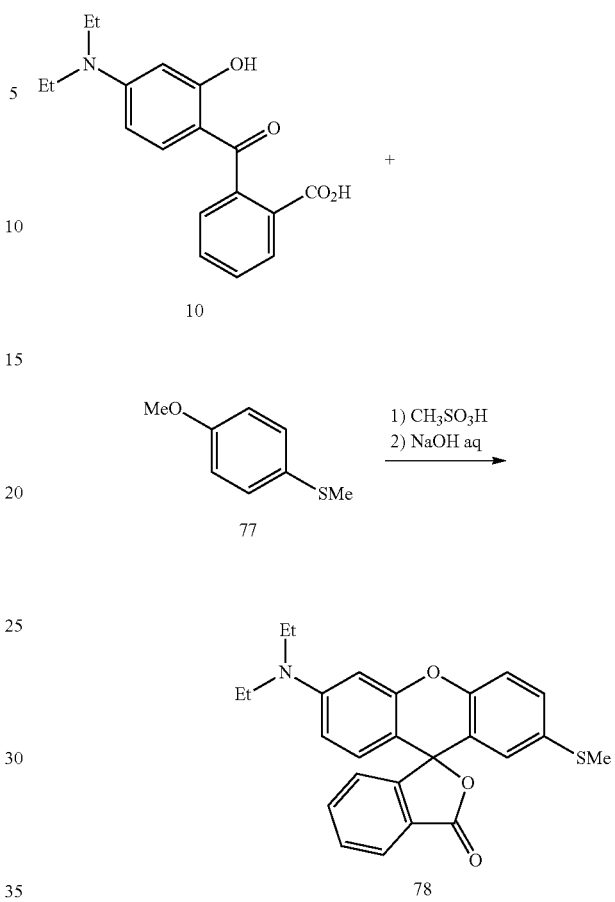

Example 39 Synthesis of a Carboxylic Acid Derivative (Compound 79)

(1) Synthesis of a Lactone Derivative (Compound 78)

Into a round-bottom flask equipped with a stirring apparatus, 3.1 g (10.0 mmol) of 2-(4-diethylamino-2-hydroxybenzoyl) benzoic acid (Compound 10: produced by Tokyo Chemical Industry Co., Ltd.), 1.5 g (10.0 mmol) of p-methoxythioanisole (Compound 77: produced by Wako Pure Chemical Industries, Ltd.), and 10 mL of methanesulfonic acid (produced by Wako Pure Chemical Industries, Ltd.) were added, and the reaction was carried out at 90° C. for 7 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 2.6 g (yield: 63%) of a reddish-brown solid lactone derivative (Compound 78).

(2) Synthesis of a Carboxylic Acid Derivative (Compound 79)

Into a round-bottom flask equipped with a stirring apparatus, 1.0 g (2.5 mmol) of the lactone derivative (Compound 78) obtained in the (1), 0.5 g (4.9 mmol) of concentrated hydrochloric acid (produced by Wako Pure Chemical Industries, Ltd.), 1.9 g (2.5 mmol) of LiFABA (produced by Tosoh Finechem Corp.), and 10 mL of dichloromethane were added, and the reaction was carried out at room temperature for 6.5 hours. After dilution of the reaction solution with dichloromethane, it was washed with water. The solvent was removed from the reaction solution by concentration under reduced pressure to obtain 2.5 g (yield: 100%) of a red solid carboxylic acid derivative having a tetrakis(pentafluorophenyl)borate (IV) anion as a counter anion (Compound 79).

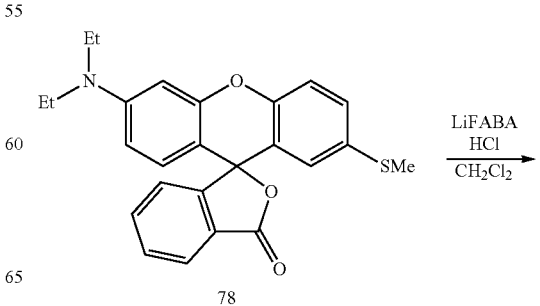

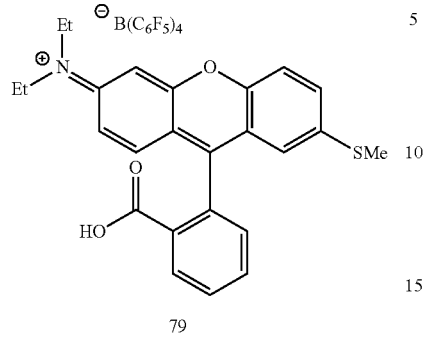

79

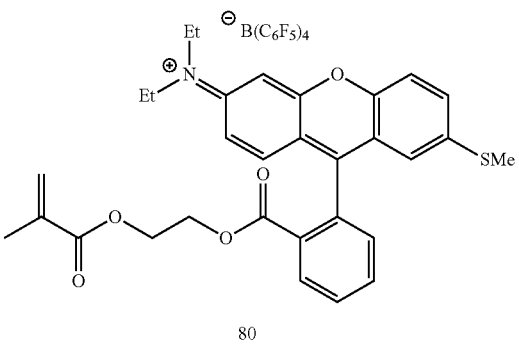

80

Example 40 Synthesis of a Monomer (Compound 80)

Into a round-bottom flask equipped with a stirring apparatus, 2.3 g (2.1 mmol) of the carboxylic acid derivative (Compound 79) obtained in Example 39, and 20 mL of dichloromethane were added for dissolution, and 0.3 g (2.5 mmol) of 2-hydroxyethyl methacrylate (Compound 16: produced by Wako Pure Chemical Industries, Ltd.), 80 mg (0.6 mmol) of DMAP (produced by Wako Pure Chemical Industries, Ltd.), and 1.0 g (5.2 mmol) of WSC (produced by Toyobo Co., Ltd.) were added, and the reaction was carried out at room temperature for 14 hours. The reaction solution was washed with water, and the solvent was removed from the reaction solution by concentration under reduced pressure to obtain a red solid. The solid was purified by a silica gel column to obtain 0.8 g (yield: 32%) of a red solid monomer (Compound 80)

Example 41 Synthesis of a Carboxylic Acid Derivative (Compound 83)

(1) Synthesis of a Lactone Derivative (Compound 82)

Into a round-bottom flask equipped with a stirring apparatus, 3.1 g (10.0 mmol) of 2-(4-diethylamino-2-hydroxybenzoyl) benzoic acid (Compound 10: produced by Tokyo Chemical Industry Co., Ltd.), 1.4 g (10.0 mmol) of p-methoxyanisole (Compound 81: produced by Wako Pure Chemical Industries, Ltd.), and 10 mL of methanesulfonic acid (produced by Wako Pure Chemical Industries, Ltd.) were added, and the reaction was carried out at 90° C. for 5 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 3.4 g (yield: 85%) of a reddish-brown solid lactone derivative (Compound 82).

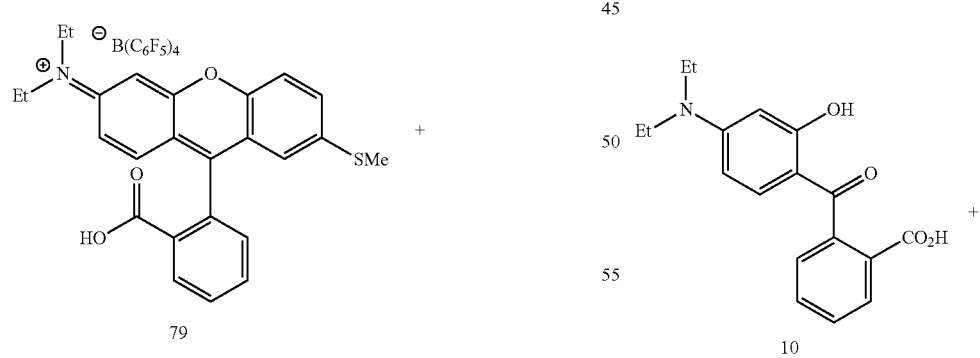

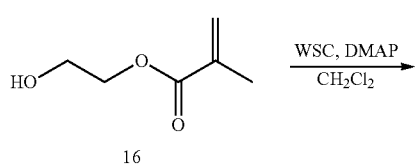

16

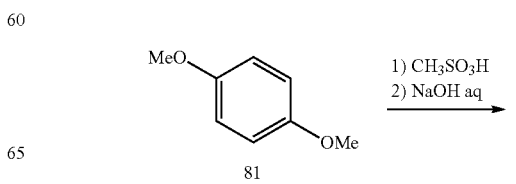

81

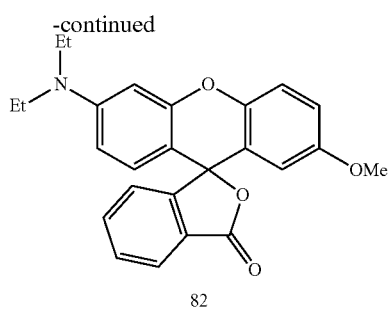

82

(2) Synthesis of a Carboxylic Acid Derivative (Compound 83)

Into a round-bottom flask equipped with a stirring apparatus, 3.3 g (8.2 mmol) of the lactone derivative (Compound 82) obtained in the (1), 1.7 g (16.3 mmol) of concentrated hydrochloric acid (produced by Wako Pure Chemical Industries, Ltd.), 6.2 g (8.2 mmol) of LiFABA (produced by Tosoh Finechem Corp.), and 10 mL of dichloromethane were added, and the reaction was carried out at room temperature for 30 minutes. After dilution of the reaction solution with dichloromethane, it was washed with water. The solvent was removed from the reaction solution by concentration under reduced pressure to obtain 8.8 g (yield: 100%) of a red solid carboxylic acid derivative having a tetrakis(pentafluorophenyl)borate (IV) anion as a counter anion (Compound 83).

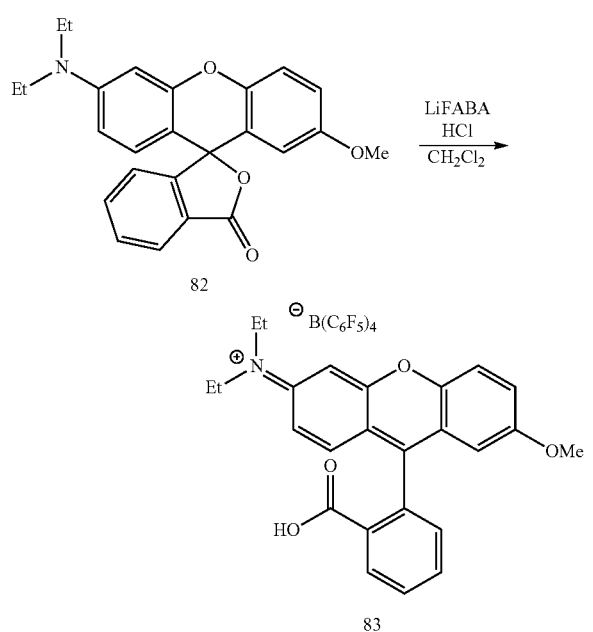

Example 42 Synthesis of a Monomer (Compound 84)

Into a round-bottom flask equipped with a stirring apparatus, 2.0 g (1.9 mmol) of the carboxylic acid derivative (Compound 83) obtained in Example 41, and 10 mL of dichloromethane were added for dissolution, and 0.3 g (2.2 mmol) of 2-hydroxyethyl methacrylate (Compound 16: produced by Wako Pure Chemical Industries, Ltd.), 70 mg (0.6 mmol) of DMAP (produced by Wako Pure Chemical Industries, Ltd.), and 0.9 g (4.6 mmol) of WSC (produced by Toyobo Co., Ltd.) were added, and the reaction was carried out at room temperature for 12 hours. The reaction solution was washed with water, and the solvent was removed from the reaction solution by concentration under reduced pressure to obtain a red solid. The solid was purified by a silica gel column to obtain 0.7 g (yield: 34%) of a red solid monomer (Compound 84).

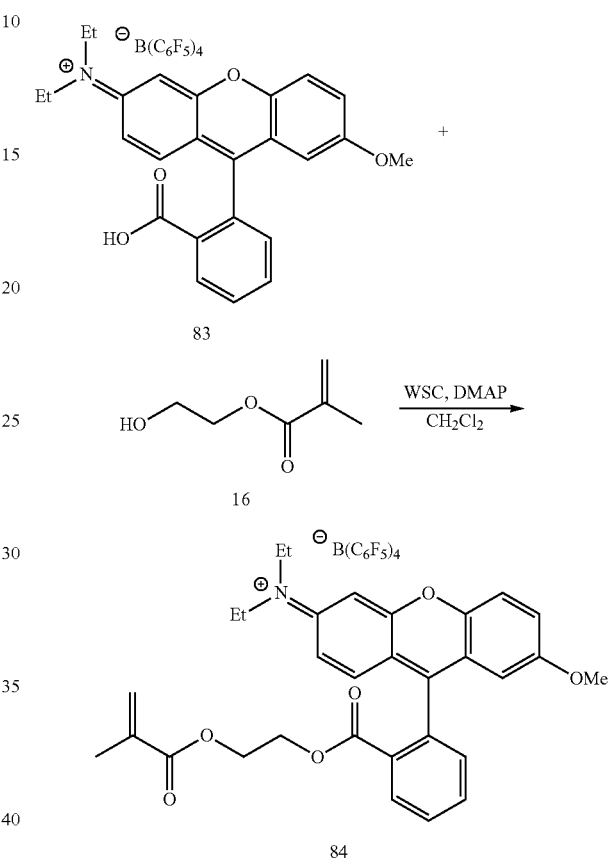

Example 43 Synthesis of a Carboxylic Acid Derivative (Compound 88)

(1) Synthesis of a Lactone Derivative (Compound 86)

Into a round-bottom flask equipped with a stirring apparatus, 9.0 g (28.7 mmol) of 2-(4-diethyl amino-2-hydroxybenzoyl) benzoic acid (Compound 10: produced by Tokyo Chemical Industry Co., Ltd.), 3.1 g (28.7 mmol) of p-methoxyaniline (Compound 85: produced by Wako Pure Chemical Industries, Ltd.), and 20 mL of methanesulfonic acid (produced by Wako Pure Chemical Industries, Ltd.) were added, and the reaction was carried out at 120° C. for 25 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with water, and the solvent was removed from the reaction solution by concentration under reduced pressure to obtain 1.7 g (yield: 44%) of a reddish-brown solid lactone derivative (Compound 86).

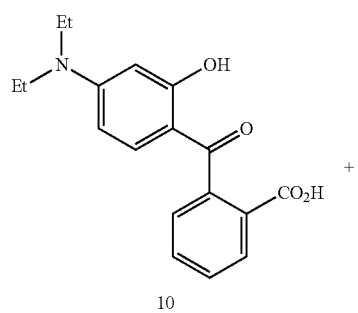

10

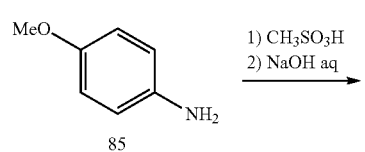

85

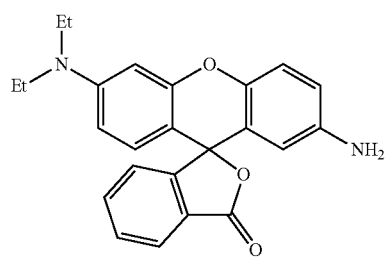

86

(2) Synthesis of a Lactone Derivative (Compound 87)

Into a round-bottom flask equipped with a stirring apparatus, 0.4 g (1.0 mmol) of the lactone derivative (Compound 86) obtained in the (1), and 10 mL of DMF were added for dissolution, and 1.0 g (6.2 mmol) of ethyl iodide (produced by Wako Pure Chemical Industries, Ltd.), 0.9 g (6.2 mmol) of potassium carbonate (produced by Wako Pure Chemical Industries, Ltd.) were added, and the reaction was carried out at room temperature for 12 hours. After completion of the reaction, ethyl acetate and water were added, and then an organic layer, obtained by solution separation, was washed with water, and the solvent was removed from the reaction solution by concentration under reduced pressure to obtain 0.4 g (yield: 87%) of a green solid spirolactone derivative (Compound 87).

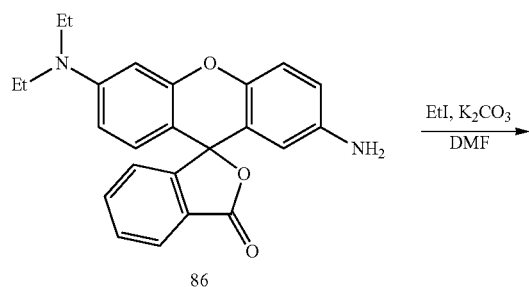

-continued

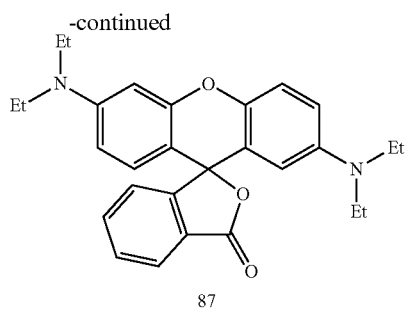

87

(3) Synthesis of a Carboxylic Acid Derivative (Compound 88)

Into a round-bottom flask equipped with a stirring apparatus, 0.3 g (0.7 mmol) of the lactone derivative (Compound 87) obtained in the (2), 0.1 g (1.3 mmol) of concentrated hydrochloric acid (produced by Wako Pure Chemical Industries, Ltd.), 0.5 g (0.7 mmol) of LiFABA (produced by Tosoh Finechem Corp.), and 10 mL of dichloromethane were added, and the reaction was carried out at room temperature for 0.5 hour. After dilution of the reaction solution with dichloromethane, it was washed with water. The solvent was removed from the reaction solution by concentration under reduced pressure to obtain 0.7 g (yield: 96%) of a green solid carboxylic acid derivative having a tetrakis(pentafluorophenyl)borate (IV) anion as a counter anion (Compound 88).

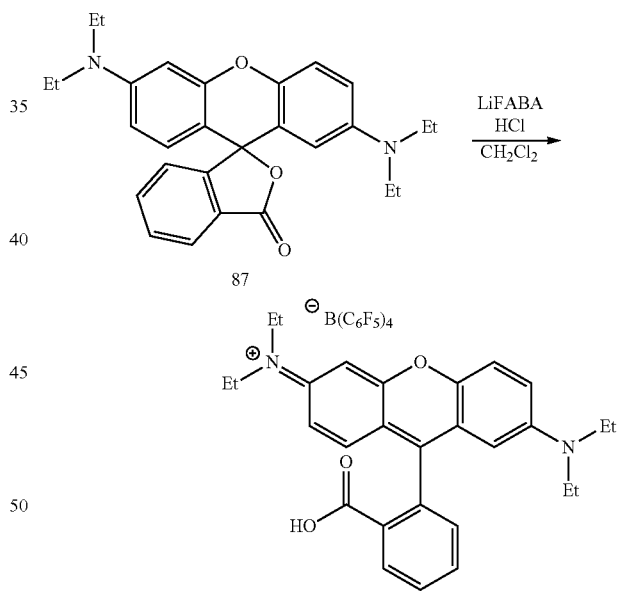

Example 44 Synthesis of a Monomer (Compound 89)

Into a round-bottom flask equipped with a stirring apparatus, 0.6 g (0.6 mmol) of the carboxylic acid derivative (Compound 88) obtained in Example 43, and 10 mL of dichloromethane were added for dissolution, and 0.1 g (0.7 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.2 g (1.0 mmol) of WSC (produced by Toyobo Co., Ltd.) were added, and the reaction was carried out at room temperature for 9 hours. The reaction solution was washed with water, and the solvent was removed from the reaction solution by concentration under reduced pressure to obtain a green solid. The solid was purified by a silica gel column to obtain 0.5 g (yield: 67%) of a green solid monomer (Compound 89).

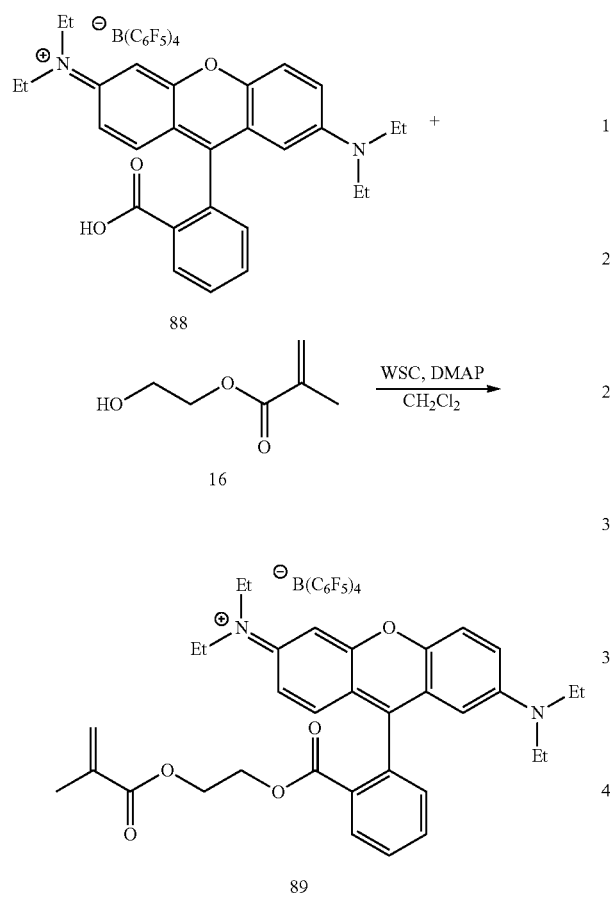

Example 45 Synthesis of a Carboxylic Acid Derivative (Compound 91)

Into a round-bottom flask equipped with a stirring apparatus, 10.6 g (20.0 mmol) of 2'-anilino-6'-(dibutylamino)-3'-methylspiro[phthalide-3,9'-xanthene] (Compound 90: trade name, Black 400; produced by Fukui Yamada Chemical Co., Ltd.), 4.2 g (40.0 mmol) of concentrated hydrochloric acid (produced by Wako Pure Chemical Industries, Ltd.), 15.2 g (20.0 mmol) of LiFABA (produced by Tosoh Finechem Corp.), and 100 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 24.3 g (yield: 100%) of a black solid carboxylic acid derivative having a tetrakis(pentafluorophenyl)borate (IV) anion as a counter anion (Compound 91).

Example 46 Synthesis of a Monomer (Compound 92)

Into a round-bottom flask equipped with a stirring apparatus, 24.3 g (20.0 mmol) of the carboxylic acid derivative (Compound 91) obtained in Example 45, and 72 mL of dichloromethane were added for dissolution, and 2.9 g (22.0 mmol) of 2-hydroxyethyl methacrylate (Compound 16: produced by Wako Pure Chemical Industries, Ltd.), 0.2 g (2.0 mmol) of DMAP (produced by Wako Pure Chemical Industries, Ltd.), and 2.8 g (22.0 mmol) of DIC (produced by Wako Pure Chemical Industries, Ltd.) were added, and the reaction was carried out at room temperature for 5 hours. The reaction solution was washed with water, and the solvent was removed from the reaction solution by concentration under reduced pressure to obtain a black solid. The solid was purified by a silica gel column to obtain 22.0 g (yield: 83%) of a black solid monomer (Compound 92).

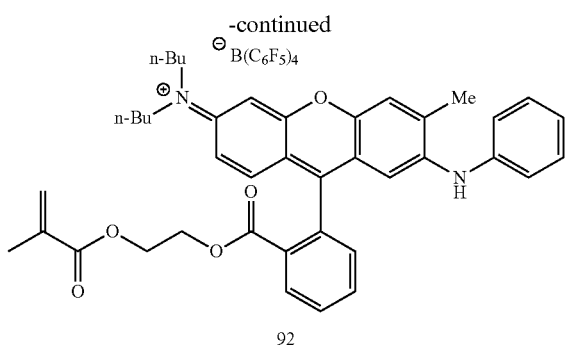

Example 47 Synthesis of a Carboxylic Acid Derivative (Compound 94)

Into a round-bottom flask equipped with a stirring apparatus, 2.59 g (5.0 mmol) of 2'-anilino-6'-(N-ethyl-N-isopentylamino)-3'-methylspiro[phthalide-3,9'-xanthene](Compound 93: trade name, S-205; produced by Fukui Yamada Chemical Co., Ltd.), 1.04 g (10.0 mmol) of concentrated hydrochloric acid (produced by Wako Pure Chemical Industries, Ltd.), 3.81 g (5.0 mmol) of LiFABA (produced by Tosoh Finechem Corp.), and 60 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 5.99 g (yield: 100%) of a black solid carboxylic acid derivative having a tetrakis(pentafluorophenyl)borate (IV) anion as a counter anion (Compound 94).

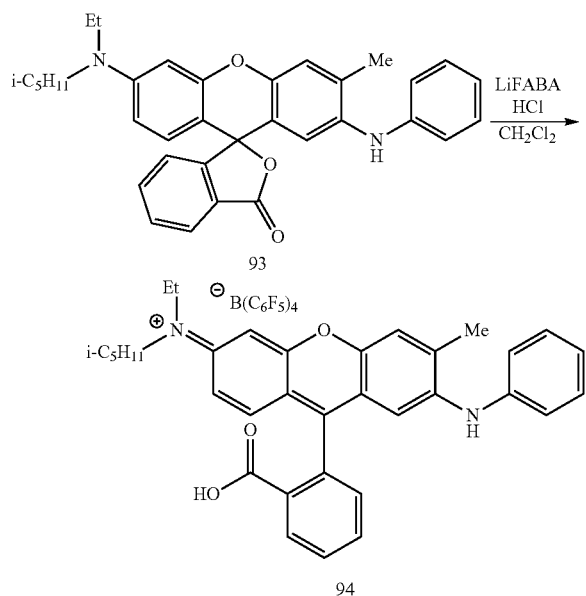

Example 48 Synthesis of a Monomer (Compound 95)

Into a round-bottom flask equipped with a stirring apparatus, 2.4 g (1.9 mmol) of the carboxylic acid derivative (Compound 94) obtained in Example 47, and 8 mL of dichloromethane were added for dissolution, and 0.3 g (2.2 mmol) of 2-hydroxyethyl methacrylate (Compound 16: produced by Wako Pure Chemical Industries, Ltd.), 20 mg (0.2 mmol) of DMAP (produced by Wako Pure Chemical Industries, Ltd.), and 0.3 g (2.2 mmol) of DIC (produced by Wako Pure Chemical Industries, Ltd.) were added, and the reaction was carried out at room temperature for 5 hours. The reaction solution was washed with water, and the solvent was removed from the reaction solution by concentration under reduced pressure to obtain a black solid. The solid was purified by a silica gel column to obtain 2.1 g (yield: 79%) of a black solid monomer (Compound 95).

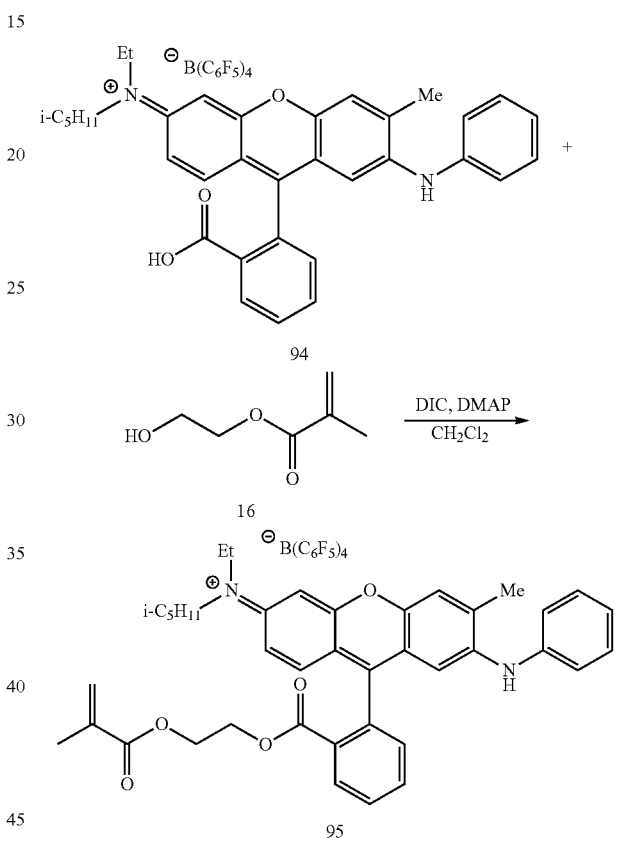

Example 49 Synthesis of a Carboxylic Acid Derivative (Compound 97)

Into a round-bottom flask equipped with a stirring apparatus, 1.6 g (3.0 mmol) of 2'-anilino-6'-[N-ethyl-N-(4-tolyl)amino]-3'-methyl-3H-spiro[phthalide-3,9'-xanthene] (Compound 96: trade name, ETAC; produced by Fukui Yamada Chemical Co., Ltd.), 0.6 g (6.0 mmol) of concentrated hydrochloric acid (produced by Wako Pure Chemical Industries, Ltd.), 2.3 g (3.0 mmol) of LiFABA (produced by Tosoh Finechem Corp.), and 35 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 3.7 g (yield: 100%) of a black solid carboxylic acid derivative having a tetrakis(pentafluorophenyl)borate (IV) anion as a counter anion (Compound 97).

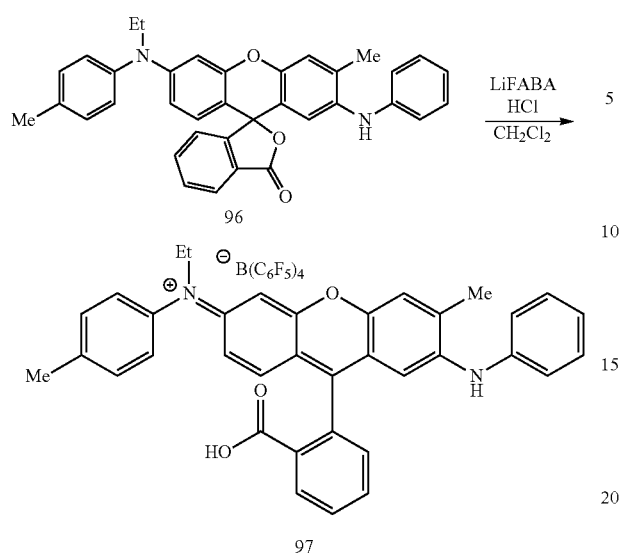

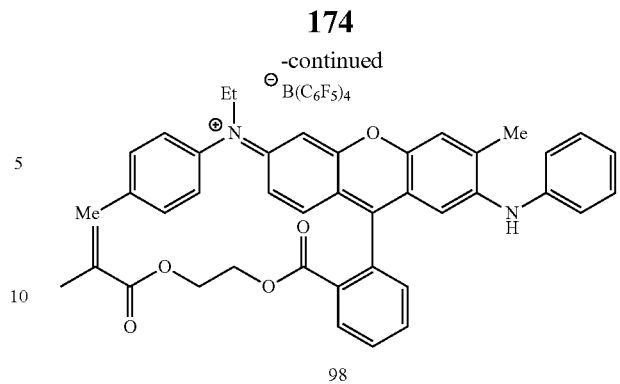

Example 51 Synthesis of a Carboxylic Acid Derivative (Compound 99)

Into a round-bottom flask equipped with a stirring apparatus, 11.7 g (30.0 mmol) of the lactone derivative (Compound 12) obtained in Example 7, 6.3 g (60.0 mmol) of concentrated hydrochloric acid (produced by Wako Pure Chemical Industries, Ltd.), 8.6 g (30.0 mmol) of LiN(SO$_2$CF$_3$)$_2$ (produced by Wako Pure Chemical Industries, Ltd.), and 190 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 20.1 g (yield: 100%) of a red solid carboxylic acid derivative having a bis(trifluoromethanesulfonyl)imide anion as a counter anion (Compound 99).

Example 50 Synthesis of a Monomer (Compound 98)

Into a round-bottom flask equipped with a stirring apparatus, 3.9 g (3.2 mmol) of the carboxylic acid derivative (Compound 97) obtained in Example 49, and 12 mL of dichloromethane were added for dissolution, and 0.5 g (3.5 mmol) of 2-hydroxyethyl methacrylate (Compound 16: produced by Wako Pure Chemical Industries, Ltd.), 40 mg (0.3 mmol) of DMAP (produced by Wako Pure Chemical Industries, Ltd.), and 0.4 g (3.5 mmol) of DIC (produced by Wako Pure Chemical Industries, Ltd.) were added, and the reaction was carried out at room temperature for 4 hours. The reaction solution was washed with water, and the solvent was removed from the reaction solution by concentration under reduced pressure to obtain a black solid. The solid was purified by a silica gel column to obtain 3.0 g (yield: 70%) of a black solid monomer (Compound 98).

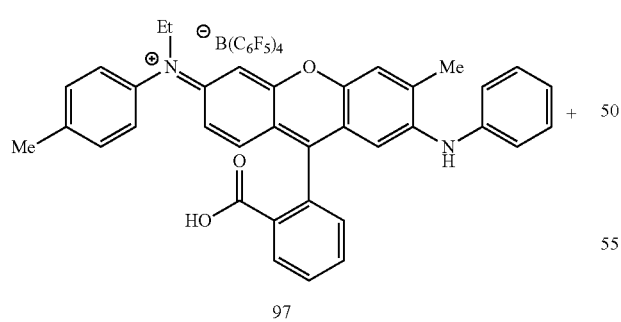

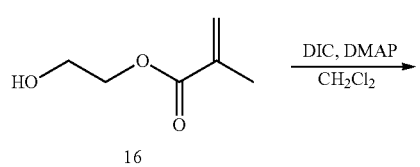

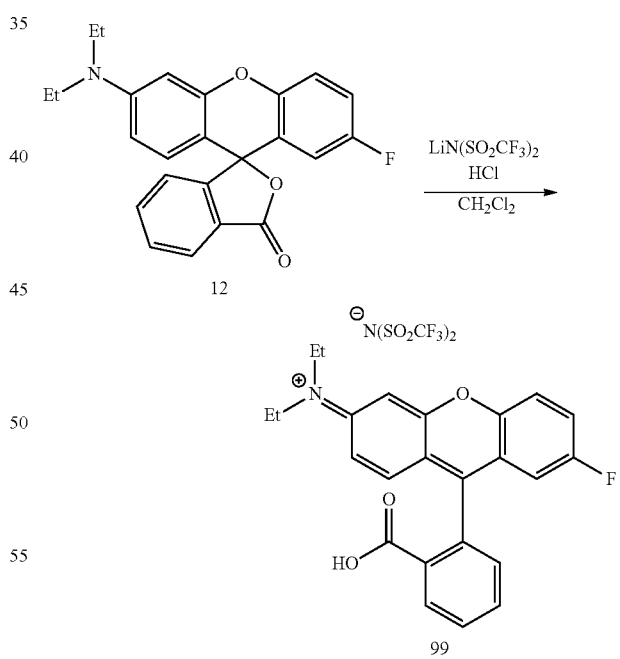

Example 52 Synthesis of a Monomer (Compound 100)

Into a round-bottom flask equipped with a stirring apparatus, 13.4 g (20.0 mmol) of the carboxylic acid derivative (Compound 99) obtained in Example 51, and 40 mL of dichloromethane were added for dissolution, and 3.1 g (24.0 mmol) of 2-hydroxyethyl methacrylate (Compound 16: produced by Wako Pure Chemical Industries, Ltd.), 0.7 g (6.0 mmol) of DMAP (produced by Wako Pure Chemical Industries, Ltd.), and 6.5 g (34.0 mmol) of WSC (produced by Toyobo Co., Ltd.) were added, and the reaction was carried out at room temperature for 4 hours. The reaction solution was washed with water, and the solvent was removed from the reaction solution by concentration under reduced pressure to obtain a red oily material. The oily material was purified by a silica gel column to obtain 11.3 g (yield: 72%) of a red solid monomer (Compound 100).

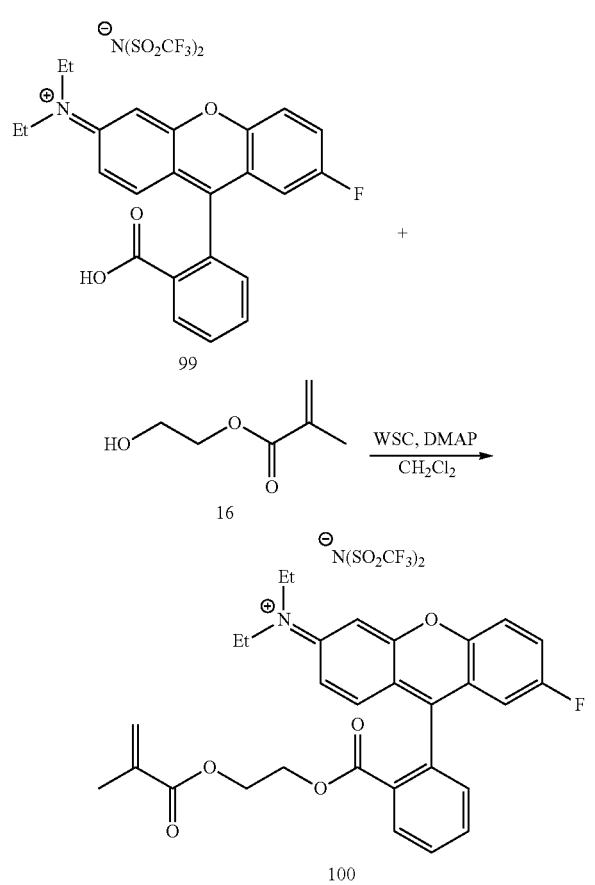

Example 53 Synthesis of a Carboxylic Acid Derivative (Compound 101)

Into a round-bottom flask equipped with a stirring apparatus, 2.5 g (5.3 mmol) of the lactone derivative (Compound 36) obtained in Example 19, 3.1 g (21.3 mmol) of a 60% hexafluorophosphate solution (produced by Wako Pure Chemical Industries, Ltd.), and 20 mL of dichloromethane were added, and the reaction was carried out at room temperature for 2 hours. After dilution of the reaction solution with dichloromethane, it was washed sequentially with water and saturated saline. The solvent was removed from the reaction solution by concentration under reduced pressure to obtain 3.3 g (yield: 100%) of a red solid carboxylic acid derivative having a hexafluorophosphate anion as a counter anion (Compound 101).

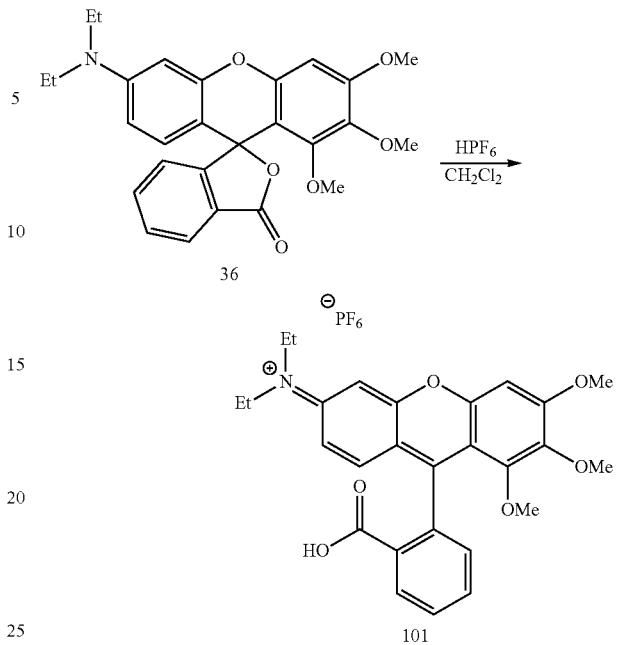

Example 54 Synthesis of a Monomer (Compound 102)

Into a round-bottom flask equipped with a stirring apparatus, 0.5 g (0.8 mmol) of the carboxylic acid derivative (Compound 101) obtained in Example 53, and 10 mL of dichloromethane were added for dissolution, and 0.1 g (1.0 mmol) of 2-hydroxyethyl methacrylate (Compound 16: produced by Wako Pure Chemical Industries, Ltd.), 0.1 g (1.0 mmol) of DMAP (produced by Wako Pure Chemical Industries, Ltd.), and 0.3 g (1.7 mmol) of WSC (produced by Toyobo Co., Ltd.) were added, and the reaction was carried out at room temperature for 14 hours. The reaction solution was washed sequentially with water and saturated saline, and the solvent was removed from the reaction solution by concentration under reduced pressure to obtain a purple solid. The solid was purified by a silica gel column to obtain 13 mg (yield: 2%) of a red solid monomer (Compound 102).

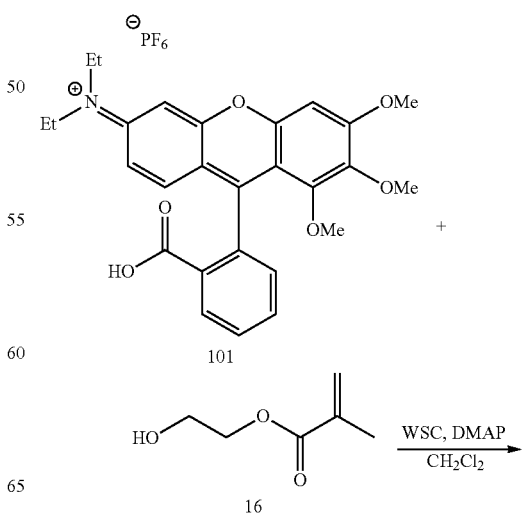

-continued

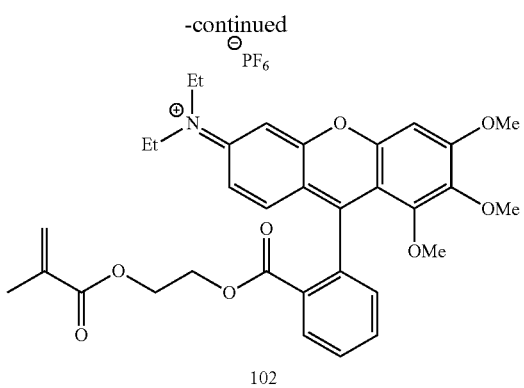
102

Example 55 Synthesis of a Carboxylic Acid Derivative (Compound 106)

(1) Synthesis of a Diethyl Derivative (Compound 104)

Into a round-bottom flask equipped with a stirring apparatus, 10.0 g (65.3 mmol) of 2,5-dimethoxyaniline (Compound 103: produced by Wako Pure Chemical Industries, Ltd.), 46.3 g (653.0 mmol) of potassium carbonate (produced by Wako Pure Chemical Industries, Ltd.), 102.0 g (653.0 mmol) of ethyl iodide (produced by Wako Pure Chemical Industries, Ltd.), and 100 mL of DMF (produced by Wako Pure Chemical Industries, Ltd.) were added, and the reaction was carried out at room temperature for 37 hours. After completion of the reaction, dichloromethane and water were added, and then an organic layer, obtained by solution separation, was washed with water, and the solvent was removed from the reaction solution by concentration under reduced pressure to obtain black liquid. The liquid was purified by a silica gel column to obtain 9.0 g (yield: 66%) of a colorless liquid diethyl derivative (Compound 104).

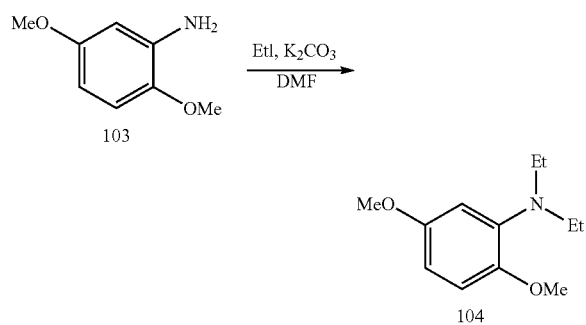

(2) Synthesis of a Lactone Derivative (Compound 105)

Into a round-bottom flask equipped with a stirring apparatus, 2.1 g (10.0 mmol) of the diethyl derivative (Compound 104) obtained in the (1), 3.1 g (10.0 mmol) of 2-(4-diethylamino-2-hydroxybenzoyl) benzoic acid (Compound 10: produced by Tokyo Chemical Industry Co., Ltd.), and 10 mL of concentrated sulfuric acid (produced by Wako Pure Chemical Industries, Ltd.) were added, and the reaction was carried out at 90° C. for 8 hours. After completion of the reaction, dichloromethane and water were added, and then a 25% aqueous sodium hydroxide was added for neutralization, and a reaction was carried out at room temperature for 1 hour. An organic layer, obtained by solution separation, was washed with saturated saline, and the solvent was removed from the reaction solution by concentration under reduced pressure to obtain 3.6 g (yield: 77%) of a purple solid lactone derivative (Compound 105).

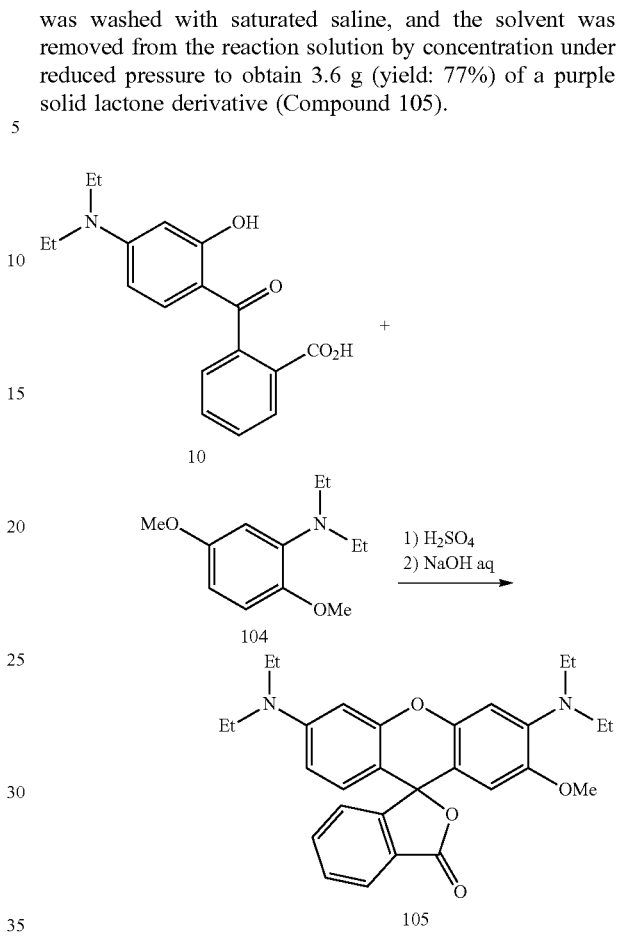

(3) Synthesis of a Carboxylic Acid Derivative (Compound 106)

Into a round-bottom flask equipped with a stirring apparatus, 1.1 g (2.4 mmol) of the lactone derivative (Compound 105) obtained in the (2), 0.5 g (4.8 mmol) of concentrated hydrochloric acid (produced by Wako Pure Chemical Industries, Ltd.), 2.0 g (2.6 mmol) of LiFABA (produced by Tosoh Finechem Corp.), and 10 mL of dichloromethane were added, and the reaction was carried out at room temperature for 1 hour. After dilution of the reaction solution with dichloromethane, it was washed sequentially with water and saturated saline. The solvent was removed from the reaction solution by concentration under reduced pressure to obtain 2.8 g (yield: 100%) of a purple solid carboxylic acid derivative having a tetrakis(pentafluorophenyl)borate (IV) anion as a counter anion (Compound 106).

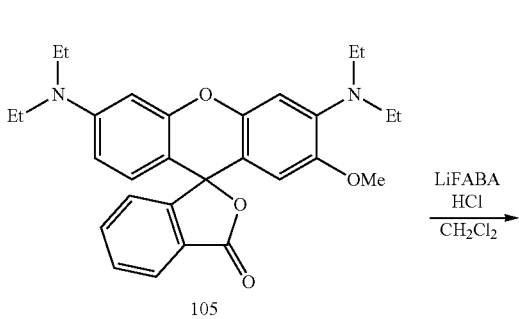

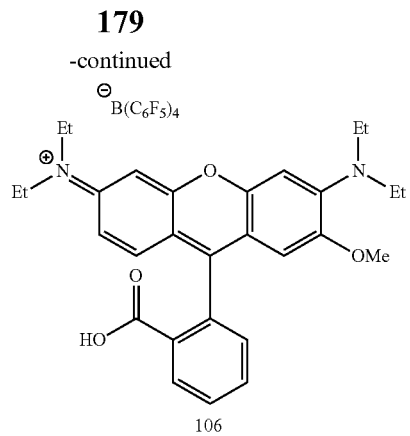

106

Example 56 Synthesis of a Monomer (Compound 107)

Into a round-bottom flask equipped with a stirring apparatus, 2.0 g (1.7 mmol) of the carboxylic acid derivative (Compound 106) obtained in Example 55, and 10 mL of dichloromethane were added for dissolution, and 0.5 g (3.5 mmol) of 2-hydroxyethyl methacrylate (Compound 16: produced by Wako Pure Chemical Industries, Ltd.), 60 mg (0.5 mmol) of DMAP (produced by Wako Pure Chemical Industries, Ltd.), and 0.4 g (1.9 mmol) of WSC (produced by Toyobo Co., Ltd.) were added, and the reaction was carried out at room temperature for 25 hours. The reaction solution was washed with water, and the solvent was removed from the reaction solution by concentration under reduced pressure to obtain a purple solid. The solid was purified by a silica gel column to obtain 1.4 g (yield: 62%) of a purple solid monomer (Compound 107).

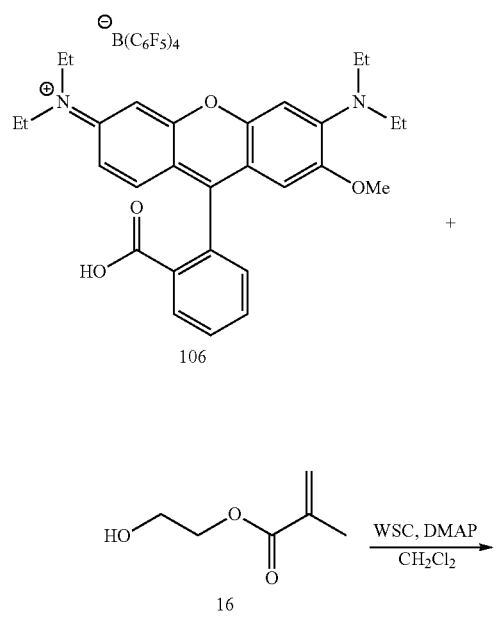

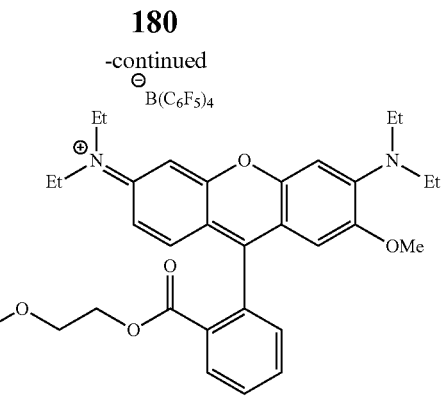

107

Example 57 Synthesis of a Carboxylic Acid Derivative (Compound 108)

Into a round-bottom flask equipped with a stirring apparatus, 1.9 g (4.0 mmol) of the lactone derivative (Compound 105) obtained in Example 55, 0.5 g (4.4 mmol) of concentrated hydrochloric acid (produced by Wako Pure Chemical Industries, Ltd.), 1.2 g (4.4 mmol) of potassium hexafluoroantimonate (produced by Morita Chemical Industries Co., Ltd.), and 15 mL of dichloromethane were added, and the reaction was carried out at room temperature for 2 hours. After dilution of the reaction solution with dichloromethane, it was washed with water. The solvent was removed from the reaction solution by concentration under reduced pressure to obtain 2.7 g (yield: 95%) of a purple solid carboxylic acid derivative having a hexafluoroantimonate anion as a counter anion (Compound 108).

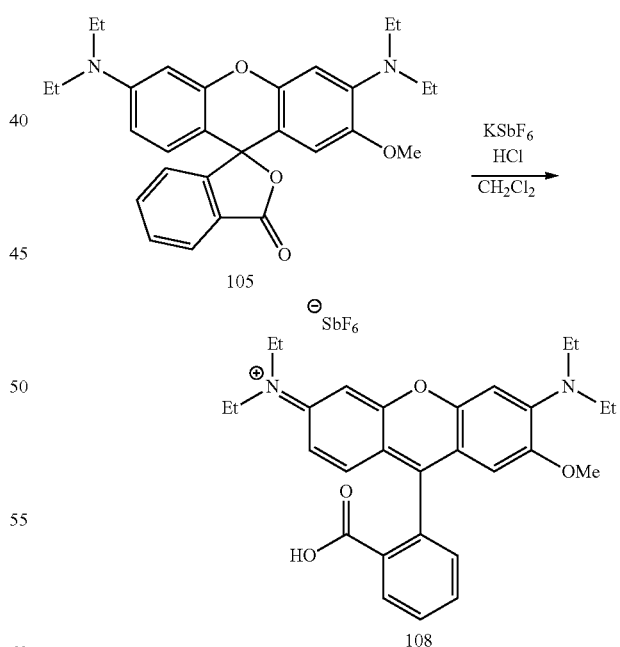

Example 58 Synthesis of a Monomer (Compound 109)

Into a round-bottom flask equipped with a stirring apparatus, 2.6 g (3.7 mmol) of the carboxylic acid derivative (Compound 108) obtained in Example 57, and 24 mL of dichloromethane were added for dissolution, and 0.6 g (4.4 mmol) of 2-hydroxyethyl methacrylate (Compound 16: produced by Wako Pure Chemical Industries, Ltd.), 50 mg (0.4 mmol) of DMAP (produced by Wako Pure Chemical Industries, Ltd.), and 1.2 g (6.3 mmol) of WSC (produced by Toyobo Co., Ltd.) were added, and the reaction was carried out at room temperature for 6 hours. The reaction solution was washed with water, and the solvent was removed from the reaction solution by concentration under reduced pressure to obtain a purple solid. The solid was purified by a silica gel column to obtain 2.5 g (yield: 82%) of a purple solid monomer (Compound 109).

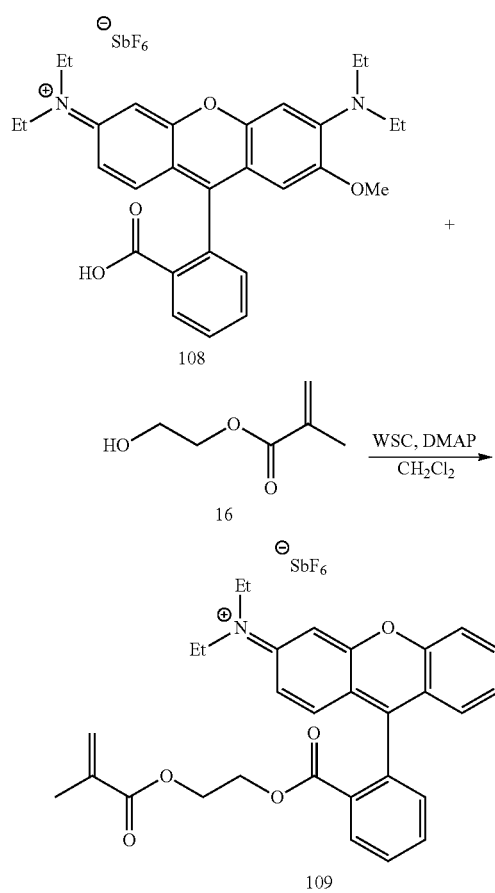

Example 59 Synthesis of a Carboxylic Acid Derivative (Compound 110)

Into a round-bottom flask equipped with a stirring apparatus, 1.7 g (4.0 mmol) of 6'-(diethylamino)-1',2'-benzofluoran (Compound 1: produced by Tokyo Chemical Industry Co., Ltd.), 0.7 g (4.0 mmol) of perchloric acid (produced by Wako Pure Chemical Industries, Ltd.), and 15 mL of dichloromethane were added, and the reaction was carried out at room temperature for 2 hours. The precipitated crystal, by the addition of water to the reaction solution, was filtrated and dried to obtain 1.7 g (yield: 82%) of a brown carboxylic acid derivative having a perchloric acid anion as a counter anion (Compound 110).

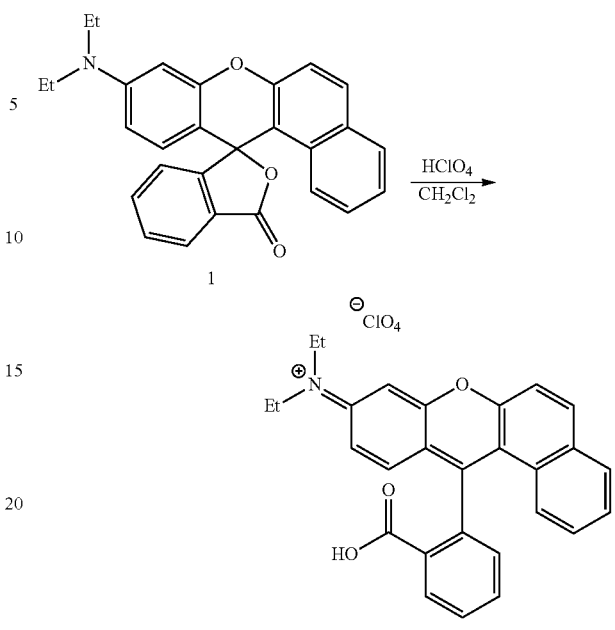

Example 60 Synthesis of a Monomer (Compound 112)

Into a round-bottom flask equipped with a stirring apparatus, 0.32 g (0.28 mmol) of the carboxylic acid derivative (Compound 106) obtained in Example 55, and 10 mL of dichloromethane were added for dissolution, and 0.05 g (0.56 mmol) of piperidine (Compound 111: produced by Wako Pure Chemical Industries, Ltd.), 10 mg (0.08 mmol) of DMAP (produced by Wako Pure Chemical Industries, Ltd.), and 0.11 g (0.56 mmol) of WSC (produced by Toyobo Co., Ltd.) were added, and the reaction was carried out at room temperature for 6.5 hours. The reaction solution was washed with water, and the solvent was removed from the reaction solution by concentration under reduced pressure to obtain a purple solid. The solid was purified by a silica gel column to obtain 0.21 g (yield: 62%) of a purple solid monomer (Compound 112).

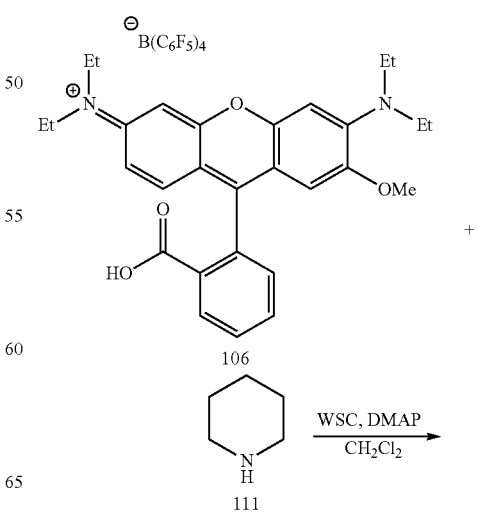

-continued

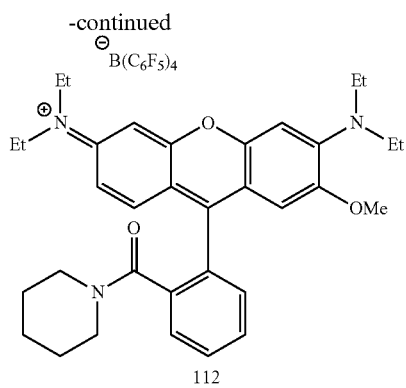

112

Experimental Example 1 Quenching Evaluation of Rhodamine B by the Monomer (Compound 17)

(1) Fluorescence Measurement of the Object Compound of Quenching

Into a volumetric flask, 13 mg (0.027 mmol) of Rhodamine B (produced by Wako Pure Chemical Industries, Ltd.) was put and diluted up to 100 mL with methanol. With a volumetric pipette, 1 mL of the solution was measured and taken, and further diluted in a volumetric flask up to 100 mL with methanol. This was referred to as an A solution. With a volumetric pipette, 2 mL of the A solution was measured and taken, and diluted in a volumetric flask up to 20 mL with methanol (concentration: $2.76 \times 10^{-7}$ mol/L). Fluorescence intensity (Ia) at the maximum fluorescence wavelength of the resulting solution was measured using a fluorescence spectrophotometer (Fluorescence Spectrophotometer F-4500, manufactured by Hitachi Ltd.).

(2) Quenching Evaluation (i)

Compound 17 obtained in Example 9 was measured and taken by 11 mg (0.0091 mmol), and diluted in a volumetric flask up to 100 mL with methanol. This was referred to as a B solution. With a volumetric pipette, 2 mL of the A solution and 10 mL of the B solution was measured and taken, and diluted in a volumetric flask up to 20 mL with methanol (concentration: $4.67 \times 10^{-5}$ mol/L). Fluorescence intensity (Ib) at the maximum fluorescence wavelength of the resulting solution was measured using a fluorescence spectrophotometer (Fluorescence Spectrophotometer F-4500, manufactured by Hitachi Ltd.). From measured values of Ia and Ib, decreasing rate (%) of fluorescence intensity was calculated by the following equation.

Decreasing rate (%) of fluorescence intensity=$(Ia-Ib)/Ia \times 100$ (3) Quenching Evaluation (ii)

Decreasing rate (%) of fluorescence intensity was calculated by a similar method as in (2), except for using 4 mL, instead of 10 mL of the B solution (concentration: $1.87 \times 10^{-5}$ mol/L).

Results of Experimental Example 1 are shown in TABLE 1.

TABLE 1

| Quenching evaluation | Concentration of compound 17 (mol/L) | Decreasing rate of fluorescence intensity (%) |
| --- | --- | --- |
| (i) | $4.67 \times 10^{-5}$ | 91.8 |
| (ii) | $1.87 \times 10^{-5}$ | 68.6 |

From the results shown in the TABLE 1, it has been revealed that the quencher of the present invention has quenching ability enough to suppress fluorescence emission of Rhodamine B having a xanthene skeleton. In addition, it has been revealed that the quenching ability depends on the concentration of the compound of the present invention, and the higher concentration provides the higher decreasing rate of fluorescence intensity (higher quenching ability).

Experimental Example 2 Quenching Evaluation of Rhodamine B by the Carboxylic Acid Derivative (Compound 2)

Compound 2 obtained in Example 1 was measured and taken by 17 mg (0.0037 mmol), and diluted in a volumetric flask up to 100 mL with methanol. This was referred to as an R solution. With a volumetric pipette, 2 mL of the resulting A solution in Experimental Example 1 and 4.0 mL of the R solution was measured and taken, and diluted in a volumetric flask up to 20 mL with methanol (concentration: $4.89 \times 10^{-5}$ mol/L). Decreasing rate of fluorescence intensity was calculated by a similar method as in (2) of Experimental Example 1, using the resulting solution.

Experimental Example 3 Quenching Evaluation of Rhodamine B by the Carboxylic Acid Derivative (Compound 3)

Decreasing rate of fluorescence intensity was calculated by a similar method as in (2) of Experimental Example 1, except for using 9.8 mg (0.0089 mmol) of Compound 3 obtained in Example 2, instead of Compound 17 (concentration: $4.45 \times 10^{-5}$ mol/L).

Experimental Example 4 Quenching Evaluation of Rhodamine B by the Carboxylic Acid Derivative (Compound 4)

Decreasing rate of fluorescence intensity was calculated by a similar method as in (2) of Experimental Example 1, except for using 17 mg (0.024 mmol) of Compound 4 obtained in Example 3, instead of Compound 17 (concentration: $8.25 \times 10^{-5}$ mol/L).

Experimental Example 5 Quenching Evaluation of Rhodamine B by the Carboxylic Acid Derivative (Compound 6)

Decreasing rate of fluorescence intensity was calculated by a similar method as in (2) of Experimental Example 1, except for using 15 mg (0.014 mmol) of Compound 6 obtained in Example 4, instead of Compound 17 (concentration: $6.76 \times 10^{-5}$ mol/L).

Experimental Example 6 Quenching Evaluation of Rhodamine B by the Carboxylic Acid Derivative (Compound 8)

Decreasing rate of fluorescence intensity was calculated by a similar method as in (2) of Experimental Example 1, except for using 12 mg (0.00095 mmol) of Compound 8 obtained in Example 5, instead of Compound 17 (concentration: $4.77 \times 10^{-5}$ mol/L).

Experimental Example 7 Quenching Evaluation of Rhodamine B by the Carboxylic Acid Derivative (Compound 9)

Decreasing rate of fluorescence intensity was calculated by a similar method as in (2) of Experimental Example 1, except for using 16.5 mg (0.019 mmol) of Compound 9 obtained in Example 6, instead of Compound 17 (concentration: $3.89 \times 10^{-5}$ mol/L).

Experimental Example 8 Quenching Evaluation of Rhodamine B by the Carboxylic Acid Derivative (Compound 13)

Decreasing rate of fluorescence intensity was calculated by a similar method as in (2) of Experimental Example 1, except for using 13.3 mg (0.012 mmol) of Compound 13 obtained in Example 7, instead of Compound 17 (concentration: $6.22 \times 10^{-5}$ mol/L).

Experimental Example 9 Quenching Evaluation of Rhodamine B by the Methyl Ester Derivative (Compound 15)

Decreasing rate of fluorescence intensity was calculated by a similar method as in (2) of Experimental Example 1, except for using 13.7 mg (0.012 mmol) of Compound 15 obtained in Example 8, instead of Compound 17 (concentration: $2.46 \times 10^{-5}$ mol/L).

Experimental Example 10 Quenching Evaluation of Rhodamine B by the Monomer (Compound 18)

Decreasing rate of fluorescence intensity was calculated by a similar method as in (2) of Experimental Example 1, except for using 12.6 mg (0.011 mmol) of Compound 18 obtained in Example 10, instead of Compound 17 (concentration: $5.29 \times 10^{-5}$ mol/L).

Experimental Example 11 Quenching Evaluation of Rhodamine B by the Monomer (Compound 19)

Compound 19 obtained in Example 11 was measured and taken by 11.2 mg (0.0082 mmol), and diluted in a volumetric flask up to 100 mL with methanol. This was referred to as an S solution. With a volumetric pipette, 2 mL of the resulting A solution in Experimental Example 1 and 12 mL of the S solution was measured and taken, and diluted in a volumetric flask up to 20 mL with methanol (concentration: $4.95 \times 10^{-5}$ mol/L). Decreasing rate of fluorescence intensity was calculated by a similar method as in (2) of Experimental Example 1, using the resulting solution.

Experimental Example 12 Quenching Evaluation of Rhodamine B by the Monomer (Compound 20)

Compound 20 obtained in Example 12 was measured and taken by 15.2 mg (0.016 mmol), and diluted in a volumetric flask up to 100 mL with methanol. This was referred to as a T solution. With a volumetric pipette, 2 mL of the resulting A solution in Experimental Example 1 and 7.0 mL of the T solution was measured and taken, and diluted in a volumetric flask up to 20 mL with methanol (concentration: $5.54 \times 10^{-5}$ mol/L). Decreasing rate of fluorescence intensity was calculated by a similar method as in (2) of Experimental Example 1, using the resulting solution.

Experimental Example 13 Quenching Evaluation of Rhodamine B by the Monomer (Compound 21)

Decreasing rate of fluorescence intensity was calculated by a similar method as in (2) of Experimental Example 1, except for using 13 mg (0.011 mmol) of Compound 21 obtained in Example 13, instead of Compound 17 (concentration: $5.50 \times 10^{-5}$ mol/L).

Experimental Example 14 Quenching Evaluation of Rhodamine B by the Monomer (Compound 28)

Decreasing rate of fluorescence intensity was calculated by a similar method as in (2) of Experimental Example 1, except for using 16.4 mg (0.014 mmol) of Compound 28 obtained in Example 15, instead of Compound 17 (concentration: $2.78 \times 10^{-5}$ mol/L).

Experimental Example 15 Quenching Evaluation of Rhodamine B by the Monomer (Compound 38)

Decreasing rate of fluorescence intensity was calculated by a similar method as in (2) of Experimental Example 1, except for using 10.1 mg (0.0081 mmol) of Compound 38 obtained in Example 20, instead of Compound 17 (concentration: $4.03 \times 10^{-5}$ mol/L).

Experimental Example 16 Quenching Evaluation of Rhodamine B by the Monomer (Compound 43)

Decreasing rate of fluorescence intensity was calculated by a similar method as in (2) of Experimental Example 1, except for using 12.0 mg (0.0096 mmol) of Compound 43 obtained in Example 22, instead of Compound 17 (concentration: $4.82 \times 10^{-5}$ mol/L).

Experimental Example 17 Quenching Evaluation of Rhodamine B by the Monomer (Compound 51)

Decreasing rate of fluorescence intensity was calculated by a similar method as in (2) of Experimental Example 1, except for using 13.0 mg (0.011 mmol) of Compound 51 obtained in Example 26, instead of Compound 17 (concentration: $5.33 \times 10^{-5}$ mol/L).

Experimental Example 18 Quenching Evaluation of Rhodamine B by the Monomer (Compound 55)

Decreasing rate of fluorescence intensity was calculated by a similar method as in (2) of Experimental Example 1, except for using 10.3 mg (0.0083 mmol) of Compound 55 obtained in Example 28, instead of Compound 17 (concentration: $4.15 \times 10^{-5}$ mol/L).

Experimental Example 19 Quenching Evaluation of Rhodamine B by the Monomer (Compound 59)

Compound 59 obtained in Example 30 was measured and taken by 11.4 mg (0.0089 mmol), and diluted in a volumetric flask up to 100 mL with methanol. This was referred to as a U solution. With a volumetric pipette, 2 mL of the resulting A solution in Experimental Example 1 and 12 mL of the U solution was measured and taken, and diluted in a volumetric flask up to 20 mL with methanol (concentration: $5.33 \times 10^{-5}$ mol/L). Decreasing rate of fluorescence intensity was calculated by a similar method as in (2) of Experimental Example 1, using the resulting solution.

Experimental Example 20 Quenching Evaluation of Rhodamine B by the Monomer (Compound 63)

Decreasing rate of fluorescence intensity was calculated by a similar method as in (2) of Experimental Example 1, except for using 8.2 mg (0.0065 mmol) of Compound 63 obtained in Example 32, instead of Compound 17 (concentration: $3.27 \times 10^{-5}$ mol/L).

Experimental Example 21 Quenching Evaluation of Rhodamine B by the Monomer (Compound 76)

Decreasing rate of fluorescence intensity was calculated by a similar method as in (2) of Experimental Example 1, except for using 9.8 mg (0.0079 mmol) of Compound 76 obtained in Example 38, instead of Compound 17 (concentration: $3.96 \times 10^{-5}$ mol/L).

Experimental Example 22 Quenching Evaluation of Rhodamine B by the Monomer (Compound 80)

Decreasing rate of fluorescence intensity was calculated by a similar method as in (2) of Experimental Example 1, except for using 10.1 mg (0.0083 mmol) of Compound 80 obtained in Example 40, instead of Compound 17 (concentration: $4.17 \times 10^{-5}$ mol/L).

Experimental Example 23 Quenching Evaluation of Rhodamine B by the Monomer (Compound 84)

Decreasing rate of fluorescence intensity was calculated by a similar method as in (2) of Experimental Example 1, except for using 9.5 mg (0.0080 mmol) of Compound 84 obtained in Example 42, instead of Compound 17 (concentration: $3.98 \times 10^{-5}$ mol/L).

Experimental Example 24 Quenching Evaluation of Rhodamine B by the Monomer (Compound 89)

Decreasing rate of fluorescence intensity was calculated by a similar method as in (2) of Experimental Example 1, except for using 10.4 mg (0.0084 mmol) of Compound 89 obtained in Example 44, instead of Compound 17 (concentration: $3.43 \times 10^{-5}$ mol/L).

Experimental Example 25 Quenching Evaluation of Rhodamine B by the Monomer (Compound 92)

Decreasing rate of fluorescence intensity was calculated by a similar method as in (2) of Experimental Example 1, except for using 9.1 mg (0.0069 mmol) of Compound 92 obtained in Example 46, instead of Compound 17 (concentration: $3.43 \times 10^{-5}$ mol/L).

Experimental Example 26 Quenching Evaluation of Rhodamine B by the Monomer (Compound 95)

Decreasing rate of fluorescence intensity was calculated by a similar method as in (2) of Experimental Example 1, except for using 11.0 mg (0.0084 mmol) of Compound 95 obtained in Example 48, instead of Compound 17 (concentration: $4.20 \times 10^{-5}$ mol/L).

Experimental Example 27 Quenching Evaluation of Rhodamine B by the Monomer (Compound 98)

Decreasing rate of fluorescence intensity was calculated by a similar method as in (2) of Experimental Example 1, except for using 11.0 mg (0.0083 mmol) of Compound 98 obtained in Example 50, instead of Compound 17 (concentration: $4.13 \times 10^{-5}$ mol/L).

Experimental Example 28 Quenching Evaluation of Rhodamine B by the Monomer (Compound 107)

Decreasing rate of fluorescence intensity was calculated by a similar method as in (2) of Experimental Example 1, except for using 13.3 mg (0.011 mmol) of Compound 107 obtained in Example 56, instead of Compound 17 (concentration: $5.26 \times 10^{-5}$ mol/L).

Experimental Example 29 Quenching Evaluation of Rhodamine B by the Monomer (Compound 109)

Decreasing rate of fluorescence intensity was calculated by a similar method as in (2) of Experimental Example 1, except for using 8.5 mg (0.010 mmol) of Compound 109 obtained in Example 58, instead of Compound 17 (concentration: $5.17 \times 10^{-5}$ mol/L).

Experimental Example 30 Quenching Evaluation of Rhodamine B by the Carboxylic Acid Derivative (Compound 110)

Compound 110 obtained in Example 59 was measured and taken by 8.6 mg (0.016 mmol), and diluted in a volumetric flask up to 100 mL with methanol. This was referred to as a V solution. With a volumetric pipette, 2 mL of the resulting A solution in Experimental Example 1 and 6 mL of the V solution was measured and taken, and diluted in a volumetric flask up to 20 mL with methanol (concentration: $4.94 \times 10^{-5}$ mol/L). Decreasing rate of fluorescence intensity was calculated by a similar method as in (2) of Experimental Example 1, using the resulting solution.

Experimental Example 31 Quenching Evaluation of Rhodamine B by the Monomer (Compound 112)

Compound 112 obtained in Example 60 was measured and taken by 9.4 mg (0.0077 mmol), and diluted in a volumetric flask up to 100 mL with methanol. This was referred to as a W solution. With a volumetric pipette, 2 mL of the resulting A solution in Experimental Example 1 and 14 mL of the W solution was measured and taken, and diluted in a volumetric flask up to 20 mL with methanol (concentration: $5.39 \times 10^{-5}$ mol/L). Decreasing rate of fluorescence intensity was calculated by a similar method as in (2) of Experimental Example 1, using the resulting solution.

Experimental Example 32 Quenching Evaluation of Rhodamine B by the Monomer (Compound 30)

Compound 30 obtained in Example 16 was measured and taken by 11.1 mg (0.0093 mmol), and diluted in a volumetric flask up to 100 mL with methanol. This was referred to as an X solution. With a volumetric pipette, 2 mL of the resulting A solution in Experimental Example 1 and 12 mL of the X solution was measured and taken, and diluted in a volumetric flask up to 20 mL with methanol (concentration: $5.55 \times 10^{-5}$ mol/L). Decreasing rate of fluorescence intensity was calculated by a similar method as in (2) of Experimental Example 1, using the resulting solution.

Comparative Example 1 Quenching Evaluation of Rhodamine B by Diethylacrylamide

Diethylacrylamide (produced by Wako Pure Chemical Industries, Ltd.) was measured and taken by 12.5 mg (0.00098 mmol), and diluted in a volumetric flask up to 100 mL with methanol. This was referred to as a B' solution. With a volumetric pipette, 2 mL of the resulting A solution in Experimental Example 1 and 1 mL of the B' solution measured and taken, and diluted in a volumetric flask up to 20 mL with methanol (concentration: $4.91 \times 10^{-5}$ mol/L). Fluorescence intensity (Ib') at the maximum fluorescence wavelength of the resulting solution was measured using a fluorescence spectrophotometer (Fluorescence Spectrophotometer F-4500, manufactured by Hitachi Ltd.). From the resulting value of Ia in Experimental Example 1, and the measured value of Ib', decreasing rate (%) of fluorescence intensity was calculated by the following equation.

Decreasing rate (%) of fluorescence intensity=(Ia−Ib')/Ia×100

Comparative Example 2 Quenching Evaluation of Rhodamine B by Pyridine

Decreasing rate of fluorescence intensity was calculated by a similar method as in Comparative Example 1, except for using 12.0 mg (0.0015 mmol) of pyridine (produced by Wako Pure Chemical Industries, Ltd.), instead of diethylacrylamide (concentration: $7.58 \times 10^{-5}$ mol/L).

Comparative Example 3 Quenching Evaluation of Rhodamine B by Triphenylamine

Decreasing rate of fluorescence intensity was calculated by a similar method as in Comparative Example 1, except for using 28.2 mg (0.0011 mmol) of triphenylamine (produced by Wako Pure Chemical Industries, Ltd.), instead of diethylacrylamide (concentration: $5.74 \times 10^{-5}$ mol/L).

Comparative Example 4 Quenching Evaluation of Rhodamine B by N,N-diethylaniline

Decreasing rate of fluorescence intensity was calculated by a similar method as in Comparative Example 1, except for using 20.0 mg (0.0013 mmol) of N,N-diethylaniline (produced by Wako Pure Chemical Industries, Ltd.), instead of diethylacrylamide (concentration: $6.70 \times 10^{-5}$ mol/L).

Comparative Example 5 Quenching Evaluation of Rhodamine B by p-Aminobenzoic Acid Decreasing rate of fluorescence intensity was calculated by a similar method as in Comparative Example 1, except for using 14.3 mg (0.0010 mmol) of p-aminobenzoic acid (produced by Wako Pure Chemical Industries, Ltd.), instead of diethylacrylamide (concentration: $5.21 \times 10^{-5}$ mol/L).

Results of Experimental Examples 2 to 32 are shown in TABLE 2. In addition, results of Comparative Examples 1 to 5 are shown in TABLE 3.

TABLE 2

| Experimental Example | Quencher | Concentration of each compound (mol/L) | Decreasing rate of fluorescence intensity (%) |
|---|---|---|---|
| Exp. Exam. 2 | Compound 2 | $4.89 \times 10^{-5}$ | 89.8 |
| Exp. Exam. 3 | Compound 3 | $4.45 \times 10^{-5}$ | 81.9 |
| Exp. Exam. 4 | Compound 4 | $8.25 \times 10^{-5}$ | 52.9 |
| Exp. Exam. 5 | Compound 6 | $6.76 \times 10^{-5}$ | 50.9 |
| Exp. Exam. 6 | Compound 8 | $4.77 \times 10^{-5}$ | 74.6 |
| Exp. Exam. 7 | Compound 9 | $3.89 \times 10^{-5}$ | 72.4 |
| Exp. Exam. 8 | Compound 13 | $6.22 \times 10^{-5}$ | 52.7 |
| Exp. Exam. 9 | Compound 15 | $2.46 \times 10^{-5}$ | 75.6 |
| Exp. Exam. 10 | Compound 18 | $5.29 \times 10^{-5}$ | 56.7 |
| Exp. Exam. 11 | Compound 19 | $4.95 \times 10^{-5}$ | 79.8 |
| Exp. Exam. 12 | Compound 20 | $5.54 \times 10^{-5}$ | 77.4 |
| Exp. Exam. 13 | Compound 21 | $5.50 \times 10^{-5}$ | 61.7 |
| Exp. Exam. 14 | Compound 28 | $2.78 \times 10^{-5}$ | 79.1 |
| Exp. Exam. 15 | Compound 38 | $4.03 \times 10^{-5}$ | 64.7 |
| Exp. Exam. 16 | Compound 43 | $4.82 \times 10^{-5}$ | 89.4 |
| Exp. Exam. 17 | Compound 51 | $5.33 \times 10^{-5}$ | 56.8 |
| Exp. Exam. 18 | Compound 55 | $4.15 \times 10^{-5}$ | 71.3 |
| Exp. Exam. 19 | Compound 59 | $5.33 \times 10^{-5}$ | 67.7 |
| Exp. Exam. 20 | Compound 63 | $3.27 \times 10^{-5}$ | 69.9 |
| Exp. Exam. 21 | Compound 76 | $3.96 \times 10^{-5}$ | 61.5 |
| Exp. Exam. 22 | Compound 80 | $4.17 \times 10^{-5}$ | 80.2 |
| Exp. Exam. 23 | Compound 84 | $3.98 \times 10^{-5}$ | 82.2 |
| Exp. Exam. 24 | Compound 89 | $3.43 \times 10^{-5}$ | 78.8 |
| Exp. Exam. 25 | Compound 92 | $3.43 \times 10^{-5}$ | 54.6 |
| Exp. Exam. 26 | Compound 95 | $4.20 \times 10^{-5}$ | 82.8 |
| Exp. Exam. 27 | Compound 98 | $4.13 \times 10^{-5}$ | 83.0 |
| Exp. Exam. 28 | Compound 107 | $5.26 \times 10^{-5}$ | 91.9 |
| Exp. Exam. 29 | Compound 109 | $5.17 \times 10^{-5}$ | 92.3 |
| Exp. Exam. 30 | Compound 110 | $4.94 \times 10^{-5}$ | 78.4 |
| Exp. Exam. 31 | Compound 112 | $5.39 \times 10^{-5}$ | 92.5 |
| Exp. Exam. 32 | Compound 30 | $5.55 \times 10^{-5}$ | 93.5 |

TABLE 3

| Comparative Example | Quencher | Concentration of each compound (mol/L) | Decreasing rate of fluorescence intensity (%) |
|---|---|---|---|
| Com. Exam. 1 | diethylacrylamide | $4.91 \times 10^{-5}$ | 2.3 |
| Com. Exam. 2 | pyridine | $7.58 \times 10^{-5}$ | 2.2 |
| Com. Exam. 3 | triphenylamine | $5.74 \times 10^{-5}$ | 5.1 |
| Com. Exam. 4 | N,N-diethylaniline | $6.70 \times 10^{-5}$ | 5.9 |
| Com. Exam. 5 | p-aminobenzoic acid | $5.21 \times 10^{-5}$ | 5.9 |

From the results shown in the TABLE 2, it has been revealed that all of the quenchers of the present invention have quenching ability enough to suppress fluorescence emission of Rhodamine B having a xanthene skeleton. Still more, from comparison of the results shown in the TABLE 2, and the results shown in the TABLE 3, it has been revealed that the quencher of the present invention exerts superior quenching effect as compared with conventional quenchers such as diethylacrylamide.

Experimental Example 33 Quenching Evaluation of Quinine Sulfate by the Monomer (Compound 17)

(1) Fluorescence Measurement of the Object Compound of Quenching

Into a volumetric flask, 10.9 mg (0.015 mmol) of quinine sulfate (produced by Wako Pure Chemical Industries, Ltd.) was put and diluted up to 100 mL with methanol. With a volumetric pipette, 10 mL of the solution was measured and taken, and further diluted in a volumetric flask up to 100 mL with methanol. This was referred to as a C solution. With a volumetric pipette, 4 mL of the C solution was measured and taken, and diluted in a volumetric flask up to 20 mL with methanol (concentration: $2.91 \times 10^{-6}$ mol/L). Fluorescence intensity (Ic) at the maximum fluorescence wavelength of the resulting solution was measured using a fluorescence spectrophotometer (Fluorescence Spectrophotometer F-4500, manufactured by Hitachi Ltd.).

(2) Quenching Evaluation (iii)

Compound 17 obtained in Example 9 was measured and taken by 21.7 mg (0.018 mmol), and diluted in a volumetric flask up to 100 mL with methanol. This was referred to as a D solution. With a volumetric pipette, 2 mL of the D solution and 4 mL of the C solution was measured and taken, and diluted in a volumetric flask up to 20 mL with methanol (concentration: $8.94 \times 10^{-5}$ mol/L). Fluorescence intensity (Id) at the maximum fluorescence wavelength of the resulting solution was measured using a fluorescence spectrophotometer (Fluorescence Spectrophotometer F-4500, manufactured by Hitachi Ltd.). From measured values of Ic and Id, decreasing rate (%) of fluorescence intensity was calculated by the following equation.

Decreasing rate (%) of fluorescence intensity= $(Ic-Id)/Ic \times 100$ (3) Quenching Evaluation (iv)

Decreasing rate (%) of fluorescence intensity was calculated by a similar method as in (2), except for using 1 mL, instead of 2 mL of the D solution (concentration: $4.47 \times 10^{-5}$ mol/L).

Experimental Example 34 Quenching Evaluation of Fluorescein by the Monomer (Compound 17)

(1) Fluorescence Measurement of the Object Compound of Quenching

Into a volumetric flask, 10.9 mg (0.033 mmol) of fluorescein (produced by Wako Pure Chemical Industries, Ltd.) was put and diluted up to 100 mL with methanol. With a volumetric pipette, 10 mL of the solution was measured and taken, and further diluted in a volumetric flask up to 100 mL with methanol. This was referred to as an E solution. With a volumetric pipette, 2 mL of the E solution was measured and taken, and diluted in a volumetric flask up to 20 mL with methanol (concentration: $3.28 \times 10^{-6}$ mol/L). Fluorescence intensity (Ie) at the maximum fluorescence wavelength of the resulting solution was measured using a fluorescence spectrophotometer (Fluorescence Spectrophotometer F-4500, manufactured by Hitachi Ltd.).

(2) Quenching Evaluation (v)

Compound 17 obtained in Example 9 was measured and taken by 14.3 mg (0.012 mmol), and diluted in a volumetric flask up to 100 mL with methanol. This was referred to as an F solution. With a volumetric pipette, 10 mL of the F solution and 2 mL of the E solution was measured and taken, and diluted in a volumetric flask up to 20 mL with methanol (concentration: $5.89 \times 10^{-5}$ mol/L). Fluorescence intensity (If) at the maximum fluorescence wavelength of the resulting solution was measured using a fluorescence spectrophotometer (Fluorescence Spectrophotometer F-4500, manufactured by Hitachi Ltd.). From measured values of Ie and If, decreasing rate (%) of fluorescence intensity was calculated by the following equation.

Decreasing rate (%) of fluorescence intensity=$(Ie-If)/Ie \times 100$ (3) Quenching Evaluation (vi)

Decreasing rate (%) of fluorescence intensity was calculated by a similar method as in (2), except for using 4 mL, instead of 10 mL of the F solution (concentration: $2.36 \times 10^{-5}$ mol/L).

(4) Quenching Evaluation (vii)

Decreasing rate (%) of fluorescence intensity was calculated by a similar method as in (2), except for using 2.5 mL, instead of 10 mL of the F solution (concentration: $1.47 \times 10^{-5}$ mol/L).

Experimental Example 35 Quenching Evaluation of Coumarin 6 by the Monomer (Compound 17)

(1) Fluorescence Measurement of the Object Compound of Quenching

Into a volumetric flask, 15.2 mg (0.043 mmol) of coumarin 6 (produced by Tokyo Chemical Industry Co., Ltd.) was put and diluted up to 100 mL with methanol. With a volumetric pipette, 1 mL of the solution was measured and taken, and further diluted in a volumetric flask up to 100 mL with methanol. This was referred to as a G solution. With a volumetric pipette, 1 mL of the G solution was measured and taken, and diluted in a volumetric flask up to 20 mL with methanol (concentration: $2.17 \times 10^{-7}$ mol/L). Fluorescence intensity (Ig) at the maximum fluorescence wavelength of the resulting solution was measured using a fluorescence spectrophotometer (Fluorescence Spectrophotometer F-4500, manufactured by Hitachi Ltd.).

(2) Quenching Evaluation (viii)

Compound 17 obtained in Example 9 was measured and taken by 12.1 mg (0.010 mmol), and diluted in a volumetric flask up to 100 mL with methanol. This was referred to as an H solution. With a volumetric pipette, 4 mL of the H solution and 1 mL of the G solution was measured and taken, and diluted in a volumetric flask up to 20 mL with methanol (concentration: $1.99 \times 10^{-5}$ mol/L). Fluorescence intensity (Ih) at the maximum fluorescence wavelength of the resulting solution was measured using a fluorescence spectrophotometer (Fluorescence Spectrophotometer F-4500, manufactured by Hitachi Ltd.). From measured values of Ig and Ih, decreasing rate (%) of fluorescence intensity was calculated by the following equation.

Decreasing rate (%) of fluorescence intensity= $(Ig-Ih)/Ig \times 100$

Experimental Example 36 Quenching Evaluation of Anthracene by the Monomer (Compound 17)

(1) Fluorescence Measurement of the Object Compound of Quenching

Into a volumetric flask, 11.5 mg (0.065 mmol) of anthracene (produced by Wako Pure Chemical Industries, Ltd.) was put and diluted up to 100 mL with methanol. With a volumetric pipette, 1 mL of the solution was measured and taken, and further diluted in a volumetric flask up to 100 mL with methanol. This was referred to as an I solution. With a volumetric pipette, 1 mL of the I solution was measured and taken, and diluted in a volumetric flask up to 20 mL with methanol (concentration: $3.23 \times 10^{-7}$ mol/L). Fluorescence intensity (Ii) at the maximum fluorescence wavelength of the resulting solution was measured using a fluorescence spectrophotometer (Fluorescence Spectrophotometer F-4500, manufactured by Hitachi Ltd.).

(2) Quenching Evaluation (ix)

Compound 17 obtained in Example 9 was measured and taken by 12.1 mg (0.010 mmol), and diluted in a volumetric flask up to 100 mL with methanol. This was referred to as a J solution. With a volumetric pipette, 10 mL of the J solution and 1 mL of the I solution was measured and taken, and diluted in a volumetric flask up to 20 mL with methanol (concentration: $4.99 \times 10^{-5}$ mol/L). Fluorescence intensity (Ij) at the maximum fluorescence wavelength of the resulting solution was measured using a fluorescence spectrophotometer (Fluorescence Spectrophotometer F-4500, manufactured by Hitachi Ltd.). From measured values of Ii and Ij, decreasing rate (%) of fluorescence intensity was calculated by the following equation.

Decreasing rate (%) of fluorescence intensity= $(Ii-Ij)/Ii \times 100$ (3) Quenching Evaluation (x)

Decreasing rate (%) of fluorescence intensity was calculated by a similar method as in (2), except for using 4 mL, instead of 10 mL of the J solution (concentration: $1.99 \times 10^{-5}$ mol/L).

Results of Experimental Examples 33 to 36 are shown in TABLE 4.

TABLE 4

| Experimental Example | Quenching evaluation | Quenching object compound | Concentration of compound 17 (mol/L) | Decreasing rate of fluorescence intensity (%) |
|---|---|---|---|---|
| Exp. Example 33 | (iii) (iv) | quinine sulfate | $8.94 \times 10^{-5}$ $4.47 \times 10^{-5}$ | 95.6 84.2 |
| Exp. Example 34 | (v) (vi) (vii) | fluorescein | $5.89 \times 10^{-5}$ $2.36 \times 10^{-5}$ $1.47 \times 10^{-5}$ | 98.7 80.9 61.8 |
| Exp. Example 35 | (viii) | coumarin 6 | $1.99 \times 10^{-5}$ | 55.4 |
| Exp. Example 36 | (ix) (x) | anthracene | $4.99 \times 10^{-5}$ $1.99 \times 10^{-5}$ | 82.2 52.8 |

From the results shown in the TABLE 4, it has been revealed that the quencher of the present invention has quenching ability enough to suppress fluorescence emission of various compounds having fluorescent property, such as anthracene, quinine sulfate having a quinoline skeleton, fluorescein having a xanthene skeleton, and coumarin 6 having a coumarin skeleton.

Experimental Example 37 Heat Resistance Evaluation (at 230° C., for 0.5 Hour) of the Monomer (Compound 17)

Heat resistance of Compound 17 obtained in Example 9 was evaluated as follows.
(1) Synthesis of a Polymer not Containing a Dye Into a round-bottom flask equipped with a stirring apparatus, a cooling tube, a thermometer and a nitrogen introduction tube, 98.5 g of propylene glycol monomethyl ether acetate (PGMEA) (produced by Wako Pure Chemical Industries, Ltd.) was added, and heated until inner temperature reached to 90° C. under nitrogen gas flow. Next, a solution mixed with 186.2 g of benzyl methacrylate (produced by Wako Pure Chemical Industries, Ltd.), 25.6 g of methacrylic acid (produced by Wako Pure Chemical Industries, Ltd.), and 33.9 g of 2,2'-azobis(methyl 2-methylpropionate) (trade name: V-601, produced by Wako Pure Chemical Industries, Ltd.) was dropped into heated PGMEA taking 2 hours. After that, the resulting solution was reacted at 90° C. for 2 hours. Next, temperature of the solution was heated up to 100° C., and the reaction was carried out for 1 hour. After the reaction, the solution was cooled to room temperature, and 171.5 g of PGMEA was added for dilution, to obtain a pale yellow transparent polymer solution. This was referred to as a polymer A. It should be noted that concentration of non-volatile components of the polymer A was 36.1%.
(2) Preparation of a Dye Monomer Mixture Solution A dye monomer mixed solution B was prepared by mixing 0.08 g of Compound 17 obtained in Example 9, 4.24 g of the polymer A, and 2.68 g of PGMEA.

(3) Heat Resistance Evaluation

A thin film with a film thickness of 1 μm was obtained by spin coating the dye monomer mixed solution B onto 3 inch glass wafer (Eagle XG, manufactured by Corning Inc.), and then by drying for 90 seconds on a hot plate heated at 90° C. Absorbance ($\lambda$a) at the maximum absorption wavelength of the resulting thin film was measured using a spectrophotometer (Spectrophotometer UV-2550, manufactured by Shimadzu Corp.), and then, after heating for 30 minutes on the hot plate heated at 230° C., absorbance ($\lambda$b) at the maximum absorption wavelength was measured again. From values of $\lambda$a and $\lambda$b, dye residual ratio (%) was calculated by the following equation.

Dye residual ratio (%)=($\lambda b/\lambda a$)$\times 100$

Experimental Example 38 Heat Resistance Evaluation (at 230° C., for 0.5 Hour) of the Monomer (Compound 18)

Heat resistance was evaluated by a similar method as in (2) of Experimental Example 37, except for using 0.08 g of Compound 18 obtained in Example 10, instead of Compound 17.

Experimental Example 39 Heat Resistance Evaluation (at 230° C., for 0.5 Hour) of the Monomer (Compound 21)

Heat resistance was evaluated by a similar method as in (2) of Experimental Example 37, except for using 0.08 g of Compound 21 obtained in Example 13, instead of Compound 17.

Experimental Example 40 Heat Resistance Evaluation (at 230° C., for 0.5 Hour) of the Monomer (Compound 28)

Heat resistance was evaluated by a similar method as in (2) of Experimental Example 37, except for using 0.08 g of Compound 28 obtained in Example 15, instead of Compound 17.

Experimental Example 41 Heat Resistance Evaluation (at 230° C., for 0.5 Hour) of the Monomer (Compound 30)

Heat resistance was evaluated by a similar method as in (2) of Experimental Example 37, except for using 0.08 g of Compound 30 obtained in Example 16, instead of Compound 17.

Experimental Example 42 Heat Resistance Evaluation (at 230° C., for 0.5 Hour) of the Monomer (Compound 92)

Heat resistance was evaluated by a similar method as in (2) of Experimental Example 37, except for using 0.08 g of Compound 92 obtained in Example 46, instead of Compound 17.

Experimental Example 43 Heat Resistance Evaluation (at 170° C., for 0.5 Hour) of the Monomer (Compound 100)

Heat resistance was evaluated by a similar method as in (2) of Experimental Example 37, except for using 0.08 g of Compound 100 obtained in Example 52, instead of Compound 17, and for setting heating temperature at 170° C., instead of 230° C.

Comparative Example 6 Heat Resistance Evaluation (at 230° C., for 0.5 Hour) of the Monomer (Rhodamine 6G)

Heat resistance was evaluated by a similar method as in (2) of Experimental Example 37, except for using Rhodamine 6G, instead of Compound 17.

Results of Experimental Examples 37 to 43 and Comparative Example 6 are shown in TABLE 5.

TABLE 5

| Experimental Example | Compound | Dye residual ratio (%) |
|---|---|---|
| Exp. Example 37 | Compound 17 | 98 |
| Exp. Example 38 | Compound 18 | 93 |
| Exp. Example 39 | Compound 21 | 90 |
| Exp. Example 40 | Compound 28 | 86 |
| Exp. Example 41 | Compound 30 | 93 |
| Exp. Example 42 | Compound 92 | 97 |
| Exp. Example 43 | Compound 100 | 95 |
| Com. Example 6 | Rhodamine 6G | 18 |

It has been revealed that, by observation of the glass wafers after heating, the coating film was remained on each glass wafer in Experimental Examples 37 to 43, whereas the dye was decomposed and changed to be a colorless and transparent state in Comparative Example 6. It has been revealed that the compound of the present invention showed superior heat resistance, as compared with Rhodamine 6G, which is a general dye not having a polymerizable group, from this observation result and from the results of dye residual ratio shown in the TABLE 5.

Experimental Example 44 Elution Resistance Test of the Polymer (Derived from Compound 21)

(1) Synthesis of a Polymer (Derived from Compound 21)

Into a 2000 mL round-bottom flask equipped with a stirring apparatus, a cooling tube, a thermometer and a nitrogen introduction tube, 105 g of PGMEA (produced by Daicel Corp.) was charged, and heated until inner temperature reached to 95° C. under nitrogen gas flow. Next, 15 g of the monomer (Compound 21) obtained in Example 13, 285 g of methyl methacrylate (MMA) (produced by Wako Pure Chemical Industries, Ltd.), and 15 g of 2,2'-azobis (methyl 2-methylpropionate) (trade name: V-601, produced by Wako Pure Chemical Industries, Ltd.) were mixed, and the mixed solution was dropped into the round-bottom flask at 95° C. taking 2 hours. After that, the resulting solution was reacted at 95° C. for 2 hours. After the reaction, the resulting solution was cooled to room temperature, and dissolved into 1000 g of ethyl acetate. The mixed solution was charged into 4600 mL of n-hexane, and then a generated precipitate was filtrated and dried under reduced pressure to obtain 314 g of a polymer (derived from Compound 21) containing about 5 parts by weight of the monomer (Compound 21).

(2) Molding of a Colored Plate

Colored resin pellets were obtained by melt blending 0.5 part by weight of the polymer (derived from Compound 21) obtained in (1), and 99.5 parts by weight of a commercially available methyl methacrylate resin (ACRYPET MD001, produced by Mitsubishi Rayon Co., Ltd.), using a same direction rotation type twin screw extruder. Next, a colored plate, having a size of 150 mm×150 mm x t 2 mm, was prepared by molding the resulting resin pellets using an electromotive injection molding machine.

(3) Elution Resistance Test

The molded plate prepared in (2) was cut to a size of 40 mm×30 mm x t 2 mm, and then immersed in 80 mL of an aqueous ethanol solution, which was prepared by mixing 50 parts of ethanol and 50 parts of deionized water, and stored in a thermostatic bath at 40° C. for 200 hours. The aqueous ethanol solution was taken out to measure an optical spectrum thereof using a spectrophotometer (Spectrophotometer UV-2500, manufactured by Shimadzu Corp.). Weight of the monomer (Compound 21) eluted into the aqueous ethanol solution was calculated, using absorbance ($\lambda a$) of the measurement sample at the maximum absorption wavelength, and gram absorption coefficient ($\varepsilon$) measured in advance, to calculate elution ratio (%), based on weight of the monomer (Compound 21) contained in the resin plate immersed, by the following equation.

Elution ratio (%)=[($\lambda a$×0.08/$\varepsilon$)/(weight of the dye contained in the colored plate)]×100

Weight of the dye contained in the colored plate=weight of the plate x 0.00025

Experimental Example 45 Elution Resistance Test of the Polymer (Derived from Compound 17)

Elution ratio was calculated by a similar method as in (1) of Experimental Example 44, except for using 15 g of Compound 17 obtained in Example 9, instead of Compound 21.

Experimental Example 46 Elution Resistance Test of the Polymer (Derived from Compound 92)

Elution ratio was calculated by a similar method as in (1) of Experimental Example 44, except for using 15 g of Compound 92 obtained in Example 46, instead of Compound 21.

Experimental Example 47 Elution Resistance Test of the Polymer (Derived from Compound 100)

Elution ratio was calculated by a similar method as in (1) of Experimental Example 44, except for using 15 g of Compound 100 obtained in Example 52, instead of Compound 21.

Results of Experimental Examples 44 to 47 are shown in TABLE 6.

TABLE 6

| Experimental Example | Colored plate | Elution ratio (%) |
|---|---|---|
| Exp. Exam. 44 | Colored plate containing polymer (derived from compound 21) | 0.3 |
| Exp. Exam. 45 | Colored plate containing polymer (derived from compound 17) | 2.4 |
| Exp. Exam. 46 | Colored plate containing polymer (derived from compound 92) | 0.9 |
| Exp. Exam. 47 | Colored plate containing polymer (derived from compound 100) | 0.3 |

From the results shown in the TABLE 6, it has been revealed that the polymer of the present invention little elutes from the colored plate, even in contact with a solvent.

Experimental Example 48 Weather Resistance Test of the Polymer (Derived from Compound 21)

The colored plate prepared in (2) of Experimental Example 44 was cut to a size of 65 mm×65 mm×t 2 mm, and subjected to an accelerated weather resistance test by a xenon arc lamp type under the following conditions, using an apparatus (Ci4000, manufactured by Atlas Material Testing Technology, Ltd.) specified in JIS B7754: 1991.
(1) Test Conditions
Irradiance: 50 w/m² (300 to 400 nm)
Filter glass: (inside) borosilicate S-type, (outside) soda lime
Black panel temperature: 63±2° C.
Chamber temperature: 38±2° C.
Relative humidity: 50±10% RH
Test time: 50 hours
(2) Color Measurement Conditions
Measurement: reflection measurement (8°: de)
Standard light: $D_{65}$
Measurement hole diameter: φ5 mm
As for the molded plate before the test and after the test for 50 hours, color difference was measured, according to the L*a*b* color system of JIS Z8730:2009, using a color meter CC-i (manufactured by Suga Test Instruments Co., Ltd.) to calculate ΔL*, Δa* and Δb*, which indicate amount of change of L* value, a* value and b* value before and after the test; and color difference (ΔE*ab) was calculated by the following equation.

Color difference $(\Delta E^*ab) = [(\Delta L^*)^2 + (\Delta a^*)^2 + (\Delta b^*)^2]^{1/2}$ Experimental Example 49 Weather Resistance Test of the Polymer (Derived from Compound 17)

The accelerated weather resistance test was carried out by a similar method as in Experimental Example 44, except for using the colored plate prepared in Experimental Example 45, instead of the colored plate prepared in (2) of Experimental Example 44.

Experimental Example 50 Weather Resistance Test of the Polymer (Derived from Compound 92)

The accelerated weather resistance test was carried out by a similar method as in Experimental Example 44, except for using the colored plate prepared in Experimental Example 46, instead of the colored plate prepared in (2) of Experimental Example 44.

Experimental Example 51 Weather Resistance Test of the Polymer (Derived from Compound 100)

The accelerated weather resistance test was carried out by a similar method as in Experimental Example 44, except for using the colored plate prepared in Experimental Example 47, instead of the colored plate prepared in (2) of Experimental Example 44.
Results of Experimental Examples 48 to 51 are shown in TABLE 7.

TABLE 7

| Experimental Example | Test time: 0 hr | | | Test time: 50 hr | | | Color difference |
|---|---|---|---|---|---|---|---|
| | L* | a* | b* | L* | a* | b* | ΔE*ab |
| Exp. Exam. 48 | 52.04 | 50.92 | 33.99 | 54.29 | 50.04 | 31.16 | 3.72 |
| Exp. Exam. 49 | 37.05 | 65.23 | −7.37 | 35.92 | 60.64 | −5.89 | 4.95 |
| Exp. Exam. 50 | 44.28 | 51.35 | 38.81 | 42.56 | 46.72 | 34.57 | 6.5 |
| Exp. Exam. 51 | 5.07 | 10.11 | 5.65 | 6.01 | 11.08 | 7.38 | 2.2 |

From the results shown in the TABLE 7, it has been revealed that the colored plate containing the polymer of the present invention has superior weather resistance.

Example 61 Synthesis of a Dye Polymer (Derived from MMA/Compound 1001)

(1) Synthesis of a Dye Monomer (Compound 1001)
The dye polymer (Compound 1001) was synthesized, in accordance with a method described in WO2014/126167 publication.

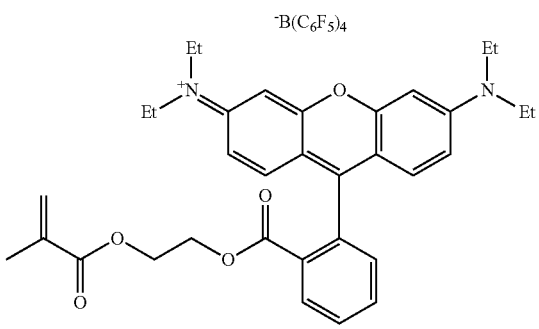

1001

(2) Synthesis of a Dye Polymer (Derived from MMA/Compound 1001)
Into a round-bottom flask equipped with a stirring apparatus, 105 g of PGMEA (produced by Daicel Corp.) was added and heated to 95° C. after nitrogen purge. Into an Erlenmeyer flask, 15 g (12.1 mmol) of the dye monomer (Compound 1001) obtained in (1) of Example 61, 285.03 g (2.85 mol) of MMA (produced by Wako Pure Chemical Industries, Ltd.), 15 g (65.1 mmol) of 2,2'-azobis(methyl 2-methylpropionate) (trade name: V-601, produced by Wako Pure Chemical Industries, Ltd.), and 105 g of PGMEA were added for dissolution, and dropped into the round-bottom flask at 95° C. taking 2 hours. After the dropping, a reaction was carried out at 95° C. for 2 hours. After completion of the reaction, 1200 g of ethyl acetate was added, and then it was dropped into 5.2 L of hexane for reprecipitation. The reprecipitated polymer was filtrated and dried under reduced pressure to obtain 322.06 g (yield: 100%) of a red dye polymer (derived from MMA/Compound 1001).

Example 62 Synthesis of Dye Polymer Solution (Derived from MMA/Compound 1001)

Into a round-bottom flask equipped with a stirring apparatus, 70.00 g of PGMEA (produced by Daicel Corp.) was added and heated to 95° C. after nitrogen purge. Into an Erlenmeyer flask, 0.01 g (0.0081 mmol) of the dye monomer (Compound 1001) obtained in (1) of Example 61, 199.99 g (2.00 mol) of MMA (produced by Wako Pure Chemical Industries, Ltd.), 10.00 g (43.4 mmol) of 2,2'-azobis(methyl 2-methylpropionate) (trade name: V-601, produced by Wako Pure Chemical Industries, Ltd.), and 70.00 g of PGMEA were added for dissolution, and dropped into the round-bottom flask at 95° C. taking 2 hours. After the dropping, a reaction was carried out at 95° C. for 2 hours to obtain 345.16 g (yield: 99%) of a red dye polymer solution (derived from MMA/Compound 1001).

Example 63 Synthesis of a Dye Polymer (MMA/Compound 21=95:5)

Into a round-bottom flask equipped with a stirring apparatus, 105.93 g of PGMEA (produced by Daicel Corp.) was added and heated to 95° C. after nitrogen purge. Into an Erlenmeyer flask, 15.11 g (12.8 mmol) of the monomer (Compound 21) obtained in Example 13, 285.02 g (2.85 mol) of MMA (produced by Wako Pure Chemical Industries, Ltd.), 15.00 g (60.4 mmol) of 2,2'-azobis(methyl 2-methylpropionate) (trade name: V-601, produced by Wako Pure Chemical Industries, Ltd.), and 105.54 g of PGMEA were added for dissolution, and dropped into the round-bottom flask at 95° C. taking 2 hours. After the dropping, a reaction was carried out at 95° C. for 2 hours. After completion of the reaction, 1000 g of ethyl acetate was added, and then dropped into 4.6 L of hexane for reprecipitation. The reprecipitated polymer was filtrated and dried under reduced pressure to obtain 314.37 g (yield: 100%) of a red dye polymer (derived from MMA/Compound 21, MMA:Compound 21=95:5).

Example 64 Synthesis of a Dye Polymer (MMA/Compound 21=30:70)

Into a round-bottom flask equipped with a stirring apparatus, 7.29 g of PGMEA (produced by Daicel Corp.) was added and heated to 95° C. after nitrogen purge. Into an Erlenmeyer flask, 13.98 g (11.8 mmol) of the monomer (Compound 21) obtained in Example 13, 6.00 g (59.9 mol) of MMA (produced by Wako Pure Chemical Industries, Ltd.), 1.01 g (4.03 mmol) of 2,2'-azobis(methyl 2-methylpropionate) (trade name: V-601, produced by Wako Pure Chemical Industries, Ltd.), and 21.28 g of PGMEA were added for dissolution, and dropped into the round-bottom flask at 95° C. taking 2 hours. After the dropping, a reaction was carried out at 95° C. for 2 hours, and after completion of the reaction, 14.50 g of PGMEA was added for dilution to obtain 62.1 g (yield: 97%) of a red polymer (derived from MMA/Compound 21, MMA:Compound 21=30:70).

Example 65 Synthesis of a Copolymer (Derived from MMA/Compound 21/Compound 1001)

Into a round-bottom flask equipped with a stirring apparatus, 70.00 g of PGMEA (produced by Daicel Corp.) was added and heated to 95° C. after nitrogen purge. Into an Erlenmeyer flask, 9.99 g (8.45 mmol) of the monomer (Compound 21) obtained in Example 13, 0.01 g (0.0081 mmol) of the dye monomer (Compound 1001) obtained in (1) of Example 61, 190.00 g (1.90 mol) of MMA (produced by Wako Pure Chemical Industries, Ltd.), 10.00 g (43.4 mmol) of 2,2'-azobis(methyl 2-methylpropionate) (trade name: V-601, produced by Wako Pure Chemical Industries, Ltd.), and 70.00 g of PGMEA were added for dissolution, and dropped into the round-bottom flask at 95° C. taking 2 hours. After the dropping, a reaction was carried out at 95° C. for 2 hours to obtain 345.9 g (yield: 99%) of a red copolymer (derived from MMA/Compound 21/Compound 1001).

Experimental Example 52 Quenching Evaluation of a Dye Polymer by the Monomer (Compound 21)

(1) Fluorescence Measurement of Object of Fluorescence Quenching

Into a volumetric flask, 12.5 mg (contained Compound 1001: $5.06 \times 10^{-7}$ mol) of the dye polymer (derived from MMA/Compound 1001) obtained in Example 61 was put and diluted up to 100 mL with PGMEA. This was referred to as an M solution. With a volumetric pipette, 1 mL of the M solution was measured and taken, and diluted in a volumetric flask up to 20 mL with PGMEA (concentration of Compound 1001: $2.53 \times 10^{-7}$ mol/L). Fluorescence intensity (Im) at the maximum fluorescence wavelength of the resulting solution was measured using a fluorescence spectrophotometer (Fluorescence Spectrophotometer F-4500, manufactured by Hitachi Ltd.).

(2) Quenching Evaluation

Compound 21 obtained in Example 13 was measured and taken by 32.2 mg (0.027 mmol), and diluted in a volumetric flask up to 20 mL with methanol. This was referred to as an N solution. With a volumetric pipette, 1 mL of the M solution and 4 mL of the N solution was measured and taken, and diluted in a volumetric flask up to 20 mL with methanol (concentration: $2.64 \times 10^{-4}$ mol/L). Fluorescence intensity (In) at the maximum fluorescence wavelength of the resulting solution was measured using a fluorescence spectrophotometer (Fluorescence Spectrophotometer F-4500, manufactured by Hitachi Ltd.). From measured values of Im and In, decreasing rate (%) of fluorescence intensity was calculated by the following equation.

Decreasing rate (%) of fluorescence intensity= $(Im-In)/Im \times 100$

Experimental Example 53 Quenching Evaluation of a Dye Polymer by the Polymer (MMA/Compound 21=95:5)

The polymer (MMA: the compound 21=95:5) obtained in Example 63 was measured and taken by 132.1 mg (contained Compound 21: $5.6 \times 10^{-6}$ mol), and 1 mL of the M solution was measured and taken with volumetric pipette, and diluted in a volumetric flask up to 20 mL with PGMEA (concentration: $2.79 \times 10^{-4}$ mol/L). Fluorescence intensity (In) at the maximum fluorescence wavelength of the resulting solution was measured using a fluorescence spectrophotometer (Fluorescence Spectrophotometer F-4500, manufactured by Hitachi Ltd.). From the resulting value of Im in Experimental Example 52, and the measured value of In, decreasing rate (%) of fluorescence intensity was calculated by the following equation.

Decreasing rate (%) of fluorescence intensity= $(Im-In)/In \times 100$

Experimental Example 54 Quenching Evaluation of a Dye Polymer by the Polymer (MMA/Compound 21=30:70)

Decreasing rate of fluorescence intensity was calculated by a similar method as in Experimental Example 53 (concentration: $3.04 \times 10^{-4}$ mol/L), except for using 32.4 mg (contained Compound 21: $6.1 \times 10^{-6}$ mol) of the polymer (MMA:Compound 21=30:70) obtained in Example 64, instead of the polymer (MMA:Compound 21=95:5).

Experimental Example 55 Quenching Evaluation of a Dye Polymer by the Polymer (MMA/Compound 21=95:5)

(1) Fluorescence Measurement of Object of Fluorescence Quenching

Into a volumetric flask, 12.1 mg (contained Compound 1001: $9.83 \times 10^{-6}$ mol) of the dye monomer (Compound 1001) obtained in (1) of Example 61 was put and diluted up to 100 mL with PGMEA. With a volumetric pipette, 2.5 mL of this solution was measured and taken, and diluted in a volumetric flask up to 100 mL with PGMEA. This was referred to as an O solution. With a volumetric pipette, 2 mL of the O solution was measured and taken, and diluted in a volumetric flask up to 20 mL with PGMEA (concentration of Compound 1001: $2.46 \times 10^{-7}$ mol/L). Fluorescence intensity (Io) at the maximum fluorescence wavelength of the resulting solution was measured using a fluorescence spectrophotometer (Fluorescence Spectrophotometer F-4500, manufactured by Hitachi Ltd.).

(2) Quenching Evaluation

The polymer (MMA:Compound 21=95:5) obtained in Example 63 was measured and taken by 123.6 mg (contained Compound 21: $5.2 \times 10^{-6}$ mol), and 2 mL of the O solution was measured and taken with volumetric pipette, and diluted in a volumetric flask up to 20 mL with PGMEA (concentration: $2.62 \times 10^{-4}$ mol/L). Fluorescence intensity (Ip) at the maximum fluorescence wavelength of the resulting solution was measured using a fluorescence spectrophotometer (Fluorescence Spectrophotometer F-4500, manufactured by Hitachi Ltd.). From measured values of Io and Ip, decreasing rate (%) of fluorescence intensity was calculated by the following equation.

Decreasing rate (%) of fluorescence intensity= $(Io-Ip)/Io \times 100$

Experimental Example 56 Quenching Evaluation of a Dye Polymer by the Polymer (MMA/Compound 21=30:70)

Decreasing rate of fluorescence intensity was calculated by a similar method as in (2) of Experimental Example 55 (concentration: $3.04 \times 10^{-4}$ mol/L), except for using 32.4 mg (contained Compound 21: $6.1 \times 10^{-6}$ mol) of the polymer (MMA:Compound 21=30:70) obtained in Example 64, instead of the polymer (MMA:Compound 21=95:5).

Experimental Example 57 Quenching Evaluation of a Dye Polymer by the Copolymer (Derived from MMA/Compound 21/Compound 1001)

(1) Fluorescence Measurement of Object of Fluorescence Quenching

Into a volumetric flask, 2.06 g (contained Compound 1001: $5.98 \times 10^{-5}$ mol) of the dye polymer solution (derived from MMA/Compound 1001) obtained in Example 62 was put and diluted up to 20 mL with PGMEA. This was referred to as a Q solution. With a volumetric pipette, 2 mL of the Q solution was measured and taken, and diluted in a volumetric flask up to 20 mL with PGMEA (concentration of Compound 1001: $2.42 \times 10^{-7}$ mol/L). Fluorescence intensity (Iq) at the maximum fluorescence wavelength of the resulting solution was measured using a fluorescence spectrophotometer (Fluorescence Spectrophotometer F-4500, manufactured by Hitachi Ltd.).

(2) Quenching Evaluation

Into a volumetric flask, 2.19 g of the copolymer (derived from MMA/Compound 21/Compound 1001) obtained in Example 65 was put and diluted up to 20 mL with PGMEA. With a volumetric pipette, 2 mL of the solution was measured and taken, and diluted in a volumetric flask up to 20 mL with PGMEA (concentration of Compound 1001: $2.56 \times 10^{-7}$ mol/L, concentration of Compound 21: $2.68 \times 10^{-4}$ mol/L). Fluorescence intensity (Ir) at the maximum fluorescence wavelength of the resulting solution was measured using a fluorescence spectrophotometer (Fluorescence Spectrophotometer F-4500, manufactured by Hitachi Ltd.). From measured values of Ia and Ib, decreasing rate (%) of fluorescence intensity was calculated by the following equation.

Decreasing rate (%) of fluorescence intensity= $(Iq-Ir)/Iq \times 100$

Results of Experimental Examples 52 to 57 are shown in TABLE 8.

TABLE 8

| Experimental Example | Quencher | Dye having fluorescent property | Concentration of compound 21 (mol/L) | Decreasing rate of fluorescence intensity (%) |
| --- | --- | --- | --- | --- |
| Exp. Exam. 52 | Compound of the present invention (monomer) | Polymer | $2.64 \times 10^{-4}$ | 98.1 |
| Exp. Exam. 53 | Polymer of the present invention | Polymer | $2.79 \times 10^{-4}$ | 85.1 |
| Exp. Exam. 54 | Polymer of the present invention | Polymer | $3.04 \times 10^{-4}$ | 89.4 |
| Exp. Exam. 55 | Polymer of the present invention | Monomer | $2.62 \times 10^{-4}$ | 83.2 |
| Exp. Exam. 56 | Polymer of the present invention | Monomer | $3.04 \times 10^{-4}$ | 90.0 |
| Exp. Exam. 57 | Copolymer of the present invention (Copolymer of quencher and dye) | | $2.68 \times 10^{-4}$ | 97.5 |

From the result shown in Experimental Example 52 of the TABLE 8, it has been revealed that the compound of the present invention exerts quenching effect not only to a dye monomer having fluorescent property but also to a dye polymer having fluorescent property. In addition, from the result shown by Experimental Examples 53 to 56 of the TABLE 8, it has been revealed that also the polymer of the present invention exerts sufficient quenching effect both to a dye monomer and to a dye polymer having fluorescent property. Still more, from the result represented by Experimental Example 57 of the TABLE 8, it has been revealed that, in the copolymer of the present invention, the compound (the monomer) of the present invention contained in the copolymer is capable of suppressing fluorescence, which is emitted by the fluorescent dye contained in the copolymer, inside the copolymer molecule.

The invention claimed is:
1. A quencher comprising a compound represented by formula (3);

(1)

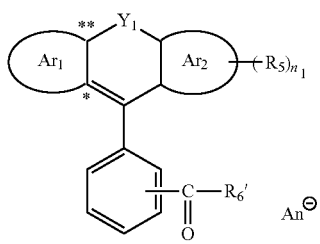

wherein $n_1$ pieces of $R_5$ each independently represent a halogen atom; an alkyl group having 1 to 20 carbon atoms; an alkoxy group having 1 to 20 carbon atoms; an alkylthio group having 1 to 20 carbon atoms; an amino group having an alkyl group having 1 to 20 carbon atoms, a halogenated alkyl group having 1 to 20 carbon atoms, an aryl group having 6 to 10 carbon atoms, or an arylalkyl group having 7 to 13 carbon atoms, as a substituent, or not having a substituent; a hydroxy group; an aryl group having 6 to 14 carbon atoms; an aryloxy group having 6 to 14 carbon atoms; or an arylalkyl group having 7 to 20 carbon atoms; $R_6'$ represents a group having an acryloyl group, a methacryloyl group, a vinylaryl group, a vinyloxy group, or an allyl group; $Y_1$ represents an oxygen atom; $R_{32}$ represents an alkyl group having 1 to 6 carbon atoms; $An^-$ represents an anion; $Ar_1$ represents a ring structure represented by formula (1-1);

(1-1)

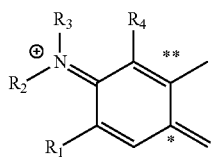

wherein $R_1$ and $R_4$ represent a hydrogen atom; $R_2$ and $R_3$ each independently represent an alkyl group having 1 to 20 carbon atoms, or an aryl group having 6 to 14 carbon atoms which has an alkyl group having 1 to 20 carbon atoms as a substituent or no substituent; $R_1$ and $R_2$ may form an alkylene group having 2 to 4 carbon atoms; and $R_3$ and $R_4$ may form an alkylene group having 2 to 4 carbon atoms,

* and ** represent each binding position; $Ar_2$ represents a benzene ring, a naphthalene ring or an anthracene ring; when $Ar_2$ is the benzene ring, $n_1$ represents an integer of 0 to 4, when $Ar_2$ is the naphthalene ring, $n_1$ represents an integer of 0 to 6, and when $Ar_2$ is the anthracene ring, $n_1$ represents an integer of 0 to 8;
and a structure (1-10) in the formula (3) is an asymmetric structure;

(1-10)

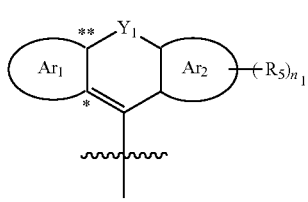

wherein $n_1$ pieces of $R_5$, $Y_1$, $Ar_1$, $Ar_2$, $n_1$, * and ** are the same as described above.

2. The quencher according to claim 1, wherein $An^-$ is an anion containing an aryl group having an electron withdrawing substituent, a sulfonyl group having an electron withdrawing substituent, a halogenated alkyl group, or a halogeno group; a halogen oxoacid anion; or a sulfonate anion.

3. The quencher according to claim 1, wherein $An^-$ is an anion represented by formulae (16) to (19);

(16)

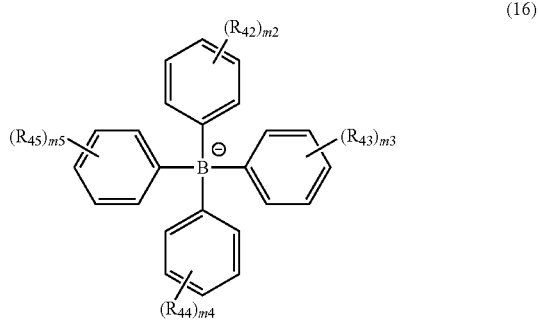

wherein $R_{42}$ to $R_{45}$ each independently represent a halogenated alkyl group having 1 to 3 carbon atoms, a halogen atom, or a nitro group; $m_2$ to $m_5$ each independently represent an integer of 1 to 5; and $m_2$ pieces of $R_{42}$, $m_3$ pieces of $R_{43}$, $m_4$ pieces of $R_{44}$ and $m_5$ pieces of $R_{45}$ each independently may be the same or different, (17)

wherein 4 pieces of $R_{46}$ each independently represent a halogenated alkyl group having 1 to 3 carbon atoms, or a halogen atom, (18)

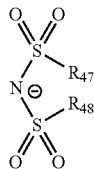

wherein $R_{47}$ and $R_{48}$ each independently represent a halogenated alkyl group having 1 to 3 carbon atoms, or a halogen atom; and $R_{47}$ and $R_{48}$ may form a halogenated alkylene group having 2 to 3 carbon atoms, (19)

$$\begin{array}{c} X \\ X_{\diagdown} \overset{|}{\underset{|}{R_{49}}} {\mathbin{\!\!\!\ominus}} \overset{\mathllap{\text{\tiny\textbackslash}}}{\phantom{R}} X \\ X \overset{|}{\phantom{R}} X \\ X \end{array}$$

wherein $R_{49}$ represents a phosphorus atom or an antimony atom; and 6 pieces of X all represent the same halogen atom.

4. The quencher according to claim 1, wherein $R_6'$ is a group having an acryloyl group or a methacryloyl group.

5. The quencher according to claim 1, wherein $R_6'$ is a group represented by formula (2);

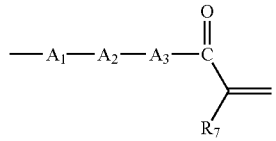
(2)

wherein $R_7$ represents a hydrogen atom or a methyl group; $A_1$ represents —O—, or a group represented by formula (2-1);

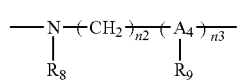
(2-1)

wherein $R_8$ and $R_9$ each independently represent a hydrogen atom, or an alkyl group having 1 to 12 carbon atoms; $A_4$ represents a nitrogen atom, or a group represented by formula (2-2);

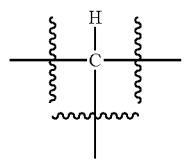
(2-2)

$n_2$ represents an integer of 0 to 3; $R_8$ and $R_9$ may form a ring structure of a 5 to 6-membered ring together with —N(CH$_2$)$_{n2}$-(A$_4$)$_{n3}$- bonding thereto; when the ring structure of the 5 to 6-membered ring is formed by $R_8$, $R_9$ and —N(CH$_2$)$_{n2}$-(A$_4$)$_{n3}$-, $n_3$ represents 1, and when the ring structure of the 5 to 6-membered ring is not formed, $n_3$ represents 0 or 1, $A_2$ represents an alkylene group having 1 to 21 carbon atoms which has at least one group selected from —O—, —COO—, —COO—, —NHCO—, —CONH—, —NHCONH— and an arylene group in a chain; an alkylene group having 1 to 21 carbon atoms which has at least one group selected from —O—, —COO—, —COO—, —NHCO—, —CONH—, —NHCONH— and an arylene group in a chain, and also has a hydroxy group as a substituent; an alkylene group having 1 to 21 carbon atoms which has a hydroxy group as a substituent; or an alkylene group having 1 to 21 carbon atoms; $A_3$ represents —NR$_{10}$— or —O—; and $R_{10}$ represents a hydrogen atom or an alkyl group having 1 to 12 carbon atoms.

6. A compound represented by formula (3);

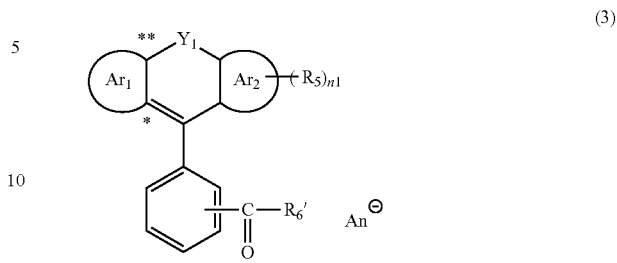
(3)

wherein $n_1$ pieces of $R_5$ each independently represent a halogen atom; an alkyl group having 1 to 20 carbon atoms; an alkoxy group having 1 to 20 carbon atoms; an alkylthio group having 1 to 20 carbon atoms; an amino group having an alkyl group having 1 to 20 carbon atoms, a halogenated alkyl group having 1 to 20 carbon atoms, an aryl group having 6 to 10 carbon atoms, or an arylalkyl group having 7 to 13 carbon atoms, as a substituent, or not having a substituent; a hydroxy group; an aryl group having 6 to 14 carbon atoms; an aryloxy group having 6 to 14 carbon atoms; or an arylalkyl group having 7 to 20 carbon atoms; $R_6'$ represents a group having an acryloyl group, a methacryloyl group, a vinylaryl group, a vinyloxy group, or an allyl group; $Y_1$ represents an oxygen atom; $R_{32}$ represents an alkyl group having 1 to 6 carbon atoms; An$^-$ represents an anion; $Ar_1$ represents a ring structure represented by formula (1-1);

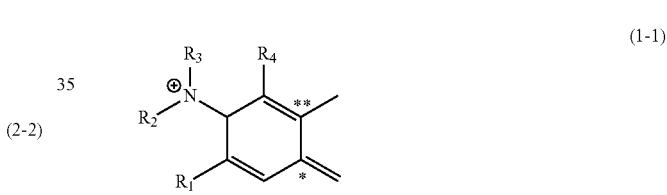
(1-1)

wherein $R_1$ and $R_4$ represent a hydrogen atom; $R_2$ and $R_3$ each independently represent an alkyl group having 1 to 20 carbon atoms, or an aryl group having 6 to 14 carbon atoms which has an alkyl group having 1 to 20 carbon atoms as a substituent or no substituent; $R_1$ and $R_2$ may form an alkylene group having 2 to 4 carbon atoms; and $R_3$ and $R_4$ may form an alkylene group having 2 to 4 carbon atoms,

* and ** represent each binding position; $Ar_2$ represents a benzene ring, a naphthalene ring or an anthracene ring; when $Ar_2$ is the benzene ring, $n_1$ represents an integer of 0 to 4, when $Ar_2$ is the naphthalene ring, $n_1$ represents an integer of 0 to 6, and when $Ar_2$ is the anthracene ring, $n_1$ represents an integer of 0 to 8;

and a structure (1-10) in the formula (3) is an asymmetric structure;

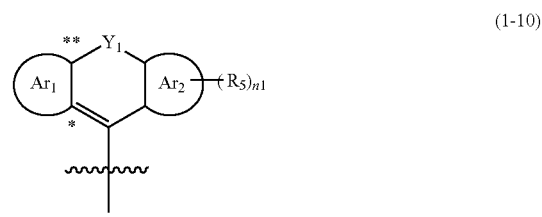
(1-10)

wherein $n_1$ pieces of $R_5$, $Y_1$, $Ar_1$, $Ar_2$, $n_1$, * and ** are the same as described above.

7. The compound according to claim 6, wherein $An^-$ is an anion containing an aryl group having an electron withdrawing substituent, a sulfonyl group having an electron withdrawing substituent, a halogenated alkyl group, or a halogeno group.

8. The compound according to claim 6, wherein $An^-$ is an anion represented by formulae (16) to (19);

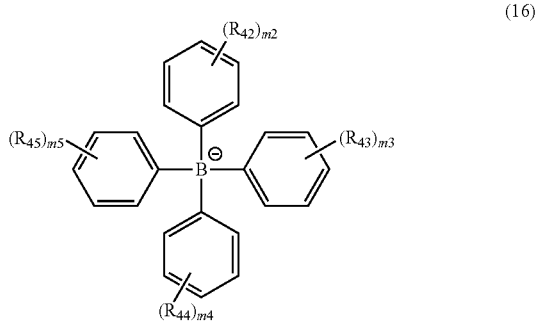

(16)

wherein $R_{42}$ to $R_{45}$ each independently represent a halogenated alkyl group having 1 to 3 carbon atoms, a halogen atom, or a nitro group; $m_2$ to $m_5$ each independently represent an integer of 1 to 5; and $m_2$ pieces of $R_{42}$, $m_3$ pieces of $R_{43}$, $m_4$ pieces of $R_{44}$ and $m_5$ pieces of $R_{45}$ each independently may be the same or different,

(17)

wherein 4 pieces of $R_{46}$ each independently represent a halogenated alkyl group having 1 to 3 carbon atoms, or a halogen atom,

(18)

wherein $R_{47}$ and $R_{48}$ each independently represent a halogenated alkyl group having 1 to 3 carbon atoms, or a halogen atom; and $R_{47}$ and $R_{48}$ may form a halogenated alkylene group having 2 to 3 carbon atoms,

(19)

wherein $R_{49}$ represents a phosphorus atom or an antimony atom; and 6 pieces of X all represent the same halogen atom.

9. The compound according to claim 6, wherein $R_6'$ is a group having an acryloyl group or a methacryloyl group.

10. The compound according to claim 6, wherein $R_6'$ is a group represented by formula (2);

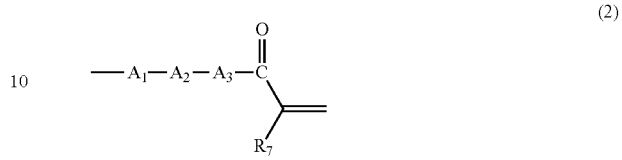

(2)

wherein $R_7$ represents a hydrogen atom or a methyl group; $A_1$ represents —O—, or a group represented by formula (2-1);

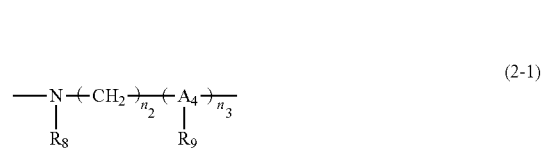

(2-1)

wherein $R_8$ and $R_9$ each independently represent a hydrogen atom, or an alkyl group having 1 to 12 carbon atoms; $A_4$ represents a nitrogen atom, or a group represented by formula (2-2);

(2-2)

$n_2$ represents an integer of 0 to 3; $R_8$ and $R_9$ may form a ring structure of a 5 to 6-membered ring together with —$N(CH_2)_{n2}$-$(A_4)_{n3}$- bonding thereto; when the ring structure of the 5 to 6-membered ring is formed by $R_8$, $R_9$ and —$N(CH_2)_{n2}$-$(A_4)_{n3}$-, $n_3$ represents 1, and when the ring structure of the 5 to 6-membered ring is not formed, $n_3$ represents 0 or 1, $A_2$ represents an alkylene group having 1 to 21 carbon atoms which has at least one group selected from —O—, —COO—, —COO—, —NHCO—, —CONH—, —NHCONH— and an arylene group in a chain; an alkylene group having 1 to 21 carbon atoms which has at least one group selected from —O—, —COO—, —COO—, —NHCO—, —CONH—, —NHCONH— and an arylene group in a chain, and also has a hydroxy group as a substituent; an alkylene group having 1 to 21 carbon atoms which has a hydroxy group as a substituent; or an alkylene group having 1 to 21 carbon atoms; $A_3$ represents —$NR_{10}$— or —O—; and $R_{10}$ represents a hydrogen atom or an alkyl group having 1 to 12 carbon atoms.

11. A polymer having a monomer unit derived from a compound represented by formula (3);

(3)

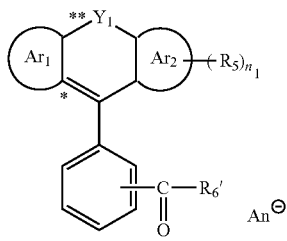

wherein $n_1$ pieces of $R_5$ each independently represent a halogen atom; an alkyl group having 1 to 20 carbon atoms; an alkoxy group having 1 to 20 carbon atoms; an alkylthio group having 1 to 20 carbon atoms; an amino group having an alkyl group having 1 to 20 carbon atoms, a halogenated alkyl group having 1 to 20 carbon atoms, an aryl group having 6 to 10 carbon atoms, or an arylalkyl group having 7 to 13 carbon atoms, as a substituent, or not having a substituent; a hydroxy group; an aryl group having 6 to 14 carbon atoms; an aryloxy group having 6 to 14 carbon atoms; or an arylalkyl group having 7 to 20 carbon atoms; $R_6'$ represents a group having an acryloyl group, a methacryloyl group, a vinylaryl group, a vinyloxy group, or an allyl group; $Y_1$ represents an oxygen atom; $R_{32}$ represents an alkyl group having 1 to 6 carbon atoms; $An^-$ represents an anion; $Ar_1$ represents a ring structure represented by formula (1-1);

(1-1)

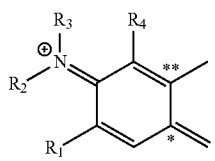

wherein $R_1$ and $R_4$ represent a hydrogen atom; $R_2$ and $R_3$ each independently represent an alkyl group having 1 to 20 carbon atoms, or an aryl group having 6 to 14 carbon atoms which has an alkyl group having 1 to 20 carbon atoms as a substituent or no substituent; $R_1$ and $R_2$ may form an alkylene group having 2 to 4 carbon atoms; and $R_3$ and $R_4$ may form an alkylene group having 2 to 4 carbon atoms,

* and ** represent each binding position; $Ar_2$ represents a benzene ring, a naphthalene ring or an anthracene ring; when $Ar_2$ is the benzene ring, $n_1$ represents an integer of 0 to 4, when $Ar_2$ is the naphthalene ring, $n_1$ represents an integer of 0 to 6, and when $Ar_2$ is the anthracene ring, $n_1$ represents an integer of 0 to 8;

and a structure (1-10) in the formula (3) is an asymmetric structure;

(1-10)

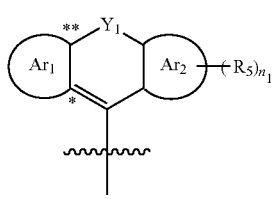

wherein $n_1$ pieces of $R_5$, $Y_1$, $Ar_1$, $Ar_2$, $n_1$, * and ** are the same as described above.

12. The polymer according to claim 11, wherein $An^-$ is an anion containing an aryl group having an electron withdrawing substituent, a sulfonyl group having an electron withdrawing substituent, a halogenated alkyl group, or a halogeno group.

13. The polymer according to claim 11, wherein $An^-$ is an anion represented by formulae (16) to (19);

(16)

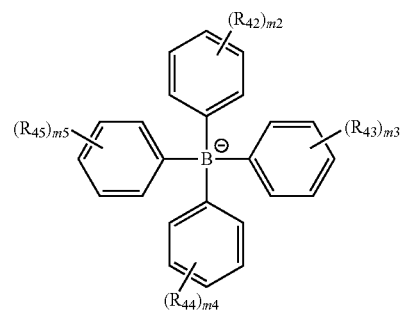

wherein $R_{42}$ to $R_{45}$ each independently represent a halogenated alkyl group having 1 to 3 carbon atoms, a halogen atom, or a nitro group; $m_2$ to $m_5$ each independently represent an integer of 1 to 5; and $m_2$ pieces of $R_{42}$, $m_3$ pieces of $R_{43}$, $m_4$ pieces of $R_{44}$ and $m_5$ pieces of $R_{45}$ each independently may be the same or different, (17)

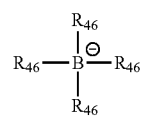

wherein 4 pieces of $R_{46}$ each independently represent a halogenated alkyl group having 1 to 3 carbon atoms, or a halogen atom, (18)

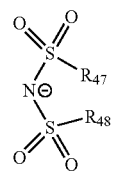

wherein $R_{47}$ and $R_{48}$ each independently represent a halogenated alkyl group having 1 to 3 carbon atoms, or a halogen atom; and $R_{47}$ and $R_{48}$ may form a halogenated alkylene group having 2 to 3 carbon atoms, (19)

wherein $R_{49}$ represents a phosphorus atom or an antimony atom; and 6 pieces of X all represent the same halogen atom.

14. The polymer according to claim 11, wherein $R_6'$ is a group having an acryloyl group or a methacryloyl group.

15. The polymer according to claim 11, wherein $R_6'$ is a group represented by formula (2);

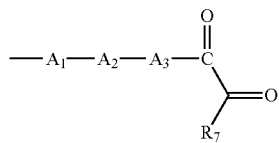

(2)

wherein $R_7$ represents a hydrogen atom or a methyl group; $A_1$ represents —O—, or a group represented by formula (2-1);

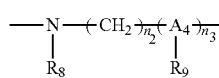

(2-1)

wherein $R_8$ and $R_9$ each independently represent a hydrogen atom, or an alkyl group having 1 to 12 carbon atoms; $A_4$ represents a nitrogen atom, or a group represented by formula (2-2);

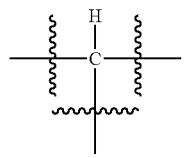

(2-2)

$n_2$ represents an integer of 0 to 3; $R_8$ and $R_9$ may form a ring structure of a 5 to 6-membered ring together with —N(CH$_2$)$_{n2}$-(A$_4$)$_{n3}$- bonding thereto; when the ring structure of the 5 to 6-membered ring is formed by $R_8$, $R_9$ and —N(CH$_2$)$_{n2}$-(A$_4$)$_{n3}$-, $n_3$ represents 1, and when the ring structure of the 5 to 6-membered ring is not formed, $n_3$ represents 0 or 1, $A_2$ represents an alkylene group having 1 to 21 carbon atoms which has at least one group selected from —O—, —COO—, —COO—, —NHCO—, —CONH—, —NHCONH— and an arylene group in a chain; an alkylene group having 1 to 21 carbon atoms which has at least one group selected from —O—, —COO—, —COO—, —NHCO—, —CONH—, —NHCONH— and an arylene group in a chain, and also has a hydroxy group as a substituent; an alkylene group having 1 to 21 carbon atoms which has a hydroxy group as a substituent; or an alkylene group having 1 to 21 carbon atoms; $A_3$ represents —NR$_{10}$— or —O—; and $R_{10}$ represents a hydrogen atom or an alkyl group having 1 to 12 carbon atoms.

16. The polymer according to claim 11, wherein the polymer is a copolymer.

17. The polymer according to claim 16, wherein the copolymer is a copolymer having a monomer unit derived from a fluorescent dye which has a polymerizable unsaturated group, and/or one or two kinds of monomer units derived from a compound represented by formula (4), formula (5), formula (6) or formula (7); and a monomer unit derived from the compound represented by the formula (3); as composition components;

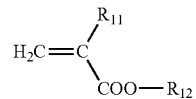

(4)

wherein $R_{11}$ represents a hydrogen atom or a methyl group; and $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 12 carbon atoms which has an oxygen atom or no oxygen atom, a dialkylaminoalkyl group having 3 to 9 carbon atoms, a fluoroalkyl group having 1 to 18 carbon atoms, an N-alkylenephthalimide group having 9 to 14 carbon atoms, a group represented by formula (4-1);

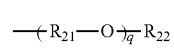

(4-1)

wherein $R_{21}$ represents an alkylene group having 1 to 3 carbon atoms which has a hydroxy group as a substituent or no substituent; $R_{22}$ represents a phenyl group having a hydroxy group as a substituent or not having a substituent, or an alkyl group having 1 to 3 carbon atoms; and q represents an integer of 1 to 3, a group represented by formula (4-2);

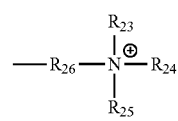

(4-2)

wherein $R_{23}$ to $R_{25}$ represent an alkyl group having 1 to 3 carbon atoms; and $R_{26}$ represents an alkylene group having 1 to 3 carbon atoms, or a group represented by formula (4-3);

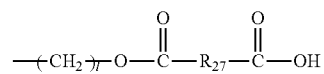

(4-3)

wherein l represents an integer of 1 to 6; and $R_{27}$ represents a phenylene group or a cyclohexylene group,

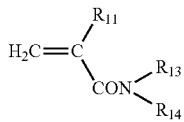

(5)

wherein $R_{11}$ is the same as described above; $R_{13}$ represents a hydrogen atom, or an alkyl group having 1 to 3 carbon atoms; $R_{14}$ represents a hydrogen atom, an alkyl group having 1 to 3 carbon atoms, a dialkylaminoalkyl group having 3 to 9 carbon atoms, or a hydroxyalkyl group having 1 to 6 carbon atoms; and $R_{13}$ and $R_{14}$ may form a morpholino group together with a nitrogen atom adjacent thereto,

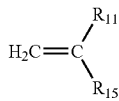

(6)

wherein $R_{15}$ represents a phenyl group or a pyrrolidino group; and $R_{11}$ is the same as described above,

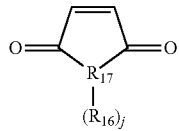

(7)

wherein $R_{17}$ represents a nitrogen atom or an oxygen atom; when $R_{17}$ is the oxygen atom, j represents 0, and when $R_{17}$ is the nitrogen atom, j represents 1; and $R_{16}$ represents a hydrogen atom, an alkyl group having 1 to 20 carbon atoms, a hydroxyalkyl group having 1 to 10 carbon atoms, a halogenated alkyl group having 1 to 10 carbon atoms, an alkylcycloalkyl group having 6 to 10 carbon atoms, a halogenated cycloalkyl group having 6 to 7 carbon atoms, an aryl group having 6 to 10 carbon atoms, an aryl group having 6 to 10 carbon atoms which has an alkyl group having 1 to 6 carbon atoms as a substituent, or a halogenated aryl group having 6 to 10 carbon atoms.

\* \* \* \* \*